(12) United States Patent
Tabuchi et al.

(10) Patent No.: US 9,499,618 B2
(45) Date of Patent: *Nov. 22, 2016

(54) METHOD OF PRODUCING HETEROGENEOUS PROTEIN

(71) Applicant: Chugai Seiyaku Kabushiki Kaisha, Tokyo (JP)

(72) Inventors: Hisahiro Tabuchi, Tokyo (JP); Tomoya Sugiyama, Tokyo (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/800,924

(22) Filed: Jul. 16, 2015

(65) Prior Publication Data

US 2015/0315624 A1 Nov. 5, 2015

Related U.S. Application Data

(62) Division of application No. 14/225,833, filed on Mar. 26, 2014, now Pat. No. 9,284,374, which is a division of application No. 12/733,052, filed as application No. PCT/JP2008/064095 on Aug. 6, 2008, now Pat. No. 8,697,397.

(30) Foreign Application Priority Data

Aug. 7, 2007 (JP) ................. 2007-205158

(51) Int. Cl.
| | | |
|---|---|---|
| C12P 21/00 | (2006.01) | |
| C12P 21/08 | (2006.01) | |
| C12N 5/02 | (2006.01) | |
| C12N 5/16 | (2006.01) | |
| C07K 16/28 | (2006.01) | |
| C07K 14/47 | (2006.01) | |
| C12N 9/10 | (2006.01) | |
| C12P 21/02 | (2006.01) | |

(52) U.S. Cl.
CPC ............. C07K 16/28 (2013.01); C07K 14/47 (2013.01); C12N 9/1096 (2013.01); C12P 21/02 (2013.01); C12Y 206/01002 (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 5,658,786 A | 8/1997 | Smith et al. | |
| 6,184,007 B1 | 2/2001 | Dusch et al. | |
| 6,225,115 B1 | 5/2001 | Smith et al. | |
| 6,251,613 B1 | 6/2001 | Kishimoto et al. | |
| 6,316,238 B1 | 11/2001 | Nakamura et al. | |
| 6,812,339 B1 | 11/2004 | Venter et al. | |
| 7,413,536 B1 | 8/2008 | Dower et al. | |
| 7,919,086 B2 | 4/2011 | Nakano et al. | |
| 8,697,397 B2 | 4/2014 | Tabuchi et al. | |
| 2003/0165495 A1 | 9/2003 | Carulli et al. | |
| 2005/0221466 A1 | 10/2005 | Liao et al. | |
| 2005/0265983 A1 | 12/2005 | Melamed et al. | |
| 2006/0014937 A1 | 1/2006 | Kang et al. | |
| 2007/0056507 A1 | 3/2007 | Kordina | |
| 2007/0162995 A1 | 7/2007 | Good et al. | |
| 2007/0166362 A1 | 7/2007 | Sakuma et al. | |
| 2007/0190599 A1 | 8/2007 | Nakano et al. | |
| 2009/0191591 A1 | 7/2009 | Tabuchi et al. | |
| 2009/0221442 A1 | 9/2009 | Dower et al. | |
| 2010/0233759 A1 | 9/2010 | Tabuchi et al. | |
| 2010/0248359 A1 | 9/2010 | Nakano et al. | |
| 2011/0003334 A1 | 1/2011 | Tabuchi et al. | |
| 2011/0014654 A1 | 1/2011 | Tabuchi et al. | |
| 2012/0045795 A1 | 2/2012 | Tabuchi et al. | |
| 2012/0142057 A1 | 6/2012 | Tabuchi et al. | |
| 2015/0315624 A1* | 11/2015 | Tabuchi ................ | C07K 14/47 435/69.6 |

FOREIGN PATENT DOCUMENTS

| | | |
|---|---|---|
| CN | 1612689 A | 5/2005 |
| CN | 1838969 A | 9/2006 |
| EP | 1 212 619 B1 | 5/2007 |
| EP | 2 213 746 A1 | 8/2010 |
| JP | 08-191693 A | 7/1996 |
| JP | 10-075787 A | 3/1998 |
| JP | 10-191984 A | 7/1998 |
| JP | 2000-228990 A | 8/2000 |
| JP | 2005-525100 A | 8/2005 |
| JP | 2006-506086 A | 2/2006 |
| WO | WO-92/04381 A1 | 3/1992 |
| WO | WO-97/27485 A1 | 7/1997 |
| WO | WO-01/20331 A1 | 3/2001 |
| WO | WO-02/092768 A2 | 11/2002 |
| WO | WO-03/039485 A2 | 5/2003 |
| WO | WO-2005/076015 A1 | 8/2005 |

(Continued)

OTHER PUBLICATIONS

Alper, Seth L., "Molecular physiology of SLC4 anion exchangers," Exp. Physiol., 2006, 91:153-161.

Arden et al., "Life and death in mammalian cell culture: strategies for apoptosis inhibition," Trends in Biotechnology, Apr. 2004, 22(4):174-180.

Beckmann et al., "Coexpression of band 3 mutants and Rh polypeptides: differential effects of band 3 on the expression of the Rh complex containing D polypeptide and the Rh complex containing CcEe polypeptide," Blood, Apr. 15, 2001, 97(8)2496-2505.

(Continued)

Primary Examiner — Michael Burkhart
(74) Attorney, Agent, or Firm — Foley & Lardner LLP

(57) ABSTRACT

The present invention provides a method capable of producing a natural or recombinant protein in high yield. The present invention relates to a method of producing a polypeptide, comprising culturing a cell which strongly expresses alanine aminotransferase and has a transferred DNA encoding a desired polypeptide and thereby allowing the cell to produce the polypeptide.

14 Claims, 13 Drawing Sheets

(56) References Cited

FOREIGN PATENT DOCUMENTS

| WO | WO-2006/006693 A1 | 1/2006 |
|---|---|---|
| WO | WO-2006/119115 A2 | 11/2006 |
| WO | WO-2007/056507 A1 | 5/2007 |
| WO | WO-2007/119774 A1 | 10/2007 |
| WO | WO-2008/114673 A1 | 9/2008 |
| WO | WO-2009/020144 A1 | 2/2009 |
| WO | WO-2009/051109 A1 | 4/2009 |
| WO | WO-2009/054433 A1 | 4/2009 |

OTHER PUBLICATIONS

Bell et al., "Genetic Engineering of Hybridoma Glutamine Metabolism," Enzyme and Microbial Technology, 1995, 17(2):98-106.

Butler, Michael, "Animal cell cultures: recent achievements and perspectives in the production of biopharmaceuticals," Appl. Microbiol. Biotechnol., Aug. 2005, 68(3):283-291.

Chambard et al., "Sugar transport by mammalian members of the SLC26 superfamily of anion-bicarbonate exchangers," J. Physiol., 2003, 550:667-677.

Christensen et al., "High expression of the taurine transporter TauT in primary cilic of NIH3T3 fibroblasts," Cell Biology International, 2005, 29:347-351.

Christie et al., "The Adaptation of BHK Cells to a Non-Ammoniagenic Glutamate-Based Culture Medium," Biotechnology and Bioengineering, Aug. 5, 1999, 64(3):298-309.

Database DDBJ/EMBL/GenBank [online], Accession No. NM_000342, uploaded Sep. 25, 2007, Keskanokwong et al., Definition: *Homo sapiens* solute carrier family 4, anion exchanger, membrane 1 (erythrocyte membrane protein band 3, Diego blood group) (SLC4A1), mRNA, retrieved Nov. 11, 2008, 12 pages.

Database EMBL [Online] Jul. 23, 1992, XP002593029, retrieved from EBI accession No. EMBL:M95495, 3 pages.

Database Uniprot [Online] Jan. 10, 2006, XP002593032, retrieved from EBI accession No. UNIPROT:Q2VRP7, 1 page.

Database UniProt [Online] Jul. 1, 1993, XP002593028, retrieved from EBI accession No. UNIPROT:Q00589, 2 pages.

Database UniProt [Online] Jun. 1, 2001, "RecName: Full=Cysteine sulfinic acid decarboxylase; EC=4.1.1.29; AltName: Full=Cysteinesulfinate decarboxylase; AltName: Full=Sulfinoalanine decarboxylase;" XP002597738 retrieved from EBI accession No. UNIPROT:Q9DBE0 Database accession No. Q9DBE0, 2 pages.

Database Uniprot [Online] Mar. 15, 2005, XP002593030, retrieved from EBI accession No. UNIPROT:Q5F431, 1 page.

Database Uniprot [Online] Oct. 1, 2000, XP002593031, retrieved from EBI accession No. UNIPROT:Q9MZ34, 2 pages.

de la Cruz Edmonds et al., "Development of Transfection and High-Producer Screening Protocols for the CHOK1SV Cell System," Molecular Biology, Oct. 1, 2006, 34(2):179-190.

de la Rosa et al., "Evidence for a Rate-Limiting Role of Cysteinesulfinate Decarboxylase Activity in Taurine Biosynthesis In Vivo," Comp. Biochem. Physiol., 1985, 81B(3):565-571.

Dusch et al., "Expression of the Corynebacterium glutamicum panD Gene Encoding L-Aspartate-alpha-Decarboxylase Leads to Pantothenate Overproduction in *Escherichia coli*," Applied and Environmental Microbiology, Apr. 1999, 65(4):1530-1539.

Final Office Action dated Dec. 17, 2010 in U.S. Appl. No. 12/226,195.

Final Office Action dated Mar. 2, 2012 in U.S. Appl. No. 12/734,283.

Final Office Action dated May 24, 2013 in U.S. Appl. No. 13/368,945.

Final Office Action dated Aug. 23, 2011 in U.S. Appl. No. 12/733,815.

Fu et al., "Direct interaction and cooperative role of tumor suppressor p16 with band 3 (AE1)," FEBS Letters, 2005, 579(10):2105-2110.

Ganapathy et al., "Expression and Regulation of the Taurine Transporter in Cultured Cell Lines of Human Origin," Advances in Experimental Medicine and Biology, 1994, 359:51-57, XP009123192.

GenBank Accession No. AEQ38544, Oct. 2011, 2 pages.

GenBank Accession No. EGW01898, Aug. 2011, 2 pages.

Good et al., "Engineering nitrogen use efficiency with alanine aminotransferase," Canadian Journal of Botany, Mar. 1, 2007, 85(3):252-262.

Griffith, Owen W., "Crysteinesulfinate Metabolism, Altered Partitioning Between Transamination and Decarboxylation Following Administration of β-Methyleneaspartate," J. Biol. Chem., Feb. 10, 1983, 258(3):1591-1598.

Hammer et al., "β-Alanine but not taurine can function as an organic osmolyte in preimplantation mouse embryos cultured from fertilized eggs," Molecular Reproduction and Development, Oct. 2003, 66(2):153-161.

Han et al., "Is TauT an Anti-Apoptotic Gene?" Taurine 6, Oja et al. Eds., 2006, 59-67.

Han et al., "Regulation of TauT by cisplatin in LLC-PK1 renal cells," Pediatr. Nephrol., 2005, 20:1067-1072.

Han et al., "Mechanisms of regulation of taurine transporter activity," Taurine 6, Edited by Oja and Saransaari, 2006, 79-90.

Herman et al., "Low dose methotrexate induces apoptosis with reactive oxygen species involvement in T lymphocytic cell lines to a greater extent than in monocytic lines," Inflammation Research, 2005, 54:273-280.

Hwang et al., "Expression and purification of recombinant human angiopoietin-2 produced in Chinese hamster ovary cells," Protein Expression and Purification, 2005, 39:175-183.

Ifandi et al., "Regulation of Cell Proliferation and Apoptosis in CHO-K1 Cells by the Coexpression of c-Myc and Bcl-2," Biotechnol. Prog., 2005, 21:671-677.

International Search Report mailed Sep. 2, 2008, in PCT/JP2008/064095, 5 pages.

Ishiguro et al., "CO2 permeability and bicarbonate transport in microperfused interlobular ducts isolated from guinea-pig pancreas," Journal of Physiology, 2000, 528.2:305-315.

Ito et al., "Expression of taurine transporter is regulated through the TonE (tonicity-responsive element)/TonEBP (TonE-binding protein) pathway and contributes to cytoprotection in HepG2 cells," Biochem. J., 2004, 382:177-182.

Kalwy et al., "Toward More Efficient Protein Expression," Molecular Biotechnology, Oct. 2006, 34(2):151-156.

Kennell et al., "Principles and Practices of Nucleic Acid Hybridization," Prog. Nucleic Acid Res. Mol. Biol., 1971, 11:259-270.

Kim et al., "Response of recombinant Chinese hamster ovary cells to hyperosmotic pressure: effect of Bcl-2 overexpression," Journal of Biotechnology, 2002, 95:237-248.

Kim et al., "Characterization of Chimeric Antibody Producing CHO Cells in the Course of Dihydrofolate Reductase-Mediated Gene Amplification and Their Stability in the Absence of Selective Pressure," Biotechnology and Bioengineering, Apr. 5, 1998, 58(1):73-84.

Kondo et al., "Modulation of apoptosis by endogenous Bcl-xL expression in MKN-45 human gastric cancer cells," Oncogene, 1998, 17:2585-2591.

Lee et al., "Development of Apoptosis-Resistant Dihydrofolate Reductase-Deficient Chinese Hamster Ovary Cell Line," Biotechnol. Bioengineer., 2003, 82:872-876.

Liu et al., "Cloning and expression of a cDNA encoding the transporter of taurine and β-alanine in mouse brain," Proc. Natl. Acad. Sci. USA, Dec. 1992, 89(24):12145-12149.

Lux et al., "Cloning and characterization of band 3, the human erythrocyte anion-exchange protein (AE1)," Proc. Natl. Acad. Sci. USA, Dec. 1989, 86:9089-9093.

Miyasaka et al., "Characterization of Human Taurine Transporter Expressed in Insect Cells Using Recombinant Baculovirus," Protein Expression and Purification, 2001, 23(3):389-397.

Morgan et al., "Interactions of transmembrane carbonic anhydrase, CAIX, with bicarbonate transporters," Am. J. Physiol. Cell Physiol., Aug. 2007, 293(2):C738-C748.

(56) References Cited

OTHER PUBLICATIONS

Mount et al., "The SLC26 gene family of multifunctional anion exchangers," Pflugers Arch.—Eur. J. Physiol., 2004, 447:710-721.
Ngo et al., "Computational Complexity, Protein Structure Prediction, and the Levinthal Paradox," The Protein Folding Problem and Tertiary Structure Prediction, Merz et al. (Eds.), 1994, 433 and 492-495.
Notice of Allowance dated Dec. 20, 2012 in U.S. Appl. No. 12/733,052.
Office Action dated Jan. 6, 2011 in U.S. Appl. No. 12/733,815.
Office Action dated Feb. 27, 2013 in U.S. Appl. No. 13/138,909.
Office Action dated May 12, 2011 in U.S. Appl. No. 12/733,052.
Office Action dated May 18, 2010 in U.S. Appl. No. 12/226,195.
Office Action dated Aug. 3, 2011 in U.S. Appl. No. 12/734,283.
Office Action dated Aug. 9, 2011 in U.S. Appl. No. 12/450,161.
Office Action dated Sep. 21, 2012 in U.S. Appl. No. 13/368,945.
Porter et al., "Non-steady-state kinetics of brain glutamate decarboxylase resulting from interconversion of the apo- and holoenzyme," Biochimica et Biophysica Acta, 1988, 874:235-244.
Pushkin et al., "SLC4 base (HCO-3, CO-23) transporters: classification, function, structure, genetic diseases, and knockout models," Am. J. Physiol. Renal Physiol., 2006, 290:F580-F599.
Ramamoorthy et al., "Functional characterization and chromosomal localization of a cloned taurine transporter from human placenta," Biochem. J., 1994, 300:893-900.
Reymond et al., "Molecular cloning and sequence analysis of the cDNA encoding rat liver cysteine sulfinate decarboxylase (CSD)," Biochimica et Biophysica Acta, 1996, 1307:152-156.
Rudinger, J., "Characteristics of the amino acids as components of a peptide hormone sequence," Peptide Hormones, Parsons (Ed.), 1976, 1-7.
Shen et al., "Expression of Anion Exchanger 1 Sequestrates p16 in the Cytoplasm in Gastric and Colonic Adenocarcinoma," Neoplasia, Oct. 2007, 9(10):812-819.
Shibayama et al., "Effect of Methotrexate Treatment on Expression Levels of Organic Anion Transporter Polypeptide 2,P-Glycoprotein and Bile Salt Export Pump in Rats," Biol. Pharm. Bull., Mar. 2009, 32(3):493-496.
Smith et al., "Cloning and Expression of a High Affinity Taurine Transporter from Rat Brain," Mol. Pharmacol., 1992, 42(4):563-569.
Supplementary European Search Report dated Aug. 3, 2010, in corresponding EP 08792251.4, 10 pages.
Tabuchi et al., "Overexpression of Taurine Transporter in Chinese Hamster Ovary cells Can Enhance Cell Viability and Product Yield, While Promoting Glutamine Consumption," Biotechnology and Bioengineering 2010, 107(6):998-1003.
Tang et al., "Protein Phosphorylation and Taurine Biosynthesis In Vivo and In Vitro," Journal of Neuroscience, Sep. 15, 1997, 17(18):6947-6951.
Tanner et al., "The complete amino acid sequence of the human erythrocyte membrane anion-transport protein deduced from the cDNA sequence," Biochem. J., 1988, 256:703-712.
Tappaz et al., "Characterization of the cDNA Coding for Rat Brain Cysteine Sulfinate Decarboxylase: Brain and Liver Enzymes are Identical Proteins Encoded by Two Distince mRNAs," J. Neurochem., 1999, 73.(3):903-912.
Tinland et al., "Agrobacterium tumefaciens transfers single-stranded transferred DNA (T-DNA) into the plant cell nucleus," Proc. Natl. Acad. Sci. USA, Aug. 1994, 91:8000-8004.
Trill et al., "Production of monoclonal antibodies in COS and CHO cells," Current Opinion in Biotechnology, 1995, 6:553-560.
Uchida et al., "Molecular cloning of the cDNA for an MDCK cell Na+- and Cl—dependent taurine transporter that is regulated by hypertonicity," Proc. Natl. Acad. Sci. USA, Sep. 1992, 89:8230-8234.
Voss et al., "Regulation of the expression and subcellular localization of the taurine transporter TauT in mouse NIH3T3 fibroblasts," Eur. J. Biochem., Dec. 2004, 271(23-24):4646-4658.
Wirth et al., "Isolation of overproducing recombinant mammalian cell lines by a fast and simple selection procedure," Gene, 1988, 73:419-426.
Wu et al., "Overexpression of Anion Exchanger 2 in Human Hepatocellular Carcinoma," Chinese Journal of Physiology, 2006, 49(4):192-198.
Yang et al., "Human Hepatitis B Viral e Antigen Interacts with Cellular Interleukin-1 Receptor Accessory Protein and Triggers Interleukin-1 Response," Journal of Biological Chemistry, Nov. 10, 2006, 281(45):34525-34536.
Yang et al., "cDNA Cloning, Genomic Structure, Chromosomal Mapping, and Functional Expression of a Novel Human Alanine Aminotransferase," Genomics, Mar. 1, 2002, 79(3):445-450.
Zhang et al., "Metabolic characteristics of recombinant Chinese hamster ovary cells expressing glutamine synthetase in presence and absence of glutamine," Cytotechnology, 2006, 51(1):21-28.
Office Action dated Apr. 27, 2016, in U.S. Appl. No. 12/733,815.
Pilbrough et al., "Intraclonal Protein Expression Heterogeneity in Recombinant CHO Cells," PLOS ONE, Dec. 2009, 4(12):e8432, 11 pages.
Jhiang et al., "Cloning of the human taurine transporter and characterization of taurine uptake in thyroid cells," FEBS, 1993, 318(2):139-144.

\* cited by examiner

Fig. 8

Mean Lactate Concentration
( n=7 )

pHyg/TauT
( 1.54±0.20 ) g/L pHyg
( 1.75±0.15 ) g/L t Test  P <0.05

Mean Antibody Yield
( n=7 )

pHyg/TauT
( 397±69 ) mg/L pHyg
( 342±55 ) mg/L

```
                        SEQUENCE LISTING

<160> NUMBER OF SEQ ID NOS: 68

<210> SEQ ID NO 1
<211> LENGTH: 1491
<212> TYPE: DNA
<213> ORGANISM: Homo sapiens

<400> SEQUENCE: 1
atggcctcga gcacaggtga ccggagccag gcggtgaggc atggactgag ggcgaaggtg      60
ctgacgctgg acggcatgaa cccgcgtgtg cggagagtgg agtacgcagt gcgtggcccc     120
atagtgcagc gagccttgga gctggagcag gagctgcgcc agggtgtgaa gaagcctttc     180
accgaggtca tccgtgccaa catcggggac gcacaggcta tggggcagag gcccatcacc     240
ttcctgcgcc aggtcttggc cctctgtgtt aaccctgatc ttctgagcag ccccaacttc     300
cctgacgatg ccaagaaaag gcggagcgc atcttgcagg cgtgtggggg ccacagtctg     360
ggggcctaca gcgtcagctc cggcatccag ctgatccggg aggacgtggc gcggtacatt     420
gagaggcgtg acggaggcat ccctgcggac cccaacaacg tcttcctgtc cacaggggcc     480
agcgatgcca tcgtgacggt gctgaagctg ctggtggccg gcgagggcca cacgcacg     540 ggtgtgctca tccccatccc ccagtaccca ctctactcgg ccacgctggc agagctgggc     600
gcagtgcagg tggattacta cctggacgag gagcgtgcct gggcgctgga cgtggccgag     660
cttcaccgtg cactgggcca ggcgcgtgac cactgccgcc ctcgtgcgct ctgtgtcatc     720
aaccctggca ccccaccgg gcaggtgcag acccgcgagt gcatcgaggc cgtgatccgc     780
ttcgccttcg aagagcggct ctttctgctg gcggacgagg tgtaccagga caacgtgtac     840
gccgcgggtt cgcagttcca ctcattcaag aaggtgctca tggagatggg gccgccctac     900
gccgggcagc aggagcttgc ctccttccac tccacctcca agggctacat gggcgagtgc     960
gggttccgcg gcggctatgt ggaggtggtg aacatggacg ctgcagtgca gcagcagatg    1020
ctgaagctga tgagtgtgcg gctgtgcccg ccggtgccag acaggccct gctggacctg    1080 gtggtcagcc cgcccgcgcc caccgacccc tcctttgcgc agttccaggc tgagaagcag    1140
gcagtgctgg cagagctggc ggccaaggcc aagctcaccg agcaggtctt caatgaggct    1200
```

```
cctggcatca gctgcaaccc agtgcagggc gccatgtact ccttcccgcg cgtgcagctg    1260
cccccgcggg cggtggagcg cgctcaggag ctgggcctgg cccccgatat gttcttctgc    1320
ctgcgcctcc tggaggagac cggcatctgc gtggtgccag ggagcggctt tgggcagcgg    1380
gaaggcacct accacttccg gatgaccatt ctgcccccct tggagaaact gcggctgctg    1440
ctggagaagc tgagcaggtt ccatgccaag ttcaccctcg agtactcctg a             1491
```

<210> SEQ ID NO 2
<211> LENGTH: 496
<212> TYPE: PRT
<213> ORGANISM: Homo sapiens

<400> SEQUENCE: 2

```
Met Ala Ser Ser Thr Gly Asp Arg Ser Gln Ala Val Arg His Gly Leu
1               5                   10                  15

Arg Ala Lys Val Leu Thr Leu Asp Gly Met Asn Pro Arg Val Arg Arg
                20                  25                  30

Val Glu Tyr Ala Val Arg Gly Pro Ile Val Gln Arg Ala Leu Glu Leu
            35                  40                  45

Glu Gln Glu Leu Arg Gln Gly Val Lys Lys Pro Phe Thr Glu Val Ile
    50                  55                  60

Arg Ala Asn Ile Gly Asp Ala Gln Ala Met Gly Gln Arg Pro Ile Thr
65                  70                  75                  80

Phe Leu Arg Gln Val Leu Ala Leu Cys Val Asn Pro Asp Leu Leu Ser
                85                  90                  95

Ser Pro Asn Phe Pro Asp Asp Ala Lys Lys Arg Ala Glu Arg Ile Leu
            100                 105                 110

Gln Ala Cys Gly Gly His Ser Leu Gly Ala Tyr Ser Val Ser Ser Gly
        115                 120                 125

Ile Gln Leu Ile Arg Glu Asp Val Ala Arg Tyr Ile Glu Arg Arg Asp
    130                 135                 140

Gly Gly Ile Pro Ala Asp Pro Asn Asn Val Phe Leu Ser Thr Gly Ala
145                 150                 155                 160

Ser Asp Ala Ile Val Thr Val Leu Lys Leu Leu Val Ala Gly Glu Gly
                165                 170                 175

His Thr Arg Thr Gly Val Leu Ile Pro Ile Pro Gln Tyr Pro Leu Tyr
            180                 185                 190

Ser Ala Thr Leu Ala Glu Leu Gly Ala Val Gln Val Asp Tyr Tyr Leu
        195                 200                 205

Asp Glu Glu Arg Ala Trp Ala Leu Asp Val Ala Glu Leu His Arg Ala
    210                 215                 220

Leu Gly Gln Ala Arg Asp His Cys Arg Pro Arg Ala Leu Cys Val Ile
225                 230                 235                 240

Asn Pro Gly Asn Pro Thr Gly Gln Val Gln Thr Arg Glu Cys Ile Glu
                245                 250                 255

Ala Val Ile Arg Phe Ala Phe Glu Glu Arg Leu Phe Leu Leu Ala Asp
            260                 265                 270

Glu Val Tyr Gln Asp Asn Val Tyr Ala Ala Gly Ser Gln Phe His Ser
        275                 280                 285

Phe Lys Lys Val Leu Met Glu Met Gly Pro Pro Tyr Ala Gly Gln Gln
    290                 295                 300

Glu Leu Ala Ser Phe His Ser Thr Ser Lys Gly Tyr Met Gly Glu Cys
305                 310                 315                 320
```

```
Gly Phe Arg Gly Gly Tyr Val Glu Val Val Asn Met Asp Ala Ala Val
            325                 330                 335

Gln Gln Gln Met Leu Lys Leu Met Ser Val Arg Leu Cys Pro Pro Val
        340                 345                 350

Pro Gly Gln Ala Leu Leu Asp Leu Val Val Ser Pro Pro Ala Pro Thr
    355                 360                 365

Asp Pro Ser Phe Ala Gln Phe Gln Ala Glu Lys Gln Ala Val Leu Ala
370                 375                 380

Glu Leu Ala Ala Lys Ala Lys Leu Thr Glu Gln Val Phe Asn Glu Ala
385                 390                 395                 400

Pro Gly Ile Ser Cys Asn Pro Val Gln Gly Ala Met Tyr Ser Phe Pro
                405                 410                 415

Arg Val Gln Leu Pro Pro Arg Ala Val Glu Arg Ala Gln Glu Leu Gly
            420                 425                 430

Leu Ala Pro Asp Met Phe Phe Cys Leu Arg Leu Leu Glu Glu Thr Gly
        435                 440                 445

Ile Cys Val Val Pro Gly Ser Gly Phe Gly Gln Arg Glu Gly Thr Tyr
    450                 455                 460

His Phe Arg Met Thr Ile Leu Pro Pro Leu Glu Lys Leu Arg Leu Leu
465                 470                 475                 480

Leu Glu Lys Leu Ser Arg Phe His Ala Lys Phe Thr Leu Glu Tyr Ser
                485                 490                 495

<210> SEQ ID NO 3
<211> LENGTH: 1572
<212> TYPE: DNA
<213> ORGANISM: Homo sapiens

<400> SEQUENCE: 3
atgcagcggg cggcggcgct ggtccggcgg ggctgtggtc cccggacccc cagctcctgg      60
ggccgcagcc agagcagcgc ggccgccgag gcctcggcgg tgctcaaggt gcggcccgag     120
cgcagccggc gcgagcgcat cctcacgctg gagtccatga cccgcaggt gaaggcggtg      180 gagtacgccg tgcggggacc catcgtgctc aaggccggcg agatcgagct cgagctgcag     240
cggggtatca aaaagccatt cacagaggtc atccgagcca catcgggga cgcccaggct     300 atggggcagc agccaatcac cttcctccgg caggtgatgg cactatgcac ctacccaaac     360
ctgctggaca gccccagctt cccagaagat gctaagaaac gtgcccggcg gatcctgcag     420
gcttgtggcg ggaacagcct ggggtcctac agtgctagcc agggtgtcaa ctgcatccgt     480
gaagatgtgg ctgcctacat caccaggagg gatggcggtg tgcctgcgga ccccgacaac     540
atctacctga ccacgggagc tagtgacggc atttctacga tcctgaagat cctcgtctcc     600
gggggcggca agtcacggac aggtgtgatg atccccatcc acaatatcc cctctattca      660 gctgtcatct ctgagctcga cgccatccag gtgaattact acctggacga ggagaactgc     720
tgggcgctga atgtgaatga gctcggcgg gcggtgcagg aggccaaaga ccactgtgat     780
cctaaggtgc tctgcataat caaccctggg aaccccacag gccaggtaca aagcagaaag     840
tgcatagaag atgtgatcca ctttgcctgg aagagaagc tctttctcct ggctgatgag     900
gtgtaccagg acaacgtgta ctctccagat gcagattcc actccttcaa gaaggtgctg     960
tacgagatgg ggcccgagta ctccagcaac gtggagctcg cctccttcca ctccacctcc    1020
aagggctaca tgggcgagtg tggttacaga ggaggctaca tggaggtgat caacctgcac    1080
cctgagatca agggccagct ggtgaagctg ctgtcggtgc gcctgtgccc ccagtgtctc    1140
```

-continued

```
gggcaggccg ccatggacat tgtcgtgaac cccccggtgg caggagagga gtcctttgag      1200
caattcagcc gagagaagga gtcggtcctg ggtaatctgg ccaaaaaagc aaagctgacg      1260
gaagacctgt ttaaccaagt cccaggaatt cactgcaacc ccttgcaggg ggccatgtac      1320
gccttccctc ggatcttcat tcctgccaaa gctgtggagg ctgctcaggc ccatcaaatg      1380
gctccagaca tgttctactg catgaagctc ctggaggaga ctggcatctg tgtcgtgccc      1440
ggcagtggct ttgggcagag gaaggcact taccacttca ggatgactat cctcccctcca     1500 gtggagaagc tgaaaacggt gctgcagaag gtgaaagact tccacatcaa cttcctggag      1560
aagtacgcgt ga                                                         1572
```

<210> SEQ ID NO 4
<211> LENGTH: 523
<212> TYPE: PRT
<213> ORGANISM: Homo sapiens

<400> SEQUENCE: 4

```
Met Gln Arg Ala Ala Leu Val Arg Arg Gly Cys Gly Pro Arg Thr
1               5                   10                  15

Pro Ser Ser Trp Gly Arg Ser Gln Ser Ala Ala Glu Ala Ser
                20                  25                  30

Ala Val Leu Lys Val Arg Pro Glu Arg Ser Arg Arg Glu Arg Ile Leu
            35                  40                  45

Thr Leu Glu Ser Met Asn Pro Gln Val Lys Ala Val Glu Tyr Ala Val
        50                  55                  60

Arg Gly Pro Ile Val Leu Lys Ala Gly Glu Ile Glu Leu Glu Leu Gln
65                  70                  75                  80

Arg Gly Ile Lys Lys Pro Phe Thr Glu Val Ile Arg Ala Asn Ile Gly
                85                  90                  95

Asp Ala Gln Ala Met Gly Gln Gln Pro Ile Thr Phe Leu Arg Gln Val
            100                 105                 110

Met Ala Leu Cys Thr Tyr Pro Asn Leu Leu Asp Ser Pro Ser Phe Pro
        115                 120                 125

Glu Asp Ala Lys Lys Arg Ala Arg Arg Ile Leu Gln Ala Cys Gly Gly
130                 135                 140

Asn Ser Leu Gly Ser Tyr Ser Ala Ser Gln Gly Val Asn Cys Ile Arg
145                 150                 155                 160

Glu Asp Val Ala Ala Tyr Ile Thr Arg Arg Asp Gly Gly Val Pro Ala
                165                 170                 175

Asp Pro Asp Asn Ile Tyr Leu Thr Thr Gly Ala Ser Asp Gly Ile Ser
            180                 185                 190

Thr Ile Leu Lys Ile Leu Val Ser Gly Gly Lys Ser Arg Thr Gly
        195                 200                 205

Val Met Ile Pro Ile Pro Gln Tyr Pro Leu Tyr Ser Ala Val Ile Ser
    210                 215                 220

Glu Leu Asp Ala Ile Gln Val Asn Tyr Tyr Leu Asp Glu Glu Asn Cys
225                 230                 235                 240

Trp Ala Leu Asn Val Asn Glu Leu Arg Arg Ala Val Gln Glu Ala Lys
                245                 250                 255

Asp His Cys Asp Pro Lys Val Leu Cys Ile Ile Asn Pro Gly Asn Pro
            260                 265                 270

Thr Gly Gln Val Gln Ser Arg Lys Cys Ile Glu Asp Val Ile His Phe
        275                 280                 285

Ala Trp Glu Glu Lys Leu Phe Leu Leu Ala Asp Glu Val Tyr Gln Asp
```

```
                290                  295                  300
Asn Val Tyr Ser Pro Asp Cys Arg Phe His Ser Phe Lys Lys Val Leu
305                 310                  315                  320

Tyr Glu Met Gly Pro Glu Tyr Ser Ser Asn Val Glu Leu Ala Ser Phe
                325                  330                  335

His Ser Thr Ser Lys Gly Tyr Met Gly Glu Cys Gly Tyr Arg Gly Gly
            340                  345                  350

Tyr Met Glu Val Ile Asn Leu His Pro Glu Ile Lys Gly Gln Leu Val
        355                  360                  365

Lys Leu Leu Ser Val Arg Leu Cys Pro Pro Val Ser Gly Gln Ala Ala
    370                  375                  380

Met Asp Ile Val Val Asn Pro Pro Val Ala Gly Glu Glu Ser Phe Glu
385                  390                  395                  400

Gln Phe Ser Arg Glu Lys Glu Ser Val Leu Gly Asn Leu Ala Lys Lys
                405                  410                  415

Ala Lys Leu Thr Glu Asp Leu Phe Asn Gln Val Pro Gly Ile His Cys
            420                  425                  430

Asn Pro Leu Gln Gly Ala Met Tyr Ala Phe Pro Arg Ile Phe Ile Pro
        435                  440                  445

Ala Lys Ala Val Glu Ala Ala Gln Ala His Gln Met Ala Pro Asp Met
    450                  455                  460

Phe Tyr Cys Met Lys Leu Leu Glu Glu Thr Gly Ile Cys Val Val Pro
465                  470                  475                  480

Gly Ser Gly Phe Gly Gln Arg Glu Gly Thr Tyr His Phe Arg Met Thr
                485                  490                  495

Ile Leu Pro Pro Val Glu Lys Leu Lys Thr Val Leu Gln Lys Val Lys
            500                  505                  510

Asp Phe His Ile Asn Phe Leu Glu Lys Tyr Ala
        515                  520

<210> SEQ ID NO 5
<211> LENGTH: 1491
<212> TYPE: DNA
<213> ORGANISM: Mus musculus

<400> SEQUENCE: 5
atggcctcac aaaggaatga ccggatccag gcttcaagga atggactgaa ggggaaggtg      60
ctaactctgg ataccatgaa cccatgtgtg cggagggtgg agtatgcagt ccgaggcccc     120
atcgtgcaac gtgccttgga gctggagcag gagctgcgcc agggtgtgaa gaagcctttt     180
actgaggtta tccgtgccaa tattggggat gcacaagcca tggggcagag acccatcacc     240
ttcttccgcc aggtcctggc cctctgtgtc taccccaatc ttctgagcag tccggacttc     300
ccagaggatg ccaagagaag ggcagaacgc atcttgcagg catgcggggg ccacagcctg     360
ggtgcctata gcattagctc tggaatccag ccgattcggg aggatgtggc gcaatatatt     420
gagaggagag acgaggcat ccctgcagac ccgaacaaca tatttctgtc cacaggggcc     480
agcgatgcca tcgtgaccat gctcaagctg ctggtagccg gcgagggccg tgcgcgaacc     540
ggtgtactca ttcccattcc tcagtaccca ctgtactcag ctgcgctggc tgagctggac     600
gccgtgcaag tggactacta cctggacgaa gagcgcgcct gggctcttga catcgctgag     660
ctgcggcgcg ctctgtgcca ggcacgtgac cgctgctgcc ctcgagtact atgcgtcatc     720
aaccccggca accccacggg gcaggtgcag accgtgaat gcatcgaggc cgtaatccgc     780
tttgctttcg aagagggact cttcctgatg gctgatgagg tataccaaga caatgtatat     840
```

```
gccgagggct ctcagttcca ttcattcaag aaggtgctca cggagatggg gccaccatat    900
gccacgcagc aggagctcgc gtctttccac tcagtctcta agggctacat gggcgagtgc    960
gggtttcgtg gtggctatgt ggaagtggta acatggatg ccgaggtgca gaaacagatg    1020
gcgaaactga tgagcgtgcg gttgtgtcca ccagtgccgg gccaggcttt gatgggcatg    1080
gtggtcagtc cgccaacccc ctcggagccg tccttcaagc agtttcaagc agagaggcag    1140
gaggtgctgg ctgaactggc agccaaggct aaactcacgg agcaggtctt caacgaggcc    1200
cccgggatcc gctgcaaccc ggtgcagggc gctatgtatt ccttccctca aattcagctg    1260
cctttgaaag cagtgcagcg tgcgcaggac ctgggcctgg cccctgacat gttcttctgt    1320
ctgtgcctcc tggaagagac tggcatctgc gttgtgcctg ggagtggctt tgggcagcag    1380
gagggcacct atcatttccg gatgaccatt ctgccccca tggagaaact gcgggtgctg    1440
ctggagaaac tgaggcactt ccatgctaaa ttcactcatg agtactcctg a    1491
```

<210> SEQ ID NO 6
<211> LENGTH: 496
<212> TYPE: PRT
<213> ORGANISM: Mus musculus

<400> SEQUENCE: 6

```
Met Ala Ser Gln Arg Asn Asp Arg Ile Gln Ala Ser Arg Asn Gly Leu
1               5                   10                  15

Lys Gly Lys Val Leu Thr Leu Asp Thr Met Asn Pro Cys Val Arg Arg
            20                  25                  30

Val Glu Tyr Ala Val Arg Gly Pro Ile Val Gln Arg Ala Leu Glu Leu
        35                  40                  45

Glu Gln Glu Leu Arg Gln Gly Val Lys Lys Pro Phe Thr Glu Val Ile
    50                  55                  60

Arg Ala Asn Ile Gly Asp Ala Gln Ala Met Gly Gln Arg Pro Ile Thr
65                  70                  75                  80

Phe Phe Arg Gln Val Leu Ala Leu Cys Val Tyr Pro Asn Leu Leu Ser
                85                  90                  95

Ser Pro Asp Phe Pro Glu Asp Ala Lys Arg Arg Ala Glu Arg Ile Leu
            100                 105                 110

Gln Ala Cys Gly Gly His Ser Leu Gly Ala Tyr Ser Ile Ser Ser Gly
        115                 120                 125

Ile Gln Pro Ile Arg Glu Asp Val Ala Gln Tyr Ile Glu Arg Arg Asp
    130                 135                 140

Gly Gly Ile Pro Ala Asp Pro Asn Asn Ile Phe Leu Ser Thr Gly Ala
145                 150                 155                 160

Ser Asp Ala Ile Val Thr Met Leu Lys Leu Leu Val Ala Gly Glu Gly
                165                 170                 175

Arg Ala Arg Thr Gly Val Leu Ile Pro Ile Pro Gln Tyr Pro Leu Tyr
            180                 185                 190

Ser Ala Ala Leu Ala Glu Leu Asp Ala Val Gln Val Asp Tyr Tyr Leu
        195                 200                 205

Asp Glu Glu Arg Ala Trp Ala Leu Asp Ile Ala Glu Leu Arg Arg Ala
    210                 215                 220

Leu Cys Gln Ala Arg Asp Arg Cys Cys Pro Arg Val Leu Cys Val Ile
225                 230                 235                 240

Asn Pro Gly Asn Pro Thr Gly Gln Val Gln Thr Arg Glu Cys Ile Glu
                245                 250                 255
```

```
Ala Val Ile Arg Phe Ala Phe Glu Glu Gly Leu Phe Leu Met Ala Asp
            260                 265                 270

Glu Val Tyr Gln Asp Asn Val Tyr Ala Glu Gly Ser Gln Phe His Ser
            275                 280                 285

Phe Lys Lys Val Leu Thr Glu Met Gly Pro Pro Tyr Ala Thr Gln Gln
        290                 295                 300

Glu Leu Ala Ser Phe His Ser Val Ser Lys Gly Tyr Met Gly Glu Cys
305                 310                 315                 320

Gly Phe Arg Gly Gly Tyr Val Glu Val Val Asn Met Asp Ala Glu Val
                325                 330                 335

Gln Lys Gln Met Ala Lys Leu Met Ser Val Arg Leu Cys Pro Pro Val
                340                 345                 350

Pro Gly Gln Ala Leu Met Gly Met Val Val Ser Pro Thr Pro Ser
            355                 360                 365

Glu Pro Ser Phe Lys Gln Phe Gln Ala Glu Arg Gln Glu Val Leu Ala
        370                 375                 380

Glu Leu Ala Ala Lys Ala Lys Leu Thr Glu Gln Val Phe Asn Glu Ala
385                 390                 395                 400

Pro Gly Ile Arg Cys Asn Pro Val Gln Gly Ala Met Tyr Ser Phe Pro
                405                 410                 415

Gln Ile Gln Leu Pro Leu Lys Ala Val Gln Arg Ala Gln Asp Leu Gly
            420                 425                 430

Leu Ala Pro Asp Met Phe Phe Cys Leu Cys Leu Leu Glu Glu Thr Gly
                435                 440                 445

Ile Cys Val Val Pro Gly Ser Gly Phe Gly Gln Gln Glu Gly Thr Tyr
        450                 455                 460

His Phe Arg Met Thr Ile Leu Pro Pro Met Glu Lys Leu Arg Val Leu
465                 470                 475                 480

Leu Glu Lys Leu Arg His Phe His Ala Lys Phe Thr His Glu Tyr Ser
            485                 490                 495

<210> SEQ ID NO 7
<211> LENGTH: 1569
<212> TYPE: DNA
<213> ORGANISM: Mus musculus

<400> SEQUENCE: 7
atgcagcggg cagcggtgct ggtgcggcgg ggctcctgcc ccgcgcctc gggcccctgg      60 ggccgtagtc acagcagcgc tgcagccgaa gcctcggcgg cgctcaaggt gcgaccggag     120
cgcagccctc gagaccgcat cctcaccctg gagtccatga cccgcaggt gaaggcggtg     180 gagtacgctg tgcggggacc catcgtgctc aaagccggcg agatcgagat ggagctgcag     240
cggggtatca aaaaccatt cactgaggta atccgagcca acattgggga tgcccatgct     300
atgggccagc agccaatcac cttcctccgt caggtgatgg cactctgcac ctacccaaac     360
ctactaaaca gccccagctt cccagaagac gctaagaaac gagcgcggcg gatcctgcag     420
gcttgtggtg gaaacagctt gggatcttac agtgctagcc aaggcgttaa ctgtatccgt     480
gaagatgtgg cagcctttat caccaggaga gatggtgtgc ctgcagaccc agacaacatt     540
tacctgacta ctggagctag cgacggtatt tctacaatcc tgaagctcct ggtctccggt     600
ggtggcaagt cacggaccgg cgtgatgatt ccatcccccc agtatcccctt gtactccgcg     660 gtcatctctg agctcgacgc ggtgcaggtc aactactatc tggatgaaga gaactgctgg     720
gctttgaatg tggacgagct ccggcgggca ttgcggcaag ccaaagacca ctgtgaccct     780
```

```
aaagttctct gcattatcaa ccccggaaac cccacaggcc aggtacaaag cagaaagtgc    840
atagaagatg tgattcactt tgcctgggaa gagaagcttt ttctcctggc tgatgaggtg    900
taccaggaca acgtgtactc tccagactgc agattccact cgtttaagaa agtgctttac    960
cagatggggc acgagtactc cagcaacgtg gagctcgcct ccttccactc cacctccaag   1020
ggctacatgg gcgagtgtgg ctacagaggg ggctacatgg aggtgatcaa tttgcacccc   1080
gagatcaaag ccagctggt gaagctactc tcggttcgcc tctgtccgcc agtgtcagga   1140
caggccgcca tggacattgt tgtgaatcca ccggaaccag agaggagtc ctttgagcaa   1200 ttcagcaggg aaaagaatt cgtccttggt aatctggcca aaaaagcaaa gctgacagaa   1260
gatctgttta accaagtccc agggatccag tgcaacccct gcaaggagc tatgtatgcg   1320 ttccctcgga ttctcatccc tgccaaggcc gtggaggcag ctcagtccca taaaatggct   1380
ccagacatgt tctactgcat gaagctcctg gaggagactg gcatctgtgt cgtgcctggc   1440
agtggctttg ggcagcgaga aggcacttac cacttcagaa tgaccattct ccctccggtg   1500
gataaactga agaccgtgct ccacaaggtg aaagactttc acctgaagtt cctggagcag   1560
tactcatga                                                           1569
```

<210> SEQ ID NO 8
<211> LENGTH: 522
<212> TYPE: PRT
<213> ORGANISM: Mus musculus

<400> SEQUENCE: 8

```
Met Gln Arg Ala Ala Val Leu Val Arg Gly Ser Cys Pro Arg Ala
1               5                   10                  15

Ser Gly Pro Trp Gly Arg Ser His Ser Ser Ala Ala Glu Ala Ser
            20                  25                  30

Ala Ala Leu Lys Val Arg Pro Glu Arg Ser Pro Arg Asp Arg Ile Leu
        35                  40                  45

Thr Leu Glu Ser Met Asn Pro Gln Val Lys Ala Val Glu Tyr Ala Val
    50                  55                  60

Arg Gly Pro Ile Val Leu Lys Ala Gly Glu Ile Glu Met Glu Leu Gln
65                  70                  75                  80

Arg Gly Ile Lys Lys Pro Phe Thr Glu Val Ile Arg Ala Asn Ile Gly
                85                  90                  95

Asp Ala His Ala Met Gly Gln Gln Pro Ile Thr Phe Leu Arg Gln Val
            100                 105                 110

Met Ala Leu Cys Thr Tyr Pro Asn Leu Leu Asn Ser Pro Ser Phe Pro
        115                 120                 125

Glu Asp Ala Lys Lys Arg Ala Arg Arg Ile Leu Gln Ala Cys Gly Gly
    130                 135                 140

Asn Ser Leu Gly Ser Tyr Ser Ala Ser Gln Gly Val Asn Cys Ile Arg
145                 150                 155                 160

Glu Asp Val Ala Ala Phe Ile Thr Arg Arg Asp Gly Val Pro Ala Asp
                165                 170                 175

Pro Asp Asn Ile Tyr Leu Thr Thr Gly Ala Ser Asp Gly Ile Ser Thr
            180                 185                 190

Ile Leu Lys Leu Leu Val Ser Gly Gly Lys Ser Arg Thr Gly Val
        195                 200                 205

Met Ile Pro Ile Pro Gln Tyr Pro Leu Tyr Ser Ala Val Ile Ser Glu
    210                 215                 220

Leu Asp Ala Val Gln Val Asn Tyr Tyr Leu Asp Glu Glu Asn Cys Trp
```

```
                225                 230                 235                 240
Ala Leu Asn Val Asp Glu Leu Arg Arg Ala Leu Arg Gln Ala Lys Asp
                    245                 250                 255

His Cys Asp Pro Lys Val Leu Cys Ile Ile Asn Pro Gly Asn Pro Thr
                260                 265                 270

Gly Gln Val Gln Ser Arg Lys Cys Ile Glu Asp Val Ile His Phe Ala
            275                 280                 285

Trp Glu Glu Lys Leu Phe Leu Leu Ala Asp Glu Val Tyr Gln Asp Asn
        290                 295                 300

Val Tyr Ser Pro Asp Cys Arg Phe His Ser Phe Lys Lys Val Leu Tyr
305                 310                 315                 320

Gln Met Gly His Glu Tyr Ser Ser Asn Val Glu Leu Ala Ser Phe His
                325                 330                 335

Ser Thr Ser Lys Gly Tyr Met Gly Glu Cys Gly Tyr Arg Gly Gly Tyr
                340                 345                 350

Met Glu Val Ile Asn Leu His Pro Glu Ile Lys Gly Gln Leu Val Lys
            355                 360                 365

Leu Leu Ser Val Arg Leu Cys Pro Pro Val Ser Gly Gln Ala Ala Met
        370                 375                 380

Asp Ile Val Val Asn Pro Pro Glu Pro Gly Glu Glu Ser Phe Glu Gln
385                 390                 395                 400

Phe Ser Arg Glu Lys Glu Phe Val Leu Gly Asn Leu Ala Lys Lys Ala
                405                 410                 415

Lys Leu Thr Glu Asp Leu Phe Asn Gln Val Pro Gly Ile Gln Cys Asn
                420                 425                 430

Pro Leu Gln Gly Ala Met Tyr Ala Phe Pro Arg Ile Leu Ile Pro Ala
            435                 440                 445

Lys Ala Val Glu Ala Ala Gln Ser His Lys Met Ala Pro Asp Met Phe
        450                 455                 460

Tyr Cys Met Lys Leu Leu Glu Glu Thr Gly Ile Cys Val Val Pro Gly
465                 470                 475                 480

Ser Gly Phe Gly Gln Arg Glu Gly Thr Tyr His Phe Arg Met Thr Ile
                485                 490                 495

Leu Pro Pro Val Asp Lys Leu Lys Thr Val Leu His Lys Val Lys Asp
                500                 505                 510

Phe His Leu Lys Phe Leu Glu Gln Tyr Ser
                515                 520

<210> SEQ ID NO 9
<211> LENGTH: 1491
<212> TYPE: DNA
<213> ORGANISM: Rattus norvegicus

<400> SEQUENCE: 9
atggcctcac gggtgaatga tcaaagccag gcttcaagga atgggctgaa gggaaaggtg      60
ctaactctgg acactatgaa cccatgtgtg cggagggtgg agtatgcagt tcgaggaccc     120
attgtgcagc gtgccttgga gctggagcag gagctgcgtc agggtgtgaa gaagccgttt     180
actgaggtca tccgtgccaa cattgggggat gcacaagcca tggggcagag acccatcacc     240
ttcttccgcc aggtcctggc cctctgtgtc taccccaatc ttctgagcag tcctgacttc     300
ccagaggatg ccaagagaag ggcagaacgc atcttgcagg cctgcggggg ccacagcctg     360
ggtgcctata gcattagctc tggaatccag ccgatccggg aggatgtggc caatacatt      420 gagagaagag acggaggcat ccccgcagac ccgaacaaca tatttctatc cacaggggcc     480
```

-continued

```
agcgatgcca tcgtgacaat gctcaagctg ctggtatctg gcgagggccg tgcacgaaca    540
ggtgtactca ttcccattcc tcagtaccca ctgtactcag ccgcgctggc tgaactggac    600
gccgtgcaag tggactacta cctggacgaa gagcgcgcct gggctctgga catcgcagag    660
ctgcggcgcg ctctgtgcca ggcacgtgac cgttgctgcc ctcgagtact gtgcgtcatc    720
aaccccggca accccactgg gcaggtgcag acccgtgagt gcatcgaggc cgtaatccgc    780
tttgctttca aagaaggact cttcttgatg gctgatgagg tataccagga caacgtgtat    840
gccgagggct ctcagttcca ttcattcaag aaggtgctca tggagatggg gccaccgtat    900
tccacgcagc aggagcttgc ttctttccac tcagtctcta aggctacat gggcgagtgc     960
gggtttcgtg gtggctatgt ggaggtggta acatggatg ctgaggtgca gaaacagatg     1020
gggaagctga tgagtgtgcg gctgtgtcca ccagtgccag ccaggcctt gatggacatg     1080
gtggtcagtc cgccaacacc ctccgagccg tccttcaagc agtttcaagc agagagacag    1140
gaggtgctgg ctgaactggc agccaaggct aagctcacgg agcaggtctt caatgaggct    1200
cccgggatcc gctgcaaccc agtgcagggc gccatgtatt ccttccctca gtgcagctg    1260
cccttgaaag cggtgcagcg tgctcaggaa ctgggcctgg cccctgacat gttcttctgc    1320
ctgtgcctcc tggaagagac tggcatctgc gttgtgcccg ggagtggctt tgggcagcag    1380
gagggcacct atcatttccg gatgaccatt ctgcccccca tggagaaact gcggctgctg    1440
ctggaaaaac tcagtcactt ccatgccaag ttcacccatg agtactcctg a             1491
```

<210> SEQ ID NO 10
<211> LENGTH: 496
<212> TYPE: PRT
<213> ORGANISM: Rattus norvegicus

<400> SEQUENCE: 10

```
Met Ala Ser Arg Val Asn Asp Gln Ser Gln Ala Ser Arg Asn Gly Leu
1               5                   10                  15

Lys Gly Lys Val Leu Thr Leu Asp Thr Met Asn Pro Cys Val Arg Arg
            20                  25                  30

Val Glu Tyr Ala Val Arg Gly Pro Ile Val Gln Arg Ala Leu Glu Leu
        35                  40                  45

Glu Gln Glu Leu Arg Gln Gly Val Lys Lys Pro Phe Thr Glu Val Ile
    50                  55                  60

Arg Ala Asn Ile Gly Asp Ala Gln Ala Met Gly Gln Arg Pro Ile Thr
65                  70                  75                  80

Phe Phe Arg Gln Val Leu Ala Leu Cys Val Tyr Pro Asn Leu Leu Ser
                85                  90                  95

Ser Pro Asp Phe Pro Glu Asp Ala Lys Arg Arg Ala Glu Arg Ile Leu
            100                 105                 110

Gln Ala Cys Gly Gly His Ser Leu Gly Ala Tyr Ser Ile Ser Ser Gly
        115                 120                 125

Ile Gln Pro Ile Arg Glu Asp Val Ala Gln Tyr Ile Glu Arg Arg Asp
    130                 135                 140

Gly Gly Ile Pro Ala Asp Pro Asn Asn Ile Phe Leu Ser Thr Gly Ala
145                 150                 155                 160

Ser Asp Ala Ile Val Thr Met Leu Lys Leu Leu Val Ser Gly Glu Gly
                165                 170                 175

Arg Ala Arg Thr Gly Val Leu Ile Pro Ile Pro Gln Tyr Pro Leu Tyr
            180                 185                 190
```

```
Ser Ala Ala Leu Ala Glu Leu Asp Ala Val Gln Val Asp Tyr Tyr Leu
            195                 200                 205

Asp Glu Glu Arg Ala Trp Ala Leu Asp Ile Ala Glu Leu Arg Arg Ala
    210                 215                 220

Leu Cys Gln Ala Arg Asp Arg Cys Cys Pro Arg Val Leu Cys Val Ile
225                 230                 235                 240

Asn Pro Gly Asn Pro Thr Gly Gln Val Gln Thr Arg Glu Cys Ile Glu
                245                 250                 255

Ala Val Ile Arg Phe Ala Phe Lys Glu Gly Leu Phe Leu Met Ala Asp
            260                 265                 270

Glu Val Tyr Gln Asp Asn Val Tyr Ala Glu Gly Ser Gln Phe His Ser
    275                 280                 285

Phe Lys Lys Val Leu Met Glu Met Gly Pro Pro Tyr Ser Thr Gln Gln
290                 295                 300

Glu Leu Ala Ser Phe His Ser Val Ser Lys Gly Tyr Met Gly Glu Cys
305                 310                 315                 320

Gly Phe Arg Gly Gly Tyr Val Glu Val Val Asn Met Asp Ala Glu Val
                325                 330                 335

Gln Lys Gln Met Gly Lys Leu Met Ser Val Arg Leu Cys Pro Pro Val
            340                 345                 350

Pro Gly Gln Ala Leu Met Asp Met Val Val Ser Pro Pro Thr Pro Ser
    355                 360                 365

Glu Pro Ser Phe Lys Gln Phe Gln Ala Glu Arg Gln Glu Val Leu Ala
370                 375                 380

Glu Leu Ala Ala Lys Ala Lys Leu Thr Glu Gln Val Phe Asn Glu Ala
385                 390                 395                 400

Pro Gly Ile Arg Cys Asn Pro Val Gln Gly Ala Met Tyr Ser Phe Pro
                405                 410                 415

Gln Val Gln Leu Pro Leu Lys Ala Val Gln Arg Ala Gln Glu Leu Gly
            420                 425                 430

Leu Ala Pro Asp Met Phe Phe Cys Leu Cys Leu Leu Glu Glu Thr Gly
    435                 440                 445

Ile Cys Val Val Pro Gly Ser Gly Phe Gly Gln Gln Glu Gly Thr Tyr
450                 455                 460

His Phe Arg Met Thr Ile Leu Pro Pro Met Glu Lys Leu Arg Leu Leu
465                 470                 475                 480

Leu Glu Lys Leu Ser His Phe His Ala Lys Phe Thr His Glu Tyr Ser
                485                 490                 495

<210> SEQ ID NO 11
<211> LENGTH: 1125
<212> TYPE: DNA
<213> ORGANISM: Canis familiaris

<400> SEQUENCE: 11
atgctggctc ttcacggggc cgtggttaag gtgaaacggg gccggctgcg tccagggctt      60
ggcgctacgc ctgatgccgg gatcgagggc ctgaccacct gttgcctcct ctttgctcag     120
ggtatcaaga aaccgttcac cgaggtcatc cgcgccaaca tcggggacgc ccaggccatg     180
ggccagcagc ctataacctt cctccgacag gtgatgcac tgtgcaccta ccccaacctg     240
ctggacagcc ccagcttccc agaagatgct aagaaacgag cccggaggat cctacaggct     300
tgtggcggga cagcctgggg tcctacagt gccagccagg gcgtcaactg catccgcgag     360
gacgtggccg cctacgtcac caggagggac ggcggggtgc ccgcggaccc cttcaacatt     420
```

-continued

```
tacctgacca ctggagccag cgacggcatt tctacgatcc tgaagatcct ggtgtccggg      480
ggtggcaagt cgcggacggg cgtgctgatc cccatcccac agtacccccct ctactcggcc     540 gtcatctccg agctcgacgc catccaggtg aactactact tggacgagga gaactgctgg     600
gccctcgacg tgaacgagct ccggcgggcc gtgcaggagg ctaaggacca ctgtaaccccc    660 aaggtgctgt gcatcatcaa ccccgggaac cccacaggtc aggtgcaaag caggaagtgc    720
atagaggacg tcatccactt tgcctgggaa gagaagctct ttctcctggc agatgaggtg    780
taccaggaca acgtgtactc tccggactgc agattccact ccttcaagaa ggtgctctac    840
gagatggggc ccgagtactc gagcaacgtg gagcttgcgt ccttccactc tacctccaag    900
ggctacatgg gcgagtacgt tggccttggc ttcctcccgc ggccccacca tcggccctg    960 cccgctggcg gcctgctgcg cggggaacac ggggcccatc tcaggggggcc tgtgcatgag   1020 ctcagccctg gtgcagggac gcccgtgcgg cgaggtcctg ctggggcccc gggctccccg   1080
cgcttcctgc cgggcccacg ctgctgccct gggactgaac cctga                    1125
```

<210> SEQ ID NO 12
<211> LENGTH: 374
<212> TYPE: PRT
<213> ORGANISM: Canis familiaris

<400> SEQUENCE: 12

```
Met Leu Ala Leu His Gly Ala Val Lys Val Lys Arg Gly Arg Leu
1               5                   10                  15

Arg Pro Gly Leu Gly Ala Thr Pro Asp Ala Gly Ile Glu Gly Leu Thr
            20                  25                  30

Thr Cys Cys Leu Leu Phe Ala Gln Gly Ile Lys Lys Pro Phe Thr Glu
        35                  40                  45

Val Ile Arg Ala Asn Ile Gly Asp Ala Gln Ala Met Gly Gln Gln Pro
    50                  55                  60

Ile Thr Phe Leu Arg Gln Val Met Ala Leu Cys Thr Tyr Pro Asn Leu
65                  70                  75                  80

Leu Asp Ser Pro Ser Phe Pro Glu Asp Ala Lys Lys Arg Ala Arg Arg
                85                  90                  95

Ile Leu Gln Ala Cys Gly Gly Asn Ser Leu Gly Ser Tyr Ser Ala Ser
            100                 105                 110

Gln Gly Val Asn Cys Ile Arg Glu Asp Val Ala Ala Tyr Val Thr Arg
        115                 120                 125

Arg Asp Gly Gly Val Pro Ala Asp Pro Phe Asn Ile Tyr Leu Thr Thr
    130                 135                 140

Gly Ala Ser Asp Gly Ile Ser Thr Ile Leu Lys Ile Leu Val Ser Gly
145                 150                 155                 160

Gly Gly Lys Ser Arg Thr Gly Val Leu Ile Pro Ile Pro Gln Tyr Pro
                165                 170                 175

Leu Tyr Ser Ala Val Ile Ser Glu Leu Asp Ala Ile Gln Val Asn Tyr
            180                 185                 190

Tyr Leu Asp Glu Glu Asn Cys Trp Ala Leu Asp Val Asn Glu Leu Arg
        195                 200                 205

Arg Ala Val Gln Glu Ala Lys Asp His Cys Asn Pro Lys Val Leu Cys
    210                 215                 220

Ile Ile Asn Pro Gly Asn Pro Thr Gly Gln Val Gln Ser Arg Lys Cys
225                 230                 235                 240

Ile Glu Asp Val Ile His Phe Ala Trp Glu Glu Lys Leu Phe Leu Leu
                245                 250                 255
```

Ala Asp Glu Val Tyr Gln Asp Asn Val Tyr Ser Pro Asp Cys Arg Phe
            260                 265                 270

His Ser Phe Lys Lys Val Leu Tyr Glu Met Gly Pro Glu Tyr Ser Ser
        275                 280                 285

Asn Val Glu Leu Ala Ser Phe His Ser Thr Ser Lys Gly Tyr Met Gly
    290                 295                 300

Glu Tyr Val Gly Leu Gly Phe Leu Pro Arg Pro His Ser Ala Leu
305                 310                 315                 320

Pro Ala Gly Gly Leu Leu Arg Gly Gly His Gly Ala His Leu Arg Gly
                325                 330                 335

Pro Val His Glu Leu Ser Pro Gly Ala Gly Thr Pro Val Arg Arg Gly
            340                 345                 350

Pro Ala Gly Ala Pro Gly Ser Pro Arg Phe Leu Pro Gly Pro Arg Cys
        355                 360                 365

Cys Pro Gly Thr Glu Pro
    370

<210> SEQ ID NO 13
<211> LENGTH: 1623
<212> TYPE: DNA
<213> ORGANISM: Xenopus laevis

<400> SEQUENCE: 13

```
atgagtattc tcaggggggtc tctgaggggg gtgctggccc ccaatgcttc tgttgtgttt        60
aggagcagat tgcccccccca gctcacttct gccctcctgt gcccccctcag gtcgctgtcg      120 ggaacgccgc tggctgaacc ggacgggaaa gttactcgca agatgtctga gaacgggaca      180
tgcaaccgga tcctgactct ggactccatg aatcccgtaa tccagaaagt ggaatacgca      240
gtgaggggcc ccatcgtcat cagggctgtg agctggaga  aagaactgca gcaggggta       300 aagaagccat tcacagaagt gatcaaagcc aatattggag atgcccatgc aatgggtcag      360
aaacccgtta ctttcctgcg ccaggtgagt gccatctgtc tgtaccccga gctcatgaat      420
gacaacaagt tcccggagga cgtgaagcag aaggcagcga ggatcctgca ggcgtgtggc      480
gggcacagca ttgggcctta cagcgccagc caagggattg aagtgatccg acaagatgtg      540
gccaagtaca ttgagagaag ggatgggggt atcctgtccg accccaacaa catctacctc      600
tccacggggg ccagtgactc tattgtgaca atgctgaagt tgctggtgtc tgggcaaggg      660
aaatcccgaa ctggggtgat gatcccgatc cctcaatacc cgctgtattc tgcggccctg      720
gcagagttgg atgccgtgca ggttaattat tatctggatg aggagaactg ctgggccctg      780
gacatcaacg agctgcggag agcactagcg gaggcccgaa acattgtgaa ccccaaagta      840
ctgtgcatta ttaacccagg aaaccctaca gggcaggtgc agagccgcaa gtgcattgag      900
gacgtgatcc gttttgctgc tgaagagaat cttttcctga tggcggatga ggtctaccaa      960
gataatgtct atgccaaggg ctgtgccttt cactccttca aaaaggttct ctttgagatg     1020
ggacccaagt attcagaaac gctggaactg gcttcttttcc actccacatc caagggatac     1080 atggagagt gcgggttcag agggggttac atggaagtga tcaatatgga tcctgctgtc     1140
aagcaacaac taaccaagtt ggtgtctgtg cgtctgtgcc ccccagtgcc ggggcaagta     1200
ttacttgatg tgattgtgaa cccaccaaag cctggggagc cctcctacaa acagttcatt     1260
tctgagaaac aggctgtgct caataacctg gctgagaaag ctcgtctcac tgaggaaatc     1320
ctaaaccaag cgcctgggat ccgctgtaac ccagtccagg gagccatgta ctcgtttcca     1380
```

```
aggatccaca tcccagagaa ggccattaaa cttgcacagg ctgagggaca ggccccagac    1440
atgttcttct gtatgaagct gctggaagag actggcattt gtgtggtacc tggaagtgga    1500
tttggacaac gtgagggcac tcaccatttc aggatgacca tcctccctcc caccgataag    1560
ctgaagagcc tgttagagcg gctgaaggat ttccaccaga aatttatgga tgagtattcc    1620
tag                                                                  1623
```

<210> SEQ ID NO 14
<211> LENGTH: 540
<212> TYPE: PRT
<213> ORGANISM: Xenopus laevis

<400> SEQUENCE: 14

```
Met Ser Ile Leu Arg Gly Ser Leu Arg Gly Val Leu Ala Pro Asn Ala
1               5                   10                  15

Ser Val Val Phe Arg Ser Arg Leu Pro Pro Gln Leu Thr Ser Ala Leu
            20                  25                  30

Leu Cys Pro Leu Arg Ser Leu Ser Gly Thr Pro Leu Ala Glu Pro Asp
        35                  40                  45

Gly Lys Val Thr Arg Lys Met Ser Glu Asn Gly Thr Cys Asn Arg Ile
    50                  55                  60

Leu Thr Leu Asp Ser Met Asn Pro Cys Ile Gln Lys Val Glu Tyr Ala
65                  70                  75                  80

Val Arg Gly Pro Ile Val Ile Arg Ala Val Glu Leu Glu Lys Glu Leu
                85                  90                  95

Gln Gln Gly Val Lys Lys Pro Phe Thr Glu Val Ile Lys Ala Asn Ile
            100                 105                 110

Gly Asp Ala His Ala Met Gly Gln Lys Pro Val Thr Phe Leu Arg Gln
        115                 120                 125

Val Ser Ala Ile Cys Leu Tyr Pro Glu Leu Met Asn Asp Asn Lys Phe
    130                 135                 140

Pro Glu Asp Val Lys Gln Lys Ala Ala Arg Ile Leu Gln Ala Cys Gly
145                 150                 155                 160

Gly His Ser Ile Gly Ala Tyr Ser Ala Ser Gln Gly Ile Glu Val Ile
                165                 170                 175

Arg Gln Asp Val Ala Lys Tyr Ile Glu Arg Arg Asp Gly Gly Ile Leu
            180                 185                 190

Ser Asp Pro Asn Asn Ile Tyr Leu Ser Thr Gly Ala Ser Asp Ser Ile
        195                 200                 205

Val Thr Met Leu Lys Leu Leu Val Ser Gly Gln Gly Lys Ser Arg Thr
    210                 215                 220

Gly Val Met Ile Pro Ile Pro Gln Tyr Pro Leu Tyr Ser Ala Ala Leu
225                 230                 235                 240

Ala Glu Leu Asp Ala Val Gln Val Asn Tyr Tyr Leu Asp Glu Glu Asn
                245                 250                 255

Cys Trp Ala Leu Asp Ile Asn Glu Leu Arg Arg Ala Leu Ala Glu Ala
            260                 265                 270

Arg Lys His Cys Asp Pro Lys Val Leu Cys Ile Ile Asn Pro Gly Asn
        275                 280                 285

Pro Thr Gly Gln Val Gln Ser Arg Lys Cys Ile Glu Asp Val Ile Arg
    290                 295                 300

Phe Ala Ala Glu Glu Asn Leu Phe Leu Met Ala Asp Glu Val Tyr Gln
305                 310                 315                 320

Asp Asn Val Tyr Ala Lys Gly Cys Ala Phe His Ser Phe Lys Lys Val
```

|  |  |  | 325 |  |  |  | 330 |  |  |  | 335 |  |
|---|---|---|---|---|---|---|---|---|---|---|---|---|
| Leu | Phe | Glu | Met | Gly | Pro | Lys | Tyr | Ser | Glu | Thr | Leu | Glu | Leu | Ala | Ser |
|  |  |  | 340 |  |  |  | 345 |  |  |  | 350 |  |

Phe His Ser Thr Ser Lys Gly Tyr Met Gly Glu Cys Gly Phe Arg Gly
            355                 360                 365

Gly Tyr Met Glu Val Ile Asn Met Asp Pro Ala Val Lys Gln Gln Leu
        370                 375                 380

Thr Lys Leu Val Ser Val Arg Leu Cys Pro Val Pro Gly Gln Val
385                 390                 395                 400

Leu Leu Asp Val Ile Val Asn Pro Pro Lys Pro Gly Glu Pro Ser Tyr
                405                 410                 415

Lys Gln Phe Ile Ser Glu Lys Gln Ala Val Leu Asn Asn Leu Ala Glu
                420                 425                 430

Lys Ala Arg Leu Thr Glu Glu Ile Leu Asn Gln Ala Pro Gly Ile Arg
                435                 440                 445

Cys Asn Pro Val Gln Gly Ala Met Tyr Ser Phe Pro Arg Ile His Ile
450                 455                 460

Pro Glu Lys Ala Ile Lys Leu Ala Gln Ala Glu Gly Gln Ala Pro Asp
465                 470                 475                 480

Met Phe Phe Cys Met Lys Leu Leu Glu Glu Thr Gly Ile Cys Val Val
                485                 490                 495

Pro Gly Ser Gly Phe Gly Gln Arg Glu Gly Thr His His Phe Arg Met
                500                 505                 510

Thr Ile Leu Pro Pro Thr Asp Lys Leu Lys Ser Leu Leu Glu Arg Leu
                515                 520                 525

Lys Asp Phe His Gln Lys Phe Met Asp Glu Tyr Ser
                530                 535                 540

<210> SEQ ID NO 15
<211> LENGTH: 1707
<212> TYPE: DNA
<213> ORGANISM: Drosophila melanogaster

<400> SEQUENCE: 15

| atgagtcgaa | tgctaattaa | acctgctgcc | gccacagttt | cggccgcatt | gcagcagcac | 60 |
| cagcgccagc | agcaacagta | cgttattcgc | cgctggaaat | cgttcctgca | caacaacagc | 120 |
| aacaatgcca | atcgacgtgc | ggcgaaatca | acggcaacag | caacggtgac | ggcagcagcg | 180 |
| acgtcgcagc | gccatggaac | aagcggcgat | tcattcaac | cgttagacgt | ccgccgttcc | 240 |
| ttttcaacca | gccacaaaat | gccgtcgtcg | tcgaaagcgc | tcacactgga | taacataaat | 300 |
| cccaacttta | ttgccatgga | atatgccgtt | cgcggtcctc | tggtgattcg | tgctggggaa | 360 |
| atcgagaagg | aactggaaaa | gggtgtcaag | aagccattcg | accaggtgat | ccgtgccaac | 420 |
| atcggtgatt | gccatgcgat | gggccagcag | cccttgacct | tcctgcgaca | gctgttggcg | 480 |
| ctgaccttcg | agacacgtct | gctggattca | ccgattatc | ccgaggacgt | caagaagcgc | 540 |
| gcctgtgcca | ttttgaacgg | ctgccagggt | caatcggtgg | ctcgtacac | cgactccgcc | 600 |
| ggtctggagg | tggtgcgtcg | ccaggttgct | cagtacatcg | agaaaaggga | tggcggcatc | 660 |
| gcctccaatt | ggcaggacat | ctatctaacc | ggcggtgcct | ctcccggcat | caagagcatt | 720 |
| ctctccatga | tcaacgccga | ggtgggatgc | aaggcgcctg | tgtcatggt | gcccattccg | 780 |
| cagtacccac | tgtactcggc | caccatctcc | gaatacggca | tgaccaaggt | ggattactat | 840 |
| ctggaggagg | agaccggttg | gagcctggac | aggaaggagc | tgcaacggtc | ctacgatgag | 900 |

```
gcgaagaagg tctgcaatcc gcgtgccctg gtcgtgatca atccgggcaa tcccaccgga    960
caggtactga cccgcgagaa catcgaggag atcattaagt tcgcacacga taacaaggtg   1020
ctggtgctgg ccgatgaggt gtaccaggac aatgtctacg acaagaactc caagttctgg   1080
tcgttcaaga aggtggccta cgaaatgggc gaccccatc gtaatctgga atggtcagt    1140 ttcctgtcca cctcgaaggg ctatctgggc gagtgcggca ttcgcggcgg ttacatggag   1200
gttctcaatc ttgatcccaa ggtcaaggcc atgctgacca gtcgataac ggcggcgctt    1260 tgcagcacca ccgctggcca ggtggccgtg agtgccctgg tcaatccacc gcagcccgga   1320
gagccatcat cgatctgta caagaaggag cgcgatggca ttctggccgc tctaaaagaa   1380
cgggccgagc tcgtccacaa ggcactgaac agcttcgaag gctacaaggt taaccccgta   1440
cagggcgcca tgtacgtctt tccacagatc gagatcccgc caaggcgat cgaggcggcc    1500 aaggccaagg gcatggcccc cgatgttttc tacgcatttg agctgctcga gcgagcggc   1560 atttgcattg ttcctggcag tggatttggt cagaagcccg gcacgtggca tttccgaagc   1620
acgatcctcc cgcaaacgga caagctgaag ctgatgatgg agaagttccg tgtgttccac   1680
gccgagttca tgaagaagta caagtag                                      1707

<210> SEQ ID NO 16
<211> LENGTH: 568
<212> TYPE: PRT
<213> ORGANISM: Drosophila melanogaster

<400> SEQUENCE: 16

Met Ser Arg Met Leu Ile Lys Pro Ala Ala Thr Val Ser Ala Ala
1               5                   10                  15

Leu Gln Gln His Gln Arg Gln Gln Gln Tyr Val Ile Arg Arg Trp
            20                  25                  30

Lys Ser Phe Leu His Asn Asn Ser Asn Ala Asn Arg Arg Ala Ala
        35                  40                  45

Lys Ser Thr Ala Thr Ala Thr Val Thr Ala Ala Thr Ser Gln Arg
    50                  55                  60

His Gly Thr Ser Gly Asp Phe Ile Gln Pro Leu Asp Val Arg Arg Ser
65                  70                  75                  80

Phe Ser Thr Ser His Lys Met Pro Ser Ser Lys Ala Leu Thr Leu
                85                  90                  95

Asp Asn Ile Asn Pro Asn Phe Ile Ala Met Glu Tyr Ala Val Arg Gly
            100                 105                 110

Pro Leu Val Ile Arg Ala Gly Glu Ile Glu Lys Glu Leu Glu Lys Gly
        115                 120                 125

Val Lys Lys Pro Phe Asp Gln Val Ile Arg Ala Asn Ile Gly Asp Cys
    130                 135                 140

His Ala Met Gly Gln Gln Pro Leu Thr Phe Leu Arg Gln Leu Leu Ala
145                 150                 155                 160

Leu Thr Phe Glu Thr Arg Leu Leu Asp Ser Pro Asp Tyr Pro Glu Asp
                165                 170                 175

Val Lys Lys Arg Ala Cys Ala Ile Leu Asn Gly Cys Gln Gly Gln Ser
            180                 185                 190

Val Gly Ser Tyr Thr Asp Ser Ala Gly Leu Glu Val Val Arg Arg Gln
        195                 200                 205

Val Ala Gln Tyr Ile Glu Lys Arg Asp Gly Gly Ile Ala Ser Asn Trp
    210                 215                 220

Gln Asp Ile Tyr Leu Thr Gly Gly Ala Ser Pro Gly Ile Lys Ser Ile
```

```
                225                 230                 235                 240
Leu Ser Met Ile Asn Ala Glu Val Gly Cys Lys Ala Pro Gly Val Met
                245                 250                 255

Val Pro Ile Pro Gln Tyr Pro Leu Tyr Ser Ala Thr Ile Ser Glu Tyr
            260                 265                 270

Gly Met Thr Lys Val Asp Tyr Leu Glu Glu Thr Gly Trp Ser
        275                 280                 285

Leu Asp Arg Lys Glu Leu Gln Arg Ser Tyr Glu Ala Lys Lys Val
    290                 295                 300

Cys Asn Pro Arg Ala Leu Val Val Ile Asn Pro Gly Asn Pro Thr Gly
305                 310                 315                 320

Gln Val Leu Thr Arg Glu Asn Ile Glu Glu Ile Ile Lys Phe Ala His
                325                 330                 335

Asp Asn Lys Val Leu Val Leu Ala Asp Glu Val Tyr Gln Asp Asn Val
                340                 345                 350

Tyr Asp Lys Asn Ser Lys Phe Trp Ser Phe Lys Lys Val Ala Tyr Glu
            355                 360                 365

Met Gly Asp Pro Tyr Arg Asn Leu Glu Met Val Ser Phe Leu Ser Thr
        370                 375                 380

Ser Lys Gly Tyr Leu Gly Glu Cys Gly Ile Arg Gly Tyr Met Glu
385                 390                 395                 400

Val Leu Asn Leu Asp Pro Lys Val Lys Ala Met Leu Thr Lys Ser Ile
                405                 410                 415

Thr Ala Ala Leu Cys Ser Thr Thr Ala Gly Gln Val Ala Val Ser Ala
                420                 425                 430

Leu Val Asn Pro Pro Gln Pro Gly Glu Pro Ser Tyr Asp Leu Tyr Lys
            435                 440                 445

Lys Glu Arg Asp Gly Ile Leu Ala Ala Leu Lys Glu Arg Ala Glu Leu
        450                 455                 460

Val His Lys Ala Leu Asn Ser Phe Glu Gly Tyr Lys Val Asn Pro Val
465                 470                 475                 480

Gln Gly Ala Met Tyr Val Phe Pro Gln Ile Glu Ile Pro Lys Ala
                485                 490                 495

Ile Glu Ala Ala Lys Ala Lys Gly Met Ala Pro Asp Val Phe Tyr Ala
                500                 505                 510

Phe Glu Leu Leu Glu Thr Ser Gly Ile Cys Ile Val Pro Gly Ser Gly
            515                 520                 525

Phe Gly Gln Lys Pro Gly Thr Trp His Phe Arg Ser Thr Ile Leu Pro
        530                 535                 540

Gln Thr Asp Lys Leu Lys Leu Met Met Glu Lys Phe Arg Val Phe His
545                 550                 555                 560

Ala Glu Phe Met Lys Lys Tyr Lys
                565

<210> SEQ ID NO 17
<211> LENGTH: 1515
<212> TYPE: DNA
<213> ORGANISM: Caenorhabditis elegans

<400> SEQUENCE: 17
atgcgaaccg tacaagcaat ttccggactc gtcacaagtc gcttttttcgg cacatccact     60 agaatcatgg ctagcggaaa gactttgaac acctccaaca tcaatccaaa tgttatcaag    120
atggagtatg ctgttcgtgg accaatcgtg atccgtgccg tggagcttga aaaagagctt    180
```

```
gcgaccggtg ctcagaagcc attcccaaat gtcatcaagg ctaatattgg agatgctcat      240
gctatgggtc aaaagccgat tactttcatt cgccagctcc tcgcgtgtat tgtcaaccca      300
gagatcatga aacggacaa atcaattcca tctgatgtta tcgaacatgc aaatgcattc       360
cttggaagtt gtggaggaaa atccgctgga gcatacagtc agagtacggg agtggaaatt      420
gtacgaaaac acgtggcaga gtatattaag agacgtgatg gaggaattcc atgcaattca      480
gaagatgtct gcttgtctgg aggagcttct gaatcaatcc gaaatgttct caaactttt       540 atcaatcata caacgcaaa gaaagtcgga gtcatgattc caattccaca atatccactc      600
tattctgcca ctatcgaaga attcggactt ggacaagttg atactatttt gagtgaatcg      660
tctaattggt ccatggatga agctgaactt gaaagatctt tcaatgatca ctgcaaagaa      720
tacgatattc gagttttgtg tatcatcaat ccaggaaatc ctaccggaca agcactttct      780
cgtgaaaata ttgagactat catcaagttt gcacaaaaga gaacctgtt  ccttatggct      840 gatgaggttt atcaagacaa cgtctacgct caaggatcgc aattccattc attcaagaag      900
gttcttgtgg agatgggaga gccatacaat aaaatggaat tggcttcttt ccattcggta      960
tccaaaggat acatgggaga atgcggaatg cgtggaggat atgttgaatt cttgaatctc     1020
gacccagaag tgtatgtcct tttcaaaaaa atgatctctg ccaaattgtg ctccacagta     1080
ctcggacaag ccgtcattga tgccgttgtg aatccaccaa aggaaggaga tgcatcgtat     1140
gctctgtgga acaagaaaaa ggatgcagta cttgcttctc ttaaggaacg tgctacactc     1200
gtcgagaagg catacagtag cattgatgga atcagctgta atccagttca aggagccatg     1260 tacgcttttcc cgcaaatcac gattccacag agagctgttg aaaaagctca gtctttgaac     1320
caacaacctg atttcttcta tgctatgcaa cttcttgaga ccaccggaat ctgtatcgtg     1380
ccaggaagtg gatttggaca aaaagacgga acttatcatt tcagaacgac aattcttcca     1440
cagccagaac tcttcaaaga catgctctcc cggttcactg atttccacca aaaattcctt     1500
gccgaataca agtag                                                      1515
```

<210> SEQ ID NO 18
<211> LENGTH: 504
<212> TYPE: PRT
<213> ORGANISM: Caenorhabditis elegans

<400> SEQUENCE: 18

Met Arg Thr Val Gln Ala Ile Ser Gly Leu Val Thr Ser Arg Phe Phe
1               5                   10                  15

Gly Thr Ser Thr Arg Ile Met Ala Ser Gly Lys Thr Leu Asn Thr Ser
            20                  25                  30

Asn Ile Asn Pro Asn Val Ile Lys Met Glu Tyr Ala Val Arg Gly Pro
        35                  40                  45

Ile Val Ile Arg Ala Val Glu Leu Glu Lys Glu Leu Ala Thr Gly Ala
    50                  55                  60

Gln Lys Pro Phe Pro Asn Val Ile Lys Ala Asn Ile Gly Asp Ala His
65                  70                  75                  80

Ala Met Gly Gln Lys Pro Ile Thr Phe Ile Arg Gln Leu Leu Ala Cys
                85                  90                  95

Ile Val Asn Pro Glu Ile Met Lys Thr Asp Lys Ser Ile Pro Ser Asp
            100                 105                 110

Val Ile Glu His Ala Asn Ala Phe Leu Gly Ser Cys Gly Gly Lys Ser
        115                 120                 125

Ala Gly Ala Tyr Ser Gln Ser Thr Gly Val Glu Ile Val Arg Lys His

```
              130                 135                 140
Val Ala Glu Tyr Ile Lys Arg Arg Asp Gly Gly Ile Pro Cys Asn Ser
145                 150                 155                 160

Glu Asp Val Cys Leu Ser Gly Ala Ser Glu Ser Ile Arg Asn Val
            165                 170                 175

Leu Lys Leu Phe Ile Asn His Asn Asn Ala Lys Lys Val Gly Val Met
            180                 185                 190

Ile Pro Ile Pro Gln Tyr Pro Leu Tyr Ser Ala Thr Ile Glu Glu Phe
            195                 200                 205

Gly Leu Gly Gln Val Gly Tyr Tyr Leu Ser Glu Ser Ser Asn Trp Ser
210                 215                 220

Met Asp Glu Ala Glu Leu Glu Arg Ser Phe Asn Asp His Cys Lys Glu
225                 230                 235                 240

Tyr Asp Ile Arg Val Leu Cys Ile Ile Asn Pro Gly Asn Pro Thr Gly
            245                 250                 255

Gln Ala Leu Ser Arg Glu Asn Ile Glu Thr Ile Ile Lys Phe Ala Gln
            260                 265                 270

Lys Lys Asn Leu Phe Leu Met Ala Asp Glu Val Tyr Gln Asp Asn Val
275                 280                 285

Tyr Ala Gln Gly Ser Gln Phe His Ser Phe Lys Lys Val Leu Val Glu
            290                 295                 300

Met Gly Glu Pro Tyr Asn Lys Met Glu Leu Ala Ser Phe His Ser Val
305                 310                 315                 320

Ser Lys Gly Tyr Met Gly Glu Cys Gly Met Arg Gly Gly Tyr Val Glu
            325                 330                 335

Phe Leu Asn Leu Asp Pro Glu Val Tyr Val Leu Phe Lys Lys Met Ile
            340                 345                 350

Ser Ala Lys Leu Cys Ser Thr Val Leu Gly Gln Ala Val Ile Asp Ala
            355                 360                 365

Val Val Asn Pro Pro Lys Glu Gly Asp Ala Ser Tyr Ala Leu Trp Lys
            370                 375                 380

Gln Glu Lys Asp Ala Val Leu Ala Ser Leu Lys Glu Arg Ala Thr Leu
385                 390                 395                 400

Val Glu Lys Ala Tyr Ser Ser Ile Asp Gly Ile Ser Cys Asn Pro Val
            405                 410                 415

Gln Gly Ala Met Tyr Ala Phe Pro Gln Ile Thr Ile Pro Gln Arg Ala
            420                 425                 430

Val Glu Lys Ala Gln Ser Leu Asn Gln Pro Asp Phe Phe Tyr Ala
            435                 440                 445

Met Gln Leu Leu Glu Thr Thr Gly Ile Cys Ile Val Pro Gly Ser Gly
450                 455                 460

Phe Gly Gln Lys Asp Gly Thr Tyr His Phe Arg Thr Thr Ile Leu Pro
465                 470                 475                 480

Gln Pro Glu Leu Phe Lys Asp Met Leu Ser Arg Phe Thr Asp Phe His
            485                 490                 495

Gln Lys Phe Leu Ala Glu Tyr Lys
            500

<210> SEQ ID NO 19
<211> LENGTH: 1458
<212> TYPE: DNA
<213> ORGANISM: Oryza sativa japonica

<400> SEQUENCE: 19
```

```
atgttcggcg gcggcggcgg cggcgggagg aagccgctgg actacgagga gctgaacgag    60
aacgtgaaga aggtgcagta cgcggtgcgg ggggagctgt acctgcgcgc ctccgagctc   120
cagaaggagg gcaagaagat catcttcacc aacgtcggca acccacacgc gctcggccag   180
aagccgctca ccttccccccg ccaggttgtg cgcgctgtgcc aggccccctt cctgctcgat   240
gatcccaacg tcggccttat cttccccgcc gacgccatcg cgcgggccaa gcactacctc   300
gccatggcac ccgtgggact aggtgcttac agtgattccc gaggtatccc tggtattagg   360
aaggaagtcg ccgagttcat cgagaggcgt gatggttatc caagtgatcc agaacttatt   420
tacctcacag atggtgccag caaaggtgtg atgcaaatgc tgaataccat tatcagaaat   480
gagagagatg ggattctggt tcctgttcca caatacccgc tttattctgc tgccatttcc   540
ctctttggtg gttctctcgt gccatactac ttagaagaag aggctaactg gggacttgac   600
ttcgtcaatc tccgacagac tgtggcgtca gcgcggtcaa agggaatcac tgttcgagca   660
atggtgatta tcaacccagg aaaccctact ggccaatgcc ttagtgaagg aaacataaag   720
gaacttctca aattctgctt ccatgagaac ttagttctgc ttgcagatga agtctatcaa   780
cagaacattt atcaagatga gcgcccattt ataagtgcta gaaaggttct gtttgacatg   840
ggtcctccta tgagcaggga agttcagctg gtttctttcc atactgtgtc aaaaggatat   900
tgggggggagt gtggacaacg tggagggtat tttgaaatga caaatcttcc tcccaagaca   960
gtagacgaga tctacaaggt tgcatcaatc gcactcagtc caaatgttcc tgggcagatc  1020
tttatgggtt taatggttaa ccctcctaag cctggagata tctcttatct gaagttttct  1080
gctgaaagca agtctatcct cgagtctttg aggaggagag cacgcctgat gacagatggg  1140
ttcaatagtt gccgaaatgt tgtctgcaat ttcacagaag gagctatgta ctctttcccc  1200
caaatacgct taccaccaaa agctatagat gcagccaaaa gggctggcaa agcggccgat  1260
gttttctact gcctcaagct tcttgaagca actggaatat ccactgttcc agggtcaggt  1320
ttcggacaaa aagaaggggt gttccacctg aggacgacca tcctgccagc tgaggaggac  1380
atgcctgcca tcatgaccag cttcaagaag ttcaacgaca ctttcatgga tcagtacgat  1440
ggctactcca ggatgtga                                                 1458
```

<210> SEQ ID NO 20
<211> LENGTH: 485
<212> TYPE: PRT
<213> ORGANISM: Oryza sativa japonica

<400> SEQUENCE: 20

```
Met Phe Gly Gly Gly Gly Gly Gly Arg Lys Pro Leu Asp Tyr Glu
1               5                   10                  15

Glu Leu Asn Glu Asn Val Lys Lys Val Gln Tyr Ala Val Arg Gly Glu
            20                  25                  30

Leu Tyr Leu Arg Ala Ser Glu Leu Gln Lys Glu Gly Lys Lys Ile Ile
        35                  40                  45

Phe Thr Asn Val Gly Asn Pro His Ala Leu Gly Gln Lys Pro Leu Thr
    50                  55                  60

Phe Pro Arg Gln Val Val Ala Leu Cys Gln Ala Pro Phe Leu Leu Asp
65                  70                  75                  80

Asp Pro Asn Val Gly Leu Ile Phe Pro Ala Asp Ala Ile Ala Arg Ala
                85                  90                  95

Lys His Tyr Leu Ala Met Ala Pro Gly Gly Leu Gly Ala Tyr Ser Asp
                100                 105                 110
```

Ser Arg Gly Ile Pro Gly Ile Arg Lys Glu Val Ala Glu Phe Ile Glu
        115                 120                 125

Arg Arg Asp Gly Tyr Pro Ser Asp Pro Glu Leu Ile Tyr Leu Thr Asp
130                 135                 140

Gly Ala Ser Lys Gly Val Met Gln Met Leu Asn Thr Ile Ile Arg Asn
145                 150                 155                 160

Glu Arg Asp Gly Ile Leu Val Pro Val Pro Gln Tyr Pro Leu Tyr Ser
                165                 170                 175

Ala Ala Ile Ser Leu Phe Gly Gly Ser Leu Val Pro Tyr Tyr Leu Glu
                180                 185                 190

Glu Glu Ala Asn Trp Gly Leu Asp Phe Val Asn Leu Arg Gln Thr Val
            195                 200                 205

Ala Ser Ala Arg Ser Lys Gly Ile Thr Val Arg Ala Met Val Ile Ile
        210                 215                 220

Asn Pro Gly Asn Pro Thr Gly Gln Cys Leu Ser Glu Gly Asn Ile Lys
225                 230                 235                 240

Glu Leu Leu Lys Phe Cys Phe His Glu Asn Leu Val Leu Leu Ala Asp
                245                 250                 255

Glu Val Tyr Gln Gln Asn Ile Tyr Gln Asp Glu Arg Pro Phe Ile Ser
                260                 265                 270

Ala Arg Lys Val Leu Phe Asp Met Gly Pro Pro Met Ser Arg Glu Val
            275                 280                 285

Gln Leu Val Ser Phe His Thr Val Ser Lys Gly Tyr Trp Gly Glu Cys
        290                 295                 300

Gly Gln Arg Gly Gly Tyr Phe Glu Met Thr Asn Leu Pro Pro Lys Thr
305                 310                 315                 320

Val Asp Glu Ile Tyr Lys Val Ala Ser Ile Ala Leu Ser Pro Asn Val
                325                 330                 335

Pro Gly Gln Ile Phe Met Gly Leu Met Val Asn Pro Pro Lys Pro Gly
                340                 345                 350

Asp Ile Ser Tyr Leu Lys Phe Ser Ala Glu Ser Lys Ser Ile Leu Glu
            355                 360                 365

Ser Leu Arg Arg Arg Ala Arg Leu Met Thr Asp Gly Phe Asn Ser Cys
370                 375                 380

Arg Asn Val Val Cys Asn Phe Thr Glu Gly Ala Met Tyr Ser Phe Pro
385                 390                 395                 400

Gln Ile Arg Leu Pro Pro Lys Ala Ile Asp Ala Ala Lys Arg Ala Gly
                405                 410                 415

Lys Ala Ala Asp Val Phe Tyr Cys Leu Lys Leu Leu Glu Ala Thr Gly
            420                 425                 430

Ile Ser Thr Val Pro Gly Ser Gly Phe Gly Gln Lys Glu Gly Val Phe
        435                 440                 445

His Leu Arg Thr Thr Ile Leu Pro Ala Glu Glu Asp Met Pro Ala Ile
    450                 455                 460

Met Thr Ser Phe Lys Lys Phe Asn Asp Thr Phe Met Asp Gln Tyr Asp
465                 470                 475                 480

Gly Tyr Ser Arg Met
                485

<210> SEQ ID NO 21
<211> LENGTH: 1452
<212> TYPE: DNA
<213> ORGANISM: Oryza sativa japonica

<400> SEQUENCE: 21

```
atggctgctc ccagcgtcgc cgtcgacaac ctcaacccca aggttttgaa ttgtgagtat      60
gcagtgcgtg gagagattgt gatccatgct cagcgcctgc agcaacagct acagactcaa     120
ccagggtctc ttccttttga tgagatccta tactgcaaca ttgggaatcc ccagtctctt     180
ggtcagaagc cagttacatt cttcagggag gttattgctc tttgtgatca tccatgcttg     240
ttggaaaagg aggaaaccaa atcattgttc agtgctgatg ccatttctcg agcaacaaca     300
attcttgcct cgattcctgg aagagcaact ggagcataca gccacagcca gggcatcaaa     360
gggctgcgtg atgcaattgc tgctggaatt gcatcacgtg acggataccc tgcaaatgca     420
gacgacattt tccttactga cggagcaagc cctggagttc acatgatgat gcagttactg     480
ataaggaacg agaaagatgg cattctctgc ccaattcctc aatatccttt gtactcagcc     540
tccattgctc ttcatggtgg agctcttgtc ccgtattatc ttaatgaatc aacaggctgg     600
ggtttggaga tctctgacct taagaagcaa ctcgaagatt ctcggttgaa aggcattgat     660
gttagggctt tggtagttat caatccagga aatccaactg gcaggttct tgctgaggaa      720
aaccaacggg acatagtgaa gttctgcaaa aatgagggac ttgttcttct ggctgatgag     780
gtgtaccaag agaacatcta tgttgacaac aagaaattta actcttcaa gaagatagcg      840
agatccatgg gatacaacga ggatgatctc cctttagtat catttcaatc tgtttctaag     900
ggatattatg gtgaatgtgg caaaagagga ggctacatgg agattactgg cttcagtgct     960
ccagttagag agcagatcta caaagtggcg tcagtgaact tatgttccaa tatcactggc    1020
cagatccttg ccagcctcgt catgaatcca ccaaaggctg gagatgcatc atatgcttca    1080
tacaaggcag agaaagatgg aatcctccaa tcattagctc gccgtgcaaa ggcattggag    1140
aatgctttca acagtcttga gggaattaca tgcaacaaaa ctgaaggagc aatgtacctc    1200
ttccctcagc ttagtctgcc acaaaaggca attgacgctg ctaaagctgc taacaaagca    1260
cctgatgctt tctatgccct tcgtctcctc gaggcaaccg gaattgttgt tgtccctgga    1320
tctggatttg gccaagttcc tggcacatgg cacatcagat gcacaatcct gccacaggag    1380
gagaagatcc ccgcgatcat ctcccgcttc aaggcattcc atgagggctt catggcagcg    1440
taccgcgact ga                                                        1452
```

<210> SEQ ID NO 22
<211> LENGTH: 483
<212> TYPE: PRT
<213> ORGANISM: Oryza sativa japonica

<400> SEQUENCE: 22

```
Met Ala Ala Pro Ser Val Ala Val Asp Asn Leu Asn Pro Lys Val Leu
1               5                   10                  15

Asn Cys Glu Tyr Ala Val Arg Gly Glu Ile Val Ile His Ala Gln Arg
                20                  25                  30

Leu Gln Gln Gln Leu Gln Thr Gln Pro Gly Ser Leu Pro Phe Asp Glu
            35                  40                  45

Ile Leu Tyr Cys Asn Ile Gly Asn Pro Gln Ser Leu Gly Gln Lys Pro
        50                  55                  60

Val Thr Phe Phe Arg Glu Val Ile Ala Leu Cys Asp His Pro Cys Leu
65                  70                  75                  80

Leu Glu Lys Glu Glu Thr Lys Ser Leu Phe Ser Ala Asp Ala Ile Ser
                85                  90                  95

Arg Ala Thr Thr Ile Leu Ala Ser Ile Pro Gly Arg Ala Thr Gly Ala
                100                 105                 110
```

Tyr Ser His Ser Gln Gly Ile Lys Gly Leu Arg Asp Ala Ile Ala Ala
    115                 120                 125

Gly Ile Ala Ser Arg Asp Gly Tyr Pro Ala Asn Ala Asp Asp Ile Phe
130                 135                 140

Leu Thr Asp Gly Ala Ser Pro Gly Val His Met Met Met Gln Leu Leu
145                 150                 155                 160

Ile Arg Asn Glu Lys Asp Gly Ile Leu Cys Pro Ile Pro Gln Tyr Pro
                165                 170                 175

Leu Tyr Ser Ala Ser Ile Ala Leu His Gly Gly Ala Leu Val Pro Tyr
            180                 185                 190

Tyr Leu Asn Glu Ser Thr Gly Trp Gly Leu Glu Ile Ser Asp Leu Lys
        195                 200                 205

Lys Gln Leu Glu Asp Ser Arg Leu Lys Gly Ile Asp Val Arg Ala Leu
    210                 215                 220

Val Val Ile Asn Pro Gly Asn Pro Thr Gly Gln Val Leu Ala Glu Glu
225                 230                 235                 240

Asn Gln Arg Asp Ile Val Lys Phe Cys Lys Asn Glu Gly Leu Val Leu
                245                 250                 255

Leu Ala Asp Glu Val Tyr Gln Glu Asn Ile Tyr Val Asp Asn Lys Lys
            260                 265                 270

Phe Asn Ser Phe Lys Lys Ile Ala Arg Ser Met Gly Tyr Asn Glu Asp
        275                 280                 285

Asp Leu Pro Leu Val Ser Phe Gln Ser Val Ser Lys Gly Tyr Tyr Gly
    290                 295                 300

Glu Cys Gly Lys Arg Gly Gly Tyr Met Glu Ile Thr Gly Phe Ser Ala
305                 310                 315                 320

Pro Val Arg Glu Gln Ile Tyr Lys Val Ala Ser Val Asn Leu Cys Ser
                325                 330                 335

Asn Ile Thr Gly Gln Ile Leu Ala Ser Leu Val Met Asn Pro Pro Lys
            340                 345                 350

Ala Gly Asp Ala Ser Tyr Ala Ser Tyr Lys Ala Glu Lys Asp Gly Ile
        355                 360                 365

Leu Gln Ser Leu Ala Arg Arg Ala Lys Ala Leu Glu Asn Ala Phe Asn
    370                 375                 380

Ser Leu Glu Gly Ile Thr Cys Asn Lys Thr Glu Gly Ala Met Tyr Leu
385                 390                 395                 400

Phe Pro Gln Leu Ser Leu Pro Gln Lys Ala Ile Asp Ala Ala Lys Ala
                405                 410                 415

Ala Asn Lys Ala Pro Asp Ala Phe Tyr Ala Leu Arg Leu Leu Glu Ala
            420                 425                 430

Thr Gly Ile Val Val Pro Gly Ser Gly Phe Gly Gln Val Pro Gly
        435                 440                 445

Thr Trp His Ile Arg Cys Thr Ile Leu Pro Gln Glu Glu Lys Ile Pro
    450                 455                 460

Ala Ile Ile Ser Arg Phe Lys Ala Phe His Glu Gly Phe Met Ala Ala
465                 470                 475                 480

Tyr Arg Asp

<210> SEQ ID NO 23
<211> LENGTH: 1722
<212> TYPE: DNA
<213> ORGANISM: Cyanidioschyzon merolae

<400> SEQUENCE: 23

```
atgcaacacg tgttggcggg tcgggtaggg cgtagaacgt ttgggctgct caatttcagt    60
tatctccgta tagggcgaag gaataggagc cacggtgtaa gcgcagggat gccgcacgaa   120
gccgacggga cgcgccggcg aaaagcgctc gacttgcgaa ccataaacca gcgcgtggta   180
gcggcgcagt acgctgtgcg tggtgaattg cccactcgcg ctgcgcgact gcaacagact   240
ctagaaaaag gaggaccaga agctgccgca ctgccgttta aggaaataat ttactgcaac   300
atcggaaatc cacaggcact tgggaacccg ccattcactt accaccggcg ggtcatggca   360
ctgtgcgact gtccggactt ggcagcggca ctcccggaga aggagcgtga aaaactgttc   420
cccgccgacg tgcgcgaagc gacggaacga atcctacgct ccgctggact cggcggtacg   480
ggagcgtact cggactccca gggagtgccg atcattcgac aagatgtggc agagttcatg   540
aacaagcggg acggcattca cgaggactcc gaatttgcag ctcgagtgaa ggatgtgttt   600
ttgacaaatg gttcatcgag cgcgatcctc atgctcatgg cgctgttgag cggttccgac   660
gcagcgctca gcgcggacgg taccaacggc gtatcgcatg gacgcgaaac acgttccatg   720
cgaccgggtg tgctgattcc agtgccacag tatccgattt actcggcgct ttgcacagtc   780
ctagggatcg aagcgctaca ctaccatctc gttcaggagc agaattggtc tattcaagtc   840
acggagctaa cggaacaggt tcgacaggca cgctcccgtg gcatcgaagc gcgcgccctg   900
gtcgtcatct caccggggaa tcctaccgga caattgcttc atccggcgaa catgcgagaa   960
ctgatggatt ttgcgtatcg agagggactc ctactcctgg ctgatgaggt ctatgcagac  1020
aacgtgtact ggatggtcg gaaattcgag tcgtttcgaa gagtgctgca ttcgagtatg  1080
ccggaggagg tccaggagtc gctggaactc gtgtcgctct actccgccag caaagggctt  1140
gtcggagagt gtggtcgccg cggcggctac atgctgttat caccgggcgt tacaaacgag  1200
gcacgtgaac aactcctgaa actcgctagt atcatgctct gcccaaacct cggcggacag  1260
gtcatgatcg actgtgtggt gcgcccgccg gagccgggcc aaccatcata tgagctctac  1320
cagaaagaga aacttgagcg ttatgaaagt ttgcggcgac gtgcgcatcg cgttgtagag  1380
gcatttaaga gtatgcgcgg tgtgcaatgc aaccctagtg agggcgccat gtacgccttt  1440
ccgagcatca ctgtgggcac gaaagcactc caggcagcgc aaaagtccaa tatgccgctg  1500
gatacgtttt actgtgtcag ccttttggaa cgaactggta tctgtgtggt gccgggcgca  1560
gggttcggca tgcattccaa tgaaccaaca tccagtgtcc cgaacggttc gtgtcggttt  1620
tacctgcgga cgactatttt gcctccggag gaaaagctcg aacccgtcat cgcgctgctt  1680
cgggctcatc acgaggagtt tcttcaaaag tatccccgg ac                      1722
```

<210> SEQ ID NO 24
<211> LENGTH: 574
<212> TYPE: PRT
<213> ORGANISM: Cyanidioschyzon merolae

<400> SEQUENCE: 24

```
Met Gln His Val Leu Ala Gly Arg Val Gly Arg Arg Thr Phe Gly Leu
1               5                   10                  15

Leu Asn Phe Ser Tyr Leu Arg Ile Gly Arg Arg Asn Arg Ser His Gly
            20                  25                  30

Val Ser Ala Gly Met Pro His Glu Ala Asp Gly Thr Arg Arg Arg Lys
        35                  40                  45

Ala Leu Asp Leu Arg Thr Ile Asn Gln Arg Val Val Ala Ala Gln Tyr
    50                  55                  60
```

-continued

```
Ala Val Arg Gly Glu Leu Pro Thr Arg Ala Ala Arg Leu Gln Gln Thr
 65                  70                  75                  80

Leu Glu Lys Gly Gly Pro Glu Ala Ala Leu Pro Phe Lys Glu Ile
                 85                  90                  95

Ile Tyr Cys Asn Ile Gly Asn Pro Gln Ala Leu Gly Asn Pro Pro Phe
                100                 105                 110

Thr Tyr His Arg Arg Val Met Ala Leu Cys Asp Cys Pro Asp Leu Ala
                115                 120                 125

Ala Ala Leu Pro Glu Lys Glu Arg Glu Lys Leu Phe Pro Ala Asp Val
            130                 135                 140

Arg Glu Ala Thr Glu Arg Ile Leu Arg Ser Ala Gly Leu Gly Gly Thr
145                 150                 155                 160

Gly Ala Tyr Ser Asp Ser Gln Gly Val Pro Ile Ile Arg Gln Asp Val
                165                 170                 175

Ala Glu Phe Met Asn Lys Arg Asp Gly Ile His Glu Asp Ser Glu Phe
                180                 185                 190

Ala Ala Arg Val Lys Asp Val Phe Leu Thr Asn Gly Ser Ser Ala
            195                 200                 205

Ile Leu Met Leu Met Ala Leu Leu Ser Gly Ser Asp Ala Ala Leu Ser
210                 215                 220

Ala Asp Gly Thr Asn Gly Val Ser His Gly Arg Glu Thr Arg Ser Met
225                 230                 235                 240

Arg Pro Gly Val Leu Ile Pro Val Pro Gln Tyr Pro Ile Tyr Ser Ala
                245                 250                 255

Leu Cys Thr Val Leu Gly Ile Glu Ala Leu His Tyr His Leu Val Gln
                260                 265                 270

Glu Gln Asn Trp Ser Ile Gln Val Thr Glu Leu Thr Glu Gln Val Arg
                275                 280                 285

Gln Ala Arg Ser Arg Gly Ile Glu Ala Arg Ala Leu Val Val Ile Ser
            290                 295                 300

Pro Gly Asn Pro Thr Gly Gln Leu Leu His Pro Ala Asn Met Arg Glu
305                 310                 315                 320

Leu Met Asp Phe Ala Tyr Arg Glu Gly Leu Leu Leu Leu Ala Asp Glu
                325                 330                 335

Val Tyr Ala Asp Asn Val Tyr Leu Asp Gly Arg Lys Phe Glu Ser Phe
                340                 345                 350

Arg Arg Val Leu His Ser Ser Met Pro Glu Glu Val Gln Glu Ser Leu
                355                 360                 365

Glu Leu Val Ser Leu Tyr Ser Ala Ser Lys Gly Leu Val Gly Glu Cys
            370                 375                 380

Gly Arg Arg Gly Gly Tyr Met Leu Leu Ser Pro Gly Val Thr Asn Glu
385                 390                 395                 400

Ala Arg Glu Gln Leu Leu Lys Leu Ala Ser Ile Met Leu Cys Pro Asn
                405                 410                 415

Leu Gly Gly Gln Val Met Ile Asp Cys Val Val Arg Pro Pro Glu Pro
                420                 425                 430

Gly Gln Pro Ser Tyr Glu Leu Tyr Gln Lys Glu Lys Leu Glu Arg Tyr
            435                 440                 445

Glu Ser Leu Arg Arg Arg Ala His Arg Val Val Glu Ala Phe Lys Ser
            450                 455                 460

Met Arg Gly Val Gln Cys Asn Pro Ser Glu Gly Ala Met Tyr Ala Phe
465                 470                 475                 480

Pro Ser Ile Thr Val Gly Thr Lys Ala Leu Gln Ala Ala Gln Lys Ser
```

```
                    485                 490                 495
Asn Met Pro Leu Asp Thr Phe Tyr Cys Val Ser Leu Leu Glu Arg Thr
            500                 505                 510

Gly Ile Cys Val Val Pro Gly Ala Gly Phe Gly Met His Ser Asn Glu
            515                 520                 525

Pro Thr Ser Ser Val Pro Asn Gly Ser Cys Arg Phe Tyr Leu Arg Thr
            530                 535                 540

Thr Ile Leu Pro Pro Glu Glu Lys Leu Glu Pro Val Ile Ala Leu Leu
545                 550                 555                 560

Arg Ala His His Glu Glu Phe Leu Gln Lys Tyr Pro Pro Asp
            565                 570

<210> SEQ ID NO 25
<211> LENGTH: 1779
<212> TYPE: DNA
<213> ORGANISM: Saccharomyces cerevisiae

<400> SEQUENCE: 25
atgttatcac tgtctgccaa aaatcacttc acagtgagta attctataac tcacgttatt      60
aagtcatatc atataaggac tctcacttca agcgcagaaa aatgccaca tatcactact      120 ccttttccta cctcagccag tagtacaaag ttaaaagctt tcaggaaagt tagacccgtc      180
ctacagagac atagctcttc ctggattgtt gctcaaaatc atagacgttc attatctggt      240
caatcttcgc taaacgacct gcgtcatttg aatcgctttc cacaccacac gttgaaaact      300
tcgaataacg agttttatcc cgccgaacaa ttgactttgg aagacgtaaa tgaaaatgtc      360
ttgaaggcta agtacgccgt tagaggtgcc atcccaatga gagctgaaga attgaaagct      420
caactggaga aggatcctca atctctgcca tttgacagga ttatcaacgc caatattggt      480
aatcctcagc aactacaaca gaaacctctg acttactaca gacaggtctt gtctctctta      540
caatacccag aactattaaa ccaaaacgaa cagcagctag ttgattcgaa attgtttaaa      600
ctagatgcca ttaaacgtgc aaagagttta atggaagata tcggtggttc tgttggtgct      660
tactcttctt ctcaaggtgt agaaggtata aggaaaagtg tcgctgaatt tataacgaag      720
agggacgaag gcgagatatc atacccagag gatatttttcc taactgctgg tgcatccgca      780
gctgtcaatt acttgttatc aatttttctgt agagggccag aaacgggtgt cttgattcca      840
attcctcaat atccattata taccgctact ctagctttga caattctca agctttacca      900 tactatttag atgagaattc aggttggtca actaatccag aagaaattga aactgtcgtc      960
aaagaggcta tacagaacga aatcaaacct acagttctag tggttatcaa tccaggtaat     1020
cctacaggag ctgtcctatc acctgagtct atagctcaga ttttttgaagt cgcagccaag     1080 tacggtacag tagtgatagc tgacgaagtt tatcaagaaa atatcttccc gggcaccaag     1140
ttccattcta tgaagaaaat tttgagacat ttacagaggg aacatccagg taaattcgat     1200
aatgttcagc tagcttcttt gcattcgact tctaagggtg tttctggtga atgtggtcaa     1260
aggggtggct acatggaact cactggattc agccatgaga tgagacaagt tatccttgaaa     1320 ctagcctcga tttcattgtg tcccgttgtc acaggtcaag ctttggttga tttgatggtt     1380
cgtccaccag tggaagggga ggaatcattc gagtcggacc aagcagaacg taactccatc     1440
catgaaaagt taattacaag agcaatgaca ctgtatgaga catttaactc tttagaaggc     1500
attgaatgtc aaaagcctca aggtgccatg tatttattcc ctaagataga cttacctttc     1560
aaggcagttc aagaagctcg ccacttagag ttaactccgg atgaatttta ttgtaagaag     1620
```

```
ttgttagaat ctactggcat ttgcactgtt cccggttctg ggtttggtca agaacctggt   1680
acttaccatt taagaacaac attttttggca cctggtctgg aatggattaa gaaatgggaa   1740
agtttccata aagaattttt tgaccaatac cgtgactga                            1779
```

<210> SEQ ID NO 26  
<211> LENGTH: 592  
<212> TYPE: PRT  
<213> ORGANISM: Saccharomyces cerevisiae

<400> SEQUENCE: 26

```
Met Leu Ser Leu Ser Ala Lys Asn His Phe Thr Val Ser Asn Ser Ile
1               5                   10                  15

Thr His Val Ile Lys Ser Tyr His Ile Arg Thr Leu Thr Ser Ser Ala
            20                  25                  30

Glu Lys Met Pro His Ile Thr Thr Pro Phe Ser Thr Ser Ala Ser Ser
        35                  40                  45

Thr Lys Leu Lys Ala Phe Arg Lys Val Arg Pro Val Leu Gln Arg His
    50                  55                  60

Ser Ser Ser Trp Ile Val Ala Gln Asn His Arg Ser Leu Ser Gly
65                  70                  75                  80

Gln Ser Ser Leu Asn Asp Leu Arg His Leu Asn Arg Phe Pro His His
                85                  90                  95

Thr Leu Lys Thr Ser Asn Asn Glu Phe Tyr Pro Ala Glu Gln Leu Thr
            100                 105                 110

Leu Glu Asp Val Asn Glu Asn Val Leu Lys Ala Lys Tyr Ala Val Arg
        115                 120                 125

Gly Ala Ile Pro Met Arg Ala Glu Glu Leu Lys Ala Gln Leu Glu Lys
    130                 135                 140

Asp Pro Gln Ser Leu Pro Phe Asp Arg Ile Ile Asn Ala Asn Ile Gly
145                 150                 155                 160

Asn Pro Gln Gln Leu Gln Gln Lys Pro Leu Thr Tyr Tyr Arg Gln Val
                165                 170                 175

Leu Ser Leu Leu Gln Tyr Pro Glu Leu Leu Asn Gln Asn Glu Gln Gln
            180                 185                 190

Leu Val Asp Ser Lys Leu Phe Lys Leu Asp Ala Ile Lys Arg Ala Lys
        195                 200                 205

Ser Leu Met Glu Asp Ile Gly Gly Ser Val Gly Ala Tyr Ser Ser Ser
    210                 215                 220

Gln Gly Val Glu Gly Ile Arg Lys Ser Val Ala Glu Phe Ile Thr Lys
225                 230                 235                 240

Arg Asp Glu Gly Glu Ile Ser Tyr Pro Glu Asp Ile Phe Leu Thr Ala
                245                 250                 255

Gly Ala Ser Ala Ala Val Asn Tyr Leu Leu Ser Ile Phe Cys Arg Gly
            260                 265                 270

Pro Glu Thr Gly Val Leu Ile Pro Ile Pro Gln Tyr Pro Leu Tyr Thr
        275                 280                 285

Ala Thr Leu Ala Leu Asn Asn Ser Gln Ala Leu Pro Tyr Tyr Leu Asp
    290                 295                 300

Glu Asn Ser Gly Trp Ser Thr Asn Pro Glu Glu Ile Glu Thr Val Val
305                 310                 315                 320

Lys Glu Ala Ile Gln Asn Glu Ile Lys Pro Thr Val Leu Val Val Ile
                325                 330                 335

Asn Pro Gly Asn Pro Thr Gly Ala Val Leu Ser Pro Glu Ser Ile Ala
            340                 345                 350
```

```
Gln Ile Phe Glu Val Ala Ala Lys Tyr Gly Thr Val Ile Ala Asp
        355                 360                 365
Glu Val Tyr Gln Glu Asn Ile Phe Pro Gly Thr Lys Phe His Ser Met
370                 375                 380
Lys Lys Ile Leu Arg His Leu Gln Arg Glu His Pro Gly Lys Phe Asp
385                 390                 395                 400
Asn Val Gln Leu Ala Ser Leu His Ser Thr Ser Lys Gly Val Ser Gly
                405                 410                 415
Glu Cys Gly Gln Arg Gly Gly Tyr Met Glu Leu Thr Gly Phe Ser His
                420                 425                 430
Glu Met Arg Gln Val Ile Leu Lys Leu Ala Ser Ile Ser Leu Cys Pro
            435                 440                 445
Val Val Thr Gly Gln Ala Leu Val Asp Leu Met Val Arg Pro Pro Val
        450                 455                 460
Glu Gly Glu Glu Ser Phe Glu Ser Asp Gln Ala Glu Arg Asn Ser Ile
465                 470                 475                 480
His Glu Lys Leu Ile Thr Arg Ala Met Thr Leu Tyr Glu Thr Phe Asn
                485                 490                 495
Ser Leu Glu Gly Ile Glu Cys Gln Lys Pro Gln Gly Ala Met Tyr Leu
                500                 505                 510
Phe Pro Lys Ile Asp Leu Pro Phe Lys Ala Val Gln Glu Ala Arg His
            515                 520                 525
Leu Glu Leu Thr Pro Asp Glu Phe Tyr Cys Lys Lys Leu Leu Glu Ser
        530                 535                 540
Thr Gly Ile Cys Thr Val Pro Gly Ser Gly Phe Gly Gln Glu Pro Gly
545                 550                 555                 560
Thr Tyr His Leu Arg Thr Thr Phe Leu Ala Pro Gly Leu Glu Trp Ile
                565                 570                 575
Lys Lys Trp Glu Ser Phe His Lys Glu Phe Phe Asp Gln Tyr Arg Asp
                580                 585                 590

<210> SEQ ID NO 27
<211> LENGTH: 1524
<212> TYPE: DNA
<213> ORGANISM: Saccharomyces cerevisiae

<400> SEQUENCE: 27
atgacaatga cacaccaaca ggatttgaaa ggtgtgttca ccgcaaagga tttggatttt      60
aagcccgctg gcaagattac taaaaaagat ttgaatacag gtgtcactaa ggcagaatat     120
gctgtaagag gagctattcc aaccagagct gacgagctaa agaggaatt gaaaaaaaac     180 ccagaagttt tgcctttcga tgatattatc aatgcgaaca ttggtaatcc gcagcaactg     240
gatcagaagc cttttgaccct taccaggcaa gtactggcca tcctggagta cccggaaatt     300
ttacgagtag ccataatga actggcttct tgaacttgt tttccaggga cgccttggaa     360
agagctgagc gcctcttgaa tgatattggc ggttctatag gggcatattc gcattctcaa     420
ggtgtgccag gaataaggca acagttgct gacttcatta ctagaagaga cggcggtgag     480
cccgctacac cggaagatat ttatttaacc actggcgctt cgtccgcggc aacttctttg     540
ttatctttat tgtgtaaaga ttctcaaaca ggcctgctga ttccaattcc gcagtatccg     600
ctttatactg catccgcatc tcttttcaat gcacaagtgc tgccatacta cttagatgag     660
gagtcaaatt ggtctacaaa cagcgacgaa attgaaaaag tagtgcaaga tgctttgaaa     720
aaacagatca gaccatctgt gctgatagtt attaatccag gtaacccaac cggtgcagtt     780
```

```
ctttctgaag aaaccattgc caggatctgt ttgatcgctg cgaaatacgg cattacaatc    840
atttctgatg aggtctatca agaaaacatt ttcaacgatg ttaaatttca ttcgatgaag    900
aaagtcctaa gaaaattgca gcatctttat ccaggaaaat tcgataacgt tcagctcgcc    960
tctttacact ccatttctaa aggattcatg gatgagtgcg gccaaagagg cggttacatg   1020
gaaattattg ggttttctca agaaataaga gatgctcttt tcaaactcat gtctatatcc   1080
atatgttctg ttgtcacagg acaagctgtg gttgatttaa tggtcaaacc accccagcct   1140
ggagacgagt cctatgaaca agatcatgac gaaaggctga aaattttca tgaaatgcgt    1200 acgagagcaa acttattgta cgagacgttt aaggaactag agggtatcga atgccaaaaa   1260
cctcagggtg caatgtatct tttccctagg cttgttttac ctaagaaagc tctttgtgaa   1320
agcgaacgcc ttggcatcga acctgatgag ttctattgca catctttgct agaatctaca   1380
ggtatttgta ctgtcccagg gtctgggttc ggacaaagac ccgggactta tcatgtgcga   1440
acaacgtttt tggctccagg gactaaatgg attcaagact ggaaagaatt tcatcaagat   1500
ttcttcagca agtatcgtaa ttga                                           1524
```

<210> SEQ ID NO 28
<211> LENGTH: 507
<212> TYPE: PRT
<213> ORGANISM: Saccharomyces cerevisiae

<400> SEQUENCE: 28

```
Met Thr Met Thr His Gln Gln Asp Leu Lys Gly Val Phe Thr Ala Lys
1               5                   10                  15

Asp Leu Asp Phe Lys Pro Ala Gly Lys Ile Thr Lys Lys Asp Leu Asn
            20                  25                  30

Thr Gly Val Thr Lys Ala Glu Tyr Ala Val Arg Gly Ala Ile Pro Thr
        35                  40                  45

Arg Ala Asp Glu Leu Lys Glu Leu Lys Lys Asn Pro Glu Val Leu
    50                  55                  60

Pro Phe Asp Asp Ile Ile Asn Ala Asn Ile Gly Asn Pro Gln Gln Leu
65                  70                  75                  80

Asp Gln Lys Pro Leu Thr Phe Thr Arg Gln Val Leu Ala Ile Leu Glu
                85                  90                  95

Tyr Pro Glu Ile Leu Arg Val Gly His Asn Glu Leu Ala Ser Leu Asn
            100                 105                 110

Leu Phe Ser Arg Asp Ala Leu Glu Arg Ala Glu Arg Leu Leu Asn Asp
        115                 120                 125

Ile Gly Gly Ser Ile Gly Ala Tyr Ser His Ser Gln Gly Val Pro Gly
    130                 135                 140

Ile Arg Gln Thr Val Ala Asp Phe Ile Thr Arg Arg Asp Gly Gly Glu
145                 150                 155                 160

Pro Ala Thr Pro Glu Asp Ile Tyr Leu Thr Thr Gly Ala Ser Ser Ala
                165                 170                 175

Ala Thr Ser Leu Leu Ser Leu Leu Cys Lys Asp Ser Gln Thr Gly Leu
            180                 185                 190

Leu Ile Pro Ile Pro Gln Tyr Pro Leu Tyr Thr Ala Ser Ala Ser Leu
        195                 200                 205

Phe Asn Ala Gln Val Leu Pro Tyr Tyr Leu Asp Glu Glu Ser Asn Trp
    210                 215                 220

Ser Thr Asn Ser Asp Glu Ile Glu Lys Val Val Gln Asp Ala Leu Lys
225                 230                 235                 240
```

Lys Gln Ile Arg Pro Ser Val Leu Ile Val Ile Asn Pro Gly Asn Pro
            245                 250                 255

Thr Gly Ala Val Leu Ser Glu Glu Thr Ile Ala Arg Ile Cys Leu Ile
            260                 265                 270

Ala Ala Lys Tyr Gly Ile Thr Ile Ile Ser Asp Glu Val Tyr Gln Glu
            275                 280                 285

Asn Ile Phe Asn Asp Val Lys Phe His Ser Met Lys Lys Val Leu Arg
            290                 295                 300

Lys Leu Gln His Leu Tyr Pro Gly Lys Phe Asp Asn Val Gln Leu Ala
305                 310                 315                 320

Ser Leu His Ser Ile Ser Lys Gly Phe Met Asp Glu Cys Gly Gln Arg
                325                 330                 335

Gly Gly Tyr Met Glu Ile Ile Gly Phe Ser Gln Glu Ile Arg Asp Ala
                340                 345                 350

Leu Phe Lys Leu Met Ser Ile Ser Ile Cys Ser Val Val Thr Gly Gln
                355                 360                 365

Ala Val Val Asp Leu Met Val Lys Pro Pro Gln Pro Gly Asp Glu Ser
            370                 375                 380

Tyr Glu Gln Asp His Asp Glu Arg Leu Lys Ile Phe His Glu Met Arg
385                 390                 395                 400

Thr Arg Ala Asn Leu Leu Tyr Glu Thr Phe Lys Glu Leu Glu Gly Ile
                405                 410                 415

Glu Cys Gln Lys Pro Gln Gly Ala Met Tyr Leu Phe Pro Arg Leu Val
                420                 425                 430

Leu Pro Lys Lys Ala Leu Cys Glu Ser Glu Arg Leu Gly Ile Glu Pro
            435                 440                 445

Asp Glu Phe Tyr Cys Thr Ser Leu Leu Glu Ser Thr Gly Ile Cys Thr
            450                 455                 460

Val Pro Gly Ser Gly Phe Gly Gln Arg Pro Gly Thr Tyr His Val Arg
465                 470                 475                 480

Thr Thr Phe Leu Ala Pro Gly Thr Lys Trp Ile Gln Asp Trp Lys Glu
                485                 490                 495

Phe His Gln Asp Phe Phe Ser Lys Tyr Arg Asn
            500                 505

<210> SEQ ID NO 29
<211> LENGTH: 1566
<212> TYPE: DNA
<213> ORGANISM: Ashbya gossypii

<400> SEQUENCE: 29
atggcaatag ggatgctgag aagaaatagc agcggcaccg ccgtgagcgt tctacagggg     60
cgtgtgcttc gcactcgtag attgagctca gtaaaggacg ggtcgcggtt tgtgcctgcg    120
gaaccgatga cactagcgga cgtgaacgaa aacgtggtca aggcgaagta cgcggtgcgg    180
gggaagattc aacgcgtgc agaggagctg agcggcggc tggaggagca cccgggctcg     240
ctgccgttca gcaaaatcat ccaagcgaac atcggcaatc gcagcagct gggccagaag     300 ccgctgacat tctaccggca agtgatctcg ctgatgcaga atccacagtt gctggagatg    360
cccgcagaat ggctgcagca ggcgttcaag gcggatgtgg tggtgcgtgc gcggaggatg    420
ctgcaggacg ccggaggctc cgtgggagcg tactcggcgt cgcagggtgt gaaaggctac    480
cggcgcacgg ttgcgcagtt tattgagcgg cgcgatggga tcccagcgaa tccagacaac    540
gtgtacctga ccgcgggtgc gtcctctgct gtgtcttgtc tgctgtcgac attctgcaag    600

-continued

```
ggaccggaga caggcgtgtt gatcccaatc cctcagtacc cgctgtacac tgctacgatc    660
acacagaata acgcggttgc gctgccgtac tacctaaatg aggctgatgg gtggtctacg    720
aatccagatg agatggaacg tgtcatcctc gattctaaga agaggaacat cgcgcccaaa    780
tgtctggttg tgattaaccc tgggaatccc actggttccg tactgtctgt aaaggatatg    840
gaggctattc taacacttgc tgcgaagtat gggattgtcg ttattgcgga cgaggtatac    900
caggataatg tgtttggcga tgccaagttc cactctatgc gtaaggtgct gaaaaacctt    960
caactcagag agccaacgct ctacaagaat gtccagttag cctctcttca ctcgatctcg   1020
aaggggctct ccggcgaatg tggccagcgt ggtggctaca tggaattgat cggtttccgt   1080
gaggagctca ggaaggtttt cgttaagttg gcttctatat ctctttgtcc agtggttacc   1140
ggacaagctc tagtcgacct tatggttggg cctcccagcc aagggatcc atcctatgag   1200 caatatcccc aggaaacaag gagtatctat cacgaattgg aggaacggtc gcaactgctg   1260
tggaaaacgt tctgttcctt ggagggtata gaatgcaata tgccacaagg tgctctatat   1320
ctattcccta agttgcatct tccacagaaa gctattgaag cggcgcaaaa gctgggtata   1380
ccagcggatg agctctactg tagcgaatta cttgatgaaa caggcatctg cactgtccct   1440
ggaactggtt tcggccaaat cccgggcaca tatcacgtta gaactacgtt tttgccacct   1500
ggtactaagt ggatcgaaag ttggaaggac ttccacaaga aattttatga caagtatagg   1560
gactaa                                                              1566
```

<210> SEQ ID NO 30
<211> LENGTH: 521
<212> TYPE: PRT
<213> ORGANISM: Ashbya gossypii

<400> SEQUENCE: 30

```
Met Ala Ile Gly Met Leu Arg Arg Asn Ser Ser Gly Thr Ala Val Ser
1               5                   10                  15

Val Leu Gln Gly Arg Val Leu Arg Thr Arg Arg Leu Ser Ser Val Lys
            20                  25                  30

Asp Gly Ser Arg Phe Val Pro Ala Glu Pro Met Thr Leu Ala Asp Val
        35                  40                  45

Asn Glu Asn Val Val Lys Ala Lys Tyr Ala Val Arg Gly Lys Ile Pro
    50                  55                  60

Thr Arg Ala Glu Glu Leu Glu Arg Arg Leu Glu Glu His Pro Gly Ser
65                  70                  75                  80

Leu Pro Phe Ser Lys Ile Ile Gln Ala Asn Ile Gly Asn Pro Gln Gln
                85                  90                  95

Leu Gly Gln Lys Pro Leu Thr Phe Tyr Arg Gln Val Ile Ser Leu Met
            100                 105                 110

Gln Asn Pro Gln Leu Leu Glu Met Pro Ala Glu Trp Leu Gln Gln Ala
        115                 120                 125

Phe Lys Ala Asp Val Val Arg Ala Arg Arg Met Leu Gln Asp Ala
    130                 135                 140

Gly Gly Ser Val Gly Ala Tyr Ser Ala Ser Gln Gly Val Lys Gly Tyr
145                 150                 155                 160

Arg Arg Thr Val Ala Gln Phe Ile Glu Arg Arg Asp Gly Ile Pro Ala
                165                 170                 175

Asn Pro Asp Asn Val Tyr Leu Thr Ala Gly Ala Ser Ser Ala Val Ser
            180                 185                 190
```

| | | | | | | | | | | | |
|---|---|---|---|---|---|---|---|---|---|---|---|
|Cys|Leu|Leu|Ser|Thr|Phe|Cys|Lys|Gly|Pro|Glu|Thr|Gly|Val|Leu|Ile|
| |195| | | |200| | | |205| | |

Pro Ile Pro Gln Tyr Pro Leu Tyr Thr Ala Thr Ile Thr Gln Asn Asn
210 215 220

Ala Val Ala Leu Pro Tyr Tyr Leu Asn Glu Ala Asp Gly Trp Ser Thr
225 230 235 240

Asn Pro Asp Glu Met Glu Arg Val Ile Leu Asp Ser Lys Lys Arg Asn
245 250 255

Ile Ala Pro Lys Cys Leu Val Val Ile Asn Pro Gly Asn Pro Thr Gly
260 265 270

Ser Val Leu Ser Val Lys Asp Met Glu Ala Ile Leu Thr Leu Ala Ala
275 280 285

Lys Tyr Gly Ile Val Val Ile Ala Asp Glu Val Tyr Gln Asp Asn Val
290 295 300

Phe Gly Asp Ala Lys Phe His Ser Met Arg Lys Val Leu Lys Asn Leu
305 310 315 320

Gln Leu Arg Glu Pro Thr Leu Tyr Lys Asn Val Gln Leu Ala Ser Leu
325 330 335

His Ser Ile Ser Lys Gly Leu Ser Gly Glu Cys Gly Gln Arg Gly Gly
340 345 350

Tyr Met Glu Leu Ile Gly Phe Arg Glu Glu Leu Arg Lys Val Phe Val
355 360 365

Lys Leu Ala Ser Ile Ser Leu Cys Pro Val Val Thr Gly Gln Ala Leu
370 375 380

Val Asp Leu Met Val Gly Pro Pro Ser Gln Gly Asp Pro Ser Tyr Glu
385 390 395 400

Gln Tyr Thr Gln Glu Thr Arg Ser Ile Tyr His Glu Leu Glu Glu Arg
405 410 415

Ser Gln Leu Leu Trp Lys Thr Phe Cys Ser Leu Glu Gly Ile Glu Cys
420 425 430

Asn Met Pro Gln Gly Ala Leu Tyr Leu Phe Pro Lys Leu His Leu Pro
435 440 445

Gln Lys Ala Ile Glu Ala Ala Gln Lys Leu Gly Ile Pro Ala Asp Glu
450 455 460

Leu Tyr Cys Ser Glu Leu Leu Asp Glu Thr Gly Ile Cys Thr Val Pro
465 470 475 480

Gly Thr Gly Phe Gly Gln Ile Pro Gly Thr Tyr His Val Arg Thr Thr
485 490 495

Phe Leu Pro Pro Gly Thr Lys Trp Ile Glu Ser Trp Lys Asp Phe His
500 505 510

Lys Lys Phe Tyr Asp Lys Tyr Arg Asp
515 520

<210> SEQ ID NO 31
<211> LENGTH: 1563
<212> TYPE: DNA
<213> ORGANISM: Candida albicans

<400> SEQUENCE: 31

```
atgcttagag taaattcacg attattaact actcgaaaat ctcaatttat gttcacttct      60
aattccttaa ggttttttagc aacctttaaa cctgcggatc cattgactac tcatgatatc    120
aacccacaaa cggtcgaggc aaaatacgct gtacgtggga aaatcccaat tattgccgat    180
gaattgaatg aattgattca aaagcaacca cagctgcatg gattaccatt tagcaaaatc    240
```

| | | |
|---|---|---|
| attaatgcca acattggtaa cccacagcaa ttggaacaac gtccattgac atggtatcgt | 300 | |
| caagtattgt ctcttttaca atacccggat ttattgaaaa atggagaccc tgaaaccgtt | 360 | |
| aaatcacttt atcctgaaga tgtgattgag cgagcacaat caattttgaa acacattgga | 420 | |
| tcaatagggg catactctca ttctcagggt gccagttatt ccgacaatc tattgctgaa | 480 | |
| tttataacta accgtgatgg tggttatgta tcccacgcca acaacatttt tttaacttcc | 540 | |
| ggggcatcaa ctgcagtgtc gtatttatta caaattttgt ctgtcaatga aaactccggg | 600 | |
| ttcttaattc cgatcccaca gtatcctttg tatactgcca ctattgcctt gaataatgcc | 660 | |
| aagccaattg ttattatct cgatgagtcg aaccattggt caaccaatcc tcaagagatt | 720 | |
| agagaattga tcgaaaccaa tcaactgcaa ggtattaaca tcaaggcatt ggtggtgatt | 780 | |
| aacccgggga acccaacggg ggcaatttta tcatcacaag atataattga attgatagat | 840 | |
| attgctgctg aatatggaat tgtattaatt gccgatgagg tttatcaaga aaatatttc | 900 | |
| aaagggaaat ttgtttcatt caagaagatt ttgtcggaat taattgagca agaccctcaa | 960 | |
| acttataaac atgttcaatt agcatcatta cactcgacat cgaaaggtgt tagtggagaa | 1020 | |
| tgtggacaac gtggtggata tatggaatta gttgggttca aaccggaagt taaagatgtg | 1080 | |
| gttttcaaat tggcatcgat taatttatgt tctgttgtct ctggtcaagc attaatggag | 1140 | |
| ttaatgatta atcctcctca agaaggtgat cctagttacc ccttgtacaa aagcgaaacc | 1200 | |
| gaatcaatcc ataacgattt ggaatcaaga gcagaatcac tctatcaagc ttttttacaa | 1260 | |
| atggaagata tcaaatgtaa taaaccaatg ggggccatgt atattttccc cactttagat | 1320 | |
| tttgatccag cccgatacca taagttatat tcgagagcta agaattccaa tttacaaatt | 1380 | |
| gatgatattt attgtatcga gttattagaa ggtacaggta tttgttgtgt tcctggtaat | 1440 | |
| ggatttggtc agaaaccaga tacttatcat ttaagaacaa catttttacc accaggtaaa | 1500 | |
| gaatggattg ataaatggat aaatttccat aaatcattta ttaaaaaata taagatgaa | 1560 | |
| tag | 1563 | |

<210> SEQ ID NO 32
<211> LENGTH: 520
<212> TYPE: PRT
<213> ORGANISM: Candida albicans

<400> SEQUENCE: 32

Met Leu Arg Val Asn Ser Arg Leu Leu Thr Thr Arg Lys Ser Gln Phe
1               5                   10                  15

Met Phe Thr Ser Asn Ser Leu Arg Phe Leu Ala Thr Phe Lys Pro Ala
            20                  25                  30

Asp Pro Leu Thr Thr His Asp Ile Asn Pro Gln Thr Val Glu Ala Lys
        35                  40                  45

Tyr Ala Val Arg Gly Lys Ile Pro Ile Ala Asp Glu Leu Asn Glu
    50                  55                  60

Leu Ile Gln Lys Gln Pro Gln Ser His Gly Leu Pro Phe Ser Lys Ile
65                  70                  75                  80

Ile Asn Ala Asn Ile Gly Asn Pro Gln Gln Leu Glu Gln Arg Pro Leu
                85                  90                  95

Thr Trp Tyr Arg Gln Val Leu Ser Leu Gln Tyr Pro Asp Leu Leu
            100                 105                 110

Lys Asn Gly Asp Pro Glu Thr Val Lys Ser Leu Tyr Pro Glu Asp Val
        115                 120                 125

Ile Glu Arg Ala Gln Ser Ile Leu Lys His Ile Gly Ser Ile Gly Ala

```
            130                 135                 140
Tyr Ser His Ser Gln Gly Ala Ser Tyr Phe Arg Gln Ser Ile Ala Glu
145                 150                 155                 160

Phe Ile Thr Asn Arg Asp Gly Tyr Val Ser His Ala Asn Asn Ile
                165                 170                 175

Phe Leu Thr Ser Gly Ala Ser Thr Ala Val Ser Tyr Leu Leu Gln Ile
                180                 185                 190

Leu Ser Val Asn Glu Asn Ser Gly Phe Leu Ile Pro Ile Pro Gln Tyr
            195                 200                 205

Pro Leu Tyr Thr Ala Thr Ile Ala Leu Asn Asn Ala Lys Pro Ile Gly
            210                 215                 220

Tyr Tyr Leu Asp Glu Ser Asn His Trp Ser Thr Asn Pro Gln Glu Ile
225                 230                 235                 240

Arg Glu Leu Ile Glu Thr Asn Gln Ser Gln Gly Ile Asn Ile Lys Ala
                245                 250                 255

Leu Val Val Ile Asn Pro Gly Asn Pro Thr Gly Ala Ile Leu Ser Ser
                260                 265                 270

Gln Asp Ile Ile Glu Leu Ile Asp Ile Ala Ala Glu Tyr Gly Ile Val
            275                 280                 285

Leu Ile Ala Asp Glu Val Tyr Gln Glu Asn Ile Phe Lys Gly Lys Phe
            290                 295                 300

Val Ser Phe Lys Lys Ile Leu Ser Glu Leu Ile Glu Gln Asp Pro Gln
305                 310                 315                 320

Thr Tyr Lys His Val Gln Leu Ala Ser Leu His Ser Thr Ser Lys Gly
                325                 330                 335

Val Ser Gly Glu Cys Gly Gln Arg Gly Gly Tyr Met Glu Leu Val Gly
                340                 345                 350

Phe Lys Pro Glu Val Lys Asp Val Val Phe Lys Leu Ala Ser Ile Asn
            355                 360                 365

Leu Cys Ser Val Val Ser Gly Gln Ala Leu Met Glu Leu Met Ile Asn
            370                 375                 380

Pro Pro Gln Glu Gly Asp Pro Ser Tyr Pro Leu Tyr Lys Ser Glu Thr
385                 390                 395                 400

Glu Ser Ile His Asn Asp Leu Glu Ser Arg Ala Glu Ser Leu Tyr Gln
                405                 410                 415

Ala Phe Leu Gln Met Glu Asp Ile Lys Cys Asn Lys Pro Met Gly Ala
            420                 425                 430

Met Tyr Ile Phe Pro Thr Leu Asp Phe Asp Pro Ala Arg Tyr His Lys
            435                 440                 445

Leu Tyr Ser Arg Ala Lys Asn Ser Asn Leu Gln Ile Asp Asp Ile Tyr
            450                 455                 460

Cys Ile Glu Leu Leu Glu Gly Thr Gly Ile Cys Cys Val Pro Gly Asn
465                 470                 475                 480

Gly Phe Gly Gln Lys Pro Asp Thr Tyr His Leu Arg Thr Thr Phe Leu
                485                 490                 495

Pro Pro Gly Lys Glu Trp Ile Asp Lys Trp Ile Asn Phe His Lys Ser
                500                 505                 510

Phe Ile Lys Lys Tyr Lys Asp Glu
            515                 520

<210> SEQ ID NO 33
<211> LENGTH: 1518
<212> TYPE: DNA
<213> ORGANISM: Schizosaccharomyces pombe
```

<400> SEQUENCE: 33

```
atgtttacag attatccaaa tgatattaac tgtgagtctc caagaatgtc ggaccttgat    60
ggattttgtc aaaatgcgtt ctcagacctt aattctttga atcaacaagt atttaaggca   120
aattacgccg tccgtggagc tttagccatt cttgcgacg agatccaaga tgatttactt    180
gaaaatcctt cttcatatcc tttcagtgag atcgtctatg caaacatcgg taatcctcag   240
cagatgggac agtctcctat tacattcgtt cgacaggttt tatctctttg ccagtaccct   300
accttgttag accatgctga ggaaaagtgg tttcaaaatt tgttccctac ggatgtcgta   360
caacgatcca aaatgctctt aaaggaatct ggaagtttgg gtgcctatag tgcttctcaa   420
ggtattccgc ttgtaaggcg acatgttgcg gatttcatta gagcgagaga tggatttgat   480
tgcgagccat ctgacatata tttgactagt ggtgcctcac acgctgcccg gcttataatg   540
actttgataa tcgctaggcc aacagatggt gtaatggttc ccgctcctca atatcctttg   600
tacggtgccc aaattgatct catgagtgga tctatggtat cttacagcct ctccgaggaa   660
aataattggg acattgattt tgaccaattt aaaaaatcat tgatgaagc atctaaaaaa    720
ggtatcaacg ttcgtttatg cgtggttatt aatcccggta atcctactgg agcttgcatt   780
tctgaaaata gcatggaaaa agtttgcgc tttgctaagg caaagggcat agtattgctt    840
gccgacgaag tctatcaaaa caatatttac caaaacaagt tcattctttt taggagaaaa   900
cttggtgaat aagagaaaa ggaacccgac aatcattggg accaagtttc gcttatttcc    960
gtaaattctg ttagcaaagg tcaatttggt gaatgtggtc aaagaggtgg atatttggac  1020
gttgttaata ttccagagcc cgctaaggat caaatcctca actagctac cattgacatt   1080
tgtccaccag ttgctggtca attattagta gacatgctag taaatcctcc taaacctggt  1140
gatcccagtt atgatttgtt catcaaagaa gttgatgaga ttcatgaagc actgcgttta  1200
caatgccgtc agctctacga gggaacaaag cgcatgaaga gagtttcatg tttagaaccc  1260
cacggggcca tgtatttgca tcccagcgtc tcacttcccg aaaagttaat cactacagcc  1320
aaagctcaga aaattcaacc tgacgaattc tatgcgatag aattgcttaa gcgttcaggt  1380
atatgtgttg ttcctggaag tggatttggg caaccagaag gtgattatca tattcgaatc  1440
acgttttttgg ctaaaggaac tgaatacatt gaacgatttg tcaaagctca taatgaaata  1500
atggacctct atgaataa                                                1518
```

<210> SEQ ID NO 34
<211> LENGTH: 505
<212> TYPE: PRT
<213> ORGANISM: Schizosaccharomyces pombe

<400> SEQUENCE: 34

```
Met Phe Thr Asp Tyr Pro Asn Asp Ile Asn Cys Glu Ser Pro Arg Met
1               5                   10                  15

Ser Asp Leu Asp Gly Phe Cys Gln Asn Ala Phe Ser Asp Leu Asn Ser
            20                  25                  30

Leu Asn Gln Gln Val Phe Lys Ala Asn Tyr Ala Val Arg Gly Ala Leu
        35                  40                  45

Ala Ile Leu Ala Asp Glu Ile Gln Asp Leu Leu Glu Asn Pro Ser
    50                  55                  60

Ser Tyr Pro Phe Ser Glu Ile Val Tyr Ala Asn Ile Gly Asn Pro Gln
65                  70                  75                  80

Gln Met Gly Gln Ser Pro Ile Thr Phe Val Arg Gln Val Leu Ser Leu
```

```
                85                  90                  95
Cys Gln Tyr Pro Thr Leu Leu Asp His Ala Glu Glu Lys Trp Phe Gln
            100                 105                 110

Asn Leu Phe Pro Thr Asp Val Val Gln Arg Ser Lys Met Leu Leu Lys
            115                 120                 125

Glu Ser Gly Ser Leu Gly Ala Tyr Ser Ala Ser Gln Gly Ile Pro Leu
            130                 135                 140

Val Arg Arg His Val Ala Asp Phe Ile Arg Ala Arg Asp Gly Phe Asp
145                 150                 155                 160

Cys Glu Pro Ser Asp Ile Tyr Leu Thr Ser Gly Ala Ser His Ala Ala
            165                 170                 175

Arg Leu Ile Met Thr Leu Ile Ile Ala Arg Pro Thr Asp Gly Val Met
            180                 185                 190

Val Pro Ala Pro Gln Tyr Pro Leu Tyr Gly Ala Gln Ile Asp Leu Met
            195                 200                 205

Ser Gly Ser Met Val Ser Tyr Ser Leu Ser Glu Glu Asn Asn Trp Asp
            210                 215                 220

Ile Asp Phe Asp Gln Phe Lys Lys Ser Phe Asp Glu Ala Ser Lys Lys
225                 230                 235                 240

Gly Ile Asn Val Arg Leu Cys Val Val Ile Asn Pro Gly Asn Pro Thr
            245                 250                 255

Gly Ala Cys Ile Ser Glu Asn Ser Met Glu Lys Val Leu Arg Phe Ala
            260                 265                 270

Lys Ala Lys Gly Ile Val Leu Leu Ala Asp Glu Val Tyr Gln Asn Asn
            275                 280                 285

Ile Tyr Gln Asn Lys Phe His Ser Phe Arg Arg Lys Leu Gly Glu Leu
            290                 295                 300

Arg Glu Lys Glu Pro Asp Asn His Trp Asp Gln Val Ser Leu Ile Ser
305                 310                 315                 320

Val Asn Ser Val Ser Lys Gly Gln Phe Gly Glu Cys Gly Gln Arg Gly
            325                 330                 335

Gly Tyr Leu Asp Val Val Asn Ile Pro Glu Pro Ala Lys Asp Gln Ile
            340                 345                 350

Leu Lys Leu Ala Thr Ile Asp Ile Cys Pro Pro Val Ala Gly Gln Leu
            355                 360                 365

Leu Val Asp Met Leu Val Asn Pro Pro Lys Pro Gly Asp Pro Ser Tyr
            370                 375                 380

Asp Leu Phe Ile Lys Glu Val Asp Glu Ile His Glu Ala Leu Arg Leu
385                 390                 395                 400

Gln Cys Arg Gln Leu Tyr Glu Gly Thr Lys Arg Met Lys Arg Val Ser
            405                 410                 415

Cys Leu Glu Pro His Gly Ala Met Tyr Leu His Pro Ser Val Ser Leu
            420                 425                 430

Pro Glu Lys Leu Ile Thr Thr Ala Lys Ala Gln Lys Ile Gln Pro Asp
            435                 440                 445

Glu Phe Tyr Ala Ile Glu Leu Leu Lys Arg Ser Gly Ile Cys Val Val
            450                 455                 460

Pro Gly Ser Gly Phe Gly Gln Pro Glu Gly Asp Tyr His Ile Arg Ile
465                 470                 475                 480

Thr Phe Leu Ala Lys Gly Thr Glu Tyr Ile Glu Arg Phe Val Lys Ala
            485                 490                 495

His Asn Glu Ile Met Asp Leu Tyr Glu
            500                 505
```

<210> SEQ ID NO 35
<211> LENGTH: 1500
<212> TYPE: DNA
<213> ORGANISM: Aspergillus nidulans

<400> SEQUENCE: 35

```
atgacgaccc gaacgacagt tcctaatgcc tcgcaacgcg ctctatccac tgcggctgtt      60
cgttgcctga ccctagacaa catcaattcg aacgtcaagg ctgccaagta tgctgttcgt     120
ggagaactcg ccgttaaggc ggaggaatac cgtgtgaggc tggctcaggg agacaagaca     180
ctgccgtttg acagcgttat tttcgccaac atcggcaatc ctcagcagct cgaccaaaag     240
cccatcactt tcttccgtca agtcctcagt cttatggaaa accctctact gttaagcaac     300
aaagatgccc ttcgtacgtc tttcggctat caggatgatg ttatcgagcg ggccgagaag     360
cttctggccg aagtccagag tgttggtgca tacagtcaca gccaaggtgc tcccctgatt     420
cgcgagagtg tggccaagtt cattgaagaa cgtgatggct ccccgccga ccctcagtcg      480
ctttacctta ctggtggtgc ctcttccggt gtaaacacca ttctgaacgt catttgtaat     540
gggccaaatg ctggtgtcct agttccgatt ccccagtatc ctctgtacac agccactta     600
tccctcttga atgctcagtg tgttccttac cacttagaag agcagaaggc ttggggtacc     660
gacatcggta caatcaagaa gtcattggaa caggccaagg ctgcaggcac tgacgttcgc     720
gccattgttg ttatcaaccc tggcaaccccg acgggcgctt ctttgagtcc agctgatatc     780
aagagcgtcc ttgacatcgc gcggaagag aagctcgtcg taattgcgga cgaggtatac     840
cagacaaatg tgtttatcgg agaattcaca tcgttcaaaa agaggctccg ggagctgcag     900
caagaagtac ctggtaaata cgacaatgtc gagcttgttt cccttcacag tacttccaag     960
ggtatggttg gtgaatgtgg ccatcgcgga ggttacttcg aactggttgg atttgatccc    1020
ttggttgctg cccaggtcta caagttcatc agcatcatgc tctgccctcc tgtcatcggg    1080
caatgtttgg ttgaactgat ggtgaaccct ccaaaggagg gcgagcccag ccatgagttg    1140
tatcagaagg agtacaacgg catccgggaa ggactgcgcc agcgcgcctt tgccctctat    1200
gaagcttttc aacggatgga gggtgtcgag tgccaagagc tcagggtgc catgtacctt     1260
ttccctacta tctcactgcc tcccaaggct attgaagccg ctgccgctga aaccgcgcc     1320
gcagacgaat tctactgcct ccgtctcctt gacgccactg tgtttgcgt cgtccctggc     1380
tccggcttcg gtcagaagga gaacacgctc cacttccgca ctactttcct cgcaccaggc    1440
acggactggg tggagcgtat cgtgaagttc cattccgagt tcatggccaa atacaaatag    1500
```

<210> SEQ ID NO 36
<211> LENGTH: 499
<212> TYPE: PRT
<213> ORGANISM: Aspergillus nidulans

<400> SEQUENCE: 36

```
Met Thr Thr Arg Thr Thr Val Pro Asn Ala Ser Gln Arg Ala Leu Ser
1               5                   10                  15

Thr Ala Ala Val Arg Cys Leu Thr Leu Asp Asn Ile Asn Ser Asn Val
            20                  25                  30

Lys Ala Ala Lys Tyr Ala Val Arg Gly Glu Leu Ala Val Lys Ala Glu
        35                  40                  45

Glu Tyr Arg Val Arg Leu Ala Gln Gly Asp Lys Thr Leu Pro Phe Asp
    50                  55                  60
```

```
Ser Val Ile Phe Ala Asn Ile Gly Asn Pro Gln Gln Leu Asp Gln Lys
 65                  70                  75                  80

Pro Ile Thr Phe Phe Arg Gln Val Leu Ser Leu Met Glu Asn Pro Leu
                 85                  90                  95

Leu Leu Ser Asn Lys Asp Ala Leu Arg Thr Ser Phe Gly Tyr Gln Asp
            100                 105                 110

Asp Val Ile Glu Arg Ala Glu Lys Leu Leu Ala Glu Val Gln Ser Val
        115                 120                 125

Gly Ala Tyr Ser His Ser Gln Gly Ala Pro Leu Ile Arg Glu Ser Val
    130                 135                 140

Ala Lys Phe Ile Glu Glu Arg Asp Gly Phe Pro Ala Asp Pro Gln Ser
145                 150                 155                 160

Leu Tyr Leu Thr Gly Gly Ala Ser Ser Gly Val Asn Thr Ile Leu Asn
                165                 170                 175

Val Ile Cys Asn Gly Pro Asn Ala Gly Val Leu Val Pro Ile Pro Gln
            180                 185                 190

Tyr Pro Leu Tyr Thr Ala Thr Leu Ser Leu Leu Asn Ala Gln Cys Val
        195                 200                 205

Pro Tyr His Leu Glu Glu Gln Lys Ala Trp Gly Thr Asp Ile Gly Thr
    210                 215                 220

Ile Lys Lys Ser Leu Glu Gln Ala Lys Ala Ala Gly Thr Asp Val Arg
225                 230                 235                 240

Ala Ile Val Val Ile Asn Pro Gly Asn Pro Thr Gly Ala Ser Leu Ser
                245                 250                 255

Pro Ala Asp Ile Lys Ser Val Leu Asp Ile Ala Ala Glu Glu Lys Leu
            260                 265                 270

Val Val Ile Ala Asp Glu Val Tyr Gln Thr Asn Val Phe Ile Gly Glu
        275                 280                 285

Phe Thr Ser Phe Lys Lys Arg Leu Arg Glu Leu Gln Gln Glu Val Pro
    290                 295                 300

Gly Lys Tyr Asp Asn Val Glu Leu Val Ser Leu His Ser Thr Ser Lys
305                 310                 315                 320

Gly Met Val Gly Glu Cys Gly His Arg Gly Gly Tyr Phe Glu Leu Val
                325                 330                 335

Gly Phe Asp Pro Leu Val Ala Ala Gln Val Tyr Lys Phe Ile Ser Ile
            340                 345                 350

Met Leu Cys Pro Pro Val Ile Gly Gln Cys Leu Val Glu Leu Met Val
        355                 360                 365

Asn Pro Pro Lys Glu Gly Glu Pro Ser His Glu Leu Tyr Gln Lys Glu
    370                 375                 380

Tyr Asn Gly Ile Arg Glu Gly Leu Arg Gln Arg Ala Phe Ala Leu Tyr
385                 390                 395                 400

Glu Ala Phe Gln Arg Met Glu Gly Val Glu Cys Gln Glu Pro Gln Gly
                405                 410                 415

Ala Met Tyr Leu Phe Pro Thr Ile Ser Leu Pro Pro Lys Ala Ile Glu
            420                 425                 430

Ala Ala Ala Ala Glu Asn Arg Ala Ala Asp Glu Phe Tyr Cys Leu Arg
        435                 440                 445

Leu Leu Asp Ala Thr Gly Val Cys Val Val Pro Gly Ser Gly Phe Gly
    450                 455                 460

Gln Lys Glu Asn Thr Leu His Phe Arg Thr Thr Phe Leu Ala Pro Gly
465                 470                 475                 480

Thr Asp Trp Val Glu Arg Ile Val Lys Phe His Ser Glu Phe Met Ala
```

Lys Tyr Lys

<210> SEQ ID NO 37
<211> LENGTH: 1506
<212> TYPE: DNA
<213> ORGANISM: Aspergillus fumigatus

<400> SEQUENCE: 37

| | | | | | |
|---|---|---|---|---|---|
| atgatcacag | aacccaccat | gaccgtgcca | tataccacca | agcggaccgc | ttctgatctc | 60 |
| ggccctcgtc | gtctccgtgc | cgataatatc | aatcccaacg | tcaaggcggc | caagtatgct | 120 |
| gtccgtggtg | agcttgccgt | caaggcggag | gaataccgtg | tgagattggc | caagggagac | 180 |
| aagtctttgc | cctttgacag | tgtcattttc | gccaatattg | caacccccca | gcagctggat | 240 |
| caaaaaccca | tcaccttctt | ccgtcaagta | ctcagtcttc | tcgagaacac | cgcattgctt | 300 |
| gaaaaaccgg | aggtcctgcg | gtcgtctttc | ggctacaacc | aggacgtcat | tgaccgggct | 360 |
| aagaagcttc | ttgcggacat | tcagagcgtc | ggtgcctaca | gtcacagcca | gggagcacca | 420 |
| gtaattcggg | agagcgtggc | caaattcatc | gaggagcgtg | atggcttccc | cgccaacccg | 480 |
| caagacctgt | acctctgcgc | tggtgcgtcg | tccggtgtta | gcacgctgct | gaatgtcatc | 540 |
| tgcaacggtc | ccaccgccgg | tgtccttgtg | ccgattcccc | aatatcctct | gtacaccgcc | 600 |
| accctgtccc | ttctcaatgc | acagtgcgtc | ccataccatt | tagaggagga | caaggcctgg | 660 |
| ggtaccgacg | tggaggccat | ccggcaatct | ctggtgcgcg | ccaaggccga | gggcactgag | 720 |
| gttcgtgcta | tcgtcgtcat | caaccccggt | aacccgacgg | tgcctcgct | cagccccgag | 780 |
| gacatcaaga | gcgtgcttga | catcgccgcc | gaggagaagc | tggtcgtcat | cgccgacgag | 840 |
| gtgtaccaga | ccaacgtctt | cgtgggcgag | ttcacatcct | tcaagaagag | actgcgccaa | 900 |
| ctccagcagg | aggtgcctgg | caagtacgac | aatgtcgaac | ttgcttctct | gcacagtgtg | 960 |
| tccaagggta | tggtgggcga | atgcggtcac | cgaggcggtt | actttgaact | cgtcggattc | 1020 |
| gaccccttgg | tcgcggccga | gatttacaag | tttgttagca | ttatgctgtg | cccgccggtg | 1080 |
| atcggtcagt | gcctggtcga | acttatggtg | aacccaccca | agaagggcga | gcccagttac | 1140 |
| gagttgtatc | agaaggagta | caacagcatt | agcgatggcc | tacacaagcg | tgccctcgcc | 1200 |
| ctgtacgaag | ccttcaagca | gatggagggc | gttgaatgcc | aggagcctca | gggcgccatg | 1260 |
| tacctcttcc | ccagcatcac | cctgcccccc | aaggccgtcg | aagccgccgc | tgccgaaggt | 1320 |
| cggaacgccg | acgaattcta | ctgtctcgcc | ctcctcgacg | caacgggtgt | tgcgtggtc | 1380 |
| cccggttccg | gctttggaca | gaaggagaac | acgctccact | tccgcacaac | cttccttgcc | 1440 |
| cccggcactg | actgggtcga | gcggatcgtc | aagttccacg | ccgagttcat | ggccaagtat | 1500 |
| aaatag | | | | | | 1506 |

<210> SEQ ID NO 38
<211> LENGTH: 501
<212> TYPE: PRT
<213> ORGANISM: Aspergillus fumigatus

<400> SEQUENCE: 38

Met Ile Thr Glu Pro Thr Met Thr Val Pro Tyr Thr Thr Lys Arg Thr
1               5                   10                  15

Ala Ser Asp Leu Gly Pro Arg Arg Leu Arg Ala Asp Asn Ile Asn Pro
            20                  25                  30

Asn Val Lys Ala Ala Lys Tyr Ala Val Arg Gly Glu Leu Ala Val Lys

```
                35                  40                  45
Ala Glu Glu Tyr Arg Val Arg Leu Ala Lys Gly Asp Lys Ser Leu Pro
 50                  55                  60

Phe Asp Ser Val Ile Phe Ala Asn Ile Gly Asn Pro Gln Gln Leu Asp
65                   70                  75                  80

Gln Lys Pro Ile Thr Phe Phe Arg Gln Val Leu Ser Leu Leu Glu Asn
                 85                  90                  95

Thr Ala Leu Leu Glu Lys Pro Glu Val Leu Arg Ser Ser Phe Gly Tyr
            100                 105                 110

Asn Gln Asp Val Ile Asp Arg Ala Lys Lys Leu Leu Ala Asp Ile Gln
        115                 120                 125

Ser Val Gly Ala Tyr Ser His Ser Gln Gly Ala Pro Val Ile Arg Glu
    130                 135                 140

Ser Val Ala Lys Phe Ile Glu Glu Arg Asp Gly Phe Pro Ala Asn Pro
145                 150                 155                 160

Gln Asp Leu Tyr Leu Cys Ala Gly Ala Ser Ser Gly Val Ser Thr Leu
                165                 170                 175

Leu Asn Val Ile Cys Asn Gly Pro Thr Ala Gly Val Leu Val Pro Ile
            180                 185                 190

Pro Gln Tyr Pro Leu Tyr Thr Ala Thr Leu Ser Leu Leu Asn Ala Gln
        195                 200                 205

Cys Val Pro Tyr His Leu Glu Glu Asp Lys Ala Trp Gly Thr Asp Val
    210                 215                 220

Glu Ala Ile Arg Gln Ser Leu Val Arg Ala Lys Ala Glu Gly Thr Glu
225                 230                 235                 240

Val Arg Ala Ile Val Val Ile Asn Pro Gly Asn Pro Thr Gly Ala Ser
                245                 250                 255

Leu Ser Pro Glu Asp Ile Lys Ser Val Leu Asp Ile Ala Ala Glu Glu
            260                 265                 270

Lys Leu Val Val Ile Ala Asp Glu Val Tyr Gln Thr Asn Val Phe Val
        275                 280                 285

Gly Glu Phe Thr Ser Phe Lys Lys Arg Leu Arg Gln Leu Gln Gln Glu
    290                 295                 300

Val Pro Gly Lys Tyr Asp Asn Val Glu Leu Ala Ser Leu His Ser Val
305                 310                 315                 320

Ser Lys Gly Met Val Gly Glu Cys Gly His Arg Gly Gly Tyr Phe Glu
                325                 330                 335

Leu Val Gly Phe Asp Pro Leu Val Ala Ala Glu Ile Tyr Lys Phe Val
            340                 345                 350

Ser Ile Met Leu Cys Pro Pro Val Ile Gly Gln Cys Leu Val Glu Leu
        355                 360                 365

Met Val Asn Pro Pro Lys Lys Gly Glu Pro Ser Tyr Glu Leu Tyr Gln
    370                 375                 380

Lys Glu Tyr Asn Ser Ile Ser Asp Gly Leu His Lys Arg Ala Leu Ala
385                 390                 395                 400

Leu Tyr Glu Ala Phe Lys Gln Met Glu Gly Val Glu Cys Gln Glu Pro
                405                 410                 415

Gln Gly Ala Met Tyr Leu Phe Pro Ser Ile Thr Leu Pro Pro Lys Ala
            420                 425                 430

Val Glu Ala Ala Ala Ala Glu Gly Arg Asn Ala Asp Glu Phe Tyr Cys
        435                 440                 445

Leu Arg Leu Leu Asp Ala Thr Gly Val Cys Val Val Pro Gly Ser Gly
    450                 455                 460
```

```
Phe Gly Gln Lys Glu Asn Thr Leu His Phe Arg Thr Thr Phe Leu Ala
465                 470                 475                 480

Pro Gly Thr Asp Trp Val Glu Arg Ile Val Lys Phe His Ala Glu Phe
            485                 490                 495

Met Ala Lys Tyr Lys
            500

<210> SEQ ID NO 39
<211> LENGTH: 1497
<212> TYPE: DNA
<213> ORGANISM: Aspergillus oryzae

<400> SEQUENCE: 39
atggcgactc agactacagt gtcctacact actacacgca ccttgtccac cccggctcgt       60
tgcctgaacc ctgataacat caaccccac gtcacggagg ccaagtatgc cgtccgtggt      120
gagcttgctg tcaaggccga ggagtaccgc gtgaaactgg ccaatggaga caaatcgtta     180
cctttcgaca gtgtcatctt tgccaacatc ggcaatcccc aacagctcga ccagaaaccc     240
atcaccttct ccgccaagt actcagtctc ctcgagaacc ctcaactgtt gaacaacacg      300
gaagcacttc gtacatcctt tttttatgaa caagatgtcg ttgaccgggc caagaagctc     360
ctcgcggatg tccagagcgt tggtgcttac agtcacagcc agggagcgcc tgtgatccgc     420
caaagtatcg ccaaattcat tgaggagcgt gatggattcc cggccaaccc tcaggatttg     480
ttctgctgcg ctggtgcctc gtctggcgtc agcaccattc tcaatatcat ctgcaacggc     540
ccccaggccg gtgtcctcgt ccctattccg caataccctc tttacactgc cacccttct     600 ctcctgaatg cgcaatgtgt accctacctc ctcgaagagc aaaaggcttg gggtaccgat     660
gtgactgcca tccgtaactc gttggcgcag gcccggtcta ccggcactga cgttcgttcg     720
attgtggtca tcaaccccgg taaccctact ggtgcctctt tgagcgccga ggatatcaag     780
aatgttcttg accttgctgc ggaggagaag cttgttgtta ttgcggacga ggtttaccag     840
acgaacgttt tcgagggcga gttcatttcg ttcaagaaga ggcttcgtca gctgcaacag     900
gagacaccag gcaagtatga ttatgtggag ttggtctctc ttcacagtgt gtctaaaggt     960
atggtgggcg agtgtggcca ccgtggtggc tactttgagc tggttggatt cgaccctgag    1020
gttcaggccc agatctacaa gcttgtgagc atcggacttt gcccaccagt cattggacag    1080
tgtttgcttg agcttatggt gaacccaccc aaggagggcg aaggcagcta tgagctgtac    1140
cagaaggagt acaatggaat cagcgaggga ctgcacaagc gcgccttttgc cttatacgag    1200 gccttccaac agatggaggg cgttgagtgt cagaaacctc agggtgccat gtatctcttc    1260
cccaccatca ctctcccacc caaggccatt gaggctgcca aggctgagaa ccgtgccgcc    1320
gatgagttct actgcttgcg tctcctcgac gctaccggtg tctgtgttgt ccctggctcc    1380
ggcttcggcc agaaggagaa cactctgcac ttccgcacaa ctttcctggc ccctggcact    1440
gattgggttg aacggatcgt caagttccac tccgaattta tggccaagta caaataa      1497

<210> SEQ ID NO 40
<211> LENGTH: 498
<212> TYPE: PRT
<213> ORGANISM: Aspergillus oryzae

<400> SEQUENCE: 40

Met Ala Thr Gln Thr Thr Val Ser Tyr Thr Thr Thr Arg Thr Leu Ser
1               5                   10                  15
```

```
Thr Pro Ala Arg Cys Leu Asn Pro Asp Asn Ile Asn Pro His Val Thr
            20                  25                  30

Glu Ala Lys Tyr Ala Val Arg Gly Glu Leu Ala Val Lys Ala Glu Glu
            35                  40                  45

Tyr Arg Val Lys Leu Ala Asn Gly Asp Lys Ser Leu Pro Phe Asp Ser
 50                  55                  60

Val Ile Phe Ala Asn Ile Gly Asn Pro Gln Gln Leu Asp Gln Lys Pro
 65                  70                  75                  80

Ile Thr Phe Phe Arg Gln Val Leu Ser Leu Leu Glu Asn Pro Gln Leu
                85                  90                  95

Leu Asn Asn Thr Glu Ala Leu Arg Thr Ser Phe Phe Tyr Glu Gln Asp
                100                 105                 110

Val Val Asp Arg Ala Lys Lys Leu Leu Ala Asp Val Gln Ser Val Gly
                115                 120                 125

Ala Tyr Ser His Ser Gln Gly Ala Pro Val Ile Arg Gln Ser Ile Ala
            130                 135                 140

Lys Phe Ile Glu Glu Arg Asp Gly Phe Pro Ala Asn Pro Gln Asp Leu
145                 150                 155                 160

Phe Cys Cys Ala Gly Ala Ser Ser Gly Val Ser Thr Ile Leu Asn Ile
                165                 170                 175

Ile Cys Asn Gly Pro Gln Ala Gly Val Leu Val Pro Ile Pro Gln Tyr
            180                 185                 190

Pro Leu Tyr Thr Ala Thr Leu Ser Leu Leu Asn Ala Gln Cys Val Pro
            195                 200                 205

Tyr Leu Leu Glu Glu Gln Lys Ala Trp Gly Thr Asp Val Thr Ala Ile
 210                 215                 220

Arg Asn Ser Leu Ala Gln Ala Arg Ser Thr Gly Thr Asp Val Arg Ser
225                 230                 235                 240

Ile Val Val Ile Asn Pro Gly Asn Pro Thr Gly Ala Ser Leu Ser Ala
                245                 250                 255

Glu Asp Ile Lys Asn Val Leu Asp Leu Ala Ala Glu Glu Lys Leu Val
            260                 265                 270

Val Ile Ala Asp Glu Val Tyr Gln Thr Asn Val Phe Glu Gly Glu Phe
            275                 280                 285

Ile Ser Phe Lys Lys Arg Leu Arg Gln Leu Gln Gln Glu Thr Pro Gly
 290                 295                 300

Lys Tyr Asp Tyr Val Glu Leu Val Ser Leu His Ser Val Ser Lys Gly
305                 310                 315                 320

Met Val Gly Glu Cys Gly His Arg Gly Gly Tyr Phe Glu Leu Val Gly
                325                 330                 335

Phe Asp Pro Glu Val Gln Ala Gln Ile Tyr Lys Leu Val Ser Ile Gly
            340                 345                 350

Leu Cys Pro Pro Val Ile Gly Gln Cys Leu Leu Glu Leu Met Val Asn
            355                 360                 365

Pro Pro Lys Glu Gly Glu Gly Ser Tyr Glu Leu Tyr Gln Lys Glu Tyr
 370                 375                 380

Asn Gly Ile Ser Glu Gly Leu His Lys Arg Ala Phe Ala Leu Tyr Glu
385                 390                 395                 400

Ala Phe Gln Gln Met Glu Gly Val Glu Cys Gln Lys Pro Gln Gly Ala
                405                 410                 415

Met Tyr Leu Phe Pro Thr Ile Thr Leu Pro Pro Lys Ala Ile Glu Ala
                420                 425                 430

Ala Lys Ala Glu Asn Arg Ala Ala Asp Glu Phe Tyr Cys Leu Arg Leu
```

435                 440                 445
Leu Asp Ala Thr Gly Val Cys Val Pro Gly Ser Gly Phe Gly Gln
            450                 455                 460

Lys Glu Asn Thr Leu His Phe Arg Thr Thr Phe Leu Ala Pro Gly Thr
465                 470                 475                 480

Asp Trp Val Glu Arg Ile Val Lys Phe His Ser Glu Phe Met Ala Lys
                485                 490                 495

Tyr Lys

<210> SEQ ID NO 41
<211> LENGTH: 1542
<212> TYPE: DNA
<213> ORGANISM: Cryptococcus neoformans

<400> SEQUENCE: 41

| | | |
|---|---|---|
| atgcccagac ttagcaacgt ctattgtccc aaatcactct acaacgtca gaccatccaa | 60 |
| atcaggtcat tcagtcagac tatgtcacct ttcaaacccg cgcttactct tgataccatc | 120 |
| aaccccgcgg ttcaggctgt tcactatgct gtccgaggcg agctcgcgat caaggcggac | 180 |
| aaatatgtcc aagtccttgc cgatataact cacaagcctt gccgtttga aaagatcgtc | 240 |
| actgccaaca tcggtaatcc ccaacaacaa ggtcttgatc aagttcctct cacttattgg | 300 |
| cgacaaatta tttccttatt ggagtatccc gatctgatgc agaaacatga gcagttggcc | 360 |
| aagcagattt accctggaga tgtgattgag cgagccaggg cgttacataa cgaaattgga | 420 |
| agtacgggtg cgtacactca ttccaagggt gtgttgggta tcagaaagag agtcgccaag | 480 |
| tttattgaag aacgcgacgg ttacccggcg gaccctcaaa atatcttcct caccgccggt | 540 |
| gcttctgccg tgttgcttc gatccttggt gtcgccctcc gcagaggtga tggctgcatg | 600 |
| atccccatcc cccaatatcc cctctatacc gccaccctcg cttacctcga gtctgagcct | 660 |
| ctgccatact acctttctga gcggacgac tggtcgatga ccacgattc tttgctcaag | 720 |
| agcgtggagg aaggcaagaa gaagggtatc cccatcaagg cgcttgtaat cattaacccc | 780 |
| ggaaacccta ccggcgcatg tttgagccaa gaggcgatgg aggcggttgt gcatctctgt | 840 |
| tatgaggaag gtatcgtcct cctcgcagac gaggtttacc agatgaacgt ctttgacccc | 900 |
| gaacagcgac cgttcatttc tttcaaaaag gttttgatgg atatgcccaa ggagatcagg | 960 |
| gaaagtgtgg aactggtatc tttccattcg atctcaaaag gtgttagtgg agaatgtgga | 1020 |
| aggagaggtg gatactttga atgtgtcaac attgataagg atgtgatgga ccaggtttac | 1080 |
| aagatggcga gtgtcacttt atgtcctccc gtctcaggcc agatcggtgt cgacctcatg | 1140 |
| gtctcccctc cgaaacccgg agacgaatct taccccttat ggaaagaaga aaccgatctg | 1200 |
| atccaaaaca atctcaagtc ccgatcatat ctcatggctg agcatttcaa caaaatggaa | 1260 |
| ggtgtttctt gcaacaatgc ggaaggagcc atgtacttgt cccgaggat taatatccct | 1320 |
| cccaaagctg tagaggcggc gaagaagttg ggtaaggaac cggatgtgat gtatgctttg | 1380 |
| gatcttcttg atgcgaccgg tatctgtgcg gtggcaggca gcggttttgg ccaagaaccg | 1440 |
| gggacgttcc atttgcgagt gactgccctg tgtcccgata ctgctgaatt tatcggtcga | 1500 |
| ttccaaaagt tcaacaagga atttatggaa aagtatgcct aa | 1542 |

<210> SEQ ID NO 42
<211> LENGTH: 480
<212> TYPE: PRT
<213> ORGANISM: Cryptococcus neoformans

```
<400> SEQUENCE: 42

Met Pro Arg Leu Ser Asn Val Tyr Cys Pro Lys Ser Leu Leu Gln Arg
1               5                   10                  15

Gln Thr Ile Gln Ile Arg Ser Phe Ser Gln Thr Met Ser Pro Phe Lys
            20                  25                  30

Pro Ala Leu Thr Leu Asp Thr Ile Asn Pro Ala Val Gln Ala Val His
        35                  40                  45

Tyr Ala Val Arg Gly Glu Leu Ala Ile Lys Ala Asp Lys Tyr Val Gln
    50                  55                  60

Val Leu Ala Asp Ile Thr His Lys Pro Leu Pro Phe Glu Lys Ile Val
65                  70                  75                  80

Thr Ala Asn Ile Gly Asn Pro Gln Gln Gly Leu Asp Gln Val Pro
                85                  90                  95

Leu Thr Tyr Trp Arg Gln Ile Ile Ser Leu Leu Glu Tyr Pro Asp Leu
            100                 105                 110

Met Gln Lys His Glu Gln Leu Ala Lys Gln Ile Tyr Pro Gly Asp Val
            115                 120                 125

Ile Glu Arg Ala Arg Ala Leu His Asn Glu Ile Gly Ser Thr Gly Ala
        130                 135                 140

Tyr Thr His Ser Lys Gly Val Leu Gly Ile Arg Lys Arg Val Ala Lys
145                 150                 155                 160

Phe Ile Glu Glu Arg Asp Gly Tyr Pro Ala Asp Pro Gln Asn Ile Phe
                165                 170                 175

Leu Thr Ala Gly Ala Ser Ala Gly Val Ala Ser Ile Leu Gly Val Ala
            180                 185                 190

Leu Arg Arg Gly Asp Gly Cys Met Ile Pro Ile Pro Gln Tyr Pro Leu
        195                 200                 205

Tyr Thr Ala Thr Leu Ala Tyr Leu Glu Ser Pro Leu Pro Tyr Tyr
210                 215                 220

Leu Ser Glu Ala Asp Asp Trp Ser Met Asn His Asp Ser Leu Leu Lys
225                 230                 235                 240

Ser Val Glu Glu Gly Lys Lys Gly Ile Pro Ile Lys Ala Leu Val
                245                 250                 255

Ile Ile Asn Pro Gly Asn Pro Thr Gly Ala Cys Leu Ser Gln Glu Ala
            260                 265                 270

Met Glu Ala Val Val His Leu Cys Tyr Glu Glu Gly Ile Val Leu Leu
            275                 280                 285

Ala Asp Glu Val Tyr Gln Met Asn Val Phe Asp Pro Glu Gln Arg Pro
        290                 295                 300

Phe Ile Ser Phe Lys Lys Val Leu Met Asp Met Pro Lys Glu Ile Arg
305                 310                 315                 320

Glu Ser Val Glu Leu Val Ser Phe His Ser Ile Ser Lys Gly Val Ser
                325                 330                 335

Gly Glu Cys Gly Arg Arg Gly Gly Tyr Phe Glu Cys Val Asn Ile Asp
            340                 345                 350

Lys Asp Val Met Asp Gln Val Tyr Lys Met Ala Ser Val Thr Leu Cys
        355                 360                 365

Pro Pro Val Ser Gly Gln Ile Gly Val Asp Leu Met Val Ser Pro Pro
    370                 375                 380

Lys Pro Gly Asp Glu Ser Tyr Pro Leu Trp Lys Glu Thr Asp Leu
385                 390                 395                 400

Ile Gln Asn Asn Leu Lys Ser Arg Ser Tyr Leu Met Ala Glu His Phe
                405                 410                 415
```

```
Asn Lys Met Glu Gly Val Ser Cys Asn Asn Ala Glu Gly Ala Met Tyr
            420                 425                 430

Leu Phe Pro Arg Ile Asn Ile Pro Pro Lys Ala Val Glu Ala Ala Lys
        435                 440                 445

Lys Leu Gly Lys Glu Pro Asp Val Met Tyr Ala Leu Asp Leu Leu Asp
    450                 455                 460

Ala Thr Gly Ile Cys Ala Val Ala Gly Ser Gly Phe Gly Gln Glu Pro
465                 470                 475                 480

<210> SEQ ID NO 43
<211> LENGTH: 1605
<212> TYPE: DNA
<213> ORGANISM: Dictyostelium discoideum

<400> SEQUENCE: 43
atgttcaaaa gaagtttaaa agttttatta tcaaatccac ccatcaacag agtaaagccc      60
tcttcaacaa ttattcaacc actttcaaat actactacaa caacaataat taataataat     120
aatataacta attttgaaaa aatgacacat aaaaaatcta tgacaattga taatatttgc     180
caaaatgtaa gaaatgcaca atatgcagta cgtggtgaat tagttattcg tgcagaagca     240
atttcacatc aattacaaaa acaaaaaaca gaaggcacaa aaacattacc atttgaagag     300
attgtctatt gtaatattgg taatccacaa caattgaaac aaaaaccatt aacttatttc     360
cgtcaagttg tatcattagt tgaatgtcca gatttattag ataatccata cgttgaaaag     420
atatatccag ccgatgttat ctcacgtgct aaagagatat taggatcaat taataataca     480
acaggtgcct attccaatag tcaaggtatt ggtttagttt taagatcagt tgcagatttc     540
atagagagac gtgatggaca taatctgat ccatccgaaa ttttccttac agatggtgca      600
tcagttggtg tacaacgtat tttgaaactt ttaattaaag atcgttcaga cggtatctta     660
attccaattc cacaatatcc actctacagt gccaccattg aattatataa tggcagtcaa     720
ttagggtacc tattaaatga agagaaaggt tggtcactcg agatctccca attggagcat     780
tcctacaatg atgcagtttc aaagggtatt aatccacgtg cactcgttat catcaatcca     840
ggtaatccaa ctggtcaatg tttagataga gcaaatatgg aagagattgt caagttttgt     900
ttagaaaaga atgtagtatt attggctgat gaagtctatc aagagaatgt ttatgtcaaa     960
gagagtaaac cattcatctc attcaaaaag gttgtcaaag atatgggtgg tgattatgca    1020
gatttagaga tggtttcatt ccattcagtt agtaaaggtt cgttggtga atgtggtaaa     1080 cgtggtggtt atatggaatt aaatggtgtc actcaagatg ttaaagctga atttataaaa    1140
ctcgcatcaa ttggtttatg tccaaatgtt attggtcaat ggttgttga tttaatggtt     1200 cgtccaccag ttgctggtga acaatcacat gatctctacc ttaaagaaag agataatatc    1260
tatgaatctt taaaaaaacg tgcaaatctc ttaacaaatg ctttaaataa tcttgaaggt    1320
gtaacttgta atccatcaga aggtgcaatg tatgctttcc cacaaattcg tcttccagct    1380
aaagctgtag aatatgcaaa ttcaattggt aaagcaccag atgcttacta ttgtattcaa    1440
ttactcgaag ccactggtat ctgtgttgta ccaggtagtg gtttcggtca aaaagatggt    1500
acttggcatt ttagaactac cttccttacct tctgaagaag caattgaagg tgtttgtaag    1560
agaatcgctg atttccatca atcatttatg aataaatata ataa                     1605

<210> SEQ ID NO 44
<211> LENGTH: 534
<212> TYPE: PRT
```

<213> ORGANISM: Dictyostelium discoideum

<400> SEQUENCE: 44

```
Met Phe Lys Arg Ser Leu Lys Val Leu Leu Ser Asn Pro Pro Ile Asn
1               5                   10                  15
Arg Val Lys Pro Ser Ser Thr Ile Ile Gln Pro Leu Ser Asn Thr Thr
            20                  25                  30
Thr Thr Thr Ile Ile Asn Asn Asn Ile Thr Asn Phe Glu Lys Met
        35                  40                  45
Thr His Lys Lys Ser Met Thr Ile Asp Asn Ile Cys Gln Asn Val Arg
    50                  55                  60
Asn Ala Gln Tyr Ala Val Arg Gly Glu Leu Val Ile Arg Ala Glu Ala
65                  70                  75                  80
Ile Ser His Gln Leu Gln Lys Gln Lys Thr Glu Gly Thr Lys Thr Leu
                85                  90                  95
Pro Phe Glu Glu Ile Val Tyr Cys Asn Ile Gly Asn Pro Gln Gln Leu
            100                 105                 110
Lys Gln Lys Pro Leu Thr Tyr Phe Arg Gln Val Val Ser Leu Val Glu
        115                 120                 125
Cys Pro Asp Leu Leu Asp Asn Pro Tyr Val Glu Lys Ile Tyr Pro Ala
130                 135                 140
Asp Val Ile Ser Arg Ala Lys Glu Ile Leu Gly Ser Ile Asn Asn Thr
145                 150                 155                 160
Thr Gly Ala Tyr Ser Asn Ser Gln Gly Ile Gly Leu Val Leu Arg Ser
                165                 170                 175
Val Ala Asp Phe Ile Glu Arg Arg Asp Gly His Lys Ser Asp Pro Ser
            180                 185                 190
Glu Ile Phe Leu Thr Asp Gly Ala Ser Val Gly Val Gln Arg Ile Leu
        195                 200                 205
Lys Leu Leu Ile Lys Asp Arg Ser Asp Gly Ile Leu Ile Pro Ile Pro
210                 215                 220
Gln Tyr Pro Leu Tyr Ser Ala Thr Ile Glu Leu Tyr Asn Gly Ser Gln
225                 230                 235                 240
Leu Gly Tyr Leu Leu Asn Glu Glu Lys Gly Trp Ser Leu Glu Ile Ser
                245                 250                 255
Gln Leu Glu His Ser Tyr Asn Asp Ala Val Ser Lys Gly Ile Asn Pro
            260                 265                 270
Arg Ala Leu Val Ile Ile Asn Pro Gly Asn Pro Thr Gly Gln Cys Leu
        275                 280                 285
Asp Arg Ala Asn Met Glu Glu Ile Val Lys Phe Cys Leu Glu Lys Asn
290                 295                 300
Val Val Leu Leu Ala Asp Glu Val Tyr Gln Glu Asn Val Tyr Val Lys
305                 310                 315                 320
Glu Ser Lys Pro Phe Ile Ser Phe Lys Val Val Lys Asp Met Gly
                325                 330                 335
Gly Asp Tyr Ala Asp Leu Glu Met Val Ser Phe His Ser Val Ser Lys
            340                 345                 350
Gly Phe Val Gly Glu Cys Gly Lys Arg Gly Gly Tyr Met Glu Leu Asn
        355                 360                 365
Gly Val Thr Gln Asp Val Lys Ala Glu Ile Tyr Lys Leu Ala Ser Ile
370                 375                 380
Gly Leu Cys Pro Asn Val Ile Gly Gln Leu Val Val Asp Leu Met Val
385                 390                 395                 400
```

```
Arg Pro Pro Val Ala Gly Glu Gln Ser His Asp Leu Tyr Leu Lys Glu
                405                 410                 415

Arg Asp Asn Ile Tyr Glu Ser Leu Lys Lys Arg Ala Asn Leu Leu Thr
            420                 425                 430

Asn Ala Leu Asn Asn Leu Glu Gly Val Thr Cys Asn Pro Ser Glu Gly
        435                 440                 445

Ala Met Tyr Ala Phe Pro Gln Ile Arg Leu Pro Ala Lys Ala Val Glu
    450                 455                 460

Tyr Ala Asn Ser Ile Gly Lys Ala Pro Asp Ala Tyr Tyr Cys Ile Gln
465                 470                 475                 480

Leu Leu Glu Ala Thr Gly Ile Cys Val Val Pro Gly Ser Gly Phe Gly
                485                 490                 495

Gln Lys Asp Gly Thr Trp His Phe Arg Thr Thr Phe Leu Pro Ser Glu
                500                 505                 510

Glu Ala Ile Glu Gly Val Cys Lys Arg Ile Ala Asp Phe His Gln Ser
            515                 520                 525

Phe Met Asn Lys Tyr Lys
        530

<210> SEQ ID NO 45
<211> LENGTH: 1710
<212> TYPE: DNA
<213> ORGANISM: Trypanosoma brucei

<400> SEQUENCE: 45
atggatatat atttattttc cgtttggttt atacagaacg aggaaaagtg tttggatttt      60
ctaaacatta gtaagaagaa caaagccaag tcgagcgtac aacacattgg cgggttagcg     120
cgaaaacaga atcctgaacc acaaaaatca atttttgtgt cgagatacgg agcacgatca     180
ctgaagacct cgacaatgaa aggtaaccag gaatttttc agaagggtgg ggcccacgtt     240
tccaagggcg ttcacatcaa cccacgcgta agaaggctc agtatgccgt gcgcgggctt      300
gtgccgatgc gagccgacga atcagggag gaaatccgtt caggcacggg gaagtcgaag      360
ttctccttca cgaactggt ttactgcaac attggcaacc cccaagccct ggagcagaag      420
ccgcttacct ttcaccgcca agtgatgtcg cttatcgatg ctccatttct gcttgaggat     480
aacgccgtcg tctctcgata tccctctgat gctgtttccc gtgcgcgtct ctacttgggc     540
cacatcggcc aacgtactgg cgcctacacg gactccgcag gctatgcctt tgtacgtgac     600
atcgtcgcgc agtatgtgaa tgagcgtgac gcctatgtaa aaccgcttca ggaggcatcg     660
tcgattgtgc ttacagacgg cgcaagcact ggtgtgcgca taatcttaca gacgcttgtg     720
ggcgatgaga aggacgctgt gatgattccc atcccgcagt atccgctgta cacggcacag     780
attgcattgt tgggaggtac ccccgcgatg tattaccttc gtgagagcga aggctgggcg     840
ctgaacgttg gagagctcga ggcagtatac aaagactgtg tggcgaacgg aaacgcgacg     900
ccccgcgtgc tcgtcgtgat taaccctggt aaccctacag gtggcgtgtt ggagcgcact     960
gtgatggagg aggttgccaa gttctgttgc gatcacggtg ttgtgctcat ggccgatgag    1020
gtttaccagg aaaatatcta caccgcgacc aagcggtttg agagttttcg gaagattgtg    1080
ctcgaacttc caccaccata caacaccgac accgtgcttg tttccttgca ctccgtgtcg    1140
aagggtatta tcggtgagtg tggtcgccgt ggtgggtact tcacactcac aaacgctccg    1200
cctgagttag tggagcaggt gatgaaattg tgctctatta acctctgcag caacgtcaac    1260
ggtcagctta tgacggcact gatgtgctcc ccgccgaaac ctggcgatgc gagcttcgac    1320
```

```
cactacacgg cagagtacag tggcattttt gaaagcctta agcgccgtgc tgacctgctt    1380
gcaaaggaac tgaacaacat ccgtggtttc aagtcccaat ctgttgaggg cgccatgtac    1440
gctttcccca ctattgagct ccctcccaag tacgtgaagc acaacgatga gatgaactca    1500
aaggagggcc gacagcttgc gccggacgcg cgttgggcac tggagcttct cgagagcacc    1560
ggtattgttg tggtgccggg ttctggcttt gggcagcagc ctgggacact gcacttccgc    1620
acgacgatcc tcccacccga agcgcatatg gagcgtgtgg tgaaggctct cgccagttc    1680 caggagggca tttgggccaa gtatgcataa                                     1710
```

<210> SEQ ID NO 46
<211> LENGTH: 569
<212> TYPE: PRT
<213> ORGANISM: Trypanosoma brucei

<400> SEQUENCE: 46

```
Met Asp Ile Tyr Leu Phe Ser Val Trp Phe Ile Gln Asn Glu Glu Lys
1               5                   10                  15

Cys Leu Asp Phe Leu Asn Ile Ser Lys Lys Asn Lys Ala Lys Ser Ser
            20                  25                  30

Val Gln His Ile Gly Gly Leu Ala Arg Lys Gln Asn Pro Glu Pro Thr
        35                  40                  45

Lys Ser Ile Phe Val Ser Arg Tyr Gly Ala Arg Ser Leu Lys Thr Ser
    50                  55                  60

Thr Met Lys Gly Asn Gln Glu Phe Phe Gln Lys Gly Ala His Val
65                  70                  75                  80

Ser Lys Gly Val His Ile Asn Pro Arg Val Lys Lys Ala Gln Tyr Ala
                85                  90                  95

Val Arg Gly Leu Val Pro Met Arg Ala Asp Glu Ile Arg Glu Ile
            100                 105                 110

Arg Ser Gly Thr Gly Lys Ser Lys Phe Ser Phe Asn Glu Leu Val Tyr
        115                 120                 125

Cys Asn Ile Gly Asn Pro Gln Ala Leu Glu Gln Lys Pro Leu Thr Phe
    130                 135                 140

His Arg Gln Val Met Ser Leu Ile Asp Ala Pro Phe Leu Leu Glu Asp
145                 150                 155                 160

Asn Ala Val Val Ser Arg Tyr Pro Ser Asp Ala Val Ser Arg Ala Arg
                165                 170                 175

Leu Tyr Leu Gly His Ile Gly Gln Arg Thr Gly Ala Tyr Thr Asp Ser
            180                 185                 190

Ala Gly Tyr Ala Phe Val Arg Asp Ile Val Ala Gln Tyr Val Asn Glu
        195                 200                 205

Arg Asp Ala Tyr Val Lys Pro Leu Gln Glu Ala Ser Ser Ile Val Leu
    210                 215                 220

Thr Asp Gly Ala Ser Thr Gly Val Arg Ile Ile Leu Gln Thr Leu Val
225                 230                 235                 240

Gly Asp Glu Lys Asp Ala Val Met Ile Pro Ile Pro Gln Tyr Pro Leu
                245                 250                 255

Tyr Thr Ala Gln Ile Ala Leu Leu Gly Gly Thr Pro Ala Met Tyr Tyr
            260                 265                 270

Leu Arg Glu Ser Glu Gly Trp Ala Leu Asn Val Gly Glu Leu Glu Ala
        275                 280                 285

Val Tyr Lys Asp Cys Val Ala Asn Gly Asn Ala Thr Pro Arg Val Leu
    290                 295                 300
```

```
Val Val Ile Asn Pro Gly Asn Pro Thr Gly Gly Val Leu Glu Arg Thr
305                 310                 315                 320

Val Met Glu Glu Val Ala Lys Phe Cys Cys Asp His Gly Val Val Leu
                325                 330                 335

Met Ala Asp Glu Val Tyr Gln Glu Asn Ile Tyr Thr Ala Thr Lys Arg
            340                 345                 350

Phe Glu Ser Phe Arg Lys Ile Val Leu Glu Leu Pro Pro Pro Tyr Asn
        355                 360                 365

Thr Asp Thr Val Leu Val Ser Leu His Ser Val Ser Lys Gly Ile Ile
    370                 375                 380

Gly Glu Cys Gly Arg Arg Gly Gly Tyr Phe Thr Leu Thr Asn Ala Pro
385                 390                 395                 400

Pro Glu Leu Val Glu Gln Val Met Lys Leu Cys Ser Ile Asn Leu Cys
                405                 410                 415

Ser Asn Val Asn Gly Gln Leu Met Thr Ala Leu Met Cys Ser Pro Pro
                420                 425                 430

Lys Pro Gly Asp Ala Ser Phe Asp His Tyr Thr Ala Glu Tyr Ser Gly
            435                 440                 445

Ile Phe Glu Ser Leu Lys Arg Arg Ala Asp Leu Leu Ala Lys Glu Leu
450                 455                 460

Asn Asn Ile Arg Gly Phe Lys Ser Gln Ser Val Glu Gly Ala Met Tyr
465                 470                 475                 480

Ala Phe Pro Thr Ile Glu Leu Pro Pro Lys Tyr Val Lys His Asn Asp
                485                 490                 495

Glu Met Asn Ser Lys Gly Arg Gln Leu Ala Pro Asp Ala Arg Trp
            500                 505                 510

Ala Leu Glu Leu Leu Glu Ser Thr Gly Ile Val Val Pro Gly Ser
515                 520                 525

Gly Phe Gly Gln Gln Pro Gly Thr Leu His Phe Arg Thr Thr Ile Leu
530                 535                 540

Pro Pro Glu Ala His Met Glu Arg Val Val Lys Ala Leu Arg Gln Phe
545                 550                 555                 560

Gln Glu Gly Ile Trp Ala Lys Tyr Ala
                565

<210> SEQ ID NO 47
<211> LENGTH: 1494
<212> TYPE: DNA
<213> ORGANISM: Leishmania major

<400> SEQUENCE: 47
atgctgcgcc acgctgctcg ttgcttttca ccaaggcaat gctacgtaag ccctcgcgtc      60
atggaggcgg aatacgccgt gcgggggctg atcccggcgc gcgcggatga gatcaaggcg     120
gacttggcta caggccacgg cacctactcg ttcgaaagcc tcgtgtactg caacatcggc     180
aacccgcagt cagtggggca gatgccgcta acgttctacc gacaagtgat ggtgctcgtc     240
gatgcgccgt tcctgctgga ggatgcggaa atcgttgcgc ggctgccaga ggacgccgtt     300
gcacgcgcgc gcaggtacct ttcggagatc gggacgggca ccggcgcgta cacagagtct     360
ttcggcttcc ggtttgcccg cgctgccgtt gcggcgcaca tcaacgagct cgaccatggc     420
gtgagcccgg ctgcgacggt gaacgatatc tgtctgacag acggcgcgag catgggtgcg     480
aagctgttcc tgcagctcct tgtgggcggc gcgagcgatg ctgtgatgat cccggttccg     540
cagtatccgc tatactctgc gcagattgct ttacttggcg gggtgaaggt gccctacggc     600
```

```
ctgcacgagt ctgaggggtg ggtaatgaag ttgtcggacc ttgttgccgc gtacgagcgg    660
tgcgtgaccg agagcggcgc gacgccgcgc ttgtttgtgt gcatcaaccc cgggaacccg    720
acggggaacg tactggagcg ctgcgtgatg gaggacgtcg tgcggttctg ccacgagcgc    780
ggcatgctgc tgcttgcaga cgaggtgtac caggagaacg tgtacgacac gcgacgccgg    840
tttttgagct tccgcgaggt tgtgcttggg atgcctgagc cgtactgctc ggagacgatg    900
cttgtgtcac tgcactcgac atcgaaaggg gtgattggtg aatgcgggcg cgcggcggg     960 tatttctgca tgacgaacct gcctgctgcg ctgcgccagc aggttgtgaa gctgtgctcg   1020
atcaacctgt gtgcaaacgt gaacgggcag ttgatgactg cgctgatgtg ctcgccgccg   1080
cgcgagggcg aagcgagcta cgcgctgcac cggcgcgagt acgacgagat ctttacgggc   1140
atgaaggagc gcgctgagct gctggcgcgc gagcttgggg ctgtgcgcgg gctctcgtgc   1200
caaccggtgg agggcgcaat gtacgcgttc ccgagaattg tgttgcctga gcggtacgcc   1260
cagcggaacg aggagctgaa cgcgaaggag ggtcggcagc ttgcgctgga cgcgcgtgg    1320 gcgctggagc tgctggagtc gagcgggatc gttgttgtgc ccgggtctgg gttcgggcag   1380
gaacccggga cgctgcactt tcggatcacg attctcccgc ctcttgaaca gattgatcgg   1440
atggtgcgtg cgatccgcga gttccaggac cggatctacg agcagtacgc ttaa         1494
```

<210> SEQ ID NO 48
<211> LENGTH: 497
<212> TYPE: PRT
<213> ORGANISM: Leishmania major

<400> SEQUENCE: 48

```
Met Leu Arg His Ala Ala Arg Cys Phe Ser Pro Arg Gln Cys Tyr Val
1               5                   10                  15

Ser Pro Arg Val Met Glu Ala Glu Tyr Ala Val Arg Gly Leu Ile Pro
            20                  25                  30

Ala Arg Ala Asp Glu Ile Lys Ala Asp Leu Ala Thr Gly His Gly Thr
        35                  40                  45

Tyr Ser Phe Glu Ser Leu Val Tyr Cys Asn Ile Gly Asn Pro Gln Ser
    50                  55                  60

Val Gly Gln Met Pro Leu Thr Phe Tyr Arg Gln Val Met Val Leu Val
65                  70                  75                  80

Asp Ala Pro Phe Leu Leu Glu Asp Ala Glu Ile Val Ala Arg Leu Pro
                85                  90                  95

Glu Asp Ala Val Ala Arg Ala Arg Arg Tyr Leu Ser Glu Ile Gly Thr
            100                 105                 110

Gly Thr Gly Ala Tyr Thr Glu Ser Phe Gly Phe Arg Phe Ala Arg Ala
        115                 120                 125

Ala Val Ala Ala His Ile Asn Glu Leu Asp His Gly Val Ser Pro Ala
    130                 135                 140

Ala Thr Val Asn Asp Ile Cys Leu Thr Asp Gly Ala Ser Met Gly Ala
145                 150                 155                 160

Lys Leu Phe Leu Gln Leu Leu Val Gly Gly Ala Ser Asp Ala Val Met
                165                 170                 175

Ile Pro Val Pro Gln Tyr Pro Leu Tyr Ser Ala Gln Ile Ala Leu Leu
            180                 185                 190

Gly Gly Val Lys Val Pro Tyr Gly Leu His Glu Ser Glu Gly Trp Val
        195                 200                 205

Met Lys Leu Ser Asp Leu Val Ala Ala Tyr Glu Arg Cys Val Thr Glu
    210                 215                 220
```

```
Ser Gly Ala Thr Pro Arg Leu Phe Val Cys Ile Asn Pro Gly Asn Pro
225                 230                 235                 240

Thr Gly Asn Val Leu Glu Arg Cys Val Met Glu Asp Val Val Arg Phe
            245                 250                 255

Cys His Glu Arg Gly Met Leu Leu Ala Asp Glu Val Tyr Gln Glu
        260                 265                 270

Asn Val Tyr Asp Thr Arg Arg Phe Leu Ser Phe Arg Glu Val Val
        275                 280                 285

Leu Gly Met Pro Glu Pro Tyr Cys Ser Glu Thr Met Leu Val Ser Leu
            290                 295                 300

His Ser Thr Ser Lys Gly Val Ile Gly Glu Cys Gly Arg Gly Gly
305                 310                 315                 320

Tyr Phe Cys Met Thr Asn Leu Pro Ala Ala Leu Arg Gln Gln Val Val
                325                 330                 335

Lys Leu Cys Ser Ile Asn Leu Cys Ala Asn Val Asn Gly Gln Leu Met
            340                 345                 350

Thr Ala Leu Met Cys Ser Pro Pro Arg Glu Gly Glu Ala Ser Tyr Ala
                355                 360                 365

Leu His Arg Arg Glu Tyr Asp Glu Ile Phe Thr Gly Met Lys Glu Arg
            370                 375                 380

Ala Glu Leu Leu Ala Arg Glu Leu Gly Ala Val Arg Gly Leu Ser Cys
385                 390                 395                 400

Gln Pro Val Glu Gly Ala Met Tyr Ala Phe Pro Arg Ile Val Leu Pro
                405                 410                 415

Glu Arg Tyr Ala Gln Arg Asn Glu Glu Leu Asn Ala Lys Glu Gly Arg
            420                 425                 430

Gln Leu Ala Leu Asp Ala Arg Trp Ala Leu Glu Leu Leu Glu Ser Ser
        435                 440                 445

Gly Ile Val Val Pro Gly Ser Gly Phe Gly Gln Glu Pro Gly Thr
450                 455                 460

Leu His Phe Arg Ile Thr Ile Leu Pro Pro Leu Glu Gln Ile Asp Arg
465                 470                 475                 480

Met Val Arg Ala Ile Arg Glu Phe Gln Asp Arg Ile Tyr Glu Gln Tyr
                485                 490                 495

Ala

<210> SEQ ID NO 49
<211> LENGTH: 1455
<212> TYPE: DNA
<213> ORGANISM: Entamoeba histolytica

<400> SEQUENCE: 49
atgaaagcat tttcaagaca agtattaat ccttgtatca ttgcaactca atatgctgtt     60
agaggaaaat tagtattaga ggcaaatgag attcaaaaag aaattgaaga agcaagaaaa    120
aaaggaaaaa ataatcctta tccatttgag aaagtagttt attgtaatat tggtaatcca    180
cagatatgta accaacagcc attaacatat ccaaggcaga ttatctcaat agttgaatat    240
cctgagcttt taaatcatac aacccttttt ccgaaagatg ttatcaccca tgctaaaaaa    300
attattaata gtcttggttg tactggaaca agtggtgcat atactaattc tatgggagtt    360
attcaattca gaaatcaat ttgtaaattt ataaaacata gagatggaac tgctccatcc    420
cctgatgacg tatttataac cgatggagca tctactggaa taaaaatgat tttaaatatg    480
ttgatttcac atcctcttca tggaattatg attcctattc cacaataccc attatacagt    540
```

```
gcttcaatat ctcaattcgg aggttttcaa attaattact ttctagatga atcaaaaaaa    600
tggtcaacag atatgacatc cgtaagaaaa gtttatgaac aagcggttga aaaaggtatt    660
caagtgaaag gatttgtttg tattaaccca ggtaatccaa ctggacaagt tcttacagtc    720
caaaatatga agaaattat agaattttgc tatgaaaaaa aaatttgttt attagctgat    780
gaagtatatc aagagaatat ctacggtgaa ataccattta catcattcag aaaggtattg    840
aagtcaatga gggatgaggt gaaaaatagt gttgagctaa tctcattttt tagtgtttca    900
aaaggatttt atggtgaatg tggaaagcga ggtggatatt ccagataga aaatattaat    960 tcatttgctc gttctcagat gtataaaata gcatctacca attttatgttc aaatgtagtt   1020 ggtcaagaga tggttgaaat aatttgcaac ccaccaaaag aaggtgatga atcttatcca   1080
aaatacatga atgaaaaaat gtctatttta aactctttga aaagaaaagc caagttactc   1140
tattctgttc taaatgagtg tgaaggaatt tcttgtaatg aagctatggg tgctctttat   1200
cttttcccaa agattacatt cccaaacaaa tatattgatg agtgtaaaag aaaggatcaa   1260
aaaccagatg aattgtattg tttaaggatg ttaaaaagta taggggtgtg tgttgttcca   1320
ggatctggtt ttggtcaaaa agataatacg tatcatttta gaattgccat tctaccacca   1380
gaaaatgaaa tacagaatat tgccgtcaaa ataaaaactt ttcatacatc ttttatgaag   1440
gactattgtc actaa                                                    1455

<210> SEQ ID NO 50
<211> LENGTH: 484
<212> TYPE: PRT
<213> ORGANISM: Entamoeba histolytica

<400> SEQUENCE: 50

Met Lys Ala Phe Ser Arg Gln Ser Ile Asn Pro Cys Ile Ile Ala Thr
1               5                   10                  15

Gln Tyr Ala Val Arg Gly Lys Leu Val Leu Glu Ala Asn Glu Ile Gln
            20                  25                  30

Lys Glu Ile Glu Glu Ala Arg Lys Lys Gly Lys Asn Asn Pro Tyr Pro
        35                  40                  45

Phe Glu Lys Val Val Tyr Cys Asn Ile Gly Asn Pro Gln Ile Cys Asn
    50                  55                  60

Gln Gln Pro Leu Thr Tyr Pro Arg Gln Ile Ile Ser Ile Val Glu Tyr
65                  70                  75                  80

Pro Glu Leu Leu Asn His Thr Thr Leu Phe Pro Lys Asp Val Ile Thr
                85                  90                  95

His Ala Lys Lys Ile Ile Asn Ser Leu Gly Cys Thr Gly Thr Ser Gly
            100                 105                 110

Ala Tyr Thr Asn Ser Met Gly Val Ile Gln Phe Arg Lys Ser Ile Cys
        115                 120                 125

Lys Phe Ile Lys His Arg Asp Gly Thr Ala Pro Ser Pro Asp Asp Val
    130                 135                 140

Phe Ile Thr Asp Gly Ala Ser Thr Gly Ile Lys Met Ile Leu Asn Met
145                 150                 155                 160

Leu Ile Ser His Pro Leu His Gly Ile Met Ile Pro Ile Pro Gln Tyr
                165                 170                 175

Pro Leu Tyr Ser Ala Ser Ile Ser Gln Phe Gly Gly Phe Gln Ile Asn
            180                 185                 190

Tyr Phe Leu Asp Glu Ser Lys Lys Trp Ser Thr Asp Met Thr Ser Val
        195                 200                 205
```

```
Arg Lys Val Tyr Glu Gln Ala Val Glu Lys Gly Ile Gln Val Lys Gly
    210                 215                 220
Phe Val Cys Ile Asn Pro Gly Asn Pro Thr Gly Gln Val Leu Thr Val
225                 230                 235                 240
Gln Asn Met Lys Glu Ile Ile Glu Phe Cys Tyr Glu Lys Lys Ile Cys
                245                 250                 255
Leu Leu Ala Asp Glu Val Tyr Gln Glu Asn Ile Tyr Gly Glu Ile Pro
            260                 265                 270
Phe Thr Ser Phe Arg Lys Val Leu Lys Ser Met Arg Asp Glu Val Lys
        275                 280                 285
Asn Ser Val Glu Leu Ile Ser Phe Phe Ser Val Ser Lys Gly Phe Tyr
    290                 295                 300
Gly Glu Cys Gly Lys Arg Gly Gly Tyr Phe Gln Ile Glu Asn Ile Asn
305                 310                 315                 320
Ser Phe Ala Arg Ser Gln Met Tyr Lys Ile Ala Ser Thr Asn Leu Cys
                325                 330                 335
Ser Asn Val Val Gly Gln Glu Met Val Glu Ile Ile Cys Asn Pro Pro
            340                 345                 350
Lys Glu Gly Asp Glu Ser Tyr Pro Lys Tyr Met Asn Gly Lys Met Ser
        355                 360                 365
Ile Leu Asn Ser Leu Lys Arg Lys Ala Lys Leu Leu Tyr Ser Val Leu
    370                 375                 380
Asn Glu Cys Glu Gly Ile Ser Cys Asn Glu Ala Met Gly Ala Leu Tyr
385                 390                 395                 400
Leu Phe Pro Lys Ile Thr Phe Pro Asn Lys Tyr Ile Asp Glu Cys Lys
                405                 410                 415
Arg Lys Asp Gln Lys Pro Asp Glu Leu Tyr Cys Leu Arg Met Leu Lys
            420                 425                 430
Ser Ile Gly Val Cys Val Val Pro Gly Ser Gly Phe Gly Gln Lys Asp
        435                 440                 445
Asn Thr Tyr His Phe Arg Ile Ala Ile Leu Pro Pro Glu Asn Glu Ile
    450                 455                 460
Gln Asn Ile Ala Val Lys Ile Lys Thr Phe His Thr Ser Phe Met Lys
465                 470                 475                 480
Asp Tyr Cys His

<210> SEQ ID NO 51
<211> LENGTH: 1452
<212> TYPE: DNA
<213> ORGANISM: Entamoeba histolytica

<400> SEQUENCE: 51
atgagatcat tcgctagtga aaatattagt ccagatgtag ttgcattcca atttgctgta      60
cgtggtaaaa ttgctattgt ttcagaagaa attgataatg ctattaaaaa agcaaaagca     120
gaaggtaaac caaatcctta tccatttgaa aaagttgtta atgtaatag tggtaatcct      180
caattattaa atcaaaaacc attaactttt gttagagaaa ttacttctat ggtagaatat     240
cctcctctta cagaacatcc agaacttttc catgctgatg ctgttgctcg tgctaaagaa     300
attattaaag ctactggttg taatggaaca actggtgctt actcaccatc taaaggtctt     360
gcttatgtta gacaaacaat tgcacgtttc ttagaagaaa gagataatgt tccaatgtcc     420
ccagaagata tttatttaac tgatggtgct tctattgcta ttaagattgt tatgcaatta     480
atgctttcac atccacttca tggtattatg attccaaatc cacaatatcc attatatggt     540
```

-continued

```
gcttgtattc aacaattagg aggaaaaaca tgtcattata atttaaacga agataattat    600
tggttaccag acattaatga tattaaggaa caatatgaaa aatatcagaa tgaaggaatt    660
aaaattaagg cattagttgt tattaatcca ggaaatccat gtggagaagt tttaccagtt    720
gacactataa aagaaattat tagattctgt aacgaaaaga agatttgttt aatggctgat    780
gaagtatatc aagaaaatat ttggactgat gttccattca actcatttag aaaaattctt    840
gctacaatgg aaccagaaat tgcacatgga cttgaattaa tttctttcca ttctatttca    900
aaaggattct atggagaatg tggtaagaga ggaggaatgt ttgcatgtac caatattcca    960
gaatttgctc gtttaatgat gtataaaatt atttctacta ctttatgttc taatgttgta   1020
ggacaagttg taatgtctat aatttgtaat cttccaaaag aaggagaccc atcctatcca   1080
ttatttaaac aagaaagaga tgaaatcctt ggctctttaa aacgtaaagc agaatattta   1140
tgtgatattt tcaataagtg tgaaggtatg tcttgtaata gagctgctgg agctatgtat   1200
cttttcccaa gaattacatt accagaaaaa ttcataaaag aatgtcatga agacatgaa    1260 gatccaaatg aaacatattg tattgaaatg ttaaaaaaga ctggaattgc tgttgtaaaa   1320
gggtctggat ttggtcagaa aaagggtaca tatcatttta gaattgcttt gttaccacca   1380
gaaaatgaaa ttgaagaagt tggaaaaaga attcaagtat tccataattc tttttattcaa   1440 caatacaagt aa                                                         1452
```

<210> SEQ ID NO 52
<211> LENGTH: 483
<212> TYPE: PRT
<213> ORGANISM: Entamoeba histolytica

<400> SEQUENCE: 52

```
Met Arg Ser Phe Ala Ser Glu Asn Ile Ser Pro Asp Val Val Ala Phe
1               5                   10                  15

Gln Phe Ala Val Arg Gly Lys Ile Ala Ile Val Ser Glu Glu Ile Asp
            20                  25                  30

Asn Ala Ile Lys Lys Ala Lys Ala Glu Gly Lys Pro Asn Pro Tyr Pro
        35                  40                  45

Phe Glu Lys Val Val Lys Cys Asn Ser Gly Asn Pro Gln Leu Leu Asn
    50                  55                  60

Gln Lys Pro Leu Thr Phe Val Arg Glu Ile Thr Ser Met Val Glu Tyr
65                  70                  75                  80

Pro Pro Leu Thr Glu His Pro Glu Leu Phe His Ala Asp Ala Val Ala
                85                  90                  95

Arg Ala Lys Glu Ile Ile Lys Ala Thr Gly Cys Asn Gly Thr Thr Gly
            100                 105                 110

Ala Tyr Ser Pro Ser Lys Gly Leu Ala Tyr Val Arg Gln Thr Ile Ala
        115                 120                 125

Arg Phe Leu Glu Glu Arg Asp Asn Val Pro Met Ser Pro Glu Asp Ile
    130                 135                 140

Tyr Leu Thr Asp Gly Ala Ser Ile Ala Ile Lys Ile Val Met Gln Leu
145                 150                 155                 160

Met Leu Ser His Pro Leu His Gly Ile Met Ile Pro Asn Pro Gln Tyr
                165                 170                 175

Pro Leu Tyr Gly Ala Cys Ile Gln Gln Leu Gly Gly Lys Thr Cys His
            180                 185                 190

Tyr Asn Leu Asn Glu Asp Asn Tyr Trp Leu Pro Asp Ile Asn Asp Ile
        195                 200                 205
```

Lys Glu Gln Tyr Glu Lys Tyr Gln Asn Glu Gly Ile Lys Ile Lys Ala
    210                 215                 220

Leu Val Val Ile Asn Pro Gly Asn Pro Cys Gly Glu Val Leu Pro Val
225                 230                 235                 240

Asp Thr Ile Lys Glu Ile Ile Arg Phe Cys Asn Glu Lys Lys Ile Cys
                245                 250                 255

Leu Met Ala Asp Glu Val Tyr Gln Glu Asn Ile Trp Thr Asp Val Pro
            260                 265                 270

Phe Asn Ser Phe Arg Lys Ile Leu Ala Thr Met Glu Pro Glu Ile Ala
        275                 280                 285

His Gly Leu Glu Leu Ile Ser Phe His Ser Ile Ser Lys Gly Phe Tyr
    290                 295                 300

Gly Glu Cys Gly Lys Arg Gly Gly Met Phe Ala Cys Thr Asn Ile Pro
305                 310                 315                 320

Glu Phe Ala Arg Leu Met Met Tyr Lys Ile Ile Ser Thr Thr Leu Cys
                325                 330                 335

Ser Asn Val Val Gly Gln Val Val Met Ser Ile Ile Cys Asn Leu Pro
            340                 345                 350

Lys Glu Gly Asp Pro Ser Tyr Pro Leu Phe Lys Gln Glu Arg Asp Glu
        355                 360                 365

Ile Leu Gly Ser Leu Lys Arg Lys Ala Glu Tyr Leu Cys Asp Ile Phe
    370                 375                 380

Asn Lys Cys Glu Gly Met Ser Cys Asn Arg Ala Ala Gly Ala Met Tyr
385                 390                 395                 400

Leu Phe Pro Arg Ile Thr Leu Pro Glu Lys Phe Ile Lys Glu Cys His
                405                 410                 415

Glu Arg His Glu Asp Pro Asn Glu Thr Tyr Cys Ile Glu Met Leu Lys
            420                 425                 430

Lys Thr Gly Ile Ala Val Val Lys Gly Ser Gly Phe Gly Gln Lys Lys
        435                 440                 445

Gly Thr Tyr His Phe Arg Ile Ala Leu Leu Pro Pro Glu Asn Glu Ile
    450                 455                 460

Glu Glu Val Gly Lys Arg Ile Gln Val Phe His Asn Ser Phe Ile Gln
465                 470                 475                 480

Gln Tyr Lys

<210> SEQ ID NO 53
<211> LENGTH: 1482
<212> TYPE: DNA
<213> ORGANISM: Trypanosoma cruzi

<400> SEQUENCE: 53
atgtctgggt cacgaaagga aattcgcatc aaccccgtg tggtggcggc agagtatgcg    60
gtgcgtggga tgctccccat gcgtgcggac gagatcaggg cggccctggc gacaccggag   120
gggaaggcca agtacccctt ctccagcatt gtgtactgca acattgggaa cccgcaggca   180
ctggaacaga agccgctgac gttcttccgg caggtgatgt cgctgattga cgcgccgttc   240
ctgctggaga acgagaaggt tacgtcgcag ttcccggcgg atgcggtggc cgtgcgaggg   300
gagtatcttc gccacatcgg cgatcgcacg ggcgcctaca cggactctgc gggctacgcc   360
tttgtccgtg acatcgtggc gcggcaaatc aatgaacgcg accacgagat aaagccgctg   420
gtggacgcat cctctatttt tctgacggac ggcgcgagct cgggcgtgcg tcttttgctg   480
caggttctcg tgggtgacgc gagtgatgcg gtgatggttc ccattccgca gtaccgctg   540

-continued

```
tacacggcgc agcttacgct tcttggcggc acgcccgcga tgtactacct gtgtgagaag      600
gataactggg cactgaacgt ggaggagctg gcgtcggtgt acgacgagtg cgtggcgaag      660
aataatgcga ccccgcgcgt gctcgttgtg atcaaccctg gaacccgac tggcggcgtg       720
ctggatcgcg acgtgatgga ggccgtggcg aaattctgct gcgaccgcgg cattgtgctg      780
atggcggacg aggtgtacca ggagaacgtg tacgcggcgg aaagcgtttc cttgagcttc      840
cgggaagtgg tgcttgggct gccggcgccg tacaacacgg acacggtgct ggcctcgctg      900
cactcgacgt cgaagggcat cattggtgag tgcgggcgcc gcggcgggta cttctgcctc      960
acaaacttcc ccgcgccggt tcgggagcag gtgttaaaga tgtgctccat ggttccgtgc     1020
agcagcgtga atgggcagtt gatgacggca ctgatgtgct cgccaccgcg gcccggtgac     1080
gcgagctatg agtcatactg gcggagtac aatgggatct ttgcgagtct aaagaagcgc      1140
gccctgctgc ttgcgaagga gctgagcacg attcgcggtt tttcttgcca gccggtggaa     1200
ggggcgatgt acgcgtttcc gacgattgag ctgccggaga agtactttca gcacaatgag     1260
gagctgaacg cgaaggaggg gcgaaagctt gggcccgaca cgcgatgggc gttggagctt     1320
ctggagagca gcggggttgt tgttgtggcc ggctctgggt ttggtcagca gcccaacacg     1380
ctgcacttcc gcacgacgat cctgccgccg gagcagcaga tggaacggat ggtgaaggcg     1440
atgcgcacat tccaggaggg catttgggca aagtacgggt aa                       1482
```

<210> SEQ ID NO 54
<211> LENGTH: 493
<212> TYPE: PRT
<213> ORGANISM: Trypanosoma cruzi

<400> SEQUENCE: 54

```
Met Ser Gly Ser Arg Lys Glu Ile Arg Ile Asn Pro Arg Val Val Ala
1               5                   10                  15

Ala Glu Tyr Ala Val Arg Gly Met Leu Pro Met Arg Ala Asp Glu Ile
                20                  25                  30

Arg Ala Ala Leu Ala Thr Pro Glu Gly Lys Ala Lys Tyr Pro Phe Ser
            35                  40                  45

Ser Ile Val Tyr Cys Asn Ile Gly Asn Pro Gln Ala Leu Glu Gln Lys
        50                  55                  60

Pro Leu Thr Phe Phe Arg Gln Val Met Ser Leu Ile Asp Ala Pro Phe
65                  70                  75                  80

Leu Leu Glu Asn Glu Lys Val Thr Ser Gln Phe Pro Ala Asp Ala Val
                85                  90                  95

Ala Arg Ala Arg Glu Tyr Leu Arg His Ile Gly Asp Arg Thr Gly Ala
            100                 105                 110

Tyr Thr Asp Ser Ala Gly Tyr Ala Phe Val Arg Asp Ile Val Ala Arg
        115                 120                 125

Gln Ile Asn Glu Arg Asp His Glu Ile Lys Pro Leu Val Asp Ala Ser
    130                 135                 140

Ser Ile Phe Leu Thr Asp Gly Ala Ser Ser Gly Val Arg Leu Leu Leu
145                 150                 155                 160

Gln Val Leu Val Gly Asp Ala Ser Asp Ala Val Met Pro Ile Pro
                165                 170                 175

Gln Tyr Pro Leu Tyr Thr Ala Gln Leu Thr Leu Leu Gly Gly Thr Pro
            180                 185                 190

Ala Met Tyr Tyr Leu Cys Glu Lys Asp Asn Trp Ala Leu Asn Val Glu
        195                 200                 205
```

```
Glu Leu Ala Ser Val Tyr Asp Glu Cys Val Ala Lys Asn Asn Ala Thr
    210                 215                 220

Pro Arg Val Leu Val Val Ile Asn Pro Gly Asn Pro Thr Gly Gly Val
225                 230                 235                 240

Leu Asp Arg Asp Val Met Glu Ala Val Ala Lys Phe Cys Cys Asp Arg
                245                 250                 255

Gly Ile Val Leu Met Ala Asp Glu Val Tyr Gln Glu Asn Val Tyr Ala
                260                 265                 270

Ala Gly Lys Arg Phe Leu Ser Phe Arg Glu Val Val Leu Gly Leu Pro
            275                 280                 285

Ala Pro Tyr Asn Thr Asp Thr Val Leu Ala Ser Leu His Ser Thr Ser
        290                 295                 300

Lys Gly Ile Ile Gly Glu Cys Gly Arg Arg Gly Gly Tyr Phe Cys Leu
305                 310                 315                 320

Thr Asn Phe Pro Ala Pro Val Arg Glu Gln Val Leu Lys Met Cys Ser
                325                 330                 335

Met Val Pro Cys Ser Ser Val Asn Gly Gln Leu Met Thr Ala Leu Met
                340                 345                 350

Cys Ser Pro Pro Arg Pro Gly Asp Ala Ser Tyr Glu Ser Tyr Trp Ala
            355                 360                 365

Glu Tyr Asn Gly Ile Phe Ala Ser Leu Lys Lys Arg Ala Leu Leu Leu
        370                 375                 380

Ala Lys Glu Leu Ser Thr Ile Arg Gly Phe Ser Cys Gln Pro Val Glu
385                 390                 395                 400

Gly Ala Met Tyr Ala Phe Pro Thr Ile Glu Leu Pro Glu Lys Tyr Phe
                405                 410                 415

Gln His Asn Glu Glu Leu Asn Ala Lys Glu Gly Arg Lys Leu Gly Pro
            420                 425                 430

Asp Thr Arg Trp Ala Leu Glu Leu Leu Glu Ser Ser Gly Val Val Val
        435                 440                 445

Val Ala Gly Ser Gly Phe Gly Gln Gln Pro Asn Thr Leu His Phe Arg
450                 455                 460

Thr Thr Ile Leu Pro Pro Glu Gln Gln Met Glu Arg Met Val Lys Ala
465                 470                 475                 480

Met Arg Thr Phe Gln Glu Gly Ile Trp Ala Lys Tyr Gly
                485                 490

<210> SEQ ID NO 55
<211> LENGTH: 1494
<212> TYPE: DNA
<213> ORGANISM: Trypanosoma cruzi

<400> SEQUENCE: 55
atgctgcgca aaactctttt tggattcagg gccattcgca tcaaccccg tgtggtggcg      60 gcagagtatg cggtgcgtgg gatgctccca atgcgtgcgg acgagatcag gcggccctg    120 gcgacaccgg aggggaaggc caagtatccc ttccccagca ttgtgtactg caacattggg    180
aacccgcagg cactggaaca gaagccgctg acgttcttcc ggcaggtgat gtcgctgatt    240
gacgcgccgt tcctgctgga aaacgagaag gttacgtcgc agtacccggc ggatgcggtg    300
gcgcgtgcga gggagtatct tcgccacatc ggcgatcgca cgggcgccta cacggactct    360
gcgggctacg cctttgtccg tgacatcgtg gcgcggcaaa tcaatgaacg cgaccacgag    420
ataaagccgc tggtggacgc atcctctatt tttctgacgg acggcgcgag ctcgggcgtg    480
```

```
cgtcttttgc tgcaggttct cgtgggtgac gcgagtgatg cggtgatggt tcccattccg    540
cagtacccgc tgtacacggc gcagcttacg cttcttggcg gcacgcccgc gatgtactac    600
ctgtgtgaga aggataactg ggcactgaac gtggaggagc tggcgtcggt gtacgacgag    660
tgcgtggcga agaataatgc gactccgcgc gtgctcgttg tgatcaaccc tgggaacccg    720
actggcggcg tgctggatcg cgacgtgatg gaggctgtgg cgaaattctg ctgcgaccgc    780
ggcattgtgc tgatggcgga cgaggtgtac caggagaacg tgtacgcggc gggaaagcgt    840
ttcttgagct tccgggaagt ggtgcttggg ctgccggcgc cgtacaacac ggacacggtg    900
ctggcctcgc tgcactcgac gtcgaagggc atcattggtg agtgcgggcg ccgcggcggg    960
tacttctgcc tcacaaactt ccccgcgccg gttcgggagc aggtgttaaa gatgtgctcc   1020
atggttccgt gcagcagcgt gaatgggcag ttgatgacgg cactgatgtg ctcgccaccg   1080
cggcccggtg acgcgagcta tgagtcatac tgggcggagt acaatgggat ctttgcgagt   1140
ctaaagaagc gcgccctgct gcttgcgaag gagctgagca cgattcgcgg ttttcttgc   1200 cagccggtgg aagggggcgat gtacgcgttt ccgacgattg agctgccgga gaagtacttt   1260
cagcacaatg aggagctgaa cgcgaaggag gggcgaaagc ttgggcccga cacgcgatgg   1320
gcgttggagc ttctggagag cagcggggtt gttgttgtgg ccggctctgg gtttggtcag   1380
cagcccaaca cgctgcactt ccgcacgacg atcctgccgc cggagcagca gatggaacgg   1440
atggtgaagc cgatgcgcac attccaggag ggcatttggg caaagtacgg gtaa          1494
```

<210> SEQ ID NO 56
<211> LENGTH: 497
<212> TYPE: PRT
<213> ORGANISM: Trypanosoma cruzi

<400> SEQUENCE: 56

```
Met Leu Arg Lys Thr Leu Phe Gly Phe Arg Ala Ile Arg Ile Asn Pro
1               5                   10                  15

Arg Val Val Ala Ala Glu Tyr Ala Val Arg Gly Met Leu Pro Met Arg
            20                  25                  30

Ala Asp Glu Ile Arg Ala Ala Leu Ala Thr Pro Glu Gly Lys Ala Lys
        35                  40                  45

Tyr Pro Phe Pro Ser Ile Val Tyr Cys Asn Ile Gly Asn Pro Gln Ala
    50                  55                  60

Leu Glu Gln Lys Pro Leu Thr Phe Phe Arg Gln Val Met Ser Leu Ile
65                  70                  75                  80

Asp Ala Pro Phe Leu Leu Glu Asn Glu Lys Val Thr Ser Gln Tyr Pro
                85                  90                  95

Ala Asp Ala Val Ala Arg Ala Arg Glu Tyr Leu Arg His Ile Gly Asp
            100                 105                 110

Arg Thr Gly Ala Tyr Thr Asp Ser Ala Gly Tyr Ala Phe Val Arg Asp
        115                 120                 125

Ile Val Ala Arg Gln Ile Asn Glu Arg Asp His Glu Ile Lys Pro Leu
    130                 135                 140

Val Asp Ala Ser Ser Ile Phe Leu Thr Asp Gly Ala Ser Ser Gly Val
145                 150                 155                 160

Arg Leu Leu Leu Gln Val Leu Val Gly Asp Ala Ser Asp Ala Val Met
                165                 170                 175

Val Pro Ile Pro Gln Tyr Pro Leu Tyr Thr Ala Gln Leu Thr Leu Leu
            180                 185                 190

Gly Gly Thr Pro Ala Met Tyr Tyr Leu Cys Glu Lys Asp Asn Trp Ala
```

-continued

```
                195                 200                 205
Leu Asn Val Glu Glu Leu Ala Ser Val Tyr Asp Glu Cys Val Ala Lys
    210                 215                 220
Asn Asn Ala Thr Pro Arg Val Leu Val Val Ile Asn Pro Gly Asn Pro
225                 230                 235                 240
Thr Gly Gly Val Leu Asp Arg Asp Val Met Glu Ala Val Ala Lys Phe
                245                 250                 255
Cys Cys Asp Arg Gly Ile Val Leu Met Ala Asp Glu Val Tyr Gln Glu
                260                 265                 270
Asn Val Tyr Ala Ala Gly Lys Arg Phe Leu Ser Phe Arg Glu Val Val
                275                 280                 285
Leu Gly Leu Pro Ala Pro Tyr Asn Thr Asp Thr Val Leu Ala Ser Leu
    290                 295                 300
His Ser Thr Ser Lys Gly Ile Ile Gly Glu Cys Gly Arg Arg Gly Gly
305                 310                 315                 320
Tyr Phe Cys Leu Thr Asn Phe Pro Ala Pro Val Arg Glu Gln Val Leu
                325                 330                 335
Lys Met Cys Ser Met Val Pro Cys Ser Ser Val Asn Gly Gln Leu Met
                340                 345                 350
Thr Ala Leu Met Cys Ser Pro Arg Pro Gly Asp Ala Ser Tyr Glu
                355                 360                 365
Ser Tyr Trp Ala Glu Tyr Asn Gly Ile Phe Ala Ser Leu Lys Lys Arg
    370                 375                 380
Ala Leu Leu Leu Ala Lys Glu Leu Ser Thr Ile Arg Gly Phe Ser Cys
385                 390                 395                 400
Gln Pro Val Glu Gly Ala Met Tyr Ala Phe Pro Thr Ile Glu Leu Pro
                405                 410                 415
Glu Lys Tyr Phe Gln His Asn Glu Glu Leu Asn Ala Lys Glu Gly Arg
                420                 425                 430
Lys Leu Gly Pro Asp Thr Arg Trp Ala Leu Glu Leu Leu Glu Ser Ser
                435                 440                 445
Gly Val Val Val Ala Gly Ser Gly Phe Gly Gln Gln Pro Asn Thr
    450                 455                 460
Leu His Phe Arg Thr Thr Ile Leu Pro Pro Glu Gln Gln Met Glu Arg
465                 470                 475                 480
Met Val Lys Ala Met Arg Thr Phe Gln Glu Gly Ile Trp Ala Lys Tyr
                485                 490                 495
Gly
```

<210> SEQ ID NO 57
<211> LENGTH: 1482
<212> TYPE: DNA
<213> ORGANISM: Trypanosoma cruzi

<400> SEQUENCE: 57

```
atgtctgggt cacgaaagga aattcgcatc aaccccgtg tggtggcggc agagtatgcg    60
gtgcgtggga tgctccccat gcgtgcggac gagatcaggg cggccctggc gacaccggag   120
gggaaggcca agtacccctt ctccagcatt gtgtactgca acattgggaa cccgcaggca   180
ctggaacaga agccgctgac gttcttccgg caggtgatgt cgctgattga cgcgccgttc   240
ctgctggaga cgagaaggt tacgtcgcag ttccggcgg atgcggtggc gcgtgcgagg   300
gagtatcttc gccacatcgg cgatcgcacg ggcgcctaca cggactctgc gggctacgcc   360
tttgtccgtg acatcgtggc gcggcaaatc aatgaacgcg accacgagat aaagccgctg   420
```

```
gtggacgcat cctctatttt tctgacggac ggcgcgagct cgggcgtgcg tcttttgctg    480
caggttctcg tgggtgacgc gagtgatgcg gtgatggttc ccattccgca gtacccgctg    540
tacacggcgc agcttacgct tcttggcggc acgcccgcga tgtactacct gtgtgagaag    600
gataactggg cactgaatgt ggaggagctg gcgtcggtgt acgacgagtg cgtggcgaag    660
aataatgcga ccccgcgcgt gctcgttgtg atcaaccctg ggaacccgac tggcggcgtg    720
ctggatcgcg acgtgatgga ggctgtggcg aaattctgct cgaccgcgg cattgtgctg     780 atggcggacg aggtgtacca ggagaacgtg tacgcggcgg aaagcgtttt cttgagcttc    840
cgggaagtgg tgcttgggct gccggcgccg tacaacacgg acacggtgct ggcctcgctg    900
cactcgacgt cgaagggcat cattggtgag tgcgggcgcc gcggcgggta cttctgcctc    960
acaaacttcc ccgcgccggt gcgggagcag gtggtaaaga tgtgctccat ggttccgtgc   1020
agcagcgtga atgggcagtt gatgacggca ctgatgtgct cgccaccgcg gcccggtgac   1080
gcgagctatg agtcatactg gcggagtac aatgggatct ttgcgagtct aaagaagcgc    1140
gccctgctgc ttgcgaagga gctgggcacg attcgcggtt tttcttgcca gccggtggaa   1200
ggggcgatgt acgcgtttcc gacgattgag ctgccggaga agtactttca gcacaatgcg   1260
gagctgaacg cgaaggaggg gcgaaagctt gggcccgaca cgcgatgggc gttggagctt   1320
ctggagagca gcggggttgt tgttgtgccc ggctctgggt ttggtcagcg gcccaacacg   1380
ctgcacttcc gcacgacgat cctgccgccg gagcagcaga tggaacggat ggtgaaggcg   1440
atgcgcacat tccaggaggg catttgggca aagtacgggt aa                      1482
```

<210> SEQ ID NO 58
<211> LENGTH: 493
<212> TYPE: PRT
<213> ORGANISM: Trypanosoma cruzi

<400> SEQUENCE: 58

```
Met Ser Gly Ser Arg Lys Glu Ile Arg Ile Asn Pro Arg Val Val Ala
1               5                   10                  15

Ala Glu Tyr Ala Val Arg Gly Met Leu Pro Met Arg Ala Asp Glu Ile
            20                  25                  30

Arg Ala Leu Ala Thr Pro Glu Gly Lys Ala Lys Tyr Pro Phe Ser
        35                  40                  45

Ser Ile Val Tyr Cys Asn Ile Gly Asn Pro Gln Ala Leu Glu Gln Lys
    50                  55                  60

Pro Leu Thr Phe Phe Arg Gln Val Met Ser Leu Ile Asp Ala Pro Phe
65                  70                  75                  80

Leu Leu Glu Asn Glu Lys Val Thr Ser Gln Phe Pro Ala Asp Ala Val
                85                  90                  95

Ala Arg Ala Arg Glu Tyr Leu Arg His Ile Gly Asp Arg Thr Gly Ala
            100                 105                 110

Tyr Thr Asp Ser Ala Gly Tyr Ala Phe Val Arg Asp Ile Val Ala Arg
        115                 120                 125

Gln Ile Asn Glu Arg Asp His Glu Ile Lys Pro Leu Val Asp Ala Ser
    130                 135                 140

Ser Ile Phe Leu Thr Asp Gly Ala Ser Ser Gly Val Arg Leu Leu Leu
145                 150                 155                 160

Gln Val Leu Val Gly Asp Ala Ser Asp Ala Val Met Val Pro Ile Pro
                165                 170                 175

Gln Tyr Pro Leu Tyr Thr Ala Gln Leu Thr Leu Leu Gly Gly Thr Pro
```

180                 185                 190
Ala Met Tyr Tyr Leu Cys Glu Lys Asp Asn Trp Ala Leu Asn Val Glu
                195                 200                 205

Glu Leu Ala Ser Val Tyr Asp Glu Cys Val Ala Lys Asn Asn Ala Thr
            210                 215                 220

Pro Arg Val Leu Val Ile Asn Pro Gly Asn Pro Thr Gly Gly Val
225                 230                 235                 240

Leu Asp Arg Asp Val Met Glu Ala Val Ala Lys Phe Cys Cys Asp Arg
                245                 250                 255

Gly Ile Val Leu Met Ala Asp Glu Val Tyr Gln Glu Asn Val Tyr Ala
            260                 265                 270

Ala Gly Lys Arg Phe Leu Ser Phe Arg Glu Val Val Leu Gly Leu Pro
        275                 280                 285

Ala Pro Tyr Asn Thr Asp Thr Val Leu Ala Ser Leu His Ser Thr Ser
    290                 295                 300

Lys Gly Ile Ile Gly Glu Cys Gly Arg Arg Gly Gly Tyr Phe Cys Leu
305                 310                 315                 320

Thr Asn Phe Pro Ala Pro Val Arg Glu Gln Val Val Lys Met Cys Ser
                325                 330                 335

Met Val Pro Cys Ser Ser Val Asn Gly Gln Leu Met Thr Ala Leu Met
            340                 345                 350

Cys Ser Pro Pro Arg Pro Gly Asp Ala Ser Tyr Glu Ser Tyr Trp Ala
        355                 360                 365

Glu Tyr Asn Gly Ile Phe Ala Ser Leu Lys Lys Arg Ala Leu Leu Leu
    370                 375                 380

Ala Lys Glu Leu Gly Thr Ile Arg Gly Phe Ser Cys Gln Pro Val Glu
385                 390                 395                 400

Gly Ala Met Tyr Ala Phe Pro Thr Ile Glu Leu Pro Glu Lys Tyr Phe
                405                 410                 415

Gln His Asn Ala Glu Leu Asn Ala Lys Glu Gly Arg Lys Leu Gly Pro
            420                 425                 430

Asp Thr Arg Trp Ala Leu Glu Leu Leu Glu Ser Ser Gly Val Val Val
        435                 440                 445

Val Pro Gly Ser Gly Phe Gly Gln Arg Pro Asn Thr Leu His Phe Arg
    450                 455                 460

Thr Thr Ile Leu Pro Pro Glu Gln Gln Met Glu Arg Met Val Lys Ala
465                 470                 475                 480

Met Arg Thr Phe Gln Glu Gly Ile Trp Ala Lys Tyr Gly
                485                 490

<210> SEQ ID NO 59
<211> LENGTH: 1494
<212> TYPE: DNA
<213> ORGANISM: Trypanosoma cruzi

<400> SEQUENCE: 59
atgctacgca aaccctttt tggattcagg gccattcgca tcaaccccg tgtggtggcg        60 gcagagtatg cggtgcgtgg gatgctcccc atgcgtgcgg acgagatcag ggcggccctg     120
gcgacaccgg aggggaaggc caagtacccc ttctccagca ttgtgtactg caacattggg     180
aacccgcagg cactggaaca gaagccgctg acgttcttcc ggcaggtgat gtcgctgatt     240
gacgcgccgt tcctgctgga gaacgagaag gttacgtcgc agttccggc ggatgcggtg     300 gcgcgtgcga gggagtatct tcgccacatc ggcgatcgca cgggcgccta cacggactct     360

```
gcgggctacg cctttgcccg tgacatcgtg gcgcggcaaa tcaatgaacg cgaccacgag    420
ataaagccgc tggtggacgc atcctctatt tttctgacgg acggcgcgag ctcgggcgtg    480
cgtcttttgc tgcaggttct cgtgggtgac gcgagtgatg cggtgatggt tcccattccg    540
cagtacccgc tgtacacggc gcagcttact cttcttggcg gcacgcccgc gatgtactac    600
ctgtgtgaga aggataactg ggcactgaac gtggaggagc tggcgtcggt gtacgacgag    660
tgcgtggcga agaataatgc gaccccgcgc gtgctcgttg tgatcaaccc gggaacccg     720
actgcggcg tgctggatcg cgaagtgatg gaggccgtgg cgaaattctg ctgcgaccgc     780
ggcattgtgc tgatggcgga cgaggtgtac caggagaacg tgtacgcggc gggaaagcgt    840
ttcttgagct tccgggaagt ggtgcttggg ctgccggcgc cgtacaacac ggacacggtg    900
ctggcctcgc tgcactcgac gtcgaagggc atcattggtg agtgcgggcg ccgcggcggg    960
tacttctgcc tcacaaactt ccccgcgccg gtgcgggagc aggtggtaaa gatgtgctcc   1020
atggttccgt gcagcagcgt gaatgggcag ttgatgacgg cactgatgtg ctcgccaccg   1080
cggcccggtg acgcgagcta tgagtcatac tgggcggagt acaatgggat ctttgcgagt   1140
ctaaagaagc gcgccctgct gcttgcgaag gagctgggca cgattcgcgg ttttttcttgc  1200
cagccggtgg aagggggcgat gtacgcgttt ccgacgattg agctgccgga gaagtacttt  1260
cagcacaatg cggagctgaa cgcgaaggag gggcgaaagc ttgggcccga cacgcgatgg   1320
gcgttggagc ttctggagag cagcgggggtt gttgttgtgc ccggctctgg gtttggtcag   1380
cggcccaaca cgctgcactt ccgcacgacg atcctgccgc cggagcagca gatggaacgg   1440
atggtgaagg cgatgcgcac attccaggag ggcatttggg caaagtacgg gtaa          1494
```

<210> SEQ ID NO 60
<211> LENGTH: 497
<212> TYPE: PRT
<213> ORGANISM: Trypanosoma cruzi

<400> SEQUENCE: 60

```
Met Leu Arg Lys Thr Leu Phe Gly Phe Arg Ala Ile Arg Ile Asn Pro
1               5                   10                  15

Arg Val Ala Ala Glu Tyr Ala Val Arg Gly Met Leu Pro Met Arg
            20                  25                  30

Ala Asp Glu Ile Arg Ala Ala Leu Ala Thr Pro Glu Gly Lys Ala Lys
        35                  40                  45

Tyr Pro Phe Ser Ser Ile Val Tyr Cys Asn Ile Gly Asn Pro Gln Ala
    50                  55                  60

Leu Glu Gln Lys Pro Leu Thr Phe Phe Arg Gln Val Met Ser Leu Ile
65                  70                  75                  80

Asp Ala Pro Phe Leu Leu Glu Asn Glu Lys Val Thr Ser Gln Phe Pro
                85                  90                  95

Ala Asp Ala Val Ala Arg Ala Glu Tyr Leu Arg His Ile Gly Asp
            100                 105                 110

Arg Thr Gly Ala Tyr Thr Asp Ser Ala Gly Tyr Ala Phe Ala Arg Asp
        115                 120                 125

Ile Val Ala Arg Gln Ile Asn Glu Arg Asp His Glu Ile Lys Pro Leu
    130                 135                 140

Val Asp Ala Ser Ser Ile Phe Leu Thr Asp Gly Ala Ser Ser Gly Val
145                 150                 155                 160

Arg Leu Leu Leu Gln Val Leu Val Gly Asp Ala Ser Asp Ala Val Met
                165                 170                 175
```

Val Pro Ile Pro Gln Tyr Pro Leu Tyr Thr Ala Gln Leu Thr Leu Leu
            180                 185                 190

Gly Gly Thr Pro Ala Met Tyr Tyr Leu Cys Glu Lys Asp Asn Trp Ala
        195                 200                 205

Leu Asn Val Glu Glu Leu Ala Ser Val Tyr Asp Glu Cys Val Ala Lys
    210                 215                 220

Asn Asn Ala Thr Pro Arg Val Leu Val Val Ile Asn Pro Gly Asn Pro
225                 230                 235                 240

Thr Gly Gly Val Leu Asp Arg Glu Val Met Glu Ala Val Ala Lys Phe
                245                 250                 255

Cys Cys Asp Arg Gly Ile Val Leu Met Ala Asp Glu Val Tyr Gln Glu
                260                 265                 270

Asn Val Tyr Ala Ala Gly Lys Arg Phe Leu Ser Phe Arg Glu Val Val
            275                 280                 285

Leu Gly Leu Pro Ala Pro Tyr Asn Thr Asp Thr Val Leu Ala Ser Leu
        290                 295                 300

His Ser Thr Ser Lys Gly Ile Ile Gly Glu Cys Gly Arg Arg Gly Gly
305                 310                 315                 320

Tyr Phe Cys Leu Thr Asn Phe Pro Ala Pro Val Arg Glu Gln Val Val
                325                 330                 335

Lys Met Cys Ser Met Val Pro Cys Ser Ser Val Asn Gly Gln Leu Met
                340                 345                 350

Thr Ala Leu Met Cys Ser Pro Arg Pro Gly Asp Ala Ser Tyr Glu
            355                 360                 365

Ser Tyr Trp Ala Glu Tyr Asn Gly Ile Phe Ala Ser Leu Lys Lys Arg
        370                 375                 380

Ala Leu Leu Leu Ala Lys Glu Leu Gly Thr Ile Arg Gly Phe Ser Cys
385                 390                 395                 400

Gln Pro Val Glu Gly Ala Met Tyr Ala Phe Pro Thr Ile Glu Leu Pro
                405                 410                 415

Glu Lys Tyr Phe Gln His Asn Ala Glu Leu Asn Ala Lys Glu Gly Arg
            420                 425                 430

Lys Leu Gly Pro Asp Thr Arg Trp Ala Leu Glu Leu Leu Glu Ser Ser
        435                 440                 445

Gly Val Val Val Pro Gly Ser Gly Phe Gly Gln Arg Pro Asn Thr
    450                 455                 460

Leu His Phe Arg Thr Thr Ile Leu Pro Pro Glu Gln Gln Met Glu Arg
465                 470                 475                 480

Met Val Lys Ala Met Arg Thr Phe Gln Glu Gly Ile Trp Ala Lys Tyr
                485                 490                 495

Gly

<210> SEQ ID NO 61
<211> LENGTH: 1869
<212> TYPE: DNA
<213> ORGANISM: Cricetulus griseus

<400> SEQUENCE: 61
atggccacca aggagaagct gcagtgtctg aaagacttcc acaaagacat cctgaagcct    60
tctccaggga agagcccagg cacacggcct gaggatgagg ctgaggggaa gccccctcag   120
agggagaagt ggtccagcaa gattgacttt gtgctgtctg tggccggagg cttcgtgggt   180
ttgggcaacg tttggcgttt cccgtacctc tgctacaaaa atggtggagg tgctttcctc   240
ataccgtatt ttattttcct gtttgggagt ggcctgcctg tgttttttcct ggaggtcata   300

```
ataggccagt acacctcaga aggggggaatc acctgctggg agaagatctg ccccttgttc        360
tctggcattg gctacgcatc catcgtcatc gtgtccctcc tgaatgtgta ctacattgtc        420
atcctggcct gggccacata ctacctattt cactccttcc agacagagct tccctgggcc        480
cactgcaacc acagctggaa cacaccacat gcatggagg acaccctgcg taggaatgag         540
agtctctggg tctcccttag cgcctccaac ttcacctcgc ctgtcatcga gttctgggag        600
cgcaatgtac tcagcctgtc ttccggaatc gacgaaccag gcgctctgaa atgggacctt        660
gcgctctgcc tcctcttagt ctggcttgtc tgttttttct gcatatggaa gggtgttcga        720
tccacaggca aggttgtcta cttcaccgcc actttcccgt tgccatgct  tctggtgctg        780
ctggtccgtg gactgaccct gccgggtgct ggcgaaggca tcaaattcta cctgtaccct        840
gacatcagcc gccttgagga cccacaggtg tggatcgacg ccggaaccca gatattcttt        900
tcctatgcca tctgcctggg ggccatgacc tcactgggaa gctacaacaa gtacaagtat        960
aactcgtaca gggactgtat gctgctggga tgcctgaaca gtggtaccag ttttgtgtct       1020
ggcttcgcag tttttttccat cctgggcttc atggcacaag agcaaggggt ggacattgct       1080
gatgtggctg agtcaggtcc tggcttggcc ttcattgcct atccaaaagc tgtgactatg       1140
atgccgctgc ccacctttg gtccattctg tttttattta tgctcctctt gcttggactg       1200
gacagccagt tgttgaagt cgaaggacag atcacatcct tggttgatct ttacccgtcc       1260
ttcctaagga aggtttatcg tcgggaagtc ttcatcgcca tcctgtgtag catcagctac       1320
ctgctgggc tgtcgatggt gacggagggt ggcatgtatg tgtttcaact ctttgactac       1380
tatgcagcta gtggtgtatg ccttttgtgg gttgcattct ttgaatgttt tgttattgcc       1440
tggatatatg gtggtgataa cttatatgac ggtattgagg acatgattgg ctatcggcct       1500
gggccctgga tgaagtacag ctgggctgtc atcactccag ttctctgtgc tggatgtttc       1560
atcttctctc ttgtcaagta tgtaccccctg acctacaaca aagtctacgt gtatcctgat       1620
tgggcaattg gctgggctg gggcctggcc ctatcctcca tggtgtgtat ccccttggtc       1680
attgccatcc tcctctgccg gacggaggga ccgttccgcg tgagaatcca atacctgata       1740
acccccaggg agcccaaccg ctgggctgtg gagcgtgagg gggccacacc cttccactcc       1800
cgcacaagcc tcgtcatgaa cggcgcactc atgaaaccca gtcacgtcat tgtggagacc       1860
atgatgtga                                                                1869
```

<210> SEQ ID NO 62
<211> LENGTH: 622
<212> TYPE: PRT
<213> ORGANISM: Cricetulus griseus

<400> SEQUENCE: 62

```
Met Ala Thr Lys Glu Lys Leu Gln Cys Leu Lys Asp Phe His Lys Asp
1               5                   10                  15

Ile Leu Lys Pro Ser Pro Gly Lys Ser Pro Gly Thr Arg Pro Glu Asp
            20                  25                  30

Glu Ala Glu Gly Lys Pro Pro Gln Arg Glu Lys Trp Ser Ser Lys Ile
        35                  40                  45

Asp Phe Val Leu Ser Val Ala Gly Gly Phe Val Gly Leu Gly Asn Val
    50                  55                  60

Trp Arg Phe Pro Tyr Leu Cys Tyr Lys Asn Gly Gly Gly Ala Phe Leu
65                  70                  75                  80

Ile Pro Tyr Phe Ile Phe Leu Phe Gly Ser Gly Leu Pro Val Phe Phe
```

```
                        85                  90                  95
Leu Glu Val Ile Ile Gly Gln Tyr Thr Ser Glu Gly Gly Ile Thr Cys
                100                 105                 110
Trp Glu Lys Ile Cys Pro Leu Phe Ser Gly Ile Gly Tyr Ala Ser Ile
                115                 120                 125
Val Ile Val Ser Leu Leu Asn Val Tyr Tyr Ile Val Ile Leu Ala Trp
            130                 135                 140
Ala Thr Tyr Tyr Leu Phe His Ser Phe Gln Thr Glu Leu Pro Trp Ala
145                 150                 155                 160
His Cys Asn His Ser Trp Asn Thr Pro His Cys Met Glu Asp Thr Leu
                165                 170                 175
Arg Arg Asn Glu Ser Leu Trp Val Ser Leu Ser Ala Ser Asn Phe Thr
                180                 185                 190
Ser Pro Val Ile Glu Phe Trp Glu Arg Asn Val Leu Ser Leu Ser Ser
                195                 200                 205
Gly Ile Asp Glu Pro Gly Ala Leu Lys Trp Asp Leu Ala Leu Cys Leu
            210                 215                 220
Leu Leu Val Trp Leu Val Cys Phe Phe Cys Ile Trp Lys Gly Val Arg
225                 230                 235                 240
Ser Thr Gly Lys Val Val Tyr Phe Thr Ala Thr Phe Pro Phe Ala Met
                245                 250                 255
Leu Leu Val Leu Leu Val Arg Gly Leu Thr Leu Pro Gly Ala Gly Glu
                260                 265                 270
Gly Ile Lys Phe Tyr Leu Tyr Pro Asp Ile Ser Arg Leu Glu Asp Pro
                275                 280                 285
Gln Val Trp Ile Asp Ala Gly Thr Gln Ile Phe Phe Ser Tyr Ala Ile
            290                 295                 300
Cys Leu Gly Ala Met Thr Ser Leu Gly Ser Tyr Asn Lys Tyr Lys Tyr
305                 310                 315                 320
Asn Ser Tyr Arg Asp Cys Met Leu Leu Gly Cys Leu Asn Ser Gly Thr
                325                 330                 335
Ser Phe Val Ser Gly Phe Ala Val Phe Ser Ile Leu Gly Phe Met Ala
                340                 345                 350
Gln Glu Gln Gly Val Asp Ile Ala Asp Val Ala Glu Ser Gly Pro Gly
                355                 360                 365
Leu Ala Phe Ile Ala Tyr Pro Lys Ala Val Thr Met Met Pro Leu Pro
            370                 375                 380
Thr Phe Trp Ser Ile Leu Phe Phe Ile Met Leu Leu Leu Gly Leu
385                 390                 395                 400
Asp Ser Gln Phe Val Glu Val Glu Gly Gln Ile Thr Ser Leu Val Asp
                405                 410                 415
Leu Tyr Pro Ser Phe Leu Arg Lys Gly Tyr Arg Arg Glu Val Phe Ile
                420                 425                 430
Ala Ile Leu Cys Ser Ile Ser Tyr Leu Leu Gly Leu Ser Met Val Thr
                435                 440                 445
Glu Gly Gly Met Tyr Val Phe Gln Leu Phe Asp Tyr Tyr Ala Ala Ser
            450                 455                 460
Gly Val Cys Leu Leu Trp Val Ala Phe Glu Cys Phe Val Ile Ala
465                 470                 475                 480
Trp Ile Tyr Gly Gly Asp Asn Leu Tyr Asp Gly Ile Glu Asp Met Ile
                485                 490                 495
Gly Tyr Arg Pro Gly Pro Trp Met Lys Tyr Ser Trp Ala Val Ile Thr
                500                 505                 510
```

```
Pro Val Leu Cys Ala Gly Cys Phe Ile Phe Ser Leu Val Lys Tyr Val
        515                 520                 525

Pro Leu Thr Tyr Asn Lys Val Tyr Val Tyr Pro Asp Trp Ala Ile Gly
        530                 535                 540

Leu Gly Trp Gly Leu Ala Leu Ser Ser Met Val Cys Ile Pro Leu Val
545                 550                 555                 560

Ile Ala Ile Leu Leu Cys Arg Thr Glu Gly Pro Phe Arg Val Arg Ile
                565                 570                 575

Gln Tyr Leu Ile Thr Pro Arg Glu Pro Asn Arg Trp Ala Val Glu Arg
                580                 585                 590

Glu Gly Ala Thr Pro Phe His Ser Arg Thr Ser Leu Val Met Asn Gly
        595                 600                 605

Ala Leu Met Lys Pro Ser His Val Ile Val Glu Thr Met Met
        610                 615                 620

<210> SEQ ID NO 63
<211> LENGTH: 1866
<212> TYPE: DNA
<213> ORGANISM: Rattus norvegicus

<400> SEQUENCE: 63
```

| | | | | | |
|---|---|---|---|---|---|
| atggccacca | aggagaagct | tcaatgtctg | aaagacttcc | acaaagacat | cctgaagcct | 60 |
| tctccaggga | agagcccagg | cacgcggcct | gaggatgagg | ctgatgggaa | gccccctcag | 120 |
| agggagaagt | ggtccagcaa | gatcgacttt | gtgctgtctg | tggccggagg | cttcgtgggt | 180 |
| ttgggcaatg | tctggcgttt | cccgtacctc | tgctacaaaa | atggtggagg | tgcattcctc | 240 |
| ataccgtatt | ttatttttcct | gtttgggagc | ggcctgcctg | tgttttttcct | ggaggtcatc | 300 |
| ataggccagt | acacctcaga | aggggggcatc | acctgctggg | agaagatctg | cccccttgttc | 360 |
| tctggcattg | gctacgcgtc | catcgtcatc | gtgtccctcc | tgaatgtgta | ctacatcgtc | 420 |
| atcctggcct | gggccacata | ctacctattc | cagtctttcc | agaaggatct | tccctgggcc | 480 |
| cactgcaacc | atagctggaa | cacgccacag | tgcatggagg | acaccctgcg | taggaacgag | 540 |
| agtcactggg | tctcccttag | cgccgccaac | ttcacttcgc | ctgtgatcga | gttctgggag | 600 |
| cgcaacgtgc | tcagcctgtc | ctccggaatc | gaccacccag | gcagtctgaa | atgggacctc | 660 |
| gcgctctgcc | tcctcttagt | ctggctcgtc | tgttttttct | gcatctggaa | gggtgttcgg | 720 |
| tccacaggca | aggttgtcta | cttcactgct | actttcccgt | tgccatgct | tctggtgctg | 780 |
| ctggtccgtg | gactgaccct | gccaggtgct | ggtgaaggca | tcaaattcta | cctgtaccct | 840 |
| aacatcagcc | gccttgagga | cccacaggtg | tggatcgacg | ctggaactca | gatattcttt | 900 |
| tcctacgcta | tctgcctggg | ggccatgacc | tcactgggaa | gctataacaa | gtacaagtat | 960 |
| aactcgtaca | gggactgtat | gctgctggga | tgcctgaaca | gtggtaccag | ttttgtgtct | 1020 |
| ggcttcgcaa | ttttttccat | cctgggcttc | atggcacaag | agcaagggggt | ggacattgct | 1080 |
| gatgtggctg | agtcaggtcc | tggcttggcc | ttcattgcct | acccaaaagc | tgtgaccatg | 1140 |
| atgccgctgc | ccaccttttg | gtccattctg | tttttttatta | tgctcctctt | gcttggactg | 1200 |
| gacagccagt | tgttgaagt | cgaaggacag | atcacatcct | tggttgatct | ttacccgtcc | 1260 |
| ttcctaagga | agggttatcg | tcgggaaatc | ttcattgcca | tcgtgtgcag | catcagctac | 1320 |
| ctgctggggc | tgacgatggt | gacggagggt | ggcatgtatg | tgtttcaact | cttgactac | 1380 |
| tatgcagcta | gtggtgtatg | ccttttgtgg | gtcgcattct | ttgaatgttt | tgttattgcc | 1440 |
| tggatatatg | gcggtgataa | cttatatgac | ggtattgagg | acatgatcgg | ctatcggcct | 1500 |

```
ggaccctgga tgaagtacag ctgggctgtc atcactccag ctctctgtgt tggatgtttc    1560
atcttctctc tcgtcaagta tgtaccctg acctacaaca aagtctaccg gtaccctgat     1620
tgggcaatcg ggctgggctg gggcctggcc ctttcctcca tggtgtgtat ccccttggtc    1680
attgtcatcc tcctctgccg gacggaggga ccgctccgcg tgagaatcaa atacctgata   1740
accccagggg agcccaaccg ctgggctgtg agcgtgaag gggctacgcc ctttcactcc     1800
agagcaaccc tcatgaacgg tgcactcatg aaacccagtc acgtcattgt ggagaccatg   1860
atgtga                                                               1866
```

<210> SEQ ID NO 64
<211> LENGTH: 621
<212> TYPE: PRT
<213> ORGANISM: Rattus norvegicus

<400> SEQUENCE: 64

```
Met Ala Thr Lys Glu Lys Leu Gln Cys Leu Lys Asp Phe His Lys Asp
1               5                   10                  15

Ile Leu Lys Pro Ser Pro Gly Lys Ser Pro Gly Thr Arg Pro Glu Asp
                20                  25                  30

Glu Ala Asp Gly Lys Pro Pro Gln Arg Glu Lys Trp Ser Ser Lys Ile
            35                  40                  45

Asp Phe Val Leu Ser Val Ala Gly Gly Phe Val Gly Leu Gly Asn Val
        50                  55                  60

Trp Arg Phe Pro Tyr Leu Cys Tyr Lys Asn Gly Gly Gly Ala Phe Leu
65                  70                  75                  80

Ile Pro Tyr Phe Ile Phe Leu Phe Gly Ser Gly Leu Pro Val Phe Phe
                85                  90                  95

Leu Glu Val Ile Ile Gly Gln Tyr Thr Ser Glu Gly Gly Ile Thr Cys
            100                 105                 110

Trp Glu Lys Ile Cys Pro Leu Phe Ser Gly Ile Gly Tyr Ala Ser Ile
        115                 120                 125

Val Ile Val Ser Leu Leu Asn Val Tyr Tyr Ile Val Ile Leu Ala Trp
    130                 135                 140

Ala Thr Tyr Tyr Leu Phe Gln Ser Phe Gln Lys Asp Leu Pro Trp Ala
145                 150                 155                 160

His Cys Asn His Ser Trp Asn Thr Pro Gln Cys Met Glu Asp Thr Leu
                165                 170                 175

Arg Arg Asn Glu Ser His Trp Val Ser Leu Ser Ala Ala Asn Phe Thr
            180                 185                 190

Ser Pro Val Ile Glu Phe Trp Glu Arg Asn Val Leu Ser Leu Ser Ser
        195                 200                 205

Gly Ile Asp His Pro Gly Ser Leu Lys Trp Asp Leu Ala Leu Cys Leu
    210                 215                 220

Leu Leu Val Trp Leu Val Cys Phe Phe Cys Ile Trp Lys Gly Val Arg
225                 230                 235                 240

Ser Thr Gly Lys Val Val Tyr Phe Thr Ala Thr Phe Pro Phe Ala Met
                245                 250                 255

Leu Leu Val Leu Leu Val Arg Gly Leu Thr Leu Pro Gly Ala Gly Glu
            260                 265                 270

Gly Ile Lys Phe Tyr Leu Tyr Pro Asn Ile Ser Arg Leu Glu Asp Pro
        275                 280                 285

Gln Val Trp Ile Asp Ala Gly Thr Gln Ile Phe Phe Ser Tyr Ala Ile
    290                 295                 300
```

Cys Leu Gly Ala Met Thr Ser Leu Gly Ser Tyr Asn Lys Tyr Lys Tyr
305                 310                 315                 320

Asn Ser Tyr Arg Asp Cys Met Leu Leu Gly Cys Leu Asn Ser Gly Thr
            325                 330                 335

Ser Phe Val Ser Gly Phe Ala Ile Phe Ser Ile Leu Gly Phe Met Ala
        340                 345                 350

Gln Glu Gln Gly Val Asp Ile Ala Asp Val Ala Glu Ser Gly Pro Gly
    355                 360                 365

Leu Ala Phe Ile Ala Tyr Pro Lys Ala Val Thr Met Met Pro Leu Pro
370                 375                 380

Thr Phe Trp Ser Ile Leu Phe Phe Ile Met Leu Leu Leu Gly Leu
385                 390                 395                 400

Asp Ser Gln Phe Val Glu Val Glu Gly Gln Ile Thr Ser Leu Val Asp
                405                 410                 415

Leu Tyr Pro Ser Phe Leu Arg Lys Gly Tyr Arg Arg Glu Ile Phe Ile
            420                 425                 430

Ala Ile Val Cys Ser Ile Ser Tyr Leu Leu Gly Leu Thr Met Val Thr
        435                 440                 445

Glu Gly Gly Met Tyr Val Phe Gln Leu Phe Asp Tyr Tyr Ala Ala Ser
450                 455                 460

Gly Val Cys Leu Leu Trp Val Ala Phe Phe Glu Cys Phe Val Ile Ala
465                 470                 475                 480

Trp Ile Tyr Gly Gly Asp Asn Leu Tyr Asp Gly Ile Glu Asp Met Ile
                485                 490                 495

Gly Tyr Arg Pro Gly Pro Trp Met Lys Tyr Ser Trp Ala Val Ile Thr
            500                 505                 510

Pro Ala Leu Cys Val Gly Cys Phe Ile Phe Ser Leu Val Lys Tyr Val
        515                 520                 525

Pro Leu Thr Tyr Asn Lys Val Tyr Arg Tyr Pro Asp Trp Ala Ile Gly
530                 535                 540

Leu Gly Trp Gly Leu Ala Leu Ser Ser Met Val Cys Ile Pro Leu Val
545                 550                 555                 560

Ile Val Ile Leu Leu Cys Arg Thr Glu Gly Pro Leu Arg Val Arg Ile
                565                 570                 575

Lys Tyr Leu Ile Thr Pro Arg Glu Pro Asn Arg Trp Ala Val Glu Arg
            580                 585                 590

Glu Gly Ala Thr Pro Phe His Ser Arg Ala Thr Leu Met Asn Gly Ala
        595                 600                 605

Leu Met Lys Pro Ser His Val Ile Val Glu Thr Met Met
610                 615                 620

<210> SEQ ID NO 65
<211> LENGTH: 1866
<212> TYPE: DNA
<213> ORGANISM: Mus musculus

<400> SEQUENCE: 65
atggccacga aggagaagct gcaatgtctg aaagacttcc acaaagacat cctgaagcct    60
tctccaggga gagcccagg cacacggcct gaagatgagg cggacgggaa gccccctcag    120
agggagaagt ggtccagcaa gatcgacttt gtgctgtctg tggccggagg cttcgtgggt    180
ttgggcaacg tctggcgttt cccgtacctc tgctacaaaa atggtggagg tgcgttcctc    240
ataccgtatt ttatttttcct gtttgggagc ggcctgcctg tgttttttctt ggaggtcatc    300

| | | |
|---|---|---|
| ataggccagt acacatcaga aggggcatc acctgctggg agaagatctg tcctttgttc | 360 | |
| tctggcattg ctacgcatc catcgtcatt gtgtccctcc tgaacgtgta ctacatcgtc | 420 | |
| atcctggcct gggccacata ctacctattc cactcttcc agaaggatct tccctgggcc | 480 | |
| cactgcaacc atagctggaa cacaccacag tgcatggagg acaccctgcg taggaacgag | 540 | |
| agtcactggg tctcccttag cactgccaac ttcacctcac ccgtcatcga gttctgggag | 600 | |
| cgcaatgtgc tcagcctgtc ctccggaatc gacaacccag gcagtctgaa atgggacctc | 660 | |
| gcgctctgcc tcctcttagt ctggctcgtc tgttttttct gcatctggaa gggtgttcga | 720 | |
| tccacaggca aggttgtcta cttcaccgct actttcccgt tgccatgct tctggtgctg | 780 | |
| ctggtccgtg gactgaccct gccaggtgct ggtgaaggca tcaaattcta cctgtaccct | 840 | |
| gacatcagcc gccttgggga cccacaggtg tggatcgacg ctggaactca gatattcttt | 900 | |
| tcctacgcaa tctgcctggg ggccatgacc tcactgggaa gctataacaa gtacaagtat | 960 | |
| aactcgtaca gggactgtat gctgctggga tgcctgaaca gtggtaccag tttgtgtct | 1020 | |
| ggcttcgcaa ttttttccat cctgggcttc atggcacaag agcaagggt ggacattgct | 1080 | |
| gatgtggctg agtcaggtcc tggcttggcc ttcattgcct acccaaaagc tgtaaccatg | 1140 | |
| atgccgctgc ccacctttg gtctattctg ttttcatta tgctcctctt gcttggactg | 1200 | |
| gacagccagt tgttgaagt cgaaggacag atcacatcct tggttgatct ttacccgtcc | 1260 | |
| ttcctaagga agggttatcg tcgggaaatc ttcatagcca tcttgtgtag catcagctac | 1320 | |
| ctgctggggc tgacgatggt gacggagggt ggcatgtatg tgtttcaact ctttgactac | 1380 | |
| tatgcagcta gtggtgtatg ccttttgtgg gttgcattct ttgaatgttt tgttattgcc | 1440 | |
| tggatatatg gcggtgataa cttatatgac ggtattgagg acatgattgg ctatcggcct | 1500 | |
| gggccctgga tgaagtacag ctgggctgtc atcactccag ctctttgtgt tggatgtttc | 1560 | |
| gtcttctcgc ttgtcaagta tgtaccctg acctacaaca aagtgtaccg gtacccggat | 1620 | |
| tgggcaattg gctgggctg gggcctggcc ctttcctcca tgctgtgtat ccccttggtc | 1680 | |
| attgtcatcc tcctctgccg gacggaggga ccgctccgcg tgagaatcaa ataccctgata | 1740 | |
| accccccaggg agcccaaccg ctgggctgtg gagcgtgaag gggccacacc ctttcactcc | 1800 | |
| cgagtaaccc tcatgaacgg cgcactcatg aaacccagtc acgtcattgt ggagaccatg | 1860 | |
| atgtga | 1866 | |

<210> SEQ ID NO 66
<211> LENGTH: 621
<212> TYPE: PRT
<213> ORGANISM: Mus musculus

<400> SEQUENCE: 66

Met Ala Thr Lys Glu Lys Leu Gln Cys Leu Lys Asp Phe His Lys Asp
1               5                   10                  15

Ile Leu Lys Pro Ser Pro Gly Lys Ser Pro Gly Thr Arg Pro Glu Asp
            20                  25                  30

Glu Ala Asp Gly Lys Pro Pro Gln Arg Glu Lys Trp Ser Ser Lys Ile
        35                  40                  45

Asp Phe Val Leu Ser Val Ala Gly Gly Phe Val Gly Leu Gly Asn Val
    50                  55                  60

Trp Arg Phe Pro Tyr Leu Cys Tyr Lys Asn Gly Gly Ala Phe Leu
65                  70                  75                  80

Ile Pro Tyr Phe Ile Phe Leu Phe Gly Ser Gly Leu Pro Val Phe Phe
                85                  90                  95

-continued

```
Leu Glu Val Ile Ile Gly Gln Tyr Thr Ser Glu Gly Ile Thr Cys
            100                 105                 110

Trp Glu Lys Ile Cys Pro Leu Phe Ser Gly Ile Gly Tyr Ala Ser Ile
            115                 120                 125

Val Ile Val Ser Leu Leu Asn Val Tyr Tyr Ile Val Ile Leu Ala Trp
130                 135                 140

Ala Thr Tyr Tyr Leu Phe His Ser Phe Gln Lys Asp Leu Pro Trp Ala
145                 150                 155                 160

His Cys Asn His Ser Trp Asn Thr Pro Gln Cys Met Glu Asp Thr Leu
                165                 170                 175

Arg Arg Asn Glu Ser His Trp Val Ser Leu Ser Thr Ala Asn Phe Thr
            180                 185                 190

Ser Pro Val Ile Glu Phe Trp Glu Arg Asn Val Leu Ser Leu Ser Ser
            195                 200                 205

Gly Ile Asp Asn Pro Gly Ser Leu Lys Trp Asp Leu Ala Leu Cys Leu
            210                 215                 220

Leu Leu Val Trp Leu Val Cys Phe Phe Cys Ile Trp Lys Gly Val Arg
225                 230                 235                 240

Ser Thr Gly Lys Val Val Tyr Phe Thr Ala Thr Phe Pro Phe Ala Met
                245                 250                 255

Leu Leu Val Leu Leu Val Arg Gly Leu Thr Leu Pro Gly Ala Gly Glu
            260                 265                 270

Gly Ile Lys Phe Tyr Leu Tyr Pro Asp Ile Ser Arg Leu Gly Asp Pro
            275                 280                 285

Gln Val Trp Ile Asp Ala Gly Thr Gln Ile Phe Phe Ser Tyr Ala Ile
            290                 295                 300

Cys Leu Gly Ala Met Thr Ser Leu Gly Ser Tyr Asn Lys Tyr Lys Tyr
305                 310                 315                 320

Asn Ser Tyr Arg Asp Cys Met Leu Leu Gly Cys Leu Asn Ser Gly Thr
                325                 330                 335

Ser Phe Val Ser Gly Phe Ala Ile Phe Ser Ile Leu Gly Phe Met Ala
            340                 345                 350

Gln Glu Gln Gly Val Asp Ile Ala Asp Val Ala Glu Ser Gly Pro Gly
            355                 360                 365

Leu Ala Phe Ile Ala Tyr Pro Lys Ala Val Thr Met Met Pro Leu Pro
370                 375                 380

Thr Phe Trp Ser Ile Leu Phe Phe Ile Met Leu Leu Leu Leu Gly Leu
385                 390                 395                 400

Asp Ser Gln Phe Val Glu Val Glu Gly Gln Ile Thr Ser Leu Val Asp
                405                 410                 415

Leu Tyr Pro Ser Phe Leu Arg Lys Gly Tyr Arg Arg Glu Ile Phe Ile
            420                 425                 430

Ala Ile Leu Cys Ser Ile Ser Tyr Leu Leu Gly Leu Thr Met Val Thr
435                 440                 445

Glu Gly Gly Met Tyr Val Phe Gln Leu Phe Asp Tyr Tyr Ala Ala Ser
            450                 455                 460

Gly Val Cys Leu Leu Trp Val Ala Phe Phe Glu Cys Phe Val Ile Ala
465                 470                 475                 480

Trp Ile Tyr Gly Gly Asp Asn Leu Tyr Asp Gly Ile Glu Asp Met Ile
                485                 490                 495

Gly Tyr Arg Pro Gly Pro Trp Met Lys Tyr Ser Trp Ala Val Ile Thr
            500                 505                 510
```

```
Pro Ala Leu Cys Val Gly Cys Phe Val Phe Ser Leu Val Lys Tyr Val
        515                 520                 525
Pro Leu Thr Tyr Asn Lys Val Tyr Arg Tyr Pro Asp Trp Ala Ile Gly
    530                 535                 540
Leu Gly Trp Gly Leu Ala Leu Ser Ser Met Leu Cys Ile Pro Leu Val
545                 550                 555                 560
Ile Val Ile Leu Leu Cys Arg Thr Glu Gly Pro Leu Arg Val Arg Ile
                565                 570                 575
Lys Tyr Leu Ile Thr Pro Arg Glu Pro Asn Arg Trp Ala Val Glu Arg
            580                 585                 590
Glu Gly Ala Thr Pro Phe His Ser Arg Val Thr Leu Met Asn Gly Ala
        595                 600                 605
Leu Met Lys Pro Ser His Val Ile Val Glu Thr Met Met
    610                 615                 620

<210> SEQ ID NO 67
<211> LENGTH: 1863
<212> TYPE: DNA
<213> ORGANISM: Homo sapiens

<400> SEQUENCE: 67
atggccacca aggagaagct gcagtgtctg aaagatttcc acaaggacat cctgaagccc      60
tcaccaggga gagcccagg cacgcggcct gaggacgagg ctgagggaaa acctccgcag     120
agggagaagt ggtctagcaa gatcgacttt gtgctctctg tggctggcgg cttcgtgggc     180
ttgggcaacg tctggcgctt cccgtacctc tgctacaaga atggtggagg tgcgtttctc     240
ataccgtatt ttatttttcct gtttgggagc ggcctgcctg tgttttttctt ggagatcatc     300 ataggccagt acacctctga agggggcatc acctgctggg aaaagatctg ccccttgttc     360
tctggtatcg gctatgcctc cgttgtaatt gtgtccctcc tgaatgtcta ctacatcgtc     420
atcctggcct gggccacata ctacctgttc cagtccttcc agaaggagct gcctgggca     480 cactgcaacc acagctggaa cacacctcac tgcatggagg acaccatgcg caagaacaag     540
agtgtctgga tcaccatcag ctccaccaac ttcacctccc ctgtcatcga gttctgggag     600
cgcaacgtgc tgagcttgtc ccctggaatc gaccacccag ctctctgaa atgggacctc     660 gctctctgcc ttcttttagt ctggctagtg tgtttcttct gcatctggaa gggcgtcagg     720
tccactggga aggtcgtcta cttcacagcc acttttccat cgccatgct cctggtgctg     780 ctggtccgag gctgacgct gccgggcgcg ggcgcaggca tcaagttcta tctgtatcct     840
gacatcaccc gccttgagga cccacaggtg tggattgacg ctgggactca gatattcttc     900
tcttatgcca tctgcctggg ggctatgacc tcgctgggga gctacaacaa gtacaagtat     960
aactcgtaca gggactgtat gctgctggga tgcctgaaca gtggtaccag ttttgtgtct    1020
ggcttcgcaa tttttttccat cctgggcttc atggcacaag agcaagggt ggacattgct    1080 gatgtggctg agtcaggtcc tggcctggcc ttcattgcct acccaaaaagc tgtgacaatg    1140 atgccgctgc ccacattttg gtccattctt ttttttatta tgcttctctt gcttggactg    1200
gatagccagt tgttgaagt tgaaggacag atcacatcct tggttgatct ttacccatcc    1260
ttcctaagga agggttatcg tcgggaaatc ttcatcgcct tcgtgtgtag catcagctac    1320
ctgctggggc tgacgatggg gacggagggt ggcatgtatg tgtttcagct ctttgactac    1380
tatgcagcta gcgtgtatg cctttttgtgg gttgcattct ttgaatgttt tgttattgcc    1440
tggatatatg gaggtgataa ccttttatgat ggtattgagg acatgattgg ctatcggccc    1500
```

-continued

```
gggccctgga tgaagtacag ctgggctgtg atcactccag ttctctgtgt tggatgtttc    1560
atcttctcgc tcgtcaagta cgtacccctg acctacaaca aaacatacgt gtaccccaac    1620
tgggccattg ggctgggctg agcctggcc ctttcctcca tgctctgcgt tcccttggtc     1680
atcgtcatcc gcctctgcca gactgagggg ccgttccttg tgagagtcaa gtacctgctg    1740
accccaaggg aacccaaccg ctgggctgtg gagcgcgagg gagccacacc ttacaactct    1800
cgcaccgtca tgaacggcgc tctcgtgaaa ccgacccaca tcattgtgga gaccatgatg    1860
tga                                                                   1863
```

<210> SEQ ID NO 68
<211> LENGTH: 620
<212> TYPE: PRT
<213> ORGANISM: Homo sapiens

<400> SEQUENCE: 68

```
Met Ala Thr Lys Glu Lys Leu Gln Cys Leu Lys Asp Phe His Lys Asp
1               5                   10                  15

Ile Leu Lys Pro Ser Pro Gly Lys Ser Pro Gly Thr Arg Pro Glu Asp
            20                  25                  30

Glu Ala Glu Gly Lys Pro Pro Gln Arg Glu Lys Trp Ser Ser Lys Ile
        35                  40                  45

Asp Phe Val Leu Ser Val Ala Gly Gly Phe Val Gly Leu Gly Asn Val
    50                  55                  60

Trp Arg Phe Pro Tyr Leu Cys Tyr Lys Asn Gly Gly Gly Ala Phe Leu
65                  70                  75                  80

Ile Pro Tyr Phe Ile Phe Leu Phe Gly Ser Gly Leu Pro Val Phe Phe
                85                  90                  95

Leu Glu Ile Ile Ile Gly Gln Tyr Thr Ser Glu Gly Gly Ile Thr Cys
            100                 105                 110

Trp Glu Lys Ile Cys Pro Leu Phe Ser Gly Ile Gly Tyr Ala Ser Val
        115                 120                 125

Val Ile Val Ser Leu Leu Asn Val Tyr Tyr Ile Val Ile Leu Ala Trp
    130                 135                 140

Ala Thr Tyr Tyr Leu Phe Gln Ser Phe Gln Lys Glu Leu Pro Trp Ala
145                 150                 155                 160

His Cys Asn His Ser Trp Asn Thr Pro His Cys Met Glu Asp Thr Met
                165                 170                 175

Arg Lys Asn Lys Ser Val Trp Ile Thr Ile Ser Ser Thr Asn Phe Thr
            180                 185                 190

Ser Pro Val Ile Glu Phe Trp Glu Arg Asn Val Leu Ser Leu Ser Pro
        195                 200                 205

Gly Ile Asp His Pro Gly Ser Leu Lys Trp Asp Leu Ala Leu Cys Leu
    210                 215                 220

Leu Leu Val Trp Leu Val Cys Phe Phe Cys Ile Trp Lys Gly Val Arg
225                 230                 235                 240

Ser Thr Gly Lys Val Val Tyr Phe Thr Ala Thr Phe Pro Phe Ala Met
                245                 250                 255

Leu Leu Val Leu Leu Val Arg Gly Leu Thr Leu Pro Gly Ala Gly Ala
            260                 265                 270

Gly Ile Lys Phe Tyr Leu Tyr Pro Asp Ile Thr Arg Leu Glu Asp Pro
        275                 280                 285

Gln Val Trp Ile Asp Ala Gly Thr Gln Ile Phe Phe Ser Tyr Ala Ile
    290                 295                 300
```

-continued

```
Cys Leu Gly Ala Met Thr Ser Leu Gly Ser Tyr Asn Lys Tyr Lys Tyr
305                 310                 315                 320

Asn Ser Tyr Arg Asp Cys Met Leu Leu Gly Cys Leu Asn Ser Gly Thr
                325                 330                 335

Ser Phe Val Ser Gly Phe Ala Ile Phe Ser Ile Leu Gly Phe Met Ala
                340                 345                 350

Gln Glu Gln Gly Val Asp Ile Ala Asp Val Ala Glu Ser Gly Pro Gly
                355                 360                 365

Leu Ala Phe Ile Ala Tyr Pro Lys Ala Val Thr Met Met Pro Leu Pro
370                 375                 380

Thr Phe Trp Ser Ile Leu Phe Phe Ile Met Leu Leu Leu Leu Gly Leu
385                 390                 395                 400

Asp Ser Gln Phe Val Glu Val Glu Gly Gln Ile Thr Ser Leu Val Asp
                405                 410                 415

Leu Tyr Pro Ser Phe Leu Arg Lys Gly Tyr Arg Arg Glu Ile Phe Ile
                420                 425                 430

Ala Phe Val Cys Ser Ile Ser Tyr Leu Leu Gly Leu Thr Met Val Thr
                435                 440                 445

Glu Gly Gly Met Tyr Val Phe Gln Leu Phe Asp Tyr Tyr Ala Ala Ser
450                 455                 460

Gly Val Cys Leu Leu Trp Val Ala Phe Phe Glu Cys Phe Val Ile Ala
465                 470                 475                 480

Trp Ile Tyr Gly Gly Asp Asn Leu Tyr Asp Gly Ile Glu Asp Met Ile
                485                 490                 495

Gly Tyr Arg Pro Gly Pro Trp Met Lys Tyr Ser Trp Ala Val Ile Thr
                500                 505                 510

Pro Val Leu Cys Val Gly Cys Phe Ile Phe Ser Leu Val Lys Tyr Val
                515                 520                 525

Pro Leu Thr Tyr Asn Lys Thr Tyr Val Tyr Pro Asn Trp Ala Ile Gly
530                 535                 540

Leu Gly Trp Ser Leu Ala Leu Ser Ser Met Leu Cys Val Pro Leu Val
545                 550                 555                 560

Ile Val Ile Arg Leu Cys Gln Thr Glu Gly Pro Phe Leu Val Arg Val
                565                 570                 575

Lys Tyr Leu Leu Thr Pro Arg Glu Pro Asn Arg Trp Ala Val Glu Arg
                580                 585                 590

Glu Gly Ala Thr Pro Tyr Asn Ser Arg Thr Val Met Asn Gly Ala Leu
                595                 600                 605

Val Lys Pro Thr His Ile Ile Val Glu Thr Met Met
610                 615                 620
```

METHOD OF PRODUCING HETEROGENEOUS PROTEIN

CROSS-REFERENCE TO RELATED APPLICATIONS

This application is a Divisional of U.S. application Ser. No. 14/225,833, filed Mar. 26, 2014, which is a Divisional of U.S. application Ser. No. 12/733,052, which is a National Stage Application of PCT/JP2008/064095, filed Aug. 6, 2008, which claims priority from Japanese application JP 2007-205158, filed Aug. 7, 2007, the entire contents of which are incorporated herein by reference.

The instant application contains a Sequence Listing which has been submitted in ASCII format via EFS-WEB and is hereby incorporated by reference in its entirety. Said ASCII copy, created on Jul. 13, 2015, is named sequence.txt and is 220 KB.

TECHNICAL FIELD

The present invention relates to a method of producing a heterogenous protein, more specifically, a method of producing a polypeptide using a cell which strongly expresses alanine aminotransferase.

BACKGROUND ART

When proteins useful as pharmaceuticals are produced with the recombinant DNA technique, use of animal cells enables complicated post-translational modification and folding which prokaryotic cells can not perform. Therefore, animal cells are frequently used as host cells for producing recombinant proteins.

Recently, a large number of biopharmaceuticals, such as antibodies and physiologically active proteins, have been developed. Techniques that permit efficient production of recombinant proteins by animal cells lead to cost reduction of biopharmaceuticals and promise their stable supply to patients.

Under these circumstances, a method of protein production with higher production efficiency is desired.

Alanine is one of the proteinogenic amino acids, and is a non-essential amino acid. In a living body, it is biosynthesized by transfer of an amino group from glutamate to pyruvate, and is degraded by a reverse reaction.

As an alanine degrading enzyme, alanine aminotransferase (EC 2.6.1.2.) (Non-patent document 1) has been known. This enzyme transfers an amino group from alanine to 2-oxoglutarate to synthesize glutamate. Alanine aminotransferase is also called glutamic-pyruvic transaminase, which is abbreviated as GPT (Non-patent document 2). GPT and GOP (aspartate aminotransferase) are enzymes found in the liver. Since GPT and GOP are released into the blood when hepatic cells are destroyed, the liver is diagnosed to have some kind of disorder when abnormally high levels of GPT and GOT are observed.

As shown above, alanine aminotransferase is used as a marker of hepatic function. However, it has not been known how host cells such as CHO cells behave if alanine aminotransferase is strongly expressed in them.

[Non-Patent Document 1]
Sanjay B. J., et. al., Hepatology (2004) 39(5), 1297-1302
[Non-Patent Document 2]
Melanie M. S., et. al., Genomics (1997) 40, 247-252

DISCLOSURE OF THE INVENTION

Problem for Solution by the Invention

It is an object of the present invention to provide a method which is capable of producing a natural or recombinant protein in high yield.

Means to Solve the Problem

As a result of extensive and intensive researches toward the solution of the above problem, the present inventors have found that it is possible to increase the yield of a desired polypeptide by using a cell that strongly expresses alanine aminotransferase (hereinafter sometimes referred to as "ALT"). Thus, the present invention has been achieved. Moreover, the desired polypeptide could be produced in an even greater amount by using cells capable of co-expressing ALT and a taurine transporter. Since alanine is produced in large amount over time in cell culture, alanine accumulated in cells is secreted in the medium. If the reaction of biosynthesizing pyruvate and glutamate from alanine can be promoted by strongly expressing ALT, the products are utilized in metabolism during a TCA cycle and glucose production by glycogenesis. This will improve cell culture behavior, and thus high-yield production of the desired polypeptide is anticipated.

The present invention may be summarized as follows.

(1) A method of producing a polypeptide, comprising culturing a cell which strongly expresses alanine aminotransferase and has a transferred DNA encoding a desired polypeptide and thereby allowing the cell to produce said polypeptide.

(2) The method of (1) above, wherein the cell which strongly expresses alanine aminotransferase is a cell into which a DNA encoding the alanine aminotransferase has been transferred.

(3) The production method of (1) or (2) above, wherein the cells that strongly express alanine aminotransferase further express a taurine transporter strongly.

(4) The production method of (3) above, wherein the cells that strongly express a taurine transporter are cells into which DNA encoding a taurine transporter has been transferred.

(5) The method of (2) or (4) above, wherein the cell is Chinese hamster ovary cells.

(6) The method of any one of (1) to (5) above, wherein the desired polypeptide is an antibody.

(7) The method of any one of (2) to (6) above, wherein the DNA encoding the alanine aminotransferase is any one of the following (a) to (e):

(a) a DNA encoding a polypeptide having the amino acid sequence as shown in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60;

(b) a DNA encoding a polypeptide which has an amino acid sequence derived from the amino acid sequence as shown in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60 by substitution, deletion, addition and/or insertion of one or more amino acid residues and yet has alanine aminotransferase activity;

(c) a DNA encoding a polypeptide having 70% or more amino acid sequence homology with the amino acid sequence as shown in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60 and yet having alanine aminotransferase activity;

(d) a DNA having the nucleotide sequence as shown in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57 or 59;

(e) a DNA which hybridizes to a DNA complementary to a DNA having the nucleotide sequence as shown in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57 or 59 under stringent conditions and yet encodes a polypeptide having alanine aminotransferase activity.

(8) A method of preparing a pharmaceutical containing a polypeptide prepared by the method of any one of (1) to (7) above.

(9) A cell which has a transferred DNA encoding alanine aminotransferase and a transferred DNA encoding a desired polypeptide.

(10) The cell according to (9) above, which further has a transferred DNA encoding a taurine transporter.

(11) A cell which has a transferred DNA encoding alanine aminotransferase and a transferred DNA encoding a taurine transporter.

(12) A method of producing a polypeptide, comprising culturing in an α-ketoglutarate-containing medium a cell which strongly expresses alanine aminotransferase and has a transferred DNA encoding a desired polypeptide and thereby allowing the cell to produce said polypeptide.

Effect of the Invention

According to the present invention, it has become possible to increase the yield of a desired polypeptide.

The present specification encompasses the contents disclosed in the specification and/or the drawings of Japanese Patent Application No. 2007-205158 based on which the present patent application claims priority.

BRIEF DESCRIPTION OF THE DRAWINGS

FIG. 8 shows the nucleotide sequence of a newly cloned, CHO cell-derived hamster taurine transporter gene and the amino acid sequence deduced therefrom.

BEST MODE FOR CARRYING OUT THE INVENTION

Figure 1:
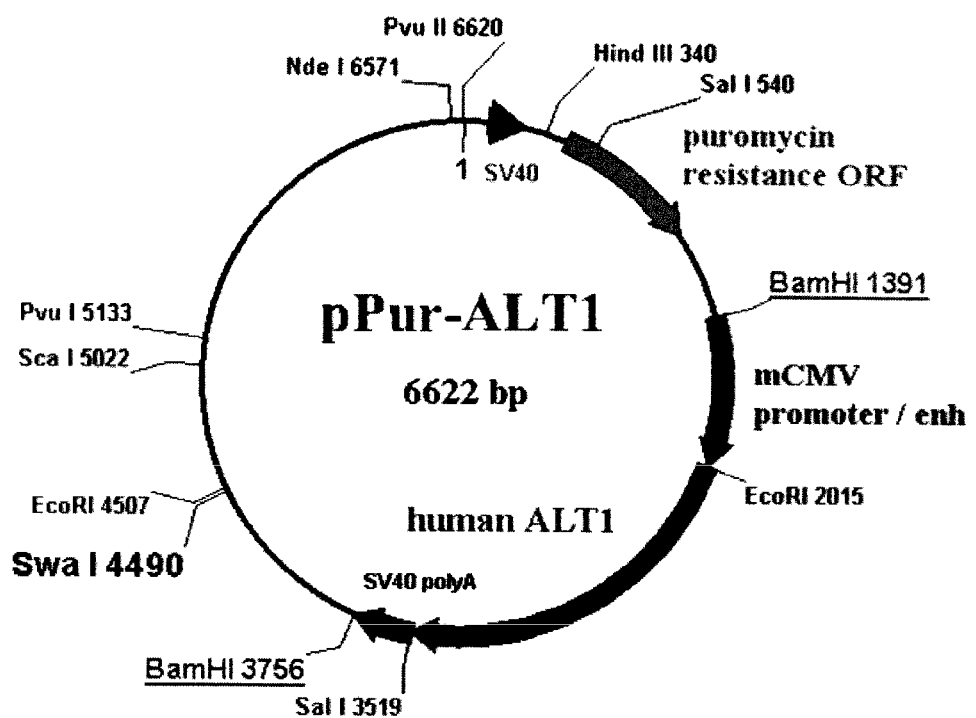
FIG. 1 shows a plasmid for Puromycin selection which was used for expressing human ALT1 (496 amino acids).

Hereinbelow, embodiments of the present invention will be described in more detail.

The present invention provides a method of producing a polypeptide, comprising culturing a cell which strongly expresses ALT and has a transferred DNA encoding a desired polypeptide and thereby allowing the cell to produce the polypeptide.

In the method of the present invention, the cell may be either a natural cell capable of producing the desired polypeptide or a transformed cell into which a DNA encoding the desired polypeptide has been transferred. Preferably, a transformed cell into which a DNA encoding the desired polypeptide has been transferred is used.

In the method of the present invention, the desired polypeptide is not particularly limited. The polypeptide may be any polypeptide such as an antibody (e.g., anti-IL-6 receptor antibody, anti-IL-6 antibody, anti-glypican-3 antibody, anti-CD3 antibody, anti-CD20 antibody, anti-GPIIb/IIIa antibody, anti-TNF antibody, anti-CD25 antibody, anti-EGFR antibody, anti-Her2/neu antibody, anti-RSV antibody, anti-CD33 antibody, anti-CD52 antibody, anti-IgE antibody, anti-CD11a antibody, anti-VEGF antibody, anti-VLA4 antibody, and the like) or a physiologically active protein (e.g., granulocyte-colony stimulating factor (G-CSF), granulocyte macrophage-colony stimulating factor (GM-CSF), erythropoietin, interferon, interleukin such as IL-1 or IL-6, t-PA, urokinase, serum albumin, blood coagulation factor, PTH, and the like). An antibody is particularly preferred, and may be any antibody such as a natural antibody, a low molecular sized antibody (e.g., Fab, scFv, sc(Fv)2), a chimeric antibody, a humanized antibody, etc.

By using strongly ALT expressing cells, the amount of a polypeptide produced by cells can be increased.

ALT is fundamentally known as an enzyme that produces glutamate by transferring an amino group from alanine to 2-oxoglutarate. The present inventors considered that if the reaction of biosynthesizing pyruvate and glutamate from alanine could be promoted by strongly expressing ALT in host cells such as CHO cells, the products might be utilized in metabolism during a TCA cycle and glucose production by glycogenesis, and this might improve cell culture behavior, leading to high-yield production of the desired polypeptide.

The strongly ALT expressing cells are not particularly limited as long as they are capable of ALT expression at higher levels than natural cells. Natural cells include, but are not particularly limited to, cells that are used as hosts in the production of recombinant proteins and may be exemplified by CHO cells.

A cell which strongly expresses ALT is not particularly limited as long as the cell has an increased expression level of ALT compared to a corresponding natural cell. The natural cell is not particularly limited. A cell which is used as a host in the production of a recombinant protein (e.g., CHO cells) may be used.

As a cell which strongly expresses ALT, a cell into which an ALT gene has been artificially transferred may be given. A cell into which an ALT gene has been artificially transferred can be prepared by methods known to those skilled in the art. For example, such a cell may be prepared by incorporating an ALT gene into a vector and transforming the vector into a cell. Furthermore, the concept of "cells into which an ALT gene has been artificially transferred" encompasses herein cells in which an endogenous ALT gene has been activated by gene activation technology (see, for example, International Publication WO94/12650) so that ALT is strongly expressed.

As ALT to be strongly expressed in a cell, ALT derived from any organism may be used. Specifically, ALTs derived from human, mouse, rat, dog, African clawed frog, fruit fly, nematode, Japanese rice, *Cyanidioschyzon merolae*, *Saccharomyces cerevisiae*, *Ashbya gossypii*, *Candida albicans*, *Schizosaccharomyces pombe*, *Aspergillus nidulans*, *Aspergillus fumigatus*, *Aspergillus oryzae*, *Cryptococcus neoformans*, *Dictyostelium discoideum*, *Trypanosoma brucei*, *Leishmania major*, *Entamoeba histolytica* and *Trypanosoma cruzi* are known and can be used. Preferably, ALT derived from human, a rodent or the same species as the host cell may be used. For example, when the cell which is allowed to strongly express ALT is Chinese hamster ovary cells (CHO cells), ALT is preferably derived from human or hamster. For ALT in humans, mice, and yeast, variants (ALT1 and ALT2) exist. ALT2 has 80% or greater homology to ALT1 at the amino acid level. ALT1 was forcedly expressed in the Examples described later.

Further, as an ALT gene to be strongly expressed in a cell, any one of the following DNAs (a) to (e) encoding ALT may be used.

(a) a DNA encoding a polypeptide having the amino acid sequence as shown in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60;

(b) a DNA encoding a polypeptide which has an amino acid sequence derived from the amino acid sequence as shown in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60 by substitution, deletion, addition and/or insertion of one or more amino acid residues and yet has alanine aminotransferase activity;

(c) a DNA encoding a polypeptide having 70% or more amino acid sequence homology with the amino acid sequence as shown in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60 and yet having alanine aminotransferase activity;

(d) a DNA having the nucleotide sequence as shown in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57 or 59;

(e) a DNA which hybridizes to a DNA complementary to a DNA having the nucleotide sequence as shown in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57 or 59 under stringent conditions and yet encodes a polypeptide having alanine aminotransferase activity.

The cell which strongly expresses ALT may be any cell, for example, eukaryotic cell such as animal, plant and yeast cells, prokaryotic cell such as *E. coli* and *B. subtilis*, etc. Preferably, animal cells such as CHO and COS cells are used, CHO cells are particularly preferred. In order to prepare a desired polypeptide, cells suitable for transfer of a gene encoding the desired polypeptide such as CHO-dhfr- cells are preferred.

Preferably, the cell of the present invention which strongly expresses ALT further expresses a taurine transporter strongly in order to prepare a desired polypeptide. By transferring a gene encoding the desired polypeptide into the cell and culturing the resultant cell in a medium, the desired polypeptide can be produced in a greater amount.

When a desired polypeptide is produced using a cell into which an ALT gene has been artificially transferred, the order of the transfer of an ALT gene and the transfer of a gene encoding a desired polypeptide is not particularly limited. A gene encoding a desired polypeptide may be transferred after the transfer of an ALT gene. Alternatively, an ALT gene may be transferred after the transfer of a gene encoding a desired polypeptide. It is also possible to transfer an ALT gene and a gene encoding a desired polypeptide simultaneously.

An ALT gene and a gene encoding a desired polypeptide may be transferred simultaneously in a single vector. Alternatively, they may be transferred separately using a plurality of vectors.

By using a cell which strongly expresses ALT and a taurine transporter, an intracellular ammonia concentration can decline.

It is known that taurine transporter is a membrane protein having the osmoregulatory function of taking up amino acids (such as taurine and β-alanine) into cells.

A cell which strongly expresses a taurine transporter is not particularly limited as long as the cell has an increased expression level of a taurine transporter compared to a corresponding natural cell. The natural cell is not particularly limited. A cell which is used as a host in the production of a recombinant protein (e.g., CHO cells) may be used.

As a cell which strongly expresses a taurine transporter, a cell into which a taurine transporter gene has been artificially transferred may be given. A cell into which a taurine transporter gene has been artificially transferred can be prepared by methods known to those skilled in the art. For example, such a cell may be prepared by incorporating a taurine transporter gene into a vector and transforming the vector into a cell.

As a taurine transporter to be strongly expressed in a cell, a taurine transporter derived from any organism may be used. Specifically, a taurine transporter derived from human or a rodent (such as mouse, rat or hamster) may be used. Preferably, a taurine transporter derived from human, a rodent or the same species as the host cell may be used. For example, when the cell which is allowed to strongly express a taurine transporter is Chinese hamster ovary cells (CHO cells), the taurine transporter is preferably derived from human or hamster.

Further, as a taurine transporter gene to be strongly expressed in a cell, any one of the following DNAs ($a_1$) to ($e_1$) encoding a taurine transporter may be used.

($a_1$) a DNA encoding a polypeptide having the amino acid sequence as shown in SEQ ID NO: 62, 64, 66 or 68;
($b_1$) a DNA encoding a polypeptide which has an amino acid sequence derived from the amino acid sequence as shown in SEQ ID NO: 62, 64, 66 or 68 by substitution, deletion, addition and/or insertion of one or more amino acid residues and yet has taurine transporter activity;
($c_1$) a DNA encoding a polypeptide having 70% or more amino acid sequence homology with the amino acid sequence as shown in SEQ ID NO: 62, 64, 66 or 68 and yet having taurine transporter activity;
($d_1$) a DNA having the nucleotide sequence as shown in SEQ ID NO: 61, 63, 65 or 67;
($e_1$) a DNA which hybridizes to a DNA complementary to a DNA having the nucleotide sequence as shown in SEQ ID NO: 61, 63, 65 or 67 under stringent conditions and yet encodes a polypeptide having taurine transporter activity.

Production of a desired polypeptide may be performed by transferring a gene encoding the desired polypeptide into a cell which strongly expresses a taurine transporter gene and an ALT gene and culturing the resultant cell in a medium. Furthermore, a desired polypeptide can be prepared by using a cell in which an endogenous gene has been activated by gene activation technology (see, for example, International Publication WO94/12650) so that a desired polypeptide has been produced.

When a desired polypeptide is produced using a cell into which a taurine transporter gene and an ALT gene have been artificially transferred, the order of the transfer of a taurine transporter gene, the transfer of an ALT gene and the transfer of a gene encoding a desired polypeptide is not particularly limited. A gene encoding a desired polypeptide may be transferred after the transfer of a taurine transporter gene and an ALT gene. Alternatively, a taurine transporter gene and an ALT gene may be transferred after the transfer of a gene encoding a desired polypeptide. It is also possible to transfer a taurine transporter gene, an ALT gene and a gene encoding a desired polypeptide simultaneously.

A taurine transporter gene, an ALT gene and a gene encoding a desired polypeptide may be transferred simultaneously in a single vector. Alternatively, they may be transferred separately using a plurality of vectors.

For culturing the cell which strongly expresses ALT (and which may strongly express a taurine transporter), media used in conventional cell culture (preferably, animal cell culture) may be used. These media usually contain amino acids, vitamins, lipid factors, energy sources, osmotic regulators, iron sources and pH regulators. The contents of these components are usually as follows: amino acids 0.05-1500 mg/L, vitamins 0.001-10 mg/L, lipid factors 0-200 mg/L, energy sources 1-20 g/L, osmotic regulators 0.1-10000 mg/L, iron sources 0.1-500 mg/L, pH regulators 1-10000 mg/L, trace metal elements 0.00001-200 mg/L, surfactants 0-5000 mg/L, growth cofactors 0.05-10000 µg/L and nucleosides 0.001-50 mg/L. However, the contents are not limited to these ranges and may be appropriately selected depending on the type of the cell to be cultured, the type of the desired polypeptide, and so on.

In addition to these components, trace metal elements, surfactants, growth cofactors, nucleosides, and the like may be added.

Specific examples of such components include amino acids, such as L-alanine, L-arginine, L-asparagine, L-aspartic acid, L-cysteine, L-cystine, L-glutamine, L-glutamic acid, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine, preferably, L-alanine, L-arginine, L-asparagine, L-aspartic acid, L-cystine, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine and L-valine; vitamins, such as i-inositol, biotin, folic acid, lipoic acid, nicotinamide, nicotinic acid, p-aminobenzoic acid, calcium pantothenate, pyridoxal hydrochloride, pyridoxine hydrochloride, riboflavin, thiamine hydrochloride, vitamin $B_{12}$ and ascorbic acid, preferably, biotin, folic acid, lipoic acid, nicotinamide, calcium pantothenate, pyridoxal hydrochloride, riboflavin, thiamine hydrochloride, vitamin $B_{12}$ and ascorbic acid; lipid factors, such as choline chloride, choline tartrate, linoleic acid, oleic acid and cholesterol, preferably, choline chloride; energy sources, such as glucose, galactose, mannose, and fructose, preferably, glucose; osmotic regulators, such as sodium chloride, potassium chloride, and potassium nitrate, preferably, sodium chloride; iron sources, such as iron EDTA, ferric citrate, ferrous chloride, ferric chloride, ferrous sulfate, ferric sulfate, and ferric nitrate, preferably, ferric chloride, iron EDTA, and ferric citrate; and pH regulators, such as sodium hydrogencarbonate, calcium chloride, sodium dihydrogen-phosphate, HEPES and MOPS, preferably, sodium hydrogencarbonate. Culture media containing any of these components may be given as examples.

Besides the above components, there may be added trace metal elements, such as copper sulfate, manganese sulfate, zinc sulfate, magnesium sulfate, nickel chloride, tin chloride, magnesium chloride and sodium subsilicate, preferably, copper sulfate, zinc sulfate and magnesium sulfate; surfactants, such as Tween 80 and Pluronic F68; growth cofactors, such as recombinant insulin, recombinant IGF-1, recombinant EGF, recombinant FGF, recombinant PDGF, recombinant TGF-α, ethanolamine hydrochloride, sodium selenite, retinoic acid and putrescine dihydrochloride, preferably, sodium selenite, ethanolamine hydrochloride, recombinant IGF-1 and putrescine dihydrochloride; and nucleosides, such as deoxyadenosine, deoxycytidine, deoxyguanosine, adenosine, cytidine, guanosine and uridine. In preferable examples of above media, antibiotics, such as streptomycin, penicillin-G potassium and gentamicin, and pH-indicators, such as Phenol Red, may be contained.

Further, α-ketoglutarate, serving as a substrate for ALT, can be added to the medium. The yield of the desired polypeptide (for example, an antibody) can be increased by addition of α-ketoglutarate. In this case, the amount of α-ketoglutarate to be added is normally in the range of 0.01 to 1000 mM, preferably 0.1 to 100 mM, and more preferably 1 to 10 mM.

The pH of the medium varies depending on the cell to be cultured. Generally, pH 6.8-7.6 is appropriate. In many cases, pH 7.0-7.4 is appropriate.

It is also possible to use a commercial medium for animal cell culture, e.g., D-MEM (Dulbecco's Modified Eagle Medium), D-MEM/F-12 1:1 Mixture (Dulbecco's Modified Eagle Medium: Nutrient Mixture F-12), RPMI1640, CHO-S-SFMII (Invitrogen), CHO-SF (Sigma-Aldrich), EX-CELL 301 (JRH Biosciences), CD-CHO (Invitrogen), IS CHO-V (Irvine Scientific), PF-ACF-CHO (Sigma-Aldrich) or the like.

Alternatively, the medium may be a serum-free medium such as CD-CHO (Invitrogen).

When the cell which strongly expresses ALT (and which may strongly express a taurine transporter) is CHO cells, CHO cells may be cultured by methods known to those skilled in the art. For example, CHO cells may be cultured usually in an atmosphere with a $CO_2$ concentration in the gas phase of 0 to 40%, preferably 2 to 10%, at 30 to 39° C., preferably about 37° C.

Moreover, in the case where the desired polypeptide such as an antibody is produced by cell culture, cells become highly confluent at the late stage of the culture (approximately $1 \times 10^7$ cells/ml), and the effect of waste products such as lactate becomes extremely high. If the desired polypeptide is produced by strongly ALT expressing cells, a high survival ratio is maintained even at the late stage of the culture, and an improvement in the yield of the desired polypeptide can also be anticipated.

An appropriate culture period for producing a desired polypeptide using the cell which strongly expresses ALT is usually 1 day to 3 months, preferably 1 day to 2 months, more preferably 1 day to 1 month.

With respect to various culture devices for animal cell culture, a fermentor type tank culture device, an air lift type culture device, a culture flask type culture device, a spinner flask type culture device, a microcarrier type culture device, a fluidized bed type culture device, a hollow fiber type culture device, a roller bottle type culture device, a packed bed type culture device, or the like may be used.

Culture may be performed by any culture method such as batch culture, fed-batch culture or continuous culture. Preferably, fed-batch culture or continuous culture is used. Fed-batch culture is more preferred.

When the cell which strongly expresses ALT (and which may strongly express a taurine transporter) is cultured, taurine may be added to the medium in order to promote taurine uptake into cells. The concentration of taurine to be added to the medium is not specifically limited, but is normally in the range of 0 g/L to 100 g/L, preferably 0 g/L to 20 g/L, and more preferably 0 g/L to 10 g/L.

When the polypeptide produced according to the method of the present invention has a biological activity useful as a pharmaceutical, it is possible to produce a pharmaceutical by mixing this polypeptide with pharmaceutically acceptable carriers or additives and formulating into a preparation.

Specific examples of pharmaceutically acceptable carriers and additives include water, organic solvents that are pharmaceutically acceptable, collagen, polyvinyl alcohol, polyvinylpyrrolidone, carboxyvinyl polymer, carboxymethylcellulose sodium, sodium polyacrylate, sodium alginate, water-soluble dextran, carboxymethyl starch sodium, pectin, methylcellulose, ethyl cellulose, xanthan gum, gum Arabic, casein, agar-agar, polyethylene glycol, diglycerin, glycerin, propylene glycol, petrolatum, paraffin, stearyl alcohol, stearic acid, human serum albumin (HSA), mannitol, sorbitol, lactose, and surfactants that are acceptable as pharmaceutical additives.

Actual additives may be selected from the above-mentioned additives singly or in combination according to the dosage form of the therapeutic of the present invention, but are not limited to those listed above. For example, when a polypeptide is used in an injectable formulation, the purified polypeptide may be dissolved in a solvent such as physiological saline, buffer or a glucose solution, and then an adsorption inhibitor such as Tween 80, Tween 20, gelatin or human serum albumin may be added to the solution. Alternatively, a freeze-dried agent may be used to prepare a dosage form which is dissolved and reconstituted prior to use. Examples of the excipient useful for freeze-drying include sugar alcohols and saccharides such as mannitol and glucose.

Effective doses of the polypeptide may be appropriately selected depending on the type of the polypeptide, the type of the disease to be treated or prevented, the age of the patient, the severity of the disease, etc. For example, when the polypeptide is anti-glypican antibody, the effective dose of anti-glypican antibody is selected within a range of 0.001 mg to 1000 mg per kg of body weight per administration. Alternatively, a dose of 0.01-100000 mg/body may be selected per patient. However, effective dose is not limited to these ranges.

The polypeptide may be administered either orally or parenterally, but parenteral administration is preferred. Specifically, injection (e.g., systemic or local administration by intravenous injection, intramuscular injection, intraperitoneal injection, subcutaneous injection, etc.), transnasal administration, transpulmonary administration, transdermal administration and the like may be enumerated.

In the present invention, as a gene encoding ALT, a DNA encoding a polypeptide having the amino acid sequence as shown in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60 may be used. Alternatively, a DNA encoding a polypeptide which has an amino acid sequence derived from the amino acid sequence as shown in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60 by substitution, deletion, addition and/or insertion of one or more amino acid residues and yet has alanine aminotransferase activity may be used.

The polypeptide which has an amino acid sequence derived from the amino acid sequence as shown in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60 by substitution, deletion, addition and/or insertion of one or more amino acid residues and yet has alanine aminotransferase activity is functionally equivalent to ALT derived from human, mouse, rat, dog, African clawed frog, fruit fly, nematode, Japanese rice, *Cyanidioschyzon merolae, Saccharomyces cerevisiae, Ashbya gossypii, Candida albicans, Schizosaccharomyces pombe, Aspergillus nidulans, Aspergillus fumigatus, Aspergillus oryzae, Cryptococcus neoformans, Dictyostelium discoideum, Trypanosoma brucei, Leishmania major, Entamoeba histolytica* or *Trypanosoma cruzi* (hereinafter sometimes referred to as "ALT derived from human or the like"). Such a polypeptide encompasses, for example, mutants of ALT derived from human or the like. In Example described below, a mutant in which four out of 496 amino acids were replaced (R53S, Q72R, F286S and M332K) was used.

As methods well-known to those skilled in the art for preparing polypeptides functionally equivalent to a specific polypeptide, methods of introducing mutations into polypeptides may be given. For example, those skilled in the art could prepare polypeptides functionally equivalent to ALT derived from human or the like by appropriately introducing mutations into amino acids of ALT derived from human or the like by site-directed mutagenesis (Hashimoto-Gotoh, T. et al. (1995) Gene 152, 271-275; Zoller, M J, and Smith, M (1983) Methods Enzymol. 100, 468-500; Kramer, W. et al. (1984) Nucleic Acids Res. 12, 9441-9456; Kramer W, and Fritz H J (1987) Methods. Enzymol. 154, 350-367; Kunkel, T A (1985) Proc Natl Acad Sci USA. 82, 488-492; Kunkel (1988) Methods Enzymol. 85, 2763-2766). Mutations in amino acids may also occur in nature.

Specific examples of polypeptides functionally equivalent to the ALT derived from human or the like include, but are not limited to, a polypeptide having an amino acid sequence derived from the amino acid sequence (e.g., SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60) of the ALT derived from human or the like by deletion of one or more amino acids, preferably 1-30 amino acids, more preferably 1-10 amino acids; a polypeptide having an amino acid sequence derived from the amino acid sequence of the ALT derived from human or the like by addition of one or more amino acids, preferably 1-30 amino acids, more preferably 1-10 amino acids; and a polypeptide having an amino acid sequence derived from the amino acid sequence of the ALT derived from human or the like by substitution of one or more amino acids, preferably 1-30 amino acids, more preferably 1-10 amino acids, with other amino acids.

Amino acid residues to be mutated are not particularly limited. Preferably, amino acid residues are mutated to other amino acids in which the nature of the initial amino acid side chain is conserved. Specific examples of the nature of amino acid side chain include hydrophobic amino acids (A, I, L, M, F, P, W, Y and V), hydrophilic amino acids (R, D, N, C, E, Q, G, H, K, S and T), amino acids with an aliphatic side chain (G, A, V, L, I and P), amino acids with a hydroxyl group-containing side chain (S, T and Y), amino acids with a sulfur atom-containing side chain (C and M), amino acids with a carboxylic acid and amide-containing side chain (D, N, E and Q), amino acids with a base-containing side chain (R, K and H) and amino acids with an aromatic-containing side chain (H, F, Y and W) (In parentheses are one-letter codes for amino acids).

It has been reported that a polypeptide having an amino acid sequence derived from an original amino acid sequence by modification (such as deletion, addition and/or substitution of one or more amino acids) maintains the biological activity of the original polypeptide (Mark, D. F. et al., Proc. Natl. Acad. Sci. USA (1984) 81, 5662-5666; Zoller, M. J. & Smith, M. Nucleic Acids Research (1982) 10, 6487-6500; Wang, A. et al., Science 224, 1431-1433; Dalbadie-McFarland, G et al., Proc. Natl. Acad. Sci. USA (1982) 79, 6409-6413).

As one example of the polypeptide in which one or more amino acid residues are added to the ALT derived from human or the like, a fusion polypeptide comprising the ALT derived from human or the like may be given. Such a fusion polypeptide is composed of the ALT derived from human or the like and other polypeptide fused thereto. Such a fusion polypeptide may be prepared by linking a gene encoding the ALT derived from human or the like in frame with a gene encoding the other polypeptide, transferring the resultant DNA into an expression vector and expressing the DNA in a host cell. Techniques known to those skilled in the art may be used. There is no limitation on the polypeptide to be fused to the ALT derived from human or the like.

Examples of polypeptides to be fused to the ALT derived from human or the like include, but are not limited to, FLAG (Hopp, T. P. et al., BioTechnology (1988) 6, 1204-1210), 6×His comprising six histidine (His) residues, 10×His, influenza hemagglutinin (HA), human c-myc fragment, VSV-GP fragment, p18HIV fragment, T7-tag, HSV-tag, E-tag, SV40T antigen fragment, lck tag, α-tubulin fragment, B-tag, protein C fragment, glutathione-S-transferase (GST), influenza hemagglutinin (HA), immunoglobulin constant region, β-galactosidase and maltose-binding protein (MBP).

A commercially available gene encoding such polypeptide is fused to the gene encoding the ALT derived from human or the like. The fused gene thus prepared is expressed to prepare a fused polypeptide.

An alternative method known to those skilled in the art for preparing polypeptides functionally equivalent to a specific polypeptide is a method using the hybridization technique (Sambrook, J et al., Molecular Cloning 2nd ed., 9.47-9.58, Cold Spring Harbor Lab. Press, 1989). Those skilled in the art could routinely isolate a DNA highly homologous to the DNA sequence (e.g., SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57 or 59) of the ALT derived from human or the like based on that DNA sequence or a part thereof, and isolate polypeptides functionally equivalent to the ALT derived from human or the like from that DNA.

Hybridization conditions for isolating a DNA encoding a polypeptide functionally equivalent to the ALT derived from human or the like can be appropriately selected by those skilled in the art. For example, low stringent hybridization conditions may be given. Low stringent hybridization conditions are, for example, 42° C., 2×SSC and 0.1% SDS, preferably 50° C., 2×SSC and 0.1% SDS. More preferably, high stringent conditions may be given. For example, high stringent conditions are 65° C., 2×SSC and 0.1% SDS. Under these conditions, as the hybridization temperature is lowered, not only DNAs with high homology but also DNAs with only low homology are obtained. Conversely, it is expected that only those DNAs with high homology are obtained as the hybridization temperature is elevated. However, not only the temperature but also a plurality of factors (such as salt concentrations) affect the stringency of hybridization. Those skilled in the art could appropriately select these factors to realize similar stringency.

The polypeptide encoded by a DNA isolated by these hybridization techniques may have 70% or more homology and usually has high homology with the ALT derived from human or the like in the amino acid sequence. The term "high homology" refers to usually 97% or more homology, preferably 98% or more homology, more preferably 99% or more homology. For determination of the homology of polypeptides, the algorithm described in Wilbur, W. J. and Lipman, D. J., Proc. Natl. Acad. Sci. USA (1983) 80, 726-730 may be followed.

The polypeptide may vary in amino acid sequence, molecular weight, isoelectric point, presence or absence of sugar chains, morphology, etc. depending on the cell or host that produce the polypeptide or the purification method that will be described later. However, as long as the resultant polypeptide has functions equivalent to the functions of the ALT derived from human or the like, DNA encoding the polypeptide can be used in the present invention. For example, when the polypeptide of the present invention is expressed in a prokaryote (e.g., Escherichia coli), a methionine reside is added to the N-terminus of the initial amino acid sequence of the polypeptide. When the polypeptide is expressed in a eukaryote (e.g., a mammalian cell), the N-terminal signal sequence is removed. These polypeptides can be used in the present invention.

The polypeptide may be prepared as a recombinant polypeptide or a natural polypeptide by methods known to those skilled in the art. A recombinant polypeptide may be prepared by incorporating a DNA encoding the polypeptide in an appropriate expression vector, introducing the vector into an appropriate host cell, collecting the resultant transformant, extracting a crude polypeptide, and then purifying the polypeptide by chromatography (such as ion exchange, reversed phase or gel filtration chromatography, or affinity chromatography in which an antibody to the polypeptide prepared by the method of the present invention is fixed in a column) or a combination of these chromatographic techniques.

When the polypeptide is expressed in a host cell (e.g., animal cell or E. coli) as a fusion polypeptide with glutathione-S-transferase polypeptide or as a recombinant polypeptide with histidine residues added thereto, the expressed polypeptide may be purified with a glutathione column or a nickel column.

After purification of a fusion polypeptide, regions other than the polypeptide of interest may be cut off by thrombin or factor Xa and removed from the fusion polypeptide.

When the polypeptide is a natural polypeptide, the polypeptide may be isolated by purification methods known to those skilled in the art. For example, an extract from tissues or cells expressing the polypeptide functionally equivalent to the ALT derived from human or the like may be applied to an affinity column to which an antibody to the ALT derived from human or the like is bound. The antibody may be either a polyclonal antibody or a monoclonal antibody.

In the present invention, as DNA encoding ALT, a DNA having the nucleotide sequence as shown in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57 or 59 may be used. Alternatively, a DNA which hybridizes to a DNA complementary to a DNA having the nucleotide sequence as shown in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57 or 59 under stringent conditions and yet encodes a polypeptide having alanine aminotransferase activity, may be used.

The DNA encoding ALT can be used in the in vivo or in vitro production of a desired polypeptide as described above. Further, the DNA encoding ALT may be used in the creation of a cell which strongly expresses ALT. The DNA encoding ALT may take any form as long as it is capable of encoding ALT. That is, the DNA may be, for example, a cDNA synthesized from mRNA, a genomic DNA or a chemically synthesized DNA. It should be noted that, as long as the DNA is capable of encoding ALT, the DNA may have any nucleotide sequence based on the degeneracy of genetic codes.

The DNA encoding ALT may be prepared by methods known to those skilled in the art. For example, the DNA may be prepared by preparing a cDNA library from a cell expressing ALT and performing hybridization using a part of the DNA sequence of ALT (e.g., SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57 or 59) as a probe. The cDNA library may be prepared, for example, by the method described in Sambrook, J. et al., Molecular Cloning, Cold Spring Harbor Laboratory Press (1989). Alternatively, a commercial cDNA library may be used. It is also possible to prepare the DNA encoding ALT by preparing RNA from a cell expressing ALT, synthesizing oligo DNA molecules based on the DNA sequence of ALT (e.g., SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57 or 59), and performing PCR using the oligo DNA molecules as primers to thereby amplify a cDNA encoding ALT.

Further, by determining the nucleotide sequence of the resultant cDNA, it is possible to determine the translation region encoding ALT and to obtain the amino acid sequence of ALT. Further, by screening a genomic library using the resultant cDNA as a probe, it is possible to isolate a genomic DNA.

Specifically, the following procedures may be used. First, mRNA is isolated from cells, tissues or the like expressing ALT. For the isolation of mRNA, the total RNA is prepared by known methods, for example, the guanidine ultracentrifugation method (Chirgwin, J. M. et al., Biochemistry (1979) 18, 5294-5299), the AGPC method (Chomczynski, P. and Sacchi, N., Anal. Biochem. (1987) 162, 156-159) or the like, and then mRNA is purified from the total RNA using mRNA Purification Kit (Pharmacia), etc. Alternatively, mRNA may be prepared directly using QuickPrep mRNA Purification Kit (Pharmacia).

From the resultant mRNA, cDNA is synthesized using a reverse transcriptase. Alternatively, cDNA may be synthesized using a kit such as AMY Reverse Transcriptase FirstStrand cDNA Synthesis Kit (SEIKAGAKU CORPORATION). It is also possible to synthesize and amplify cDNA according to the 5'-RACE method (Frohman, M. A. et al., Proc. Natl. Acad. Sci. USA (1988) 85, 8998-9002; Belyaysky, A. et al., Nucleic Acids Res. (1989) 17, 2919-2932) using 5'-Ampli FINDER RACE Kit (Clontech) and polymerase chain reaction (PCR) with primers.

A DNA fragment of interest is prepared from the resultant PCR product and ligated to a vector DNA to thereby prepare a recombinant vector. The vector is introduced into a host (e.g., E. coli), followed by selection of resultant colonies to thereby obtain a desired recombinant vector. The nucleotide sequence of the DNA of interest may be confirmed by a known method such as the dideoxynucleotide chain termination method.

Further, a nucleotide sequence of higher expression efficiency can be designed for the DNA encoding ALT by considering the frequency of codon usage in the host to be used for expression (Grantham, R. et al., Nucleic Acids Research (1981) 9, p. 43-74). Further, the DNA encoding ALT can be modified using commercially available kits or known methods. Examples of such modifications include, but are not limited to, digestion with restriction enzymes, insertion of synthetic oligonucleotides or appropriate DNA fragments, addition of linkers, and insertion of an initiation codon (ATG) and/or a termination codon (TAA, TGA or TAG).

The DNA encoding ALT also includes a DNA which hybridizes to a DNA having the nucleotide sequence as shown in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57 or 59 under stringent conditions and encodes a polypeptide functionally equivalent to ALT.

Stringent conditions can be appropriately selected by those skilled in the art, including, for example, low stringent conditions. Low stringent conditions refer to, for example, 42° C., 2×SSC and 0.1% SDS, preferably 50° C., 2×SSC and 0.1% SDS. More preferably, high stringent conditions may be selected. High stringent conditions refer to, for example, 65° C., 2×SSC and 0.1% SDS. Under these conditions, as the hybridization temperature is elevated, DNAs with a higher homology can be obtained. The above-described DNA which hybridizes is preferably a DNA derived from nature, e.g., cDNA or chromosomal DNA.

These DNAs isolated by hybridization techniques usually have a high nucleotide sequence identity with a DNA encoding the ALT derived from human or the like. The DNA encoding ALT also includes a DNA which encodes a polypeptide functionally equivalent to the ALT derived from human or the like and has high identity with a DNA encoding the ALT derived from human or the like. The term "high identity" refers to usually 96% or more homology, preferably 98% or more homology, more preferably 99% or more identity. The identity of nucleotide sequences may be determined by algorithm BLAST (Karlin and Altschul, Proc. Natl. Acad. Sci. USA 90:5873-5877, 1993). Based on this algorithm, programs such as BLASTN and BLASTX have been developed (Altschul et al. J. Mol. Biol. 215:403-410, 1990). When nucleotide sequences are analyzed by BLASTN based on BLAST, parameters may be set as score=100 and wordlength=12, for example. Specific procedures for these analysis methods are known (http://www.ncbi.nlm.nih.gov.).

The DNA encoding ALT may be inserted into a vector. When the host cell to be used is *E. coli*, it is preferable that the vector has a replication origin ("ori") so that the vector is largely amplified in *E. coli* (e.g., JM109, DH5α, HB101 and XL1-Blue) and prepared in large quantity, and also genes for selecting transformed *E. coli* (e.g., drug resistance genes that enable discrimination of transformant with some drugs such as ampicillin, tetracycline, kanamycin or chloramphenicol). Examples of preferable vectors include, but are not limited to, M13 vectors, pUC vectors, pBR322, pBluescript and pCR-Script. In addition to these vectors, pGEM-T, pDIRECT, pT7, etc. may be enumerated when the vector is used for the purpose of subcloning a cDNA and cutting off the subcloned cDNA. When the vector is used for the purpose of producing the polypeptide of the present invention, an expression vector is especially useful. When expression in *E. coli* is intended, the expression vector preferably has the above-described features so that the vector is amplified in *E. coli*, and it also preferably has a promoter which allows efficient expression in *E. coli* such as JM109, DH5α, HB101 or XL1-Blue, e.g., lacZ promoter (Ward et al, Nature (1989) 341, 544-546; FASEB J. (1992) 6, 2422-2427), araB promoter (Better et al, Science (1988) 240, 1041-1043) or T7 promoter. Specific examples of such vector include, in addition to those listed above, pGEX-5X-1 (Pharmacia), QIAexpress system (Qiagen), pEGFP, or pET (for its host, T7 RNA polymerase-expressing BL21 is preferred).

The vector may comprise signal sequences for polypeptide secretion. When the polypeptide is to be produced in the periplasm of *E. coli*, pelB signal sequence (Lei, S. P. et al., J. Bacteriol. (1987) 169, 4379) may be used as a signal sequence for polypeptide secretion. Introduction of the vector into a host cell may be performed, for example, by the calcium chloride method or electroporation.

In cases where a host cell other than *E. coli* is used, vectors useful for producing a desired polypeptide include, but are not limited to, mammal-derived expression vectors [e.g., pcDNA3 from Invitrogen; pEGF-BOS (Nucleic Acids. Res. 1990, 18(17), p. 5322); pEF, pCDM8], insect cell-derived expression vectors (e.g., Bac-to-BAC baculovairus expression system from GIBCO BRL; pBacPAK8), plant-derived expression vectors (e.g., pMH1, pMH2), animal virus-derived expression vectors (e.g., pHSV, pMV, pAdex-Lcw), retrovirus-derived expression vectors (e.g., pZIpneo), yeast-derived expression vectors (e.g., *Pichia* Expression Kit from Invitrogen; pNV11; SP-Q01), and *Bacillus subtilis*-derived expression vectors (e.g., pPL608, pKTH50).

When expression of the polypeptide in animal cells (such as CHO cells, COS cells, NIH3T3 cells, etc.) is intended, the vector preferably has a promoter necessary for expressing the polypeptide in those cells. Examples of such promoter include, but are not limited to, SV40 promoter (Mulligan et al, Nature (1979) 277, 108), MMLV-LTR promoter, EF1α promoter (Mizushima et al., Nucleic Acids Res. (1990) 18, 5322) and CMV promoter. More preferably, the vector also has genes for selecting transformed cells (e.g., drug resistance genes that enable discrimination with drugs such as neomycin or G418). Examples of vectors having such properties include, but are not limited to, pMAM, pDR2, pBK-RSV, pBK-CMV, pOPRSV and pOP13.

Further, when stable expression of a gene of interest and intracellular amplification of the copy number of the gene are indented, the following method may be used. Briefly, into CHO cells lacking a nucleic acid synthesis pathway, a vector having DHFR gene that complements the lack (e.g., pCHOI) is introduced, followed by amplification with methotrexate (MTX). On the other hand, when tentative expression of a gene of interest is intended, a method may be used in which COS cells carrying a gene expressing SV40T antigen on the chromosome is transformed with a vector having the replication origin of SV40 (e.g., pcD). As the replication origin, a replication origin derived from polyomavirus, adenovirus or bovine papillomavirus (BPV) may also be used. Further, the expression vector may contain selectable markers for amplifying the copy number of the gene in a host cell system. Examples of such selectable markers include, but are not limited to, aminoglycoside phosphotransferase (APH) gene, thymidine kinase (TK) gene, *E. coli* xanthine-guanine phosphoribosyl transferase (Ecogpt) gene and dihydrofolate reductase (dhfr) gene.

The host cell into which the DNA encoding ALT (which may be incorporated in a vector) is transferred is not particularly limited. For example, *E. coli* or various animal cells may be used. If DNA encoding a desired polypeptide is transferred into a host cell into which DNA encoding ALT is transferred, this host cell can express ALT strongly, which leads to an increased production of the desired polypeptide. DNA encoding a taurine transporter (which may be incorporated into a vector) may be further transferred into the host cell into which DNA encoding ALT is transferred. By transferring DNA encoding a desired polypeptide and DNA encoding a taurine transporter into a host cell into which DNA encoding ALT is transferred, the yield of the desired polypeptide can be increased. For the production of the polypeptide, there are in vivo and in vitro production systems. Examples of in vitro production systems include systems using eukaryotes and systems using prokaryotes.

In the present invention, as DNA encoding a taurine transporter, a DNA encoding a polypeptide having the amino acid sequence as shown in SEQ ID NO: 62, 64, 66 or 68 may be used. Alternatively, a DNA encoding a polypeptide which has an amino acid sequence derived from the amino acid sequence as shown in SEQ ID NO: 62, 64, 66 or 68 by substitution, deletion, addition and/or insertion of one or more amino acid residues and yet has taurine transporter activity may be used.

The polypeptide which has an amino acid sequence derived from the amino acid sequence as shown in SEQ ID NO: 62, 64, 66 or 68 by substitution, deletion, addition and/or insertion of one or more amino acid residues and yet has taurine transporter activity is functionally equivalent to a hamster, rat, mouse or human taurine transporter (hereinafter sometimes referred to as "taurine transporter derived from hamster or the like"). Such a polypeptide encompasses, for example, mutants of the taurine transporter derived from hamster or the like.

As methods well-known to those skilled in the art for preparing polypeptides functionally equivalent to a specific polypeptide, methods of introducing mutations into polypeptides may be given. For example, those skilled in the art could prepare polypeptides functionally equivalent to hamster taurine transporter by appropriately introducing mutations into amino acids of hamster taurine transporter by site-directed mutagenesis (Hashimoto-Gotoh, T. et al. (1995) Gene 152, 271-275; Zoller, M J, and Smith, M (1983) Methods Enzymol. 100, 468-500; Kramer, W. et al. (1984) Nucleic Acids Res. 12, 9441-9456; Kramer W, and Fritz H J (1987) Methods. Enzymol. 154, 350-367; Kunkel, T A (1985) Proc Natl Acad Sci USA. 82, 488-492; Kunkel (1988) Methods Enzymol. 85, 2763-2766). Mutations in amino acids may also occur in nature.

Specific examples of polypeptides functionally equivalent to the taurine transporter derived from hamster or the like include, but are not limited to, a polypeptide having an amino acid sequence derived from the amino acid sequence of the taurine transporter derived from hamster or the like by deletion of one or more amino acids, preferably 2-30 amino acids, more preferably 2-10 amino acids; a polypeptide having an amino acid sequence derived from the amino acid sequence of the taurine transporter derived from hamster or the like by addition of one or more amino acids, preferably 2-30 amino acids, more preferably 2-10 amino acids; and a polypeptide having an amino acid sequence derived from the amino acid sequence of the taurine transporter derived from hamster or the like by substitution of one or more amino acids, preferably 2-30 amino acids, more preferably 2-10 amino acids, with other amino acids.

Amino acid residues to be mutated are not particularly limited. Preferably, amino acid residues are mutated to other amino acids in which the nature of the initial amino acid side chain is conserved. Specific examples of the nature of amino acid side chain include hydrophobic amino acids (A, I, L, M, F, P, W, Y and V), hydrophilic amino acids (R, D, N, C, E, Q, G, H, K, S and T), amino acids with an aliphatic side chain (G, A, V, L, I and P), amino acids with a hydroxyl group-containing side chain (S, T and Y), amino acids with a sulfur atom-containing side chain (C and M), amino acids with a carboxylic acid and amide-containing side chain (D, N, E and Q), amino acids with a base-containing side chain (R, K and H) and amino acids with an aromatic-containing side chain (H, F, Y and W) (In parentheses are one-letter codes for amino acids).

As one example of the polypeptide in which one or more amino acid residues are added to the taurine transporter derived from hamster or the like, a fusion polypeptide comprising the taurine transporter derived from hamster or the like may be given. Such a fusion polypeptide is composed of the taurine transporter derived from hamster or the like and other polypeptide fused thereto. Such a fusion polypeptide is included in the present invention. Such a fusion polypeptide may be prepared by linking a gene encoding the taurine transporter derived from hamster or the like in frame with a gene encoding the other polypeptide, transferring the resultant DNA into an expression vector and expressing the DNA in a host cell. Techniques known to those skilled in the art may be used. There is no limitation on the polypeptide to be fused to the taurine transporter derived from hamster or the like.

Examples of polypeptides to be fused to the taurine transporter derived from hamster or the like include, but are not limited to, FLAG (Hopp, T. P. et al., BioTechnology (1988) 6, 1204-1210), 6×His comprising six histidine (His) residues, 10×His, influenza hemagglutinin (HA), human c-myc fragment, VSV-GP fragment, p18HIV fragment, T7-tag, HSV-tag, E-tag, SV40T antigen fragment, lck tag, α-tubulin fragment, B-tag, protein C fragment, glutathione-S-transferase (GST), influenza hemagglutinin (HA), immunoglobulin constant region, β-galactosidase and maltose-binding protein (MBP).

A commercially available gene encoding such polypeptide is fused to the gene encoding the taurine transporter derived from hamster or the like. The fused gene thus prepared is expressed to prepare a fused polypeptide.

An alternative method known to those skilled in the art for preparing polypeptides functionally equivalent to a specific polypeptide is a method using the hybridization technique (Sambrook, J et al., Molecular Cloning 2nd ed., 9.47-9.58, Cold Spring Harbor Lab. Press, 1989). Those skilled in the art could routinely isolate a DNA highly homologous to the DNA sequence of the taurine transporter derived from hamster or the like based on that DNA sequence or a part thereof, and isolate polypeptides functionally equivalent to the taurine transporter derived from hamster or the like from that DNA.

Hybridization conditions for isolating a DNA encoding a polypeptide functionally equivalent to the taurine transporter derived from hamster or the like can be appropriately selected by those skilled in the art. For example, low stringent hybridization conditions may be given. Low stringent hybridization conditions are, for example, 42° C., 2×SSC and 0.1% SDS, preferably 50° C., 2×SSC and 0.1% SDS. More preferably, high stringent conditions may be given. For example, high stringent conditions are 65° C., 2×SSC and 0.1% SDS. Under these conditions, as the hybridization temperature is lowered, not only DNAs with high homology but also DNAs with only low homology are obtained. Conversely, it is expected that only those DNAs with high homology are obtained as the hybridization temperature is elevated. However, not only the temperature but also a plurality of factors (such as salt concentrations) affect the stringency of hybridization. Those skilled in the art could appropriately select these factors to realize similar stringency.

The polypeptide encoded by a DNA isolated by these hybridization techniques may have 70% or more homology and usually has high homology with the taurine transporter derived from hamster or the like in the amino acid sequence. The polypeptide also include those polypeptides which are functionally equivalent to the taurine transporter derived from hamster or the like and have high homology with the amino acid sequence of the taurine transporter derived from hamster or the like. The term "high homology" refers to usually 97% or more homology, preferably 98% or more homology, more preferably 99% or more homology. For determination of the homology of polypeptides, the algorithm described in Wilbur, W. J. and Lipman, D. J., Proc. Natl. Acad. Sci. USA (1983) 80, 726-730 may be followed.

The polypeptide may vary in amino acid sequence, molecular weight, isoelectric point, presence or absence of sugar chains, morphology, etc. depending on the cell or host that produce the polypeptide or the purification method that will be described later. However, as long as the resultant polypeptide has functions equivalent to the functions of the taurine transporter derived from hamster or the like, a DNA encoding the polypeptide can be used in the present invention. For example, when the polypeptide is expressed in a prokaryote (e.g., Escherichia coli), a methionine reside is added to the N-terminus of the initial amino acid sequence of the polypeptide. When the polypeptide is expressed in a eukaryote (e.g., a mammalian cell), the N-terminal signal sequence is removed. DNAs encoding such polypeptides can be used in the present invention.

The polypeptide may be prepared as a recombinant polypeptide or a natural polypeptide by methods known to those skilled in the art. A recombinant polypeptide may be prepared by incorporating a DNA encoding the polypeptide in an appropriate expression vector, introducing the vector into an appropriate host cell, collecting the resultant transformant, extracting a crude polypeptide, and then purifying the polypeptide by chromatography (such as ion exchange, reversed phase or gel filtration chromatography, or affinity chromatography in which an antibody to the polypeptide is fixed in a column) or a combination of these chromatographic techniques.

When the polypeptide is expressed in a host cell (e.g., animal cell or E. coli) as a fusion polypeptide with glutathione-S-transferase polypeptide or as a recombinant polypeptide with histidine residues added thereto, the expressed polypeptide may be purified with a glutathione column or a nickel column.

After purification of a fusion polypeptide, regions other than the polypeptide of interest may be cut off by thrombin or factor Xa and removed from the fusion polypeptide.

When the polypeptide is a natural polypeptide, the polypeptide may be isolated by purification methods known to those skilled in the art. For example, an extract from tissues or cells expressing the polypeptide may be applied to an affinity column to which an antibody to the taurine transporter derived from hamster or the like described later is bound. The antibody may be either a polyclonal antibody or a monoclonal antibody.

In the present invention, as DNA encoding a taurine transporter, a DNA having the nucleotide sequence as shown in SEQ ID NO: 61, 63, 65 or 67 may be used. Alternatively, a DNA which hybridizes to a DNA complementary to a DNA having the nucleotide sequence as shown in SEQ ID NO: 61, 63, 65 or 67 under stringent conditions and yet encodes a polypeptide having taurine transporter activity may be used.

The DNA encoding a taurine transporter can be used in the in vivo or in vitro production of a desired polypeptide as described above. Further, the DNA encoding a taurine transporter may be used in the creation of a cell which strongly expresses a taurine transporter. The DNA encoding a taurine transporter may take any form as long as it is capable of encoding a taurine transporter. That is, the DNA may be, for example, a cDNA synthesized from mRNA, a genomic DNA or a chemically synthesized DNA. It should be noted that, as long as the DNA is capable of encoding a taurine transporter, the DNA may have any nucleotide sequence based on the degeneracy of genetic codes.

The DNA encoding a taurine transporter may be prepared by methods known to those skilled in the art. For example, the DNA may be prepared by preparing a cDNA library from a cell expressing a taurine transporter and performing hybridization using a part of the DNA sequence encoding a taurine transporter (e.g., SEQ ID NO: 61, 63, 65 or 67) as a probe. The cDNA library may be prepared, for example, by the method described in Sambrook, J. et al., Molecular Cloning, Cold Spring Harbor Laboratory Press (1989). Alternatively, a commercial cDNA library may be used. It is also possible to prepare the DNA encoding a taurine transporter by preparing RNA from a cell expressing the taurine transporter, synthesizing oligo DNA molecules based on the DNA sequence of the taurine transporter (e.g., SEQ ID NO: 61, 63, 65 or 67), and performing PCR using the oligo DNA molecules as primers to thereby amplify a cDNA encoding the taurine transporter.

Further, by determining the nucleotide sequence of the resultant cDNA, it is possible to determine the translation region encoding a taurine transporter and to obtain the amino acid sequence of the taurine transporter. Further, by screening a genomic library using the resultant cDNA as a probe, it is possible to isolate a genomic DNA.

Specifically, the following procedures may be used. First, mRNA is isolated from cells, tissues or the like expressing a taurine transporter. For the isolation of mRNA, the total RNA is prepared by known methods, for example, the guanidine ultracentrifugation method (Chirgwin, J. M. et al., Biochemistry (1979) 18, 5294-5299), the AGPC method (Chomczynski, P. and Sacchi, N., Anal. Biochem. (1987) 162, 156-159) or the like, and then mRNA is purified from the total RNA using mRNA Purification Kit (Pharmacia), etc. Alternatively, mRNA may be prepared directly using QuickPrep mRNA Purification Kit (Pharmacia).

From the resultant mRNA, cDNA is synthesized using a reverse transcriptase. Alternatively, cDNA may be synthesized using a kit such as AMV Reverse Transcriptase First-Strand cDNA Synthesis Kit (SEIKAGAKU CORPORATION). It is also possible to synthesize and amplify cDNA according to the 5'-RACE method (Frohman, M. A. et al., Proc. Natl. Acad. Sci. USA (1988) 85, 8998-9002; Belyavsky, A. et al., Nucleic Acids Res. (1989) 17, 2919-2932) using 5'-Ampli FINDER RACE Kit (Clontech) and polymerase chain reaction (PCR) with primers.

A DNA fragment of interest is prepared from the resultant PCR product and ligated to a vector DNA to thereby prepare a recombinant vector. The vector is introduced into a host (e.g., E. coli), followed by selection of resultant colonies to thereby obtain a desired recombinant vector. The nucleotide sequence of the DNA of interest may be confirmed by a known method such as the dideoxynucleotide chain termination method.

Further, a nucleotide sequence of a higher expression efficiency can be designed for the DNA encoding a taurine transporter by considering the frequency of codon usage in the host to be used for expression (Grantham, R. et al., Nucleic Acids Research (1981) 9, p. 43-74). Further, the DNA encoding a taurine transporter can be modified using commercially available kits or known methods. Examples of such modifications include, but are not limited to, digestion with restriction enzymes, insertion of synthetic oligonucleotides or appropriate DNA fragments, addition of linkers, and insertion of an initiation codon (ATG) and/or a termination codon (TAA, TGA or TAG).

The DNA encoding a taurine transporter also includes a DNA which hybridizes to a DNA complementary to a DNA having the nucleotide sequence as shown in SEQ ID NO: 61, 63, 65 or 67 under stringent conditions and encodes a polypeptide functionally equivalent to a taurine transporter.

Stringent conditions can be appropriately selected by those skilled in the art, including, for example, low stringent conditions. Low stringent conditions refer to, for example, 42° C., 2×SSC and 0.1% SDS, preferably 50° C., 2×SSC and 0.1% SDS. More preferably, high stringent conditions may be selected. High stringent conditions refer to, for example, 65° C., 2×SSC and 0.1% SDS. Under these conditions, as the hybridization temperature is elevated, DNAs with a higher homology can be obtained. The above-described DNA which hybridizes is preferably a DNA derived from nature, e.g., cDNA or chromosomal DNA.

These DNAs isolated by hybridization techniques usually have a high nucleotide sequence identity with a DNA encoding the taurine transporter derived from hamster, etc. The DNA also includes a DNA which encodes a polypeptide functionally equivalent to the taurine transporter derived from hamster, etc. and has high identity with a DNA encoding the taurine transporter derived from hamster, etc. The term "high identity" refers to usually 96% or more homology, preferably 98% or more homology, more preferably 99% or more identity. The identity of nucleotide sequences may be determined by algorithm BLAST (Karlin and Altschul, Proc. Natl. Acad. Sci. USA 90:5873-5877, 1993). Based on this algorithm, programs such as BLASTN and BLASTX have been developed (Altschul et al. J. Mol. Biol. 215:403-410, 1990). When nucleotide sequences are analyzed by BLASTN based on BLAST, parameters may be set as expect value=100 and word size=12, for example. Specific procedures for these analysis methods are known (http://www.ncbi.nlm.nih.gov/).

The DNA encoding a taurine transporter may be inserted into a vector.

When the host cell to be used is *E. coli*, it is preferable that the vector has a replication origin ("ori") so that the vector is largely amplified in *E. coli* (e.g., JM109, DH5α, HB101 and XL1-Blue) and prepared in large quantity, and also genes for selecting transformed *E. coli* (e.g., drug resistance genes that enable discrimination of transformant with some drugs such as ampicillin, tetracycline, kanamycin or chloramphenicol). Examples of preferable vectors include, but are not limited to, M13 vectors, pUC vectors, pBR322, pBluescript and pCR-Script. In addition to these vectors, pGEM-T, pDIRECT, pT7, etc. may be enumerated when the vector is used for the purpose of subcloning a cDNA and cutting off the subcloned cDNA. When the vector is used for the purpose of producing the polypeptide of the present invention, an expression vector is especially useful. When expression in *E. coli* is intended, the expression vector preferably has the above-described features so that the vector is amplified in *E. coli*, and it also preferably has a promoter which allows efficient expression in *E. coli* such as JM109, DH5α, HB101 or XL1-Blue, e.g., lacZ promoter (Ward et al, Nature (1989) 341, 544-546; FASEB J. (1992) 6, 2422-2427), araB promoter (Better et al, Science (1988) 240, 1041-1043) or T7 promoter. Specific examples of such vector include, in addition to those listed above, pGEX-5X-1 (Pharmacia), QIAexpress system (Qiagen), pEGFP, or pET (for its host, T7 RNA polymerase-expressing BL21 is preferred).

The vector may comprise signal sequences for polypeptide secretion. When the polypeptide is to be produced in the periplasm of *E. coli*, pelB signal sequence (Lei, S. P. et al., J. Bacteriol. (1987) 169, 4379) may be used as a signal sequence for polypeptide secretion. Introduction of the vector into a host cell may be performed, for example, by the calcium chloride method or electroporation.

In cases where a host cell other than *E. coli* is used, vectors useful for producing a desired polypeptide include, but are not limited to, mammal-derived expression vectors [e.g., pcDNA3 from Invitrogen; pEGF-BOS (Nucleic Acids. Res. 1990, 18(17), p. 5322); pEF, pCDM8], insect cell-derived expression vectors (e.g., Bac-to-BAC baculovairus expression system from GIBCO BRL; pBacPAK8), plant-derived expression vectors (e.g., pMH1, pMH2), animal virus-derived expression vectors (e.g., pHSV, pMV, pAdex-Lcw), retrovirus-derived expression vectors (e.g., pZIpneo), yeast-derived expression vectors (e.g., *Pichia* Expression Kit from Invitrogen; pNV11; SP-Q01), and *Bacillus subtilis*-derived expression vectors (e.g., pPL608, pKTH50).

When expression of the polypeptide in animal cells (such as CHO cells, COS cells, NIH3T3 cells, etc.) is intended, the vector preferably has a promoter necessary for expressing the polypeptide in those cells. Examples of such promoter include, but are not limited to, SV40 promoter (Mulligan et al, Nature (1979) 277, 108), MMLV-LTR promoter, EF1α promoter (Mizushima et al., Nucleic Acids Res. (1990) 18, 5322) and CMV promoter. More preferably, the vector also has genes for selecting transformed cells (e.g., drug resistance genes that enable discrimination with drugs such as neomycin or G418). Examples of vectors having such properties include, but are not limited to, pMAM, pDR2, pBK-RSV, pBK-CMV, pOPRSV and pOP13.

Further, when stable expression of a gene of interest and intracellular amplification of the copy number of the gene are indented, the following method may be used. Briefly, into CHO cells lacking a nucleic acid synthesis pathway, a vector having DHFR gene that complements the lack (e.g., pCHOI) is introduced, followed by amplification with methotrexate (MTX). On the other hand, when tentative expression of a gene of interest is intended, a method may be used in which COS cells carrying a gene expressing SV40T antigen on the chromosome is transformed with a vector having the replication origin of SV40 (e.g., pcD). As the replication origin, a replication origin derived from polyomavirus, adenovirus or bovine papillomavirus (BPV) may also be used. Further, the expression vector may contain selectable markers for amplifying the copy number of the gene in a host cell system. Examples of such selectable markers include, but are not limited to, aminoglycoside phosphotransferase (APH) gene, thymidine kinase (TK) gene, *E. coli* xanthine-guanine phosphoribosyl transferase (Ecogpt) gene and dihydrofolate reductase (dhfr) gene.

The present invention provides a cell which has a transferred DNA encoding ALT and a transferred DNA encoding a taurine transporter, both or either of which may be incorporated into a vector.

When eukaryotes are used, animal cells, plant cells, fungal cells, etc. may be used as the host. Specific examples of animal cells include mammalian cells, such as CHO cells (J. Exp. Med. (1995) 108, 945), COS cells, 3T3 cells, myeloma cells, BHK (baby hamster kidney) cells, HeLa cells and Vero cells; amphibian cells, such as oocytes of *Xenopus laevis* (Valle, et al., Nature (1981) 291, 358-340); or insect cells, such as sf9, sf21 and Tn5 cells. Amoung CHO cells, dhfr-CHO lacking DHFR gene (Proc. Natl. Acad. Sci. USA (1980) 77, 4216-4420) and CHO K-1 (Proc. Natl. Acad. Sci. USA (1968) 60, 1275) are used with particular advantage. When high expression is intended in an animal cell, CHO cells are especially preferred. Introduction of the DNA which may be incorporated into a vector into the host cell may be performed by such methods as the calcium phosphate method, the DEAE dextran method, a method using a cationic ribosome DOTAP (Boehringer-Mannheim), electroporation, lipofection, etc.

As plant cells for polypeptide production, a *Nicotiana tabacum*-derived cell is known as a polypeptide production system and this may be subjected to callus culture. As fungal cells for polypeptide production, specific examples include yeast belonging to the genus *Saccharomyces*, e.g., *Saccharomyces cerevisiae*, and filamentous fungi belonging to the genus *Aspergillus*, e.g., *Aspergillus niger*.

When prokaryotes are used, production systems using bacterial cells are known. Specific examples of such bacterial cells include *E. coli* (such as JM109, DH5α, HB101) and *Bacillus subtilis*.

The polypeptide encoded by a gene of interest may be obtained by transforming these cells with the gene of interest and culturing the transformed cells in vitro. The culture may be performed by known methods. For example, as a culture broth for animal cells, a medium such as DMEM, MEM, RPMI1640 or IMDM may be used. A serum supplement such as fetal calf serum (FCS) may be used jointly. Alternatively, serum-free culture may be performed. The pH during culture is preferably about 6 to 8. The culture is usually performed at about 30-40° C. for about 15-200 hours. If necessary, replacement of the medium, aeration and agitation are carried out.

On the other hand, in vivo production systems include those using animals or plants. A gene of interest is transferred into these animals or plants to produce the polypeptide in the animal bodies or plant bodies. Then, the polypeptide is collected. The term "host" as used herein includes such animals or plants.

When animals are used, available production systems include those using mammals or insects. Goat, pig, sheep, mouse and cattle may be used as mammals (Vicki Glaser, SPECTRUM Biotechnology Applications, 1993). When mammals are used, transgenic animals may be used.

First, a gene of interest is fused to a gene encoding a polypeptide produced inherently in milk (such as goat β-casein) to thereby prepare a fusion gene. A DNA fragment containing this fusion gene is injected into a goat embryo, which is then implanted in the uterus of a female goat. The polypeptide of interest can be obtained from the milk produced by transgenic goats born from the goat which accepted the embryo or the offspring of the transgenic goats. In order to increase the yield of milk containing the polypeptide produced by the transgenic goats, hormones may be appropriately administered to the transgenic goats (Ebert, K. M. et al., Bio/Technology (1994) 12, 699-702).

Examples of insects which may be used include silkworm. In this case, silkworm is infected with baculovirus carrying a transferred gene encoding the polypeptide of interest. The polypeptide of interest can be obtained from the body fluid of the silkworm (Susumu, M. et al., Nature (1985) 315, 592-594).

Furthermore, when plants are used, tobacco can typically be used. When tobacco is used, a gene encoding the polypeptide of interest is inserted into a plant expression vector (e.g., pMON 530), which is then transferred into a bacterium such as *Agrobacterium tumefaciens*. A tobacco plant (e.g., *Nicotiana tabacum*) is infected with the resultant bacterium. The polypeptide of interest can be obtained from leaves of this plant (Julian, K.-C. Ma et al., Eur. J. Immunol (1994) 24, 131-138).

The polypeptide thus obtained can be isolated from the inside of the host cell or from its outside (e.g., medium), and purified to a substantially pure and homogeneous polypeptide. Isolation and purification of polypeptides can be performed using conventional isolation and purification methods for polypeptides, and are not limited in any way. For example, polypeptides can be isolated and purified by appropriate selection and combination of various tools and techniques, such as chromatography columns, filters, ultrafiltration, salting-out, precipitation with solvent, extraction with solvent, distillation, immunoprecipitation, SDS-polyacrylamide gel electrophoresis, isoelectric focusing, dialysis, recrystallization, etc.

Examples of chromatography include affinity chromatography, ion exchange chromatography, hydrophobic chromatography, gel filtration, reverse-phase chromatography, adsorption chromatography, etc. (Strategies for Protein Purification and Characterization: A Laboratory Course Manual. Ed. Daniel R. Marshak et al., Cold Spring Harbor Laboratory Press, 1996). These chromatographic techniques can be carried out using liquid phase chromatography, for example, HPLC, FPLC, etc. The present invention also includes those polypeptides highly purified using these purification methods.

Before or after the purification, it is also possible to give optional modifications to the polypeptide or remove a partial peptide therefrom by reacting the polypeptide with an appropriate polypeptide modification enzyme. Examples of such enzyme include, but are not limited to, trypsin, chymotrypsin, lysyl endopeptidase, protein kinase and glucosidase.

In the present invention, the concept of "cells into which DNA has been transferred" encompasses not only cells into which exogenous DNA has been incorporated by genetic recombination technology; but also cells in which endogenous DNA has been activated by gene activation technology (see, for example, International Publication WO94/12650) so that expression of a protein corresponding to the endogenous DNA or transcription of the DNA has been initiated or increased.

EXAMPLES

Hereinbelow, the present invention will be described in more detail with reference to the following Examples. It should be noted that these Examples are provided only for illustrating the present invention and not for limiting the scope of the present invention.

Example 1

Cloning of Human Hepatic Cell Alanine Aminotransferase Gene

Using a commercial Human Liver QUICK-Clone cDNA (Clontech Laboratories, Inc.) as a template, alanine aminotransferase (ALT1) gene derived from a human liver was obtained by a PCR method. The gene thus cloned was sequenced and confirmed to encode ALT1 based on its homology with published human ALT1. The ALT1 gene thus obtained had mutations at five sites in the sequence of 1488 bases (c157a, a215g, c765t, t857c, t995a) and coded for 496 amino acids including four different amino acids (R53S, Q72R, F286S, M332K), but this was used as a PCR clone of the human liver derived ALT1 for cell modulation.

Example 2

Increase in Antibody Yield by Transfer of Human Alanine Aminotransferase

Figure 2:
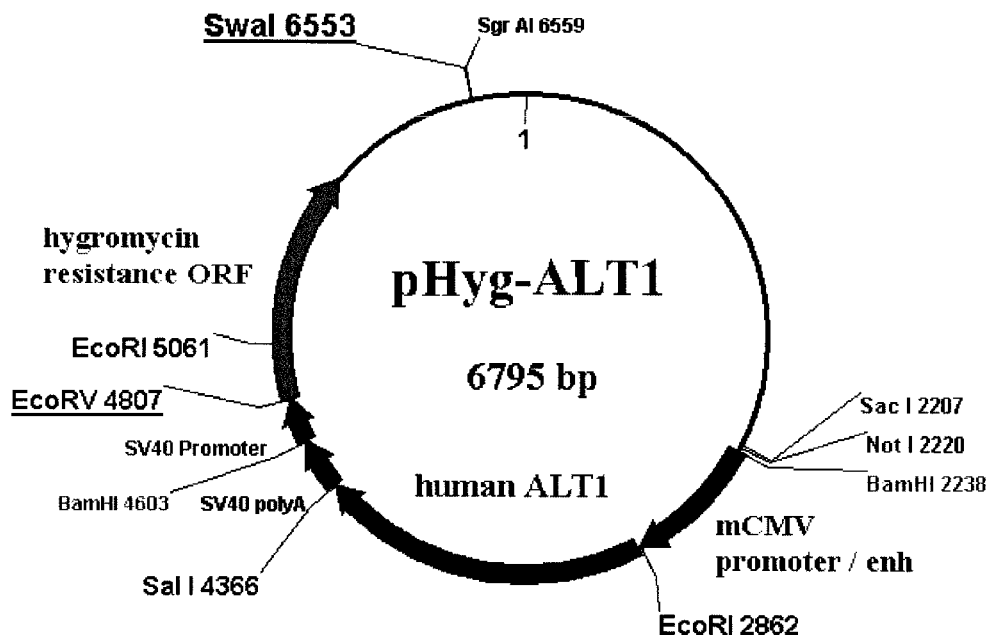
FIG. 2 shows a plasmid for Hygromycin selection which was used for expressing human ALT1 (496 amino acids).
Figure 3:
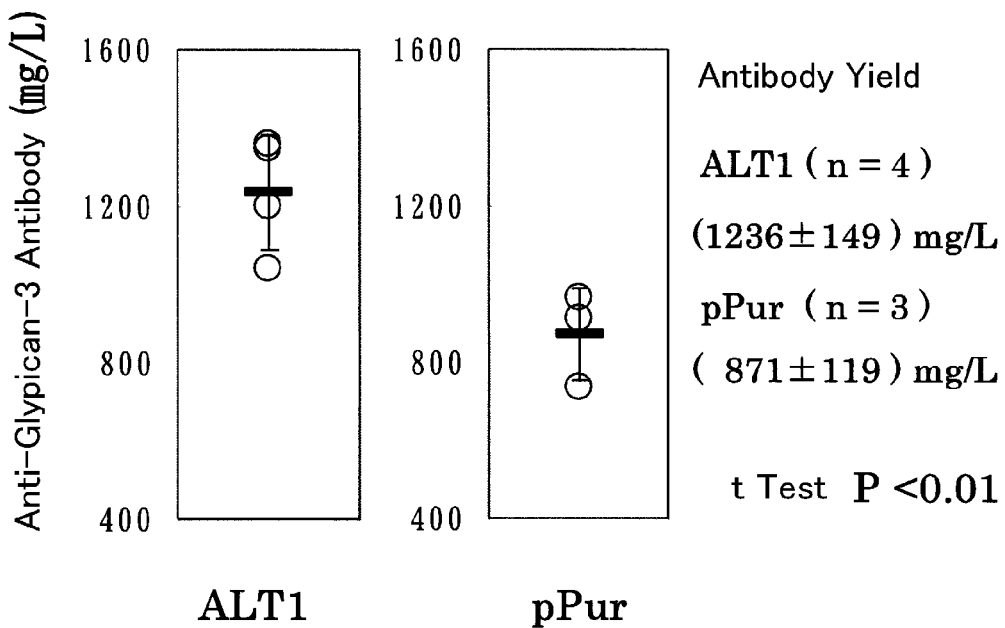
FIG. 3 shows anti-glypican-3 antibody yield plots on day 17 of 50 ml shaker flask fed-batch culture. The antibody yield in pPur-ALT1-transferred cell (n=4) was superior to that in pPur-transferred cell (n=3) (P<0.01).
C
Figure 4:
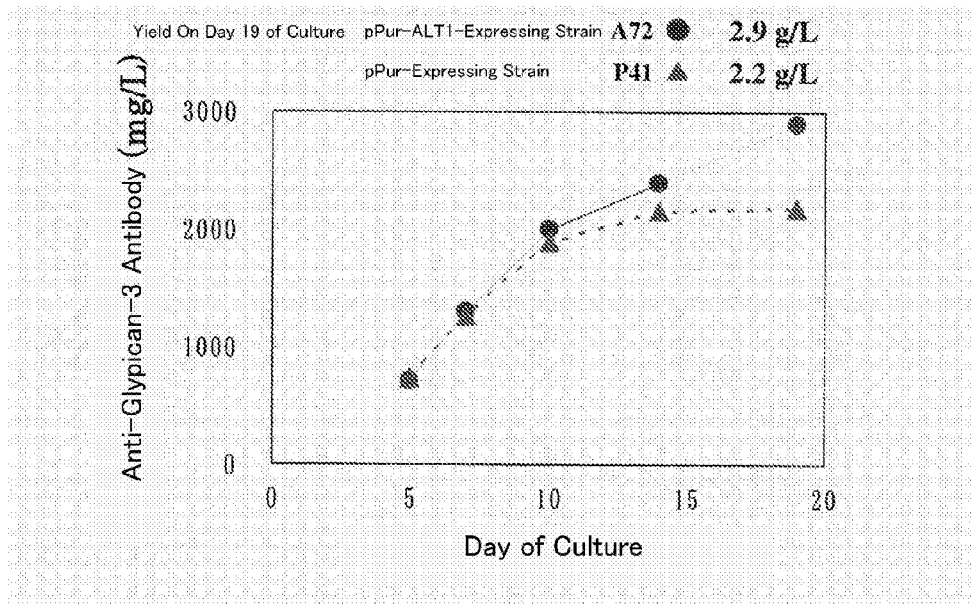
FIG. 4 is a graph showing the antibody yields of A72, which is an ALT1 expressing strain, and P41 as a control strain, in 1 L jar fed-batch culture. The anti-glypican-3 antibody yield of A72 was 2.9 g/L on day 19 of the culture, which was higher than that of P41.
Figure 5:
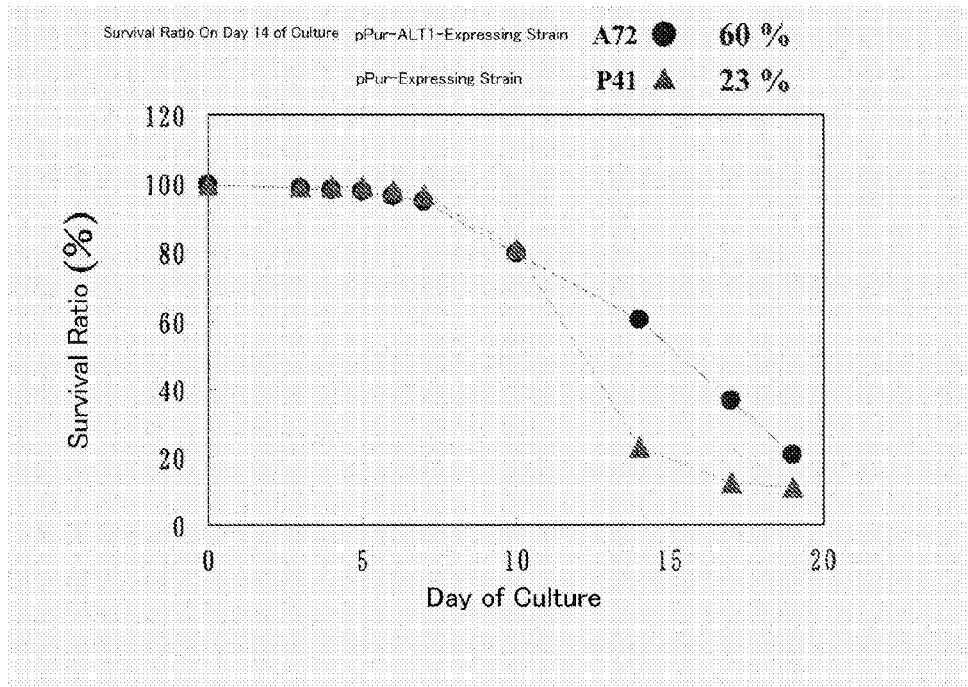
FIG. 5 is a graph showing the survival ratios of A72, which is an ALT1 expressing strain, and P41 as a control strain. The survival ratio of A72 at the late stage of the culture was higher than that of P41.

By adding a Kozak sequence to the human ALT1 obtained by cloning in Example 1 (which is hereinafter called ALT1), pPur-ALT1 (FIG. 1) and pHyg-ALT1 (FIG. 2), which were CMV promoter expression plasmids, were constructed. The pPur-ALT1 or pPur expression plasmids that did not contain the ALT1 gene were introduced into anti-glypican-3 antibody-producing CHO cells as parent strains (see International Publication WO 2006/006693) by electroporation, and cell strains that exhibited high proliferation in static culture in the presence of Puromycin (6 µg/ml) (pPur-ALT1: seven strains, pPur: three strains) were selected. After expansion, a total RNA was prepared from the pPur-ALT1 cell strains, and six strains expressing human ALT1 at high levels were selected by a TaqMan method. Further, a comparison was made for the antibody yield between pPur-transferred cells as a control (three strains) and four strains of human ALT1-transferred cells that proliferated at a level equivalent to that observed with the pPur-transferred cells during the shake culture. During fed-batch culture in a 50 ml shaker flask with an initial cell density of $2 \times 10^5$ cells/mL, the anti-glypican-3 antibody yield of pPur-ALT1-transferred cells (four strains) on day 17 at the late stage of the shaker culture was significantly higher than that of pPur-transferred cells (three strains) (t-test: p<0.01, FIG. 3). A72, a pPur-ALT1 expressing strain, and P41, a pPur expressing strain, were each found to have produced the largest amount of an antibody in the study using shaker fed-batch culture, and they were subjected to fed-batch culture in 1 L jars (an initial cell density of $10 \times 10^5$ cells/mL). As a result, the antibody yield of A72 was 2.9 g/L on day 19 of the culture, which was greater than the antibody yield of P41 (2.2 g/L) (FIG. 4). Since no increase was observed in the antibody yield of P41 on day 14 or subsequent days after the initiation of the culture, the high-yield production of an antibody by A72 was considered to be attributable to the survival ratio maintaining effect (FIG. 5). Further, pHyg/ALT-transferred cells (three strains), which were drug-selected in the presence of Hygromycin (200 µg/mL) by a method similar to the one described above, were subjected to fed-batch culture, together with the parent strain, in 15 ml tubes (an initial cell density of $1 \times 10^5$ cells/mL). As a result, the anti-glypican-3 antibody yield of the pHyg-ALT-transferred cells on day 10 at the late stage of the tube culture were 471 mg/L, 544 mg/L, and 588 mg/L, showing that the antibody yield of any one of them was greater than that of the parent strain (400 mg/L) (data not shown).

Figure 6:
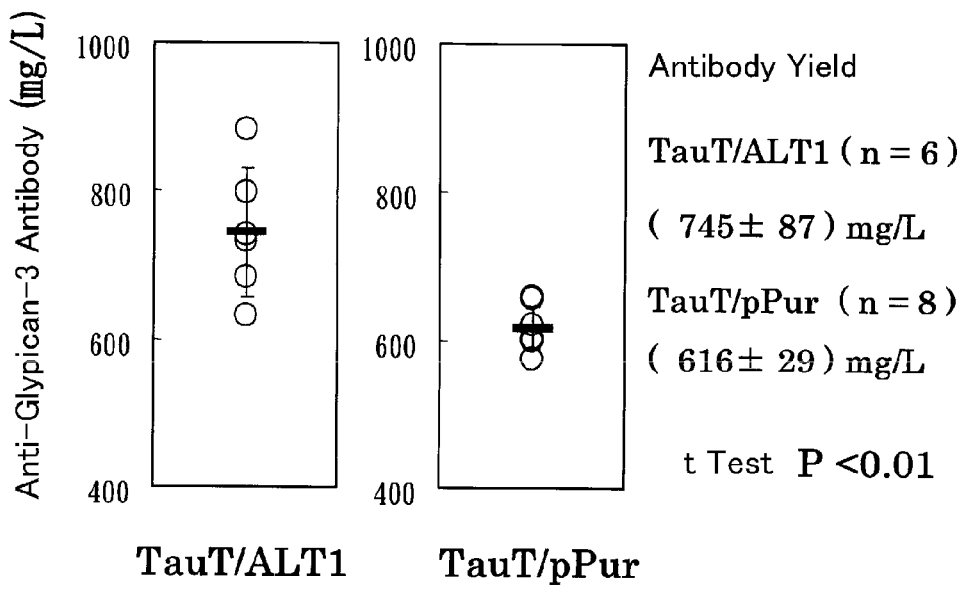
FIG. 6 shows anti-glypican-3 antibody yield plots on day 4 of 50 ml shaker flask fed-batch culture. The antibody yield in pHyg-TauT/pPur-ALT1-cotransferred cell (n=6) was superior to that in pHyg-TauT/pPur-cotransferred cell (n=8) (P<0.01).

Then, pPur-ALT1 or pPur was co-transferred into T10 which was a pHyg-TauT-transferred cell used as a parent strain (see Referential Example 2 described later). TauT/ALT1 co-expressing cells that exhibited high proliferation and expressed human ALT1 at high level (six strains) and TauT/pPur co-expressing cells that exhibited high proliferation (eight strains) were selected and subjected to fed-batch culture in 50 mL shaker flasks (an initial cell density of $10 \times 10^5$ cells/mL). The anti-glypican-3 antibody yield of TauT/ALT1 co-expressing cells, which were ALT expressing cells, on day 4 of the shaker culture was significantly higher than that of TauT/pPur cells (t-test: p<0.01, FIG. 6).

Figure 7:
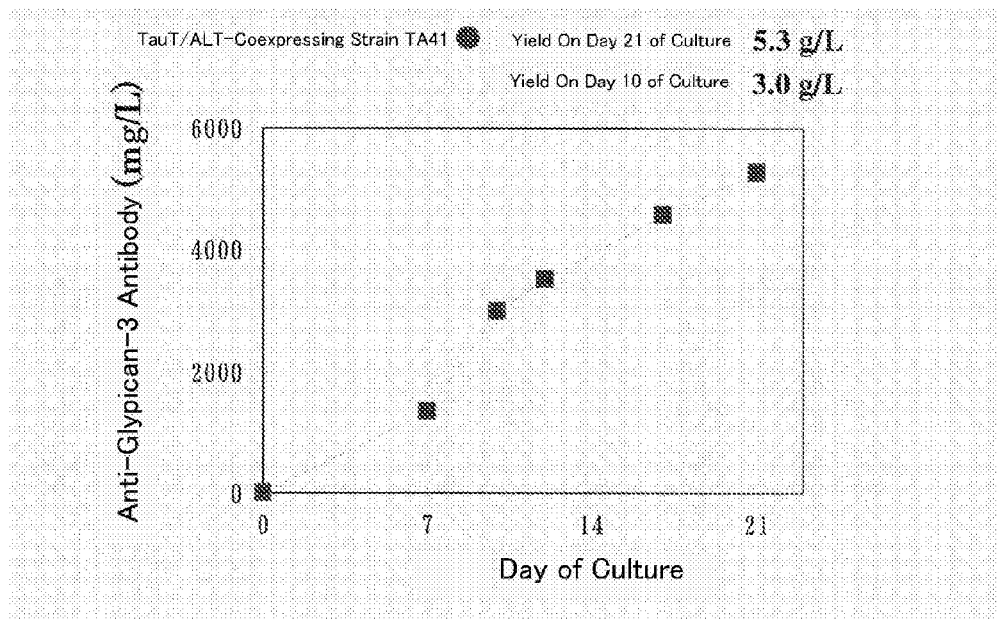
FIG. 7 is a graph showing the antibody yield of TA41, which is a TauT/ALT1 co-expressing strain, in 1 L jar fed-batch culture. The anti-glypican-3 antibody yield was 5.3 g/L on day 21 of the culture.

TA41, which was a TauT/ALT1 co-expressing strain that produced the largest amount of an antibody (881 mg/L/4 days) and expressed ALT1 mRNA at the highest level in the study using the shaker fed-batch culture, was subjected to fed-batch culture in a 1 L jar (an initial cell density of $10 \times 10^5$ cells/mL). The antibody yields were as high as 1.3 g/L on day 7 of the culture, 3.0 g/L on day 10 of the culture, 3.5 g/L on day 12 of the culture, 4.6 g/L on day 17 of the culture, and 5.3 g/L on day 21 of the culture (FIG. 7), which were clearly higher than the values for TP08 (656 mg/L/4 days), which was a control strain that produced the largest amount of an antibody among the TauT/pPur co-expressing strains (2.4 g/L on day 10 of the culture).

Figure 22:
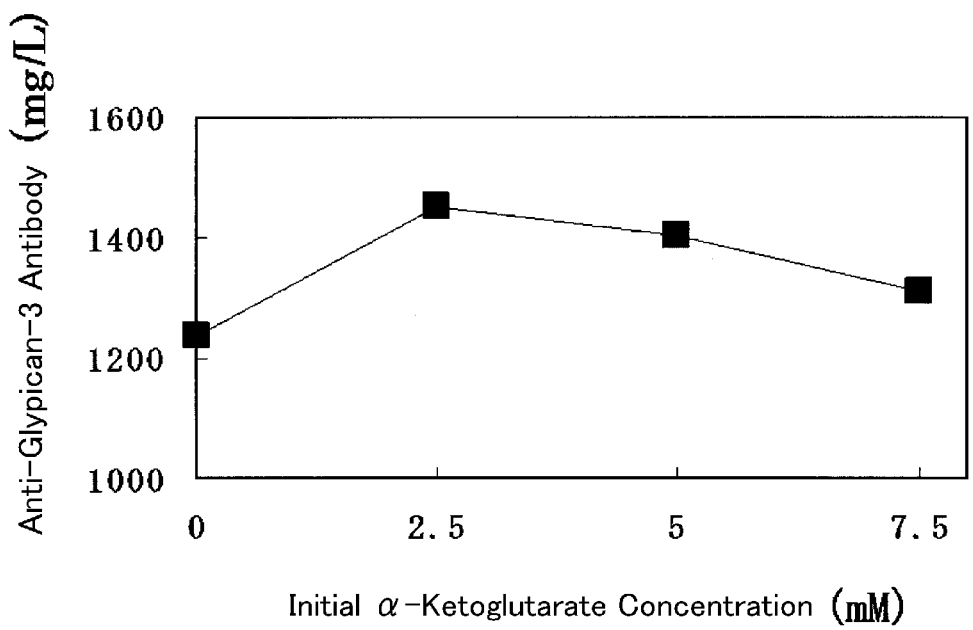
FIG. 22 shows the anti-glypican-3 antibody yield of TA41, a TauT/ALT co-expressing strain, on day 14 of fed-batch culture in a shaker. The antibody yield was increased by addition of α-ketoglutarate.

The anti-glypican-3 antibody yield of TA41, a TauT/ALT1 co-expressing strain, on day 14 of the fed-batch culture in a 50 ml shaker flask was increased by addition of α-ketoglutarate which, like alanine, served as a substrate for ALT (FIG. 22). The anti-glypican-3 antibody yield on day 14 of the culture was 1452 mg/L in the presence of 2.5 mM α-ketoglutarate, and 1239 mg/L in the absence of α-ketoglutarate.

The above results suggest that cells capable of high-yield antibody production at the late stage of culture can be obtained by artificially expressing ALT1.

The present invention is applicable to any antibody-producing cell.

Referential Example 1

Cloning of CHO Cell-Derived Hamster Taurine Transporter Gene

Figure 8:
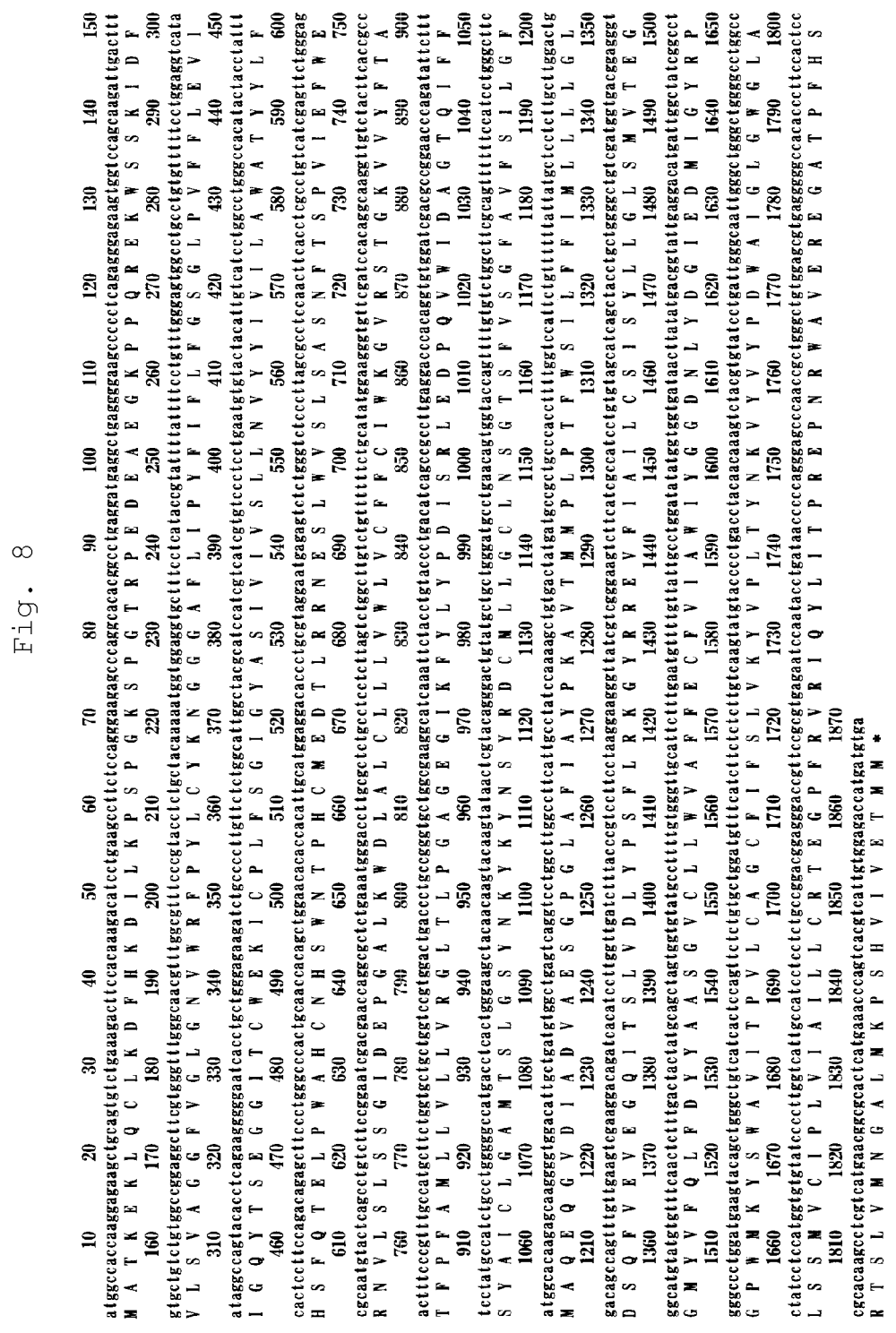
Figure 9:
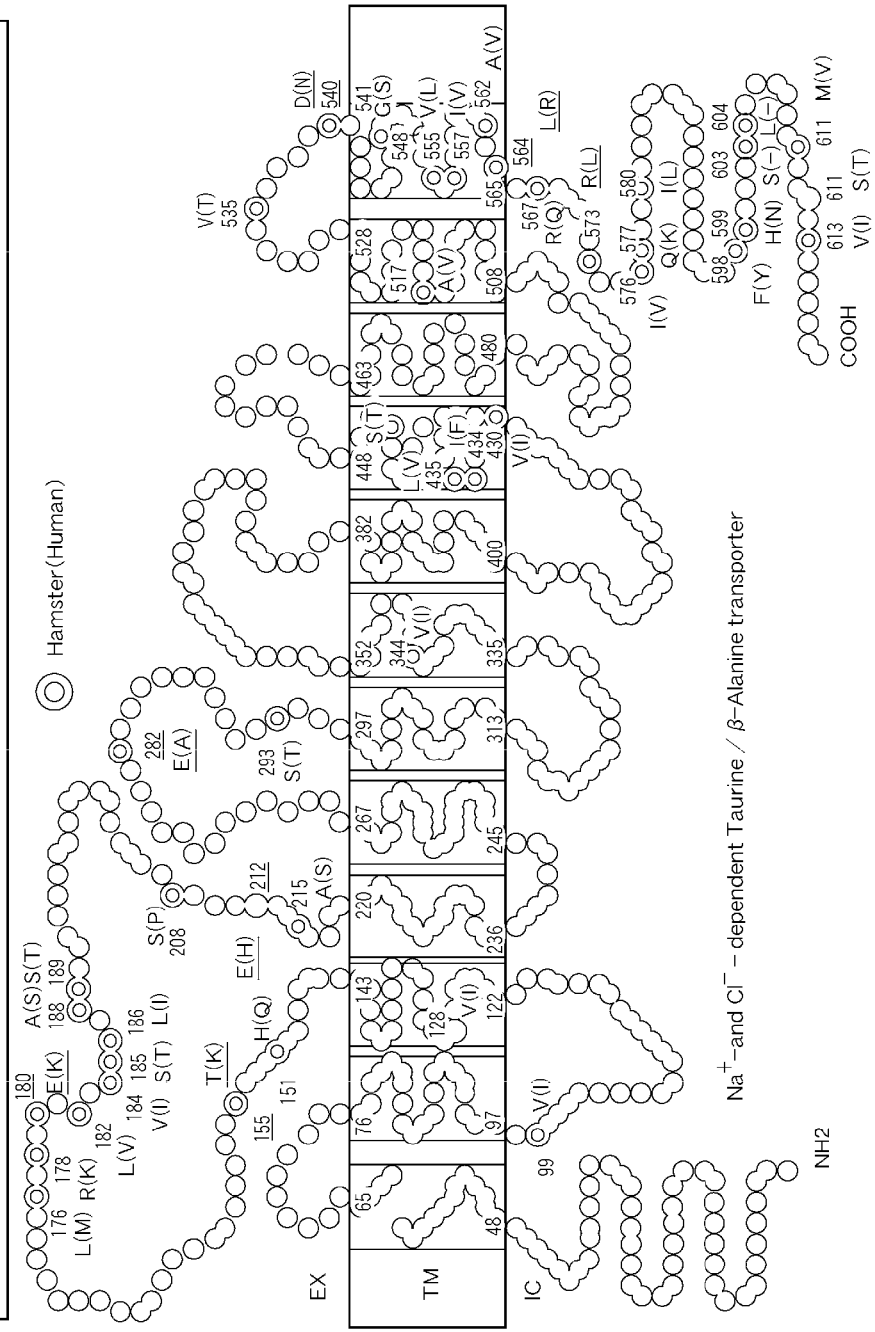
FIG. 9 is a taurine transporter membrane topology of a newly cloned, CHO cell-derived TauT.

Total RNA was extracted from anti-IL-6 receptor antibody-producing cells (A CHO DXB11 cell line into which an anti-IL-6 receptor antibody gene had been transferred) (Japanese Unexamined Patent Publication No. Hei 8-99902), and then cDNA was synthesized therefrom in a poly(A) dependent manner. Hamster taurine transporter (TauT) gene was obtained by PCR using as a template the cDNA fragmented with three restriction enzymes, SalI, XhoI and EcoRI. As PCR primers, those containing the 5'-end and the 3'-end sequence conserved between rat and mouse TauTs were designed. The nucleotide sequence of the cloned gene was determined From its homology with other TauT genes of known species, the cloned gene was confirmed to encode hamster TauT (FIG. 8). The amino acid sequence of hamster TauT has high homology with mouse TauT (96% identity), rat TauT (96% identity) and human TauT (93% identity); it was predicted that hamster TauT is a transporter with 12 transmembrane regions (FIG. 9).

Referential Example 2

Figure 10:
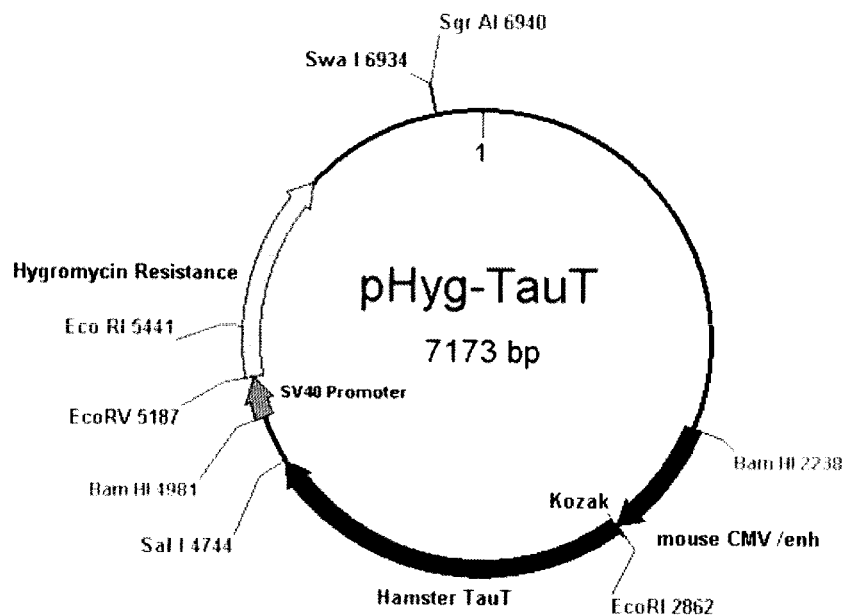
FIG. 10 shows a plasmid which was used for expressing hamster TauT (622 amino acids).
Figure 11:
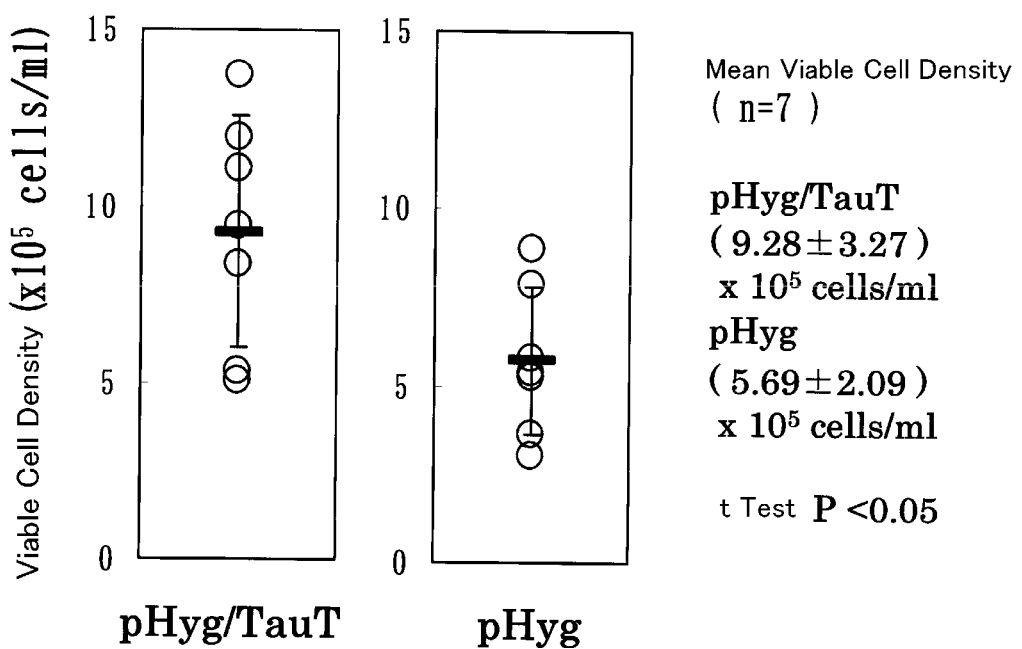
FIG. 11 shows viable cell density plots on day 7 of 50 ml shaker flask batch culture. The viable cell density in pHyg/TauT-transferred cell was superior to that in pHyg-transferred cell.
Figure 12:
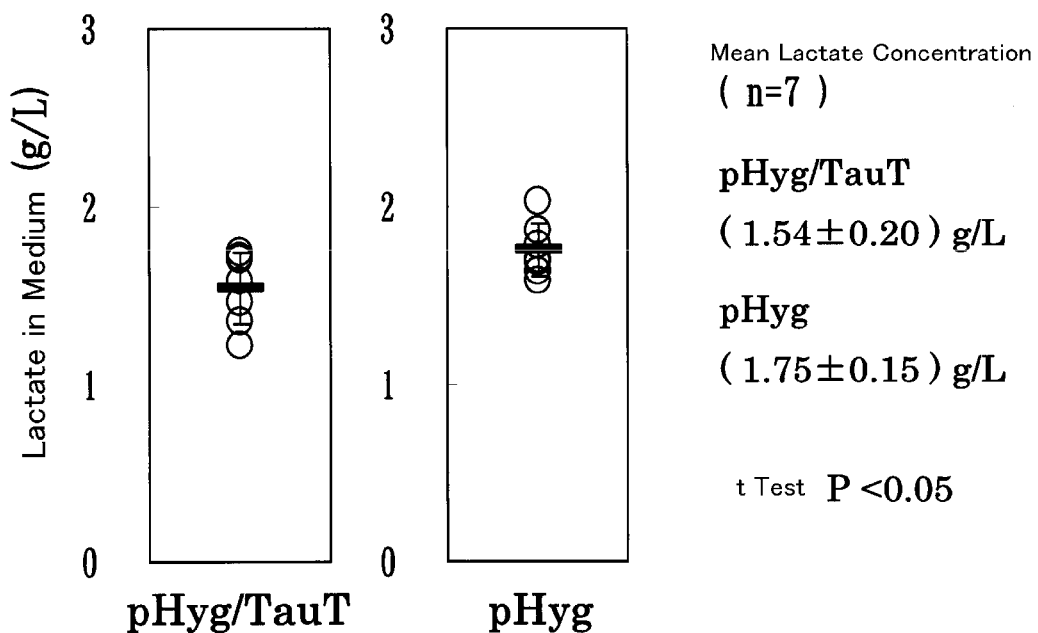
FIG. 12 shows lactate yield plots on day 7 of 50 ml shaker flask batch culture. pHyg/TauT-transferred cell produced less lactate, and was superior to pHyg-transferred cell.
Figure 13:
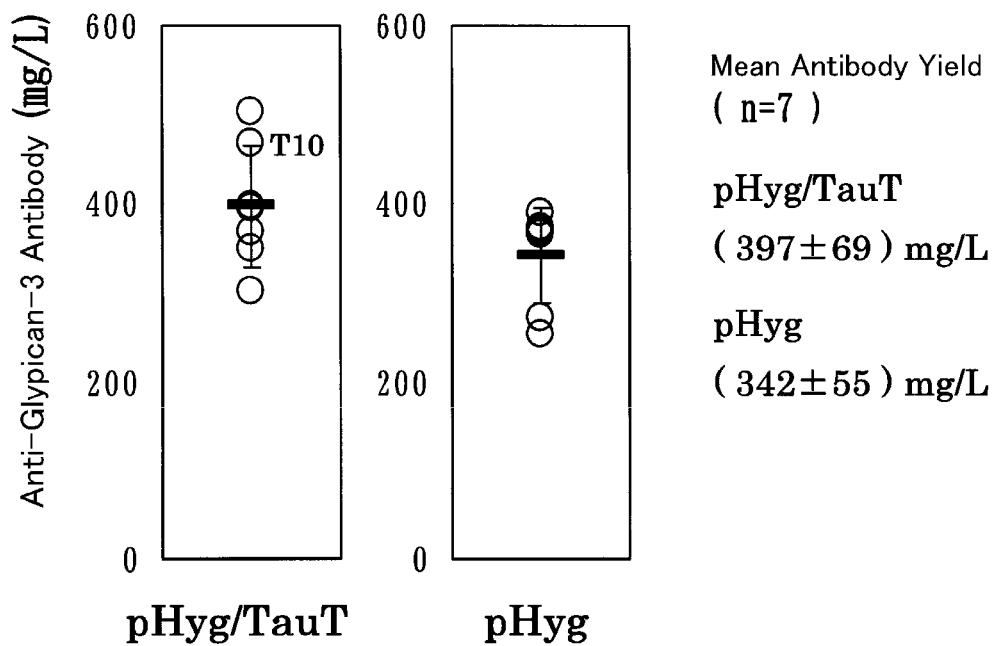
FIG. 13 shows anti-glypican-3 antibody yield plots on day 7 of 50 ml shaker flask batch culture. Four out of the 7 strains of pHyg/TauT-transferred cell showed antibody yields higher than the highest yield in pHyg-transferred cell.
Figure 14:
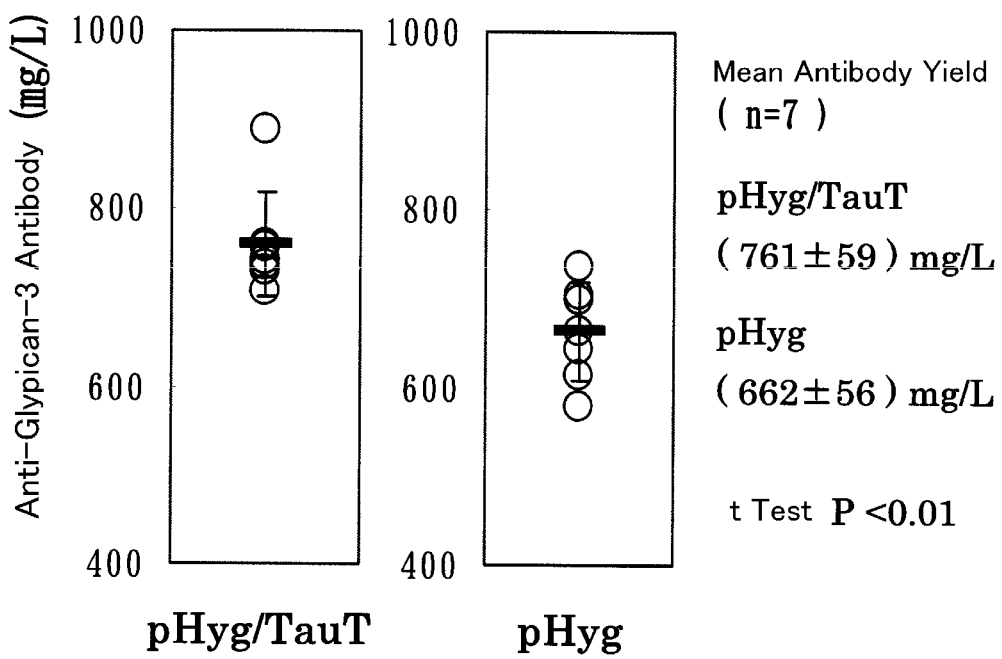
FIG. 14 shows anti-glypican-3 antibody yield plots on day 7 of 50 ml shaker flask fed-batch culture. The antibody yield in pHyg/TauT-transferred cell was superior to that in pHyg-transferred cell.
Figure 15:
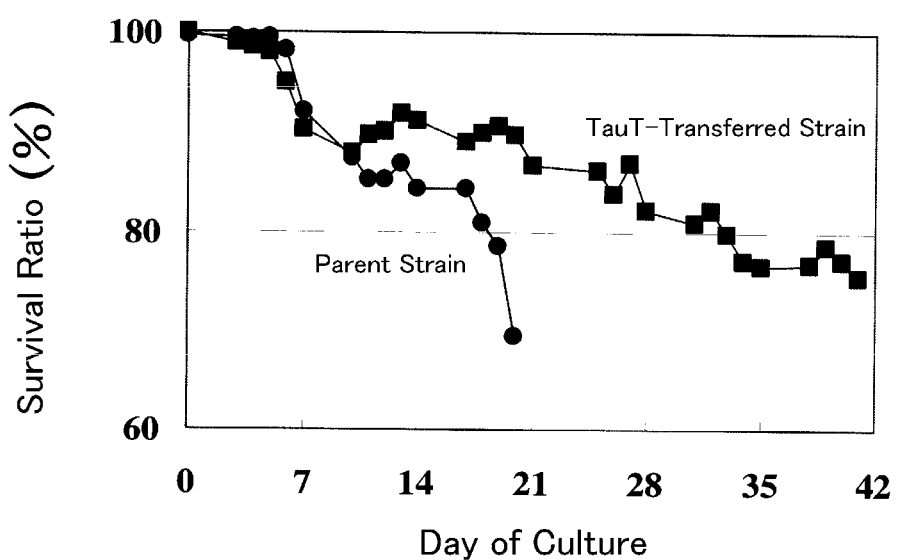
FIG. 15 is a graph showing the survival ratio of a pHyg/TauT-transferred cell T10 (which showed high growth ability) in 1 L jar fed-batch culture. The survival ratio of T10 was 80% or more even on day 32 of the culture.
Figure 16:
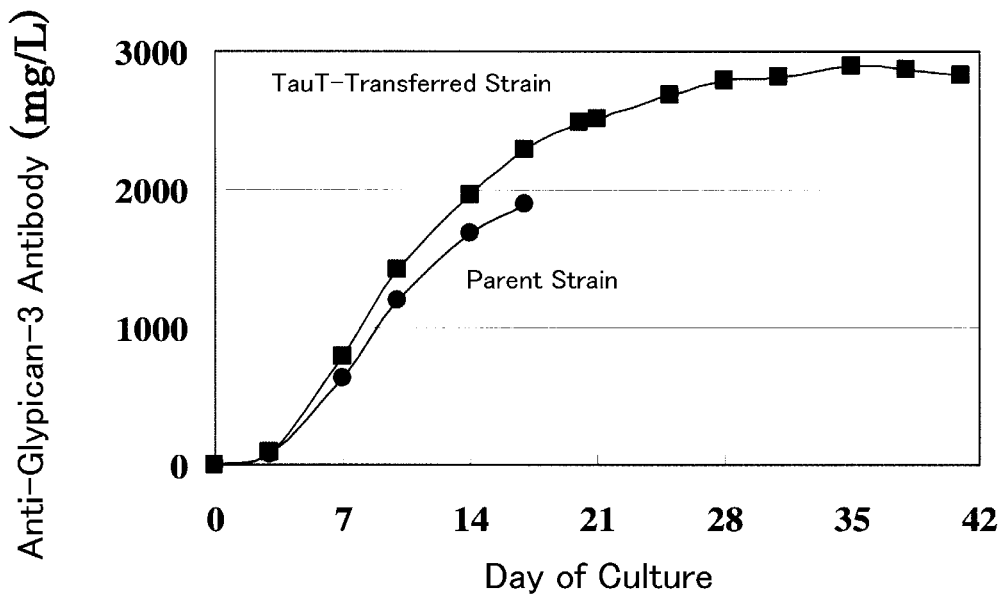
FIG. 16 is a graph showing the antibody yield of a pHyg/TauT-transferred cell T10 (which showed high growth ability during the expansion process in static culture) in 1 L jar fed-batch culture. The anti-glypican-3 antibody yield of T10 was 2.9 g/L on day 35 of the culture.
Figure 17:
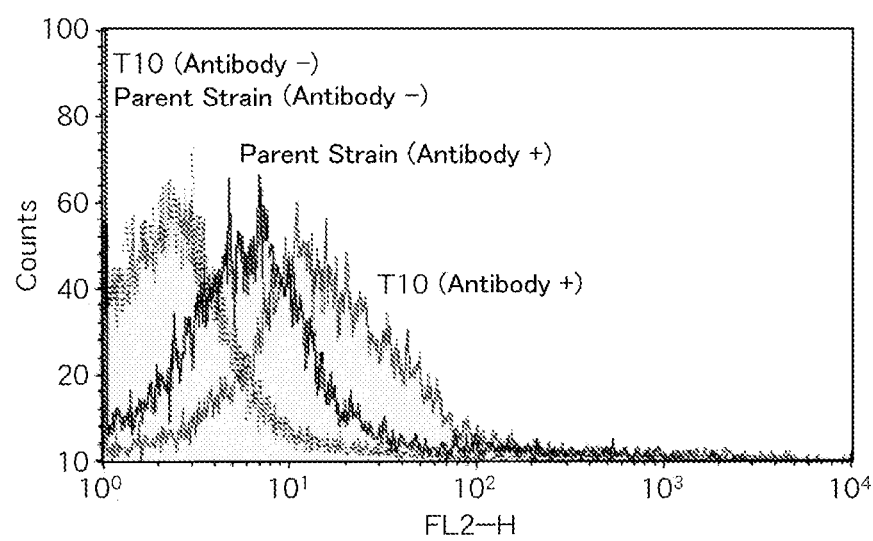
FIG. 17 shows the results of flow cytometric analysis indicating that TauT-transferred T10 cell is expressing TauT molecules on its cell membrane.

Increase in Viable Cell Density, Inhibition of Lactate Production and Increase in Antibody Yield, as Caused by Transfer of Hamster Taurine Transporter CMV promoter expression plasmid pHyg/TauT (FIG. 10) was constructed by adding Kozak sequence to the hamster TauT (hereinafter, TauT) gene obtained by cloning in Referential Example 1. Control plasmid pHyg without pHyg/TauT or TauT gene was introduced by electroporation into the parent strain anti-glypican-3 antibody producing CHO cell (see WO 2006/006693). After selection of expression plasmid-transferred cells in the presence of hygromycin (400 µg/ml), all of the stably growing cell strains were expanded (pHyg/TauT: 8 strains; pHyg: 7 strains). TauT mRNA was prepared. Subsequently, 7 strains were confirmed to express TauT more strongly than the parent strain by the TaqMan method; they were selected as pHyg/TauT transferred cells. The mean mRNA expression level of these transferred cells (7 strains) was about 40 times larger than the control (7 strains). Cells of the total 14 strains were subjected to batch culture and fed-batch culture in 50 ml shaker flasks with an initial cell density of $2 \times 10^5$ cells/ml. On day 7 of culture (late-stage), viable cell densities, lactate yields and anti-glypican-3 antibody yields in those strains were compared. In batch culture, growth inhibitory substances such as lactate accumulate in culture broth as cells grow and their growth is inhibited. However, the viable cell densities (FIG. 11) and lactate yields (FIG. 12) in pHyg/TauT transferred cells were superior to those in pHyg transferred cells (t test; p<0.05). With respect to anti-glypican-3 antibody yield, 4 out of the 7 strains of pHyg/TauT-transferred cell showed antibody yields higher than the highest yield in pHyg-transferred cell (FIG. 13). Further, since superiority of pHyg/TauT transferred cells in anti-glypican-3 antibody yield became more evident (t test; P<0.01; FIG. 14) in fed-batch culture, pHyg/TauT transferred T10 strain (which showed the highest growth ability among the above 4 strains) and the parent strain were subjected to fed-batch culture in 1 L jar. As a result, the viable ratio of T10 was maintained at 80% or more even on day 32 of culture (FIG. 15), with inhibited lactate production. Consequently, its anti-glypican-3 antibody yield achieved 2.9 g/L on day 35 of culture (FIG. 16). It was confirmed by flow cytometric analysis that TauT-transferred T10 cell was expressing TauT molecules on the cell membrane (FIG. 17). These results suggest that by artificially expressing hamster Taut, it is possible to raise the potential of antibody-producing cells and create strains capable of enhanced antibody production.

Referential Example 3

Inhibition of Ammonia Production, Taurine Uptake, Increase in Glutamine Consumption and Taurine Non-Dependent Antibody Yield in Hamster TauT Transferred Strains The parent strain and pHyg/TauT transferred strain were fed-batch cultured in 1 L jar with an initial cell density of $2 \times 10^5$ cells/ml. A part of the culture broth containing $450 \times 10^5$ cells was taken from the jar at appropriate time points. After the culture supernatant was separated by centrifugation, 1 ml of cooled sterile water containing a protease inhibitor (Complete Mini; Roche Diagnostics; Protease inhibitor cocktail tablets) was added to the cell pellet. Then, the cells were completely disrupted on ice in a sonicator (MISONIX ASTRASON MODEL XL2020) with a set of 5 seconds pulse-on and 5 seconds pulse-off being repeated 12 times. The total volume of the thus treated cells was applied to a centrifugal filter unit to thereby prepare a filtrate with a molecular weight of 5000 or less. This filtrate was used as a sample for determining intracellular amino acids. Each sample was subjected to detection and comparison of absorbance at 570 nm using a ninhydrin reagent L-8500 set (Wako Pure Chemical Industries) and an improved model of Hitachi fully automated amino acid analyzer (L-8500). Thus, various amino acid concentrations in samples were determined Since the concentrations of amino acids and ammonia in culture broth were directly measured values, concentration comparisons in the order of µM were performed. On the other hand, since intracellular concentrations were obtained after addition of 1 ml of cooled sterile water to the cell pellet and sonication thereof, the measured concentrations of various amino acids and ammonia were converted into values per cell, followed by comparison of the converted values. To determine the ammonia concentration ratios shown in FIG. 18, the detected ammonia value per $450 \times 10^5$ cells in the parent strain at the start of 1 L jar fed-batch culture was taken as 1 and compared with detected values at the start of the culture and on days 6, 12 and 18 of the culture in the transferred strain. The taurine values in FIG. 19 and the glutamine values in FIG. 20 were also determined by the above-described amino acid analysis.

Figure 18:
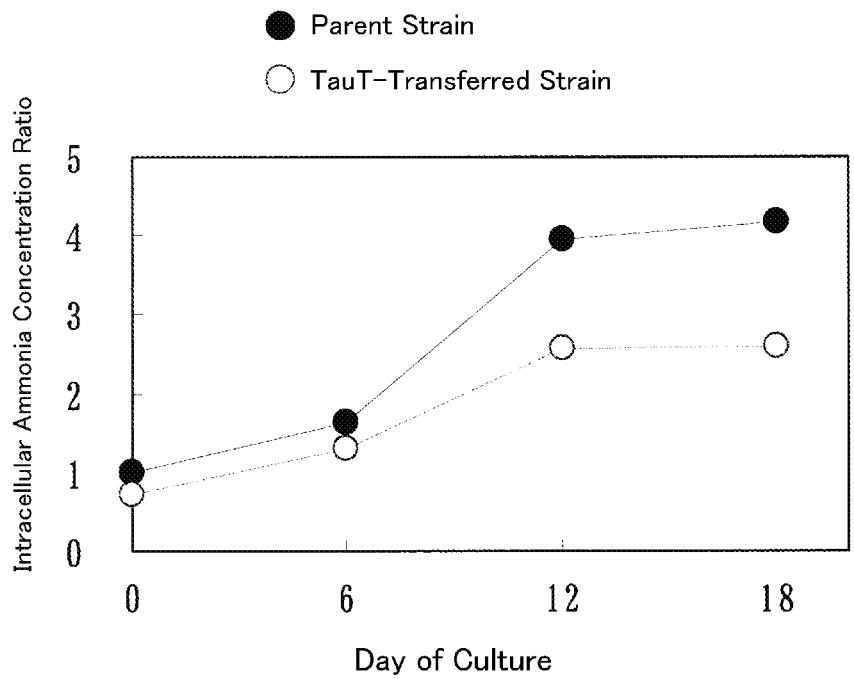
FIG. 18 is a graph showing intracellular ammonia contents (concentration ratios) in 1 L jar fed-batch culture. The ammonia inhibition in pHyg/TauT-transferred strains was remarkable compared to the parent strain.
Figure 19:
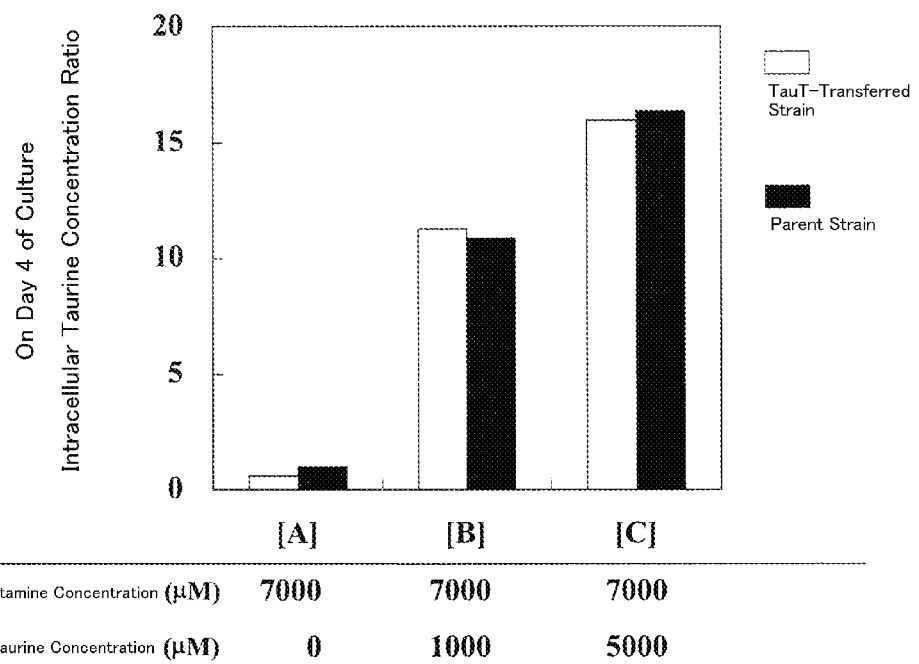
FIG. 19 is a graph showing that taurine is taken into cells depending on the taurine concentration in the medium. No difference was observed in taurine uptake between pHyg/TauT-transferred strains and the parent strain.

As a result, the intracellular ammonia in pHyg/TauT transferred strain was maintained at a low concentration at the late stage of culture; it is believed that this contributes to high antibody yield (FIG. 18).

Intracellular taurine concentration ratios were determined in the same manner as described above for ammonia concentrations (FIG. 19), except that the detected ammonia value per $200 \times 10^5$ cells in the parent strain on day 4 of 50 ml shaker batch culture was taken as 1.

Figure 20:
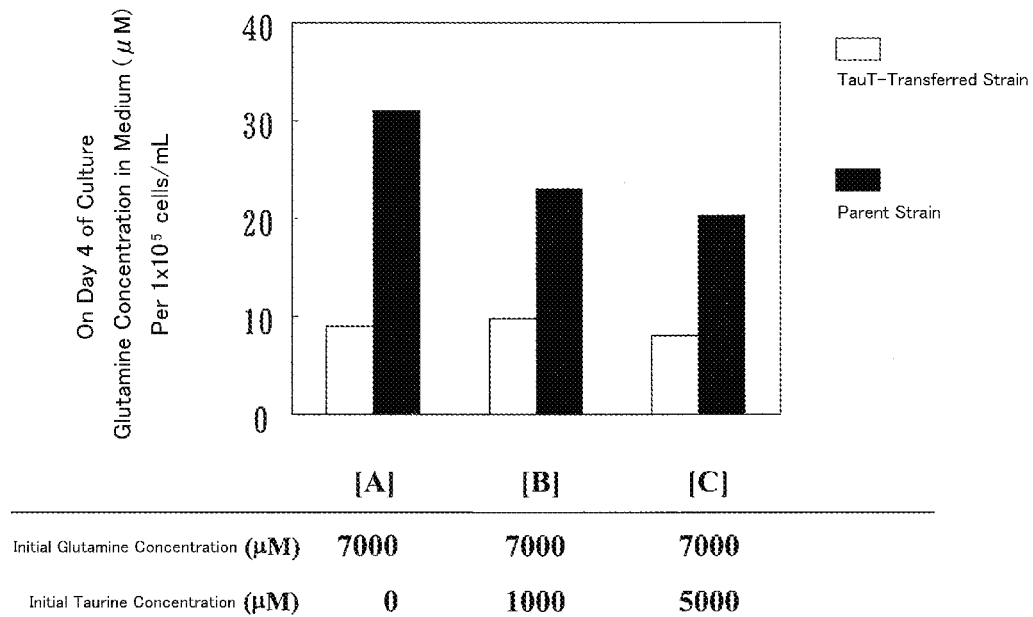
FIG. 20 is a graph showing the consumption of glutamine in the medium. Compared to the parent strain, pHyg/TauT-transferred strains showed a remarkably high glutamine consumption/cell without depending on the taurine concentration in the medium.

As a result, it was found that pHyg/TauT transferred strain had taken up taurine in a manner dependent on the amount of taurine added and that its uptake was almost equal to that by the parent strain. However, as shown in FIG. 20, glutamine consumption in pHyg/TauT transferred strain was remarkably high compared to the parent strain and was not dependent on the initial taurine concentration. It has been reported that glutamine improves cell growth, survival ratio and antibody production ability in hybridomas to thereby raise their antibody yields (Enzyme and Microbial Technology 17:47-55, 1995). Therefore, the antibody production enhancement effect of pHyg/TauT transferred strain may be caused by taurine transporter-mediated uptake of amino acids other than taurine (e.g., glutamine). The glutamine concentrations were obtained by converting the values determined by amino acid analysis of the culture broth on day 4 of culture in FIG. 19 into values per $1 \times 10^5$ cells.

Figure 21:
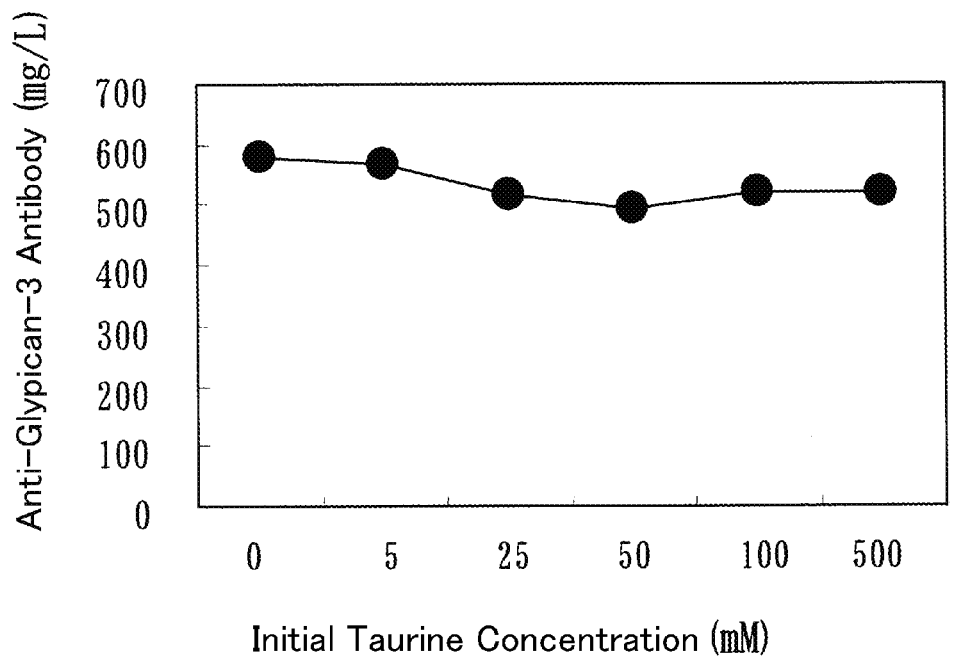
FIG. 21 is a graph showing that the anti-glypican-3 antibody yields of pHyg/TauT-transferred strains are almost equal without depending on the initial taurine concentration in the medium.

Actually, anti-glypican-3 antibody yield was not dependent on the initial taurine concentration (0-500 mM (62.575 g/L)) at the start of 50 ml shaker fed-batch culture (FIG. 21). No significant difference was observed in the parent strains in the effect of initial taurine concentration on antibody yield.

The results described so far suggest that TauT strongly expressing strains have high antibody production ability even if the medium does not contain taurine at the start of culture and that there is a possibility that such strains also promote uptake of amino acids other than taurine.

The present invention is applicable to any antibody-producing cell.

All publications, patent and patent applications cited herein are incorporated herein by reference in their entirety.

INDUSTRIAL APPLICABILITY

The present invention is applicable to production of polypeptides.

SEQUENCE LISTING FREE TEXT

<SEQ ID NO: 1>
SEQ ID NO: 1 shows the nucleotide sequence of a gene encoding human alanine aminotransferase (ALT1) (KEGG/ENZYME: 2.6.1.2/*Homo sapiens* (human): 2875).

<SEQ ID NO: 2>
SEQ ID NO: 2 shows the amino acid sequence of human alanine aminotransferase (ALT1) (KEGG/ENZYME: 2.6.1.2/*Homo sapiens* (human): 2875).

<SEQ ID NO: 3>
SEQ ID NO: 3 shows the nucleotide sequence of a gene encoding human alanine aminotransferase mutant (ALT2) (KEGG/ENZYME: 2.6.1.2/*Homo sapiens* (human): 84706).

<SEQ ID NO: 4>
SEQ ID NO: 4 shows the amino acid sequence of human alanine aminotransferase mutant (ALT2) (KEGG/ENZYME: 2.6.1.2/*Homo sapiens* (human): 84706).

<SEQ ID NO: 5>
SEQ ID NO: 5 shows the nucleotide sequence of a gene encoding mouse alanine aminotransferase (ALT1) (KEGG/ENZYME: 2.6.1.2/*Mus musculus* (mouse): 76282).

<SEQ ID NO: 6>
SEQ ID NO: 6 shows the amino acid sequence of mouse alanine aminotransferase (ALT1) (KEGG/ENZYME: 2.6.1.2/*Mus musculus* (mouse): 76282).

<SEQ ID NO: 7>
SEQ ID NO: 7 shows the nucleotide sequence of a gene encoding mouse alanine aminotransferase mutant (ALT2) (KEGG/ENZYME: 2.6.1.2/*Mus musculus* (mouse): 108682).

<SEQ ID NO: 8>
SEQ ID NO: 8 shows the amino acid sequence of mouse alanine aminotransferase mutant (ALT2) (KEGG/ENZYME: 2.6.1.2/*Mus musculus* (mouse): 108682).

<SEQ ID NO: 9>
SEQ ID NO: 9 shows the nucleotide sequence of a gene encoding rat alanine aminotransferase (ALT1) (KEGG/ENZYME: 2.6.1.2/*Rattus norvegicus* (rat): 81670).

<SEQ ID NO: 10>
SEQ ID NO: 10 shows the amino acid sequence of rat alanine aminotransferase (ALT1) (KEGG/ENZYME: 2.6.1.2/*Rattus norvegicus* (rat): 81670).

<SEQ ID NO: 11>
SEQ ID NO: 11 shows the nucleotide sequence of a gene encoding dog alanine aminotransferase (ALT1) (KEGG/ENZYME: 2.6.1.2/*Canis familiaris* (dog): 609510).

<SEQ ID NO: 12>
SEQ ID NO: 12 shows the amino acid sequence of dog alanine aminotransferase (ALT1) (KEGG/ENZYME: 2.6.1.2/*Canis familiaris* (dog): 609510).

<SEQ ID NO: 13>
SEQ ID NO: 13 shows the nucleotide sequence of a gene encoding African clawed frog alanine aminotransferase (ALT1) (KEGG/ENZYME: 2.6.1.2/*Xenopus laevis* (African clawed frog): 444533).

<SEQ ID NO: 14>
SEQ ID NO: 14 shows the amino acid sequence of African clawed frog alanine aminotransferase (ALT1) (KEGG/ENZYME: 2.6.1.2/*Xenopus laevis* (African clawed frog): 444533).

<SEQ ID NO: 15>
SEQ ID NO: 15 shows the nucleotide sequence of a gene encoding fruit fly alanine aminotransferase (ALT1) (KEGG/ENZYME: 2.6.1.2/*Drosophila melanogaster* (fruit fly): Dmel_CG1640).

<SEQ ID NO: 16>
SEQ ID NO: 16 shows the amino acid sequence of fruit fly alanine aminotransferase (ALT1) (KEGG/ENZYME: 2.6.1.2/*Drosophila melanogaster* (fruit fly): Dmel_CG1640).

<SEQ ID NO: 17>
SEQ ID NO: 17 shows the nucleotide sequence of a gene encoding nematode alanine aminotransferase (ALT1) (KEGG/ENZYME: 2.6.1.2/*Caenorhabditis elegans* (nematode): C32F10.8).

<SEQ ID NO: 18>
SEQ ID NO: 18 shows the amino acid sequence of nematode alanine aminotransferase (ALT1) (KEGG/ENZYME: 2.6.1.2/*Caenorhabditis elegans* (nematode): C32F10.8).

<SEQ ID NO: 19>
SEQ ID NO: 19 shows the nucleotide sequence of a gene encoding one of two kinds of Japanese rice alanine aminotransferases (KEGG/ENZYME: 2.6.1.2/*Oryza sativa japonica* (Japanese rice): 4342210).

<SEQ ID NO: 20>
SEQ ID NO: 20 shows the amino acid sequence of one of two kinds of Japanese rice alanine aminotransferases (KEGG/ENZYME: 2.6.1.2/*Oryza sativa japonica* (Japanese rice): 4342210).

<SEQ ID NO: 21>
SEQ ID NO: 21 shows the nucleotide sequence of a gene encoding one of two kinds of Japanese rice alanine aminotransferases (KEGG/ENZYME: 2.6.1.2/*Oryza sativa japonica* (Japanese rice): 4348524).

<SEQ ID NO: 22>
SEQ ID NO: 22 shows the amino acid sequence of one of two kinds of Japanese rice alanine aminotransferases (KEGG/ENZYME: 2.6.1.2/*Oryza sativa japonica* (Japanese rice): 4348524).

<SEQ ID NO: 23>
SEQ ID NO: 23 shows the nucleotide sequence of a gene encoding *Cyanidioschyzon merolae* alanine aminotransferase (KEGG/ENZYME: 2.6.1.2/*Cyanidioschyzon merolae*: CMM066C).

<SEQ ID NO: 24>
SEQ ID NO: 24 shows the amino acid sequence of *Cyanidioschyzon merolae* alanine aminotransferase (KEGG/ENZYME: 2.6.1.2/*Cyanidioschyzon merolae*: CMM066C).

<SEQ ID NO: 25>
SEQ ID NO: 25 shows the nucleotide sequence of a gene encoding *Saccharomyces cerevisiae* alanine aminotransferase (ALT1) (KEGG/ENZYME: 2.6.1.2/*Saccharomyces cerevisiae*: YLR089C).

<SEQ ID NO: 26>
SEQ ID NO: 26 shows the amino acid sequence of *Saccharomyces cerevisiae* alanine aminotransferase (ALT1) (KEGG/ENZYME: 2.6.1.2/*Saccharomyces cerevisiae*: YLR089C).

<SEQ ID NO: 27>
SEQ ID NO: 27 shows the nucleotide sequence of a gene encoding *Saccharomyces cerevisiae* alanine aminotransferase mutant (ALT2) (KEGG/ENZYME: 2.6.1.2/*Saccharomyces cerevisiae*: YDR111C).

<SEQ ID NO: 28>
SEQ ID NO: 28 shows the amino acid sequence of *Saccharomyces cerevisiae* alanine aminotransferase mutant (ALT2) (KEGG/ENZYME: 2.6.1.2/*Saccharomyces cerevisiae*: YDR111C).

<SEQ ID NO: 29>

SEQ ID NO: 29 shows the nucleotide sequence of a gene encoding *Ashbya gossypii* alanine aminotransferase (KEGG/ENZYME: 2.6.1.2/*Ashbya gossypii* (*Eremothecium gossypii*): AGOS_AGR085W).

<SEQ ID NO: 30>

SEQ ID NO: 30 shows the amino acid sequence of *Ashbya gossypii* alanine aminotransferase (KEGG/ENZYME: 2.6.1.2/*Ashbya gossypii* (*Eremothecium gossypii*): AGOS_AGR085W).

<SEQ ID NO: 31>

SEQ ID NO: 31 shows the nucleotide sequence of a gene encoding *Candida albicans* alanine aminotransferase (KEGG/ENZYME: 2.6.1.2/*Candida albicans*: CaO19_346).

<SEQ ID NO: 32>

SEQ ID NO: 32 shows the amino acid sequence of *Candida albicans* alanine aminotransferase (KEGG/ENZYME: 2.6.1.2/*Candida albicans*: CaO19_346).

<SEQ ID NO: 33>

SEQ ID NO: 33 shows the nucleotide sequence of a gene encoding *Schizosaccharomyces pombe* alanine aminotransferase (KEGG/ENZYME: 2.6.1.2/*Schizosaccharomyces pombe*: SPBC582.08).

<SEQ ID NO: 34>

SEQ ID NO: 34 shows the amino acid sequence of *Schizosaccharomyces pombe* alanine aminotransferase (KEGG/ENZYME: 2.6.1.2/*Schizosaccharomyces pombe*: SPBC582.08).

<SEQ ID NO: 35>

SEQ ID NO: 35 shows the nucleotide sequence of a gene encoding *Aspergillus nidulans* alanine aminotransferase (KEGG/ENZYME: 2.6.1.2/*Aspergillus nidulans*: AN1923.2).

<SEQ ID NO: 36>

SEQ ID NO: 36 shows the amino acid sequence of *Aspergillus nidulans* alanine aminotransferase (KEGG/ENZYME: 2.6.1.2/*Aspergillus nidulans*: AN1923.2).

<SEQ ID NO: 37>

SEQ ID NO: 37 shows the nucleotide sequence of a gene encoding *Aspergillus fumigatus* alanine aminotransferase (KEGG/ENZYME: 2.6.1.2/*Aspergillus fumigatus*: AFUA_6G07770).

<SEQ ID NO: 38>

SEQ ID NO: 38 shows the amino acid sequence of *Aspergillus fumigatus* alanine aminotransferase (KEGG/ENZYME: 2.6.1.2/*Aspergillus fumigatus*: AFUA_6 G07770).

<SEQ ID NO: 39>

SEQ ID NO: 39 shows the nucleotide sequence of a gene encoding *Aspergillus oryzae* alanine aminotransferase (KEGG/ENZYME: 2.6.1.2/*Aspergillus oryzae*: AO090003000164).

<SEQ ID NO: 40>

SEQ ID NO: 40 shows the amino acid sequence of *Aspergillus oryzae* alanine aminotransferase (KEGG/ENZYME: 2.6.1.2/*Aspergillus oryzae*: AO090003000164).

<SEQ ID NO: 41>

SEQ ID NO: 41 shows the nucleotide sequence of a gene encoding *Cryptococcus neoformans* alanine aminotransferase (KEGG/ENZYME: 2.6.1.2/*Cryptococcus neoformans* JEC21: CNG01490).

<SEQ ID NO: 42>

SEQ ID NO: 42 shows the amino acid sequence of *Cryptococcus neoformans* alanine aminotransferase (KEGG/ENZYME: 2.6.1.2/*Cryptococcus neoformans* JEC21: CNG01490).

<SEQ ID NO: 43>

SEQ ID NO: 43 shows the nucleotide sequence of a gene encoding *Dictyostelium discoideum* alanine aminotransferase (KEGG/ENZYME: 2.6.1.2/*Dictyostelium discoideum*: DDB 0232139).

<SEQ ID NO: 44>

SEQ ID NO: 44 shows the amino acid sequence of *Dictyostelium discoideum* alanine aminotransferase (KEGG/ENZYME: 2.6.1.2/*Dictyostelium discoideum*: DDB_0232139).

<SEQ ID NO: 45>

SEQ ID NO: 45 shows the nucleotide sequence of a gene encoding *Trypanosoma brucei* alanine aminotransferase (KEGG/ENZYME: 2.6.1.2/*Trypanosoma brucei*: Tb927.1.3950).

<SEQ ID NO: 46>

SEQ ID NO: 46 shows the amino acid sequence of *Trypanosoma brucei* alanine aminotransferase (KEGG/ENZYME: 2.6.1.2/*Trypanosoma brucei*: Tb927.1.3950).

<SEQ ID NO: 47>

SEQ ID NO: 47 shows the nucleotide sequence of a gene encoding *Leishmania major* alanine aminotransferase (KEGG/ENZYME: 2.6.1.2/*Leishmania major*: LmjF12.0630).

<SEQ ID NO: 48>

SEQ ID NO: 48 shows the amino acid sequence of *Leishmania major* alanine aminotransferase (KEGG/ENZYME: 2.6.1.2/*Leishmania major*: LmjF12.0630).

<SEQ ID NO: 49>

SEQ ID NO: 49 shows the nucleotide sequence of a gene encoding one of two kinds of *Entamoeba histolytica* alanine aminotransferases (KEGG/ENZYME: 2.6.1.2/*Entamoeba histolytica*: 233.t00009).

<SEQ ID NO: 50>

SEQ ID NO: 50 shows the amino acid sequence of one of two kinds of *Entamoeba histolytica* alanine aminotransferases (KEGG/ENZYME: 2.6.1.2/*Entamoeba histolytica*: 233.t00009).

<SEQ ID NO: 51>

SEQ ID NO: 51 shows the nucleotide sequence of a gene encoding one of two kinds of *Entamoeba histolytica* alanine aminotransferases (KEGG/ENZYME: 2.6.1.2/*Entamoeba histolytica*: 24.t00016).

<SEQ ID NO: 52>

SEQ ID NO: 52 shows the amino acid sequence of one of two kinds of *Entamoeba histolytica* alanine aminotransferases (KEGG/ENZYME: 2.6.1.2/*Entamoeba histolytica*: 24.t00016).

<SEQ ID NO: 53>

SEQ ID NO: 53 shows the nucleotide sequence of a gene encoding one of four kinds of *Trypanosoma cruzi* alanine aminotransferases (KEGG/ENZYME: 2.6.1.2/*Trypanosoma cruzi*: 506529.420).

<SEQ ID NO: 54>

SEQ ID NO: 54 shows the amino acid sequence of one of four kinds of *Trypanosoma cruzi* alanine aminotransferases (KEGG/ENZYME: 2.6.1.2/*Trypanosoma cruzi*: 506529.420).

<SEQ ID NO: 55>

SEQ ID NO: 55 shows the nucleotide sequence of a gene encoding one of four kinds of *Trypanosoma cruzi* alanine aminotransferases (KEGG/ENZYME: 2.6.1.2/*Trypanosoma cruzi*: 506529.430).

<SEQ ID NO: 56>

SEQ ID NO: 56 shows the amino acid sequence of one of four kinds of *Trypanosoma cruzi* alanine aminotransferases (KEGG/ENZYME: 2.6.1.2/*Trypanosoma cruzi*: 506529.430).

<SEQ ID NO: 57>

SEQ ID NO: 57 shows the nucleotide sequence of a gene encoding one of four kinds of *Trypanosoma cruzi* alanine aminotransferases (KEGG/ENZYME: 2.6.1.2/*Trypanosoma cruzi*: 510889.120).

<SEQ ID NO: 58>

SEQ ID NO: 58 shows the amino acid sequence of one of four kinds of *Trypanosoma cruzi* alanine aminotransferases (KEGG/ENZYME: 2.6.1.2/*Trypanosoma cruzi*: 510889.120).

<SEQ ID NO: 59>

SEQ ID NO: 59 shows the nucleotide sequence of a gene encoding one of four kinds of *Trypanosoma cruzi* alanine aminotransferases (KEGG/ENZYME: 2.6.1.2/*Trypanosoma cruzi*: 510889.140).

<SEQ ID NO: 60>

SEQ ID NO: 60 shows the amino acid sequence of one of four kinds of *Trypanosoma cruzi* alanine aminotransferases (KEGG/ENZYME: 2.6.1.2/*Trypanosoma cruzi*: 510889.140).

<SEQ ID NO: 61>

SEQ ID NO: 61 shows the nucleotide sequence of a gene encoding hamster taurine transporter.

<SEQ ID NO: 62>

SEQ ID NO: 62 shows the amino acid sequence of hamster taurine transporter.

<SEQ ID NO: 63>

SEQ ID NO: 63 shows the nucleotide sequence of a gene encoding rat taurine transporter (GenBank NM_017206).

<SEQ ID NO: 64>

SEQ ID NO: 64 shows the amino acid sequence of rat taurine transporter (GenBank NM_017206).

<SEQ ID NO: 65>

SEQ ID NO: 65 shows the nucleotide sequence of a gene encoding mouse taurine transporter (GenBank NM_009320).

<SEQ ID NO: 66>

SEQ ID NO: 66 shows the amino acid sequence of mouse taurine transporter (GenBank NM_009320).

<SEQ ID NO: 67>

SEQ ID NO: 67 shows the nucleotide sequence of a gene encoding human taurine transporter (GenBank NM_003043).

<SEQ ID NO: 68>

SEQ ID NO: 68 shows the amino acid sequence of human taurine transporter (GenBank NM_003043).

The invention claimed is:

1. A method of producing an antibody, comprising culturing an animal cell which expresses alanine aminotransferase and has a transferred DNA encoding the antibody and thereby allowing the animal cell to produce the antibody, wherein the animal cell is a cell transformed with DNA encoding the alanine aminotransferase; and
wherein the alanine aminotransferase is any one of the following (a)-(c):
 (a) a polypeptide having the amino acid sequence as shown in SEQ ID NO: 6;
 (b) a polypeptide which has an amino acid sequence derived from the amino acid sequence as shown in SEQ ID NO: 6 by substitution, deletion, addition and/or insertion of 1-5 amino acid residues and yet has alanine aminotransferase activity; and
 (c) a polypeptide having 99% or more amino acid sequence homology with the amino acid sequence as shown in SEQ ID NO: 6 and yet having alanine aminotransferase activity.

2. The method of claim 1, wherein the animal cell further expresses a taurine transporter wherein the animal cell is a cell into which DNA encoding a taurine transporter has been transferred.

3. The method of claim 1, wherein the cell is a Chinese hamster ovary cell.

4. A cultured cell transformed with DNA encoding a polypeptide having the amino acid sequence as show in SEQ ID NO: 6 and a transferred DNA encoding a desired antibody.

5. A cultured cell transformed with DNA encoding a polypeptide having the amino acid sequence as shown in SEQ ID NO: 6 and DNA encoding a taurine transporter.

6. A method of producing a desired polypeptide, comprising culturing in an α-ketoglutarate-containing medium a cell transformed with DNA encoding alanine aminotransferase and which has a transferred DNA encoding the desired polypeptide and thereby allowing the cell to produce said desired polypeptide, wherein the alanine aminotransferase is any one of the following (a)-(c):
- (a) a polypeptide having the amino acid sequence as shown in SEQ ID NO: 6;
- (b) a polypeptide which has an amino acid sequence derived from the amino acid sequence as shown in SEQ ID NO: 6 by substitution, deletion, addition and/or insertion of 1-5 amino acid residues and yet has alanine aminotransferase activity; and
- (c) a polypeptide having 99% or more amino acid sequence homology with the amino acid sequence as shown in SEQ ID NO: 6.

7. A method of producing an antibody, comprising culturing an animal cell which expresses alanine aminotransferase and has a transferred DNA encoding the antibody and thereby allowing the animal cell to produce the antibody,
wherein the animal cell is a cell transformed with exogenous DNA encoding the alanine aminotransferase; and
wherein the alanine aminotransferase is a mouse aminotransferase.

8. The method of claim 7, wherein the animal cell further expresses a taurine transporter wherein the animal cell is a cell into which DNA encoding a taurine transporter has been transferred.

9. The method of claim 7, wherein the cell is a Chinese hamster ovary cell.

10. A cultured cell transformed with exogenous DNA encoding a mouse alanine aminotransferase and a transferred DNA encoding a desired antibody.

11. The method of claim 1, wherein the animal cell further has a transferred DNA encoding a taurine transporter.

12. The method of claim 7, wherein the animal cell further has a transferred DNA encoding a taurine transporter.

13. A cultured cell transformed with DNA encoding a mouse alanine aminotransferase and DNA encoding a taurine transporter.

14. A method of producing a desired polypeptide, comprising culturing in an α-ketoglutarate-containing medium a cell transformed with exogenous DNA encoding alanine aminotransferase and which has a transferred DNA encoding the desired polypeptide and thereby allowing the cell to produce said desired polypeptide, wherein the alanine aminotransferase is a mouse alanine aminotransferase.

* * * * *